US011674125B2

(12) United States Patent
Anthony et al.

(10) Patent No.: US 11,674,125 B2
(45) Date of Patent: Jun. 13, 2023

(54) GLYCOENGINEERING

(71) Applicant: THE GENERAL HOSPITAL CORPORATION, Boston, MA (US)

(72) Inventors: Robert M. Anthony, Arlington, MA (US); Maya Kitaoka, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 225 days.

(21) Appl. No.: 16/954,814

(22) PCT Filed: Dec. 17, 2018

(86) PCT No.: PCT/US2018/066013
§ 371 (c)(1),
(2) Date: Jun. 17, 2020

(87) PCT Pub. No.: WO2019/126041
PCT Pub. Date: Jun. 27, 2019

(65) Prior Publication Data
US 2021/0207106 A1 Jul. 8, 2021

Related U.S. Application Data

(60) Provisional application No. 62/607,111, filed on Dec. 18, 2017.

(51) Int. Cl.
| | |
|---|---|
| *C12N 9/10* | (2006.01) |
| *A61P 37/06* | (2006.01) |
| *A61P 19/02* | (2006.01) |
| *A61P 13/12* | (2006.01) |
| *A61K 38/00* | (2006.01) |

(52) U.S. Cl.
CPC ............ *C12N 9/1081* (2013.01); *A61P 13/12* (2018.01); *A61P 19/02* (2018.01); *A61P 37/06* (2018.01); *C12N 9/1051* (2013.01); *C12Y 204/01038* (2013.01); *C12Y 204/99001* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 6,468,798 B1 | 10/2002 | Debs et al. | |
| 8,367,374 B2* | 2/2013 | Umana | A61P 3/10 |
| | | | 435/70.1 |
| 2006/0084162 A1 | 4/2006 | Qasba et al. | |
| 2014/0242058 A1 | 8/2014 | Lau et al. | |
| 2015/0231212 A1 | 8/2015 | Lau et al. | |
| 2016/0024179 A1* | 1/2016 | Warner | C07K 14/70503 |
| | | | 435/68.1 |
| 2016/0102298 A1* | 4/2016 | Czabany | C12N 9/1081 |
| | | | 435/320.1 |
| 2016/0108450 A1 | 4/2016 | Bhatnagar et al. | |
| 2016/0257754 A1 | 9/2016 | Schultes et al. | |
| 2017/0051328 A1 | 2/2017 | Tayi et al. | |

FOREIGN PATENT DOCUMENTS

| | | | |
|---|---|---|---|
| CN | 102333872 | 1/2012 | |
| CN | 102858949 | 1/2013 | |
| JP | 2006-516893 | 7/2006 | |
| KR | 10048311 | * 10/2016 | ............ C07K 19/00 |
| WO | WO 03/052088 | 6/2003 | |
| WO | WO 2004/065540 | 8/2004 | |

OTHER PUBLICATIONS

Kitaoka et al., "Abstract # 180: Engineering of glycosyltransferases for in-vivo glycan modification," Presented at 2018 Annual Meeting of The Society for Glycobiology, New Orleans, LA, Nov. 5-8, 2018; Glycobiology, 2018, 28(12):4073.
Pagan et al., "Engineered Sialylation of Patholgenic Antibodies In Vivo Attenuates Autoimmune Disease," Cell, 2018, 172:564-577. e13.
Partial Supplementary European Search Report in European Appln. No. 18890804.0, dated Sep. 24, 2021, 12 pages.
Ackerman, Margaret E., et al., "Natural variation in Fc glycosylation of HIV-specific antibodies impacts antiviral activity." The Journal of clinical investigation, May 2013, 123(5):2183-2192.
Alavi et al., "Serum galactosyltransferase isoform changes in rheumatoid arthritis." The Journal of rheumatology, Aug. 2004, 31(8):9 Pages.
Albert et al., "In vivo enzymatic modulation of IgG glycosylation inhibits autoimmune disease in an IgG subclass-dependent manner." Proceedings of the National Academy of Sciences, Sep. 2008, 105(39):15005-15009.
Allhorn et al., "The IgG-specific endoglycosidase EndoS inhibits both cellular and complement-mediated autoimmune hemolysis." Blood, The Journal of the American Society of Hematology, Jun. 2010, 115(24):5080-5088.
Anthony et al., "Identification of a receptor required for the anti-inflammatory activity of IVIG." Proceedings of the National Academy of Sciences, Dec. 2008, 105(50):19571-19578.
Anthony et al., "Intravenous gammaglobulin suppresses inflammation through a novel TH 2 pathway." Nature, Jun. 2011, 475(7354):110-113.
Anthony et al., "Recapitulation of IVIG anti-inflammatory activity with a recombinant IgG Fc." Science, Apr. 2008, 320(5874):5 Pages.
Appenheimer et al., "Biologic contribution of P1 promoter-mediated expression of ST6Gal I sialyltransferase." Glycobiology, Aug. 2003, 13(8):591-600.
Arnold et al., "The impact of glycosylation on the biological function and structure of human immunoglobulins." Annu. Rev. Immunol. Apr. 2007, 25:33 Pages.
Bai et al., "Self-dsDNA in the pathogenesis of systemic lupus erythematosus." Clinical & Experimental Immunology, Jan. 2018, 191(1):1-10.

(Continued)

*Primary Examiner* — Zachary S Skelding
(74) *Attorney, Agent, or Firm* — Fish & Richardson P.C.

(57) ABSTRACT

This disclosure relates to glycoengineering, and methods of utilizing glycoengineering for various therapeutic purposes.

31 Claims, 64 Drawing Sheets

Specification includes a Sequence Listing.

(56) References Cited

OTHER PUBLICATIONS

Bayry et al., "DC-Sign and α2, 6-sialylated IgG Fc interaction is dispensable for the anti-inflammatory activity of IVIg on human dendritic cells." Proceedings of the National Academy of Sciences, Mar. 2009, 106(9):E24-E24.
Beck et al., "Strategies and challenges for the next generation of therapeutic antibodies." Nature reviews immunology, May 2010, 10(5):345-352.
Benkhoucha et al., "IgG glycan hydrolysis by EndoS inhibits experimental autoimmune encephalomyelitis." Journal of neuroinflammation, Dec. 2012, 9(1):12 Pages.
Boilard et al., "Platelets amplify inflammation in arthritis via collagen-dependent microparticle production," Science, Jan. 2010, 327(5965):5 Pages.
Brockhausen et al., "O-GalNAc glycans." Essentials of Glycobiology. 2nd edition. Cold Spring Harbor Laboratory Press, 2009, 17 Pages.
Bruhns et al., "Colony-stimulating factor-1-dependent macrophages are responsible for IVIG protection in antibody-induced autoimmune disease." Immunity, Apr. 2003, 18(4):573-581.
Canty et al., "Procollagen trafficking, processing and fibrillogenesis." Journal of cell science, Apr. 2005, 118(7):1341-1353.
Chung, et al., "Polyfunctional Fc-effector profiles mediated by IgG subclass selection distinguish RV144 and VAX003 vaccines." Science translational medicine, Mar. 2014, 6(228):11 Pages.
Clark-Curtiss et al., "[23] Analysis of recombinant DNA using *Escherichia coli* minicells." Methods in enzymology, Jan. 1983, vol. 101, Academic Press, 347-362.
Clynes "Protective mechanisms of IVIG." Current opinion in immunology, 2007, 6(19):646-651.
Colley et al., "Conversion of a Golgi apparatus sialyltransferase to a secretory protein by replacement of the NH2-terminal signal anchor with a signal peptide." Journal of Biological Chemistry, Oct. 1989, 264(30):17619-17622.
Collin et al., "EndoS, a novel secreted protein from *Streptococcus pyogenes* with endoglycosidase activity on human IgG." The EMBO journal, Jun. 2001, 20(12):3046-3055.
Czajkowsky et al., "Fc-fusion proteins: new developments and future perspectives." EMBO molecular medicine, Oct. 2012, 4(10):1015-1028.
Dal et al., "Assessment of the underlying causes of the immune thrombocytopenia: Ten years experience." J Pak Med Assoc. Jul. 2017, 67(7):1004-1008.
Davies et al., "Expression of GnTIII in a recombinant anti-CD20 CHO production cell line: expression of antibodies with altered glycoforms leads to an increase in ADCC through higher affinity for FCγRIII." Biotechnology and bioengineering, Aug. 2001, 74(4):288-294.
Debre et al., "Infusion of Fcγ fragments for treatment of children with acute immune thrombocytopenic purpura." The Lancet, Oct. 1993, 342(8877):945-949.
Devi et al., "Platelet recruitment to the inflamed glomerulus occurs via an αIIbβ3/GPVI-dependent pathway." The American journal of pathology, Sep. 2010, 177(3):1131-1142.
Fan et al., "Production of multivalent protein binders using a self-trimerizing collagen-like peptide scaffold." The FASEB Journal, Nov. 2008, 22(11):3795-3804.
Ferrara et al., "Unique carbohydrate—carbohydrate interactions are required for high affinity binding between FcγRIII and antibodies lacking core fucose." Proceedings of the National Academy of Sciences, Aug. 2011, 108(31):12669-12674.
Fiebiger et al., "Protection in antibody-and T cell-mediated autoimmune diseases by antiinflammatory IgG Fcs requires type II FcRs." Proceedings of the National Academy of Sciences, May 2015, 112(18):E2385-E2394.
Fillit "Intravenous immunoglobulins for Alzheimer's disease." The Lancet Neurology, Dec. 2004, 3(12):704.
Fillit et al., "IV immunoglobulin is associated with a reduced risk of Alzheimer disease and related disorders." Neurology, Jul. 2009, 73(3):180-185.
Franklin "Structure and function of immunoglobulins." Acta Endocrinol Suppl (Copenh), Dec. 1975, 194:77-95.
Fu et al., "Autoantibodies and glomerulonephritis in systemic lupus erythematosus." Lupus, Mar. 2003, 12(3):175-180.
Gossen "Tight control of gene expression in mammalian cells by tetracycline-responsive promoters." Proceedings of the National Academy of Sciences, Jun. 1992, 89(12):5547-5551.
Hack et al., "Intravenous immunoglobulins: a treatment for Alzheimer's disease?." Journal of Neurology, Neurosurgery & Psychiatry, Oct. 2004, 75(10):1374-1375.
Hassinen et al., "Golgi N-glycosyltransferases form both homo-and heterodimeric enzyme complexes in live cells." Journal of Biological Chemistiy, Jun. 2010, 285(23):17771-17777.
Hourmant et al., "Frequency and clinical implications of development of donor-specific and non-donor-specific HLA antibodies after kidney transplantation." Journal of the American Society of Nephrology, Sep. 2005, 16(9):2804-2812.
Huber et al., "Crystallographic structure studies of an IgG molecule and an Fc fragment." Nature, Dec. 1976, 264(5585):415-420.
Hughes "Frequency of anti-DNA antibodies in SLE, RA and other diseases: experience with the ammonium sulphate precipitation technique." Scandinavian Journal of Rheumatology, Jan. 1975, 4(sup11):42-51.
Imbach et al., "High-dose intravenous gammaglobulin for idiopathic thrombocytopenic purpura in childhood." The lancet, Jun. 1981, 317(8232):1228-1231.
Ishii et al., "High-dose intravenous immunoglobulin (IVIG) therapy in autoimmune skin blistering diseases." Clinical reviews in allergy & immunology, Apr. 2010, 38(2-3):186-195.
Jefferis "Glycosylation as a strategy to improve antibody-based therapeutics." Nature reviews Drug discoveiy, Mar. 2009, 8(3):226-234.
Jefferis "Glycosylation of antibody therapeutics: optimisation for purpose." Recombinant Proteins From Plants, Humana Press, 2009, 223-238.
Jefferis "Glycosylation of recombinant antibody therapeutics." Biotechnology progress, 2005, 21(1):11-16.
Jones et al., "Anti-inflammatory IgG production requires functional P1 promoter in β-galactoside α2, 6-sialyltransferase 1 (ST6Gal-1) gene." Journal of Biological Chemistry, May 2012, 287(19):15365-15370.
Jones et al., "B-cell-independent sialylation of IgG." Proceedings of the National Academy of Sciences, Jun. 2016, 113(26):7207-7212.
Kalcheva et al., "The gene encoding [beta]-galactoside [alpha] 2, 6-sialyltransferase maps to mouse Chromosome 16." Mammalian genome, Aug. 1997, 8(8):619-620.
Kaneko et al., "Anti-inflammatory activity of immunoglobulin G resulting from Fc sialylation." Science, Aug. 2006, 313(5787):670-673.
Kaneko et al., "Pathology and protection in nephrotoxic nephritis is determined by selective engagement of specific Fc receptors." The Journal of experimental medicine, Mar. 2006, 203(3):789-797.
Kang et al., "The C-type lectin Sign-R1 mediates uptake of the capsular polysaccharide of *Streptococcus pneumoniae* in the marginal zone of mouse spleen." Proceedings of the National Academy of Sciences, Jan. 2004, 101(1):215-220.
Korganow et al., "From systemic T cell self-reactivity to organ-specific autoimmune disease via immunoglobulins." Immunity, Apr. 1999, 10(4):451-461.
Lee et al., "Platelets support extracellular sialylation by supplying the sugar donor substrate." Journal of Biological Chemistry, Mar. 2014, 289(13):8742-8748.
Lerner et al., "The role of anti-glomerlar basement membrane antibody in the pathogenesis of human glomerulonephritis." The Journal of experimental medicine, Dec. 1967, 126(6):989-1004.
Li et al., "Modulating IgG effector function by Fc glycan engineering." Proceedings of the National Academy of Sciences, Mar. 2017, 114(13):3485-3490.
Lu et al., "A functional role for antibodies in tuberculosis." Cell, Oct. 2016, 167(2):26 Pages.

(56) References Cited

OTHER PUBLICATIONS

Meng et al., "Enzymatic Basis for N-Glycan Sialylation Structure of Rat α2, 6-Sialyltransferase (ST6GAL1) Reveals Conserved and Unique Features for Glycan Sialylation." Journal of Biological Chemistry, Nov. 2013, 288(48):20 Pages.
Morrison, D. A. "Transformation in *Escherichia coli*: cryogenic preservation of competent cells." Journal of bacteriology, Oct. 1977, 132(1):349-351.
Natsume et al., "Fucose removal from complex-type oligosaccharide enhances the antibody-dependent cellular cytotoxicity of single-gene-encoded antibody comprising a single-chain antibody linked the antibody constant region." Journal of immunological methods, Nov. 2005, 306(1-2):93-103.
Neering et al., "Transduction of primitive human hematopoietic cells with recombinant adenovirus vectors." (1996): 1147-1155.
Negi et al., "Intravenous immunoglobulin: an update on the clinical use and mechanisms of action." Journal of clinical immunology, May 2007, 27(3):233-245.
Nimmerjahn et al., "Anti-inflammatory actions of intravenous immunoglobulin." Annu. Rev. Immunol., Apr. 2008, 26:23 Pages.
Nimmerjahn et al., "Fcγ receptors as regulators of immune responses." Nature Reviews Immunology, Jan. 2008, 8(1):34-47.
Nimmerjahn et al., "FcγR dependent mechanisms of cytotoxic, agonistic, and neutralizing antibody activities." Trends in immunology, Jun. 2015, 36(6):12 Pages.
Ohmi et al., "Sialylation converts arthritogenic IgG into inhibitors of collagen-induced arthritis." Nature communications, Apr. 2016, 7(1):1-12.
Okazaki et al., "Fucose depletion from human IgG1 oligosaccharide enhances binding enthalpy and association rate between IgG1 and FcγRIIIa." Journal of molecular biology, Mar. 2004, 336(5):1239-1249.
Oligino et al., "Drug inducible transgene expression in brain using a herpes simplex virus vector." Gene therapy, Apr. 1998, 5(4):491-496.
Palva et al., "Secretion of interferon by Bacillus subtilis." Gene, May 1983, 22(2-3):229-235.
PCT International Preliminary Report on Patentability in International Appln. No. PCT/US2018/066013, dated Jun. 23, 2020, 13 Pages.
PCT International Search Report and Written Opinion in International Appln. No. PCT/US2018/066013, dated May 17, 2019, 22 Pages.
Pfeifle et al., "Regulation of autoantibody activity by the IL-23-T H 17 axis determines the onset of autoimmune disease." Nature immunology, Jan. 2017, 18(1):13 Pages.
Pincetic et al., "Type I and type II Fc receptors regulate innate and adaptive immunity." Nature immunology, Aug. 2014, 15(8):707-716.
Prineas et al., "Multiple sclerosis: Serum anti-CNS autoantibodies." Multiple Sclerosis Journal, Apr. 2018, 24(5):13 Pages.
Pucci et al., "PF4 promotes platelet production and lung cancer growth." Cell reports, Nov. 2016, 17(7):1764-1772.
Querol et al., "Autoantibodies in chronic inflammatory neuropathies: diagnostic and therapeutic implications." Nature Reviews Neurology, Sep. 2017, 13(9):533-547.
Rendahl et al., "Regulation of gene expression in vivo following transduction by two separate rAAV vectors." Nature biotechnology, Aug. 1998, 16(8):757-761.
Samuelsson et al., "Anti-inflammatory activity of IVIG mediated through the inhibitory Fc receptor." Science, Jan. 2001, 291(5503):484-486.
Scallon et al., "Higher levels of sialylated Fc glycans in immunoglobulin G molecules can adversely impact functionality." Molecular immunology, Mar. 2007, 44(7):1524-1534.
Schlothauer et al., "Novel human IgG1 and IgG4 Fc-engineered antibodies with completely abolished immune effector functions." Protein Engineering, Design and Selection, Oct. 2016, 29(10):457-466.
Schrijver et al., "Anti-GBM nephritis in the mouse: role of granulocytes in the heterologous phase." Kidney international, Jul. 1990, 38(1):86-95.
Schwab et al., "Broad requirement for terminal sialic acid residues and FcγRIIB for the preventive and therapeutic activity of intravenous immunoglobulins in vivo." European journal of immunology, May 2014, 44(5):1444-1453.
Schwab et al., "Intravenous immunoglobulin therapy: how does IgG modulate the immune system?." Nature Reviews Immunology, Mar. 2013, 13(3):176-189.
Schwab et al., "IVI g-mediated amelioration of ITP in mice is dependent on sialic acid and SIGNR 1." European journal of immunology, Apr. 2012, 42(4):826-830.
Shields et al., "Lack of fucose on human IgG1 N-linked oligosaccharide improves binding to human FcγRIII and antibody-dependent cellular toxicity." Journal of Biological Chemistry, 2002, 277(30):9 Pages.
Stadlmann et al., "A close look at human IgG sialylation and subclass distribution after lectin fractionation." Proteomics, Jul. 2009, 9(17):4143-4153.
Sugimoto et al., "ST6Gal I cleavage by BACE1 enhances the sialylation of soluble glycoproteins: A novel regulatory mechanism for α2, 6-sialylation." Journal of Biological Chemistry, Sep. 2007: 9 Pages.
Tackenberg et al., "Impaired inhibitory Fcγ receptor IIB expression on B cells in chronic inflammatory demyelinating polyneuropathy." Proceedings of the National Academy of Sciences, Mar. 2009, 106(12):6 Pages.
Tackenberg et al., "Mechanisms of IVIG efficacy in chronic inflammatory demyelinating polyneuropathy," Journal of clinical immunology, May 2010, 30(1):65-69.
Tan et al., "Thrombin stimulated platelet-derived exosomes inhibit platelet-derived growth factor receptor-beta expression in vascular smooth muscle cells." Cellular Physiology and Biochemistry, 2016, 38(6):2348-2365.
Tan, Eng M. "Autoantibodies and Autoimmunity: A Three-Decade Perspective. A Tribute to Henry G. Kunkel a." Annals of the New York Academy of Sciences, Apr. 1997, 815(1):1-14.
Varki, Ajit. "Biological roles of oligosaccharides: all of the theories are correct." Glycobiology, Apr. 1993, 3(2):97-130.
Wang et al., "Anti-HA glycoforms drive B cell affinity selection and determine influenza vaccine efficacy." Cell, Jul. 2015, 162(1):11 Pages.
Wang et al., "Chromosome mapping and organization of the human beta-galactoside alpha 2, 6-sialyltransferase gene. Differential and cell-type specific usage of upstream exon sequences in B-lymphoblastoid cells." Journal of Biological Chemistiy, Feb. 1993, 268(6):4355-4361.
Wang et al., "IgG antibodies to dengue enhanced for FcγRIIIA binding determine disease severity." Science, Jan. 2017, 355(6323):5 Pages.
Wang et al., "Positive and negative regulation of gene expression in eukaryotic cells with an inducible transcriptional regulator," Gene therapy, May 1997, 4(5):432-441.
Washburn et al., "Controlled tetra-Fc sialylation of IVIg results in a drag candidate with consistent enhanced anti-inflammatory activity." Proceedings of the National Academy of Sciences, Mar. 2015, 112(11):11 Pages.
Woodard-Grice et al., "Proteolytic shedding of ST6Gal-I by BACE1 regulates the glycosylation and function of α4β1 integrins." Journal of Biological Chemistry, Sep. 2008, 283(39):11 Pages.
Xiao et al., "Precision glycocalyx editing as a strategy for cancer immunotherapy." Proceedings of the National Academy of Sciences, Sep. 2016, 113(37):10304-10309.
Yang et al., "Successful treatment of experimental glomerulonephritis with IdeS and EndoS, IgG-degrading streptococcal enzymes." Nephrology Dialysis Transplantation, Aug. 2010, 25(8):9 Pages.
Youings et al., "Site-specific glycosylation of human immunoglobulin G is altered in four rheumatoid arthritis patients." Biochemical Journal, Mar. 1996, 314(2):621-630.
Zhang et al., "Sialylated intravenous immunoglobulin suppress anti-ganglioside antibody mediated nerve injury." Experimental neurology, Aug. 2016, 282:49-55.

(56) References Cited

OTHER PUBLICATIONS

Extended European Search Report in European Appln No. 18890804.0, dated Jan. 4, 2022, 9 pages.
Office Action in Japanese Appln. No. 2020-552679, dated Dec. 20, 2022, 10 pages (with English translation).
Raymond et al., "Production of α2, 6-sialylated IgG1 in CHO cells," mAbs, 2015, 7(3):571-583.
Zhang et al., "IgG glycosylation and disease—Progress in disease-related studies," Life Sciences, Apr. 2017, 29(4):319-330 (with English abstract).

* cited by examiner

FIGS. 1D-1E

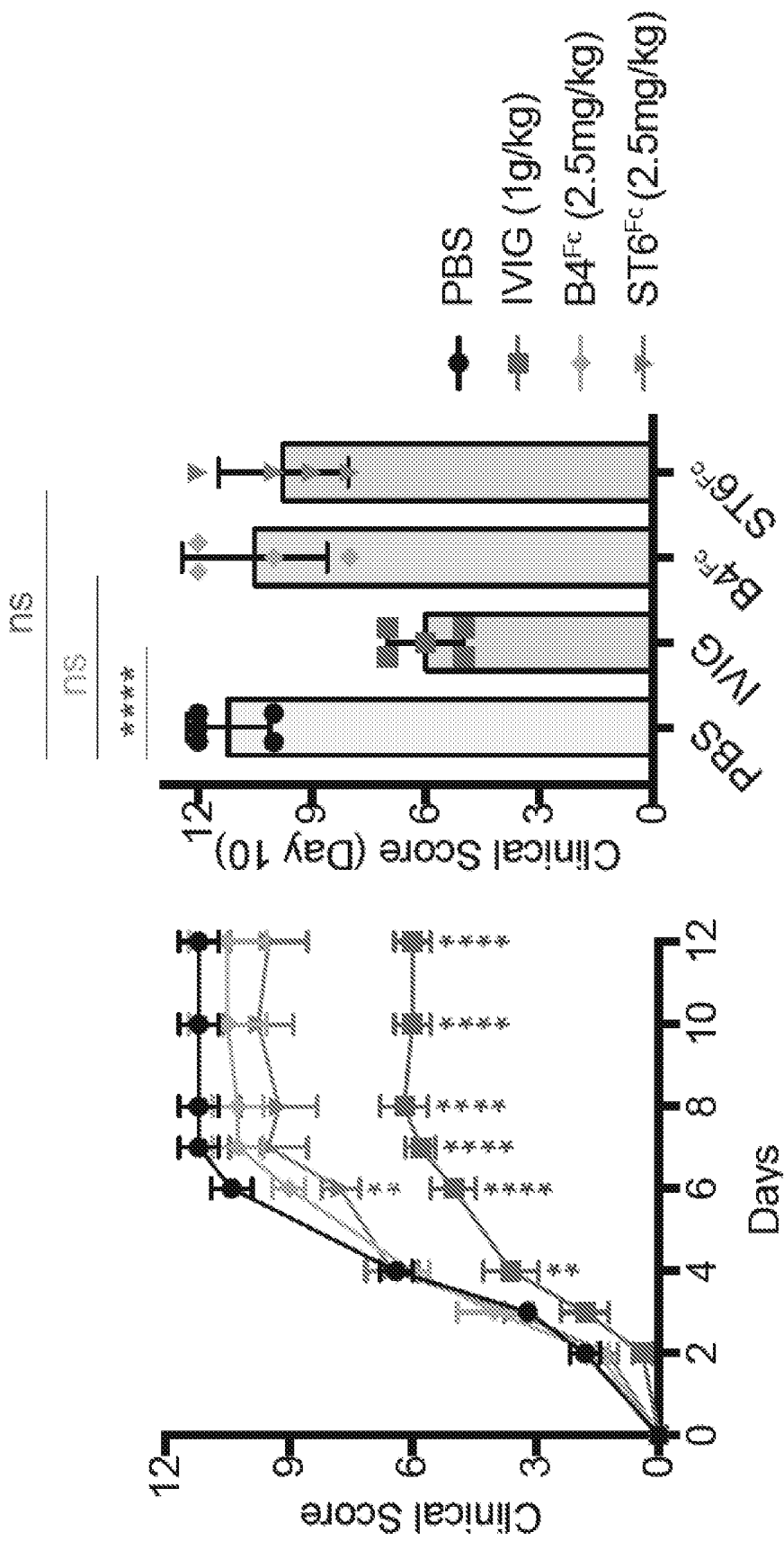

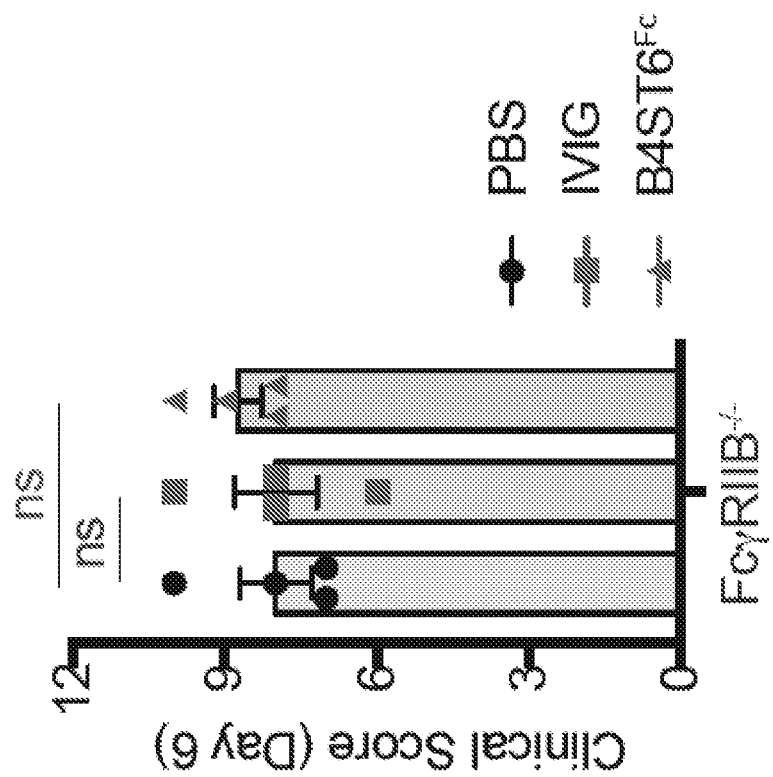
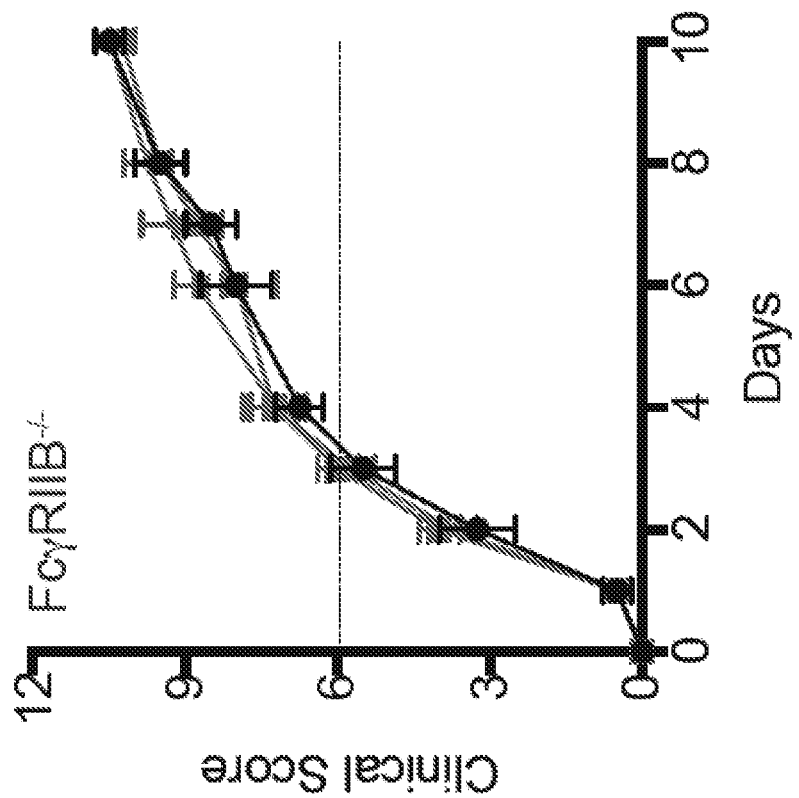
FIG. 3B
FIG. 3A

FIG. 20

SEQ ID NO: 1
hST6GAL1 (Beta-galactoside alpha-2,6-sialyltransferase 1) (Full-length)

MIHTNLKKKFSCCVLVFLLFAVICVWKEKKKGSYYDSFKLQTKEFQVLKSLGKLAMGSDSQSVSSSTQDPH
RGRQTLGSLRGLAKAKPEASFQVWNKDSSSKNLIPRLQKIWKNYLSMNKYKVSYKGPGPGIKFSAEALRCHL
RDHVNVSMVEVTDFPFNTSEWEGYLPKESIRTKAGPWGRCAVVSSAGSLKSSQLGREIDDHDAVLRFNGAPT
ANFQQDVGTKTTIRLMNSQLVTTEKRFLKDSLYNEGILIVWDPSVYHSDIPKWYQNPDYNFFNNYKTYRKLH
PNQPFYILKPQMPWELWDILQEISPEEIQPNPPSSGMLGIIMMTLCDQVDIYEFLPSKRKTDVCYYQKFF
DSACTMGAYHPLLYEKNLVKHLNQGTDEDIYLLGKATLPGFRTIHC

Glycosyltransferase domain (Amino Acids: 160-390)

SEQ ID NO: 2
hB4GALT1 (Beta-1,4-galactosyltransferase 1) (Full-length)

MRLREPLLSGSAAMPGASLQRACRLLVAVCALHLGVTLVYYLAGRDLSRLPQLVGVSTPLQGGSNSAAAIGQ
SSGELRTGGARPPPLGASSQPRPGGDSSPVVDSGPASNLTSVPVPHTTALSLPACPEESPLLVGPMLIE
FNMPVDLELVAKQNPNVKMGGRYAPRDCVSPHKVAIIPFRNRQEHLKYWLYYLHPVLQRQQLDYGIYVINQ
AGDTIFNRAKLLNVGFQEALKDYDYTCFVFSDVDLIPMNDHNAYRCFSQPRHISVAMDKFGFSLPYVQYFGG
VSALSKQQFLTINGFPNNYWGWGGEDDIFNRLVFRGMSISRPNAVVGRCRMIRHSRDKKNEPNPQRFDRIA
HTKETMLSDGLNSLTYQVLDVQRYPLYTQITVDIGTPS

Glycosyltransferase domain (Amino Acids: 185-390)

FIG. 21

SEQ ID NO: 3
Human IgG1-Fc

MYRMQLLSCIALSLALVTNSMPRGPPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK

IL2-signal sequence (Amino Acids: 1-20)
hIgGFc (Amino Acids: 26-256)

SEQ ID NO: 4
Human IgG2-Fc

METDTLLLWLLLLWVPGSTGDAAAQPARRAVRSLVPSSDPRKCCVECPPCPAPPVAGPSVFLFPPKPKDTLMI
SRTPEVTCVVVDVSHEDPEVQFNWYVDGVEVHNAKTKPREEQFNSTFRVVSVLTVVHQDWLNGKEYKCKVSN
KGLPAPIEKTISKTKGQPREPQVYTLPPSREEMTKNQVSLTCLVKGFYPSDIAVEWESNGQPENNYKTTPPM
LDSDGSFFLYSKLTVDKSRWQQGNVFSCSVMHEALHNHYTQKSLSLSPGK

κ-signal sequence (Amino Acids: 1-39)
hIgG2-Fc (Amino Acids: 52-266)

FIG. 21 (continued)

SEQ ID NO: 5
hIgG3-Fc

METDTLLLWVLLLWVPGSTGDAAQPARRAVRSLVPSSDPELKTPLGDTTHTCPRCPEPKSCDTPPPCPRCPE
PKSCDTPPPCPEPKSCDTPPPCPRCPAPELLGGPSVFLFPPKPKDTLMISRTPEVTCVVVDVSHEDPEV
QFKWYVDGVEVHNAKTKPREEQYNSTFRVVSVLTVLHQDWLNGKEYKCKVSNKALPAPIEKTISKTKGQPRE
PQVYTLPPSREEMTKNQVSLTCLVKGFYPSDIAVEWESSGQPENNYNTTPPMLDSDGSFFLYSKLTVDKSRW
QQGNIFSCSVMHEALHNRFTQKSLSLSPGK

κ-signal sequence (Amino Acids: 1-39)
         hIgG3-Fc(Amino Acids: 41-318)

SEQ ID NO: 6
hIgG4-Fc

METDTLLLWVLLLWVPGSTGDAAQPARRAVRSLVPSSDPESKYGPPCPSCPAPEFLGGPSVFLFPPKPKDTL
MISRTPEVTCVVVDVSQEDPEVQFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSPGK

κ-signal sequence (Amino Acids: 1-39)
         hIgG4-Fc(Amino Acids: 53-268)

FIG. 21 (continued)

SEQ ID NO: 7
Mouse IgG1-Fc

MYRMQLLSCIALSLALVTNSMPRGPVPRDCGCKPCICTVPEVSSVFIFPPKPKDVLTITLTPKVTCVVVDIS
KDDPEVQFSWFVDDVEVHTAQTKPREEQINSTFRSVSELPIMHQDWLNGKEFKCRVNSAAFPAPIEKTISKT
KGRPKAPQVYTIPPPKEQMAKDKVSLTCMITNFFPEDITVEWQWNGQPAENYKNTQPIMDTDGSYFVYSKLN
VQKSNWEAGNTFTCSVLHEGLHNHHTEKSLSHSPGK

IL2-signal sequence (Amino Acids: 1-20)
mIgG1-Fc (Amino Acids: 26-252)

SEQ ID NO: 8
Mouse IgG2a-Fc

MYRMQLLSCIALSLALVTNSMPRGPTIKPCPPCKCPAPNLLGGPSVFIFPPKIKDVLMISLSPIVTCVVVDV
SEDDPDVQISWFVNNVEVHTAQTQTHREDYNSTLRVVSALPIQHQDWMSGKEFKCKVNNKDLPAPIERTISK
PKGSVRAPQVYVLPPPEEEMTKKQVTLTCMVTDFMPEDIYVEWTNNGKTELNYKNTEPVLDSDGSYFMYSKL
RVEKKNWVERNSYSCSVVHEGLHNHHTTKSFSRTPGK

IL2-signal sequence (Amino Acids: 1-20)
mIgG2a-Fc (Amino Acids: 21-253)

FIG. 21 (continued)

SEQ ID NO: 9
Mouse IgG2b-Fc

MYRMQLLSCIALSLALVTNSEPSGPISTINPCPPCKECHKCPAPNLEGGPSVFIFPPNIKDVLMISLTPKVT
CVVVDVSEDDPDVRISWFVNNVEVHTAQTQTHREDYNSTIRVVSALPIQHQDWMSGKEFKCKVNNKDLPSPI
ERTISKIKGLVRAPQVYILPPPAEQLSRKDVSLTCLVVGFNPGDISVEWTSNGHTEENYKDTAPVLDSDGSY
FIYSKLDIKTSKWEKTDSFSCNVRHEGLKNYYLKKTISRSPGK

IL2-signal sequence (Amino Acids: 1-20)
mIgG2b-Fc (Amino Acids: 21-259)

SEQ ID NO: 10
Mouse IgG3-Fc

MYRMQLLSCIALSLALVTNSEPRIPKPSTPPGSSCPPGNILGGPSVFIFPPKPKDALMISLTPKVTCVVVDV
SEDDPDVHVSWFVDNKEVHTAWTQPREAQYNSTFRVVSALPIQHQDWMRGKEFKCKVNNKALPAPIERTISK
PKGRAQTPQVYTIPPPREQMSKKKVSLTCLVTNFFSEAISVEWERNGELEQDYKNTPPILDSDGTYFLYSKL
TVDTDSWLQGEIFTCSVVHEALHNHHTQKNLSRSPGK

IL2-signal sequence (Amino Acids: 1-20)
mIgG3-Fc (Amino Acids: 21-253)

FIG. 22

SEQ ID NO: 11
hIgGFc-B4GALT1 (ECD)
MYRMQLLSCIALSLALVTNSMPRGPPPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGKGAPDLKLMGRDLSRLPQLVGVSTPLQGGSNSA
AAIGQSSGELRTGGARPPPLGASSQPRPGGDSSPVVDSGPASNLTSVPVPHTTALSLPACPEESPLLVG
PMLIEFNMPVDLELVAKQNPNVKMGGRYAPRDCVSPHKVAIIPFRNRQEHLKYWLYYLHPVLQRQQLDYGI
YVINQAGDTIFNRAKLLNVGFQEALKDYDYTCFVFSDVDLIPMNDHNAYRCFSQPRHISVAMDKFGSLPYV
QYFGGVSALSKQQFLTINGFPNNYWGWGGEDDIFNRLVFRGMSISRPNAVVGRCRMIRHSRDKKNEPNPQR
FDRIAHTKETMLSDGLNSLTYQVLDVQRYPLYTQITVDIGTPS

IL2-signal sequence (Amino Acids: 1-20)
hIgGFc (Amino Acids: 26-256)
B4GALT1 (Amino Acids: 262-619)
CH2 (Amino Acids: 41-149)
CH3 (Amino Acids: 151-254)
Glycosyltransferase domain (Amino Acids: 406-611)

FIG. 22 (continued)

SEQ ID NO: 12
hIgG1Fc-ST6GAL1 (EFQ)
MYRMQLLSCIALSLALVTNSMPRGPPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGKGAPDLKLMEFQVLKSLGKLAMGSDSQSVSSSS
TQDPHRGRQTLGSLRGLAKAKPEASFQVWNKDSSSKNLIPRLQKIWKNYLSMNKYKVSYKGPGPGIKFSAEA
LRCHLRDHVNVSMVEVTDFPENTSEWEGYLPKESIRTKAGPWGRCAVVSSAGSLKSSQLGREIDDHDAVLRF
NGAPTANFQQDVGTKTTIRLMNSQLVTTEKRFLKDSLYNEGILIVWDPSVYHSDIPKWYQNPDYNFFNNYKT
YRKLHPNQPFYILKPQMPWELMDILQEISPEEIQPNPPSSGMLGIIIMMTLCDQVDIYEFLPSKRKTDVCYY
YQKFFDSACTMGAYHPLLYEKNLVKHLNQGTDEDIYLLGKATLPGFRTIHC

IL2-signal sequence (Amino Acids: 1-20)
hIgGFc (Amino Acids: 26-256)
ST6GAL1 (Amino Acids: 265-627)
CH2 (Amino Acids: 41-149)
CH3 (Amino Acids: 151-254)
Glycosyltransferase domain (Amino Acids: 381-611)

FIG. 22 (continued)

SEQ ID NO: 13
mIgG1Fc-B4GALT1

MYRMQLLSCIALSLALVTNSMVPRDCGCKPCICTVPEVSSVFIFPPKPKDVLTITLTPKVTCVVVDISKDDP
EVQFSWFVDDVEVHTAQTKPREEQINSTFRSVSELPIMHQDWLNGKEFKCRVNSAAFPAPIEKTISKTKGRP
KAPQVYTIPPPKEQMAKDKVSLTCMITNFFPEDITVEWQWNGQPAENYKNTQPIMDTDGSYFVYSKLNVQKS
NWEAGNTFTCSVLHEGLHNHHTEKSLSHSPGKGAPDLKLMGRDLSRLPQLVGVSTPLQGGSNSAAAIGQSSG
ELRTGGARPPPLGASSQPRPGGDSSPVVDSGPGPASNLTSVPVPHTTALSLPACPEESPLLVGPMLIEFNM
PVDLELVAKQNPNVKMGGRYAPRDCVSPHKVAIIPFRNRQEHLKYWLYLHPVLQRQQLDYGIYVINQAGD
TIFENRAKLLNVGFQEALKDYDYTCFVFSDVDLIPMNDHNAYRCFSQPRHISVAMDKFGFSLPYVQYFGGVSA
LSKQQFLTINGFPNNYWGWGGEDDDIFNRLVFRGMSISRPNAVVGRCRMIRHSRDKKNEPNPQRFDRIAHTK
ETMLSDGLNSLTYQVLDVQRYPLYTQITVDIGTPS

IL2-signal sequence (Amino Acids: 1-20)
mIgG1Fc (Amino Acids: 21-248)
B4GALT1 (Amino Acids: 257-611)
Glycosyltransferase domain (Amino Acids: 398-603)
CH2 (Amino Acids: 36-141)
CH3 (Amino Acids: 143-248)

FIG. 22 (continued)

SEQ ID NO: 14
mIgG1Fc-ST6GAL1

MYRMQLLSCIALSLALVTNSMPRGPVPRDCGCKPCICTVPEVSSVFIFPPKPKDVLTITLTPKVTCVVVDIS
KDDPEVQFSWFVDDVEVHTAQTKPREEQINSTFRSVSELPIMHQDWLNGKEFKCRVNSAAFPAPIEKTISKT
KGRPKAPQVYTIPPPKEQMAKDKVSLTCMITNFFPEDITVEWQWNGQPAENYKNTQPIMDTGSYFVYSKLN
VQKSNWEAGNTFTCSVLHEGLHNHHTEKSLSHSPGKGAPDLKLMEFQVLKSLGKLAMGSDSQSVSSSSTQDP
HRGRQTLGSLRGLAKAKPEASFQVWNKDSSSKNLIPRLQKIWKNYLSMNKYKVSYKGPGPGIKFSAEALRCH
LRDHVNVSMVEVTDFPNTSEWEGYLPKESIRTKAGPWGRCAVVSSAGSLKSSQLGREIDDHDAVLRFNGAP
TANFQQDVGTKTTIRLMNSQLVTTEKRFLKDSLYNEGILIVWDPSVYHSDIPKWYQNPDYNFFNNYKTYRKL
HPNQPFYILKPQMPWELWDILQEISPEEIQPNPPSSGMLGIIIMMTLCDQVDIYEFLPSKRKTDVCYYYQKF
FDSACTMGAYHPLLYEKNLVKHLNQGTDEDIYLLGKATLPGFRTIHC

IL2-signal sequence (Amino Acids: 1-20)
mIgG1-Fc (Amino Acids: 26-252)
ST6GAL1 (Amino Acids: 261-623)
Glycosyltransferase domain (Amino Acids: 377-607)
CH2 (Amino Acids: 40-145)
CH3 (Amino Acids: 147-252)

FIG. 22 (continued)

SEQ ID NO: 15
dogIgG-A (IgG1)Fc-ST6GAL1
MYRMQLLSCIALSLALVTNSPPCPVPEPLGGPSVLIFPPKPKDILRITRTPEVTCVVLDLGREDPEVQISWF
VDGKEVHTAKTQSREQQFNGTYRVVSVLPIEHQDWLTGKEFKCRVNHIDLPSPIERTISKARGRAHKPSVYV
LPPSPKELSSSDTVSITCLIKDFYPPDIDVEWQSNGQQEPERKHRMTPPQLDEDGSYFLYSKLSVDKSRWQQ
GDPFTCAVMHETLQNHYTDLSLSHSPGKEFQMVRGLEKQAATLSSTQNPPRASQALGSPRGPVKAKSEASFQ
VWNKDSSSKNLIPRLQKIWRNYLNMNKYKVSYKGPGPGVKFSAEALHCHLRDHVNVSMVEATDFPNTSEWE
GFLPKENIRTKAGPWGRCAVVSSAGSLKSSQLGREIDDHDAVLRFNGAPTASFQQDVGTKTTIRLMNSQLVT
TEGRFLKDSLYNEGILIVWDPSVYHSDIPKWYQSPDYSFFENYKSYRKLHPDQPFYILKPQMPWELWDIIQE
VSPEEIQPNPPSSGMLGIIIMMTLCDQVDIYEFLPSKRKTDVCYYQKFFDSACTMGAYHPLLFEKNLVKHL
NQGTDEDIYLLGKATLPGFRRIRC IL2-signal sequence (Amino Acids: 1-20)
dogIgG-A Fc (Amino Acids: 21-244)
ST6GAL1 (soluble)(Amino Acids: 245-600)

FIG. 22 (continued)

SEQ ID NO: 16
dogIgG-A(IgG1)Fc-B4GALT1
MYRMQLLSCIALSLALVTNSPPCPVPEPLGGPSVLIFPPKPKDILRITRTPEVTCVVLDLGREDPEVQISWF
VDGKEVHTAKTQSREQQFNGTYRVVSVLPIEHQDWLTGKEFKCRVNHIDLSPIERTISKARGRAHKPSVYV
LPPSPKELSSSDTVSITCLIKDFYPPDIDVEWQSNGQQEPERKHRMTPPQLDEDGSYFLYSKLSVDKSRWQQ
GDPFTCAVMHETLQNHYTDLSLSHSPGKMVIEFNMPVDLKLVEKQNPEVKVGGRYTPKNCISPHKVAIIPF
RNRQEHLKYWLYYLHPILQRQQLDYGIYVINQAGETMFNRAKLLNIGFQEALKDYDYNCFVFSDVDLIPMND
HNAYRCFSQPRHISVAMDKFGFSLPYVQYFGGVSALSKEQFLTINGFPNNYWGWGGEDDIYNRLVFKGMSV
SRPNAMVGKCRMIRHSRDKKNEPNPQREFDRIAHTKETMLSDGLNTLTYKVLDKERNPLYTKITVDIGTPS IL2-signal sequence (Amino Acids: 1-20)
dogIgG-A Fc (Amino Acids: 1-244)
B4GALT1 (ECD) (Amino Acids: 245-503)

FIG. 22 (continued)

SEQ ID NO: 17
catIgG1Fc-ST6GAL1

MYRMQLLSCIALSLALVTNSPKCPPPEMLGGPSIFIFPPKPKDTLSISRTPEVTCLVVDLGPDDSDVQITWF
VDNTQVYTAKTSPREEQFNSTYRVVSVLPILHQDWLKGKEFKCKVNSKSLPSPIERTISKAKGQPHEPQVYV
LPPAQEELSRNKVSVTCLIKSFHPPDIAVEWEITGQPEPENNYRTTPPQLDSDGTYFVYSKLSVDRSHWQRG
NTYTCSVSHEALHSHHTQKSLTQSPGKDFQVLRGLEKQAETSSSTQDPHRGSQALSSPRGPAKAKPEASFQV
WNKDSSSKNLIPRLQKIWRNYLNMNKYKVSYKGPGPGVKLSAEALHCHLRERVNVSMVEVTDFPFNTSEWEG
FLPKENIRTKAGPWGTCAVVSSAGSLKSSQLGREIDDHDAVLRFNGAPTANFQQDVGTKTTIRLMNSQLVTT
EGRFLKDSLYNEGILIVWDPSVYHSDIPKWYQSPDYSFFENYKSYRKLHPDQPFYILRPQMPWELWDIIQEV
SPEEIQPNPPSSGMLGIIIMMTLCDQVDIYEFLPSKRKTDVCYYQKFFDSACTMGAYHPLLFEKNLVKHLN
QGTDEDIYLLGKATLPGFRRIRC

IL2-signal sequence (Amino Acids: 1-20)
catIgG-A Fc (Amino Acids: 21-243)
ST6GAL1 (soluble) (Amino Acids: 244-599)

FIG. 22 (continued)

SEQ ID NO: 18
catIgG1Fc-B4GALT1

MYRMQLLSCIALSLALVTNSPKCPPPEMLGGPSIFIFPPKPKDTLSISRTPEVTCLVVDLGPDDSDVQITWF
VDNTQVYTAKTSPREEQFNSTYRVVSVLPILHQDWLKGKEFKCKVNSKSLPSPIERTISKAKGQPHEPQVYV
LPPAQEELSRNKVSVTCLIKSFHPPDIAVEWEITGQPEPENNYRTTPPQLDSDGTYFVYSKLSVDRSHWQRG
NTYTCSVSHEALHSHHTQKSLTQSPGKYLAGRDLNRLPQLVGVPTPLQGGSNGAAAIEQPSAELRPRGAPPL
PLLDASSELRSGRDSSPDADSHPGPASNLTSAPVPSTTVLSLLACPEESPLLVGPMVIEFNMPVDLKLVE
KQNPEVKVGGRYTPKNCISPHKVAIIPFRNRQEHLKYWLYYLHPILQRQQLDYGIYVINQAGETMFNRAKL
LNIGFQEALKDYDYNCFVFESDVDLIPMNDHNAYRCFSQPRHISVAMDKFGFSLPYVQYFGGVSALSKQQFLT
INGFPNNYWGWGGEDDIFNRLVFRGMSVSRPNAVVGKCRMIRHSRDKKNEPNPQRFDRIAHTKETMLSDGL
NTLSYKVLDIERNPLYTKITVDIGTPS

IL2-signal sequence (Amino Acids: 1-20)
catIgG-A Fc (Amino Acids: 21-243)
B4GALT1 (ECD) (Amino Acids: 244-603)

FIG. 22 (continued)

SEQ ID NO: 42
hIgGFc-B4GALT1 with Y349C/T366S/L368A/Y407V (EU numbering) mutations MYRMQLLSCIALSLALVTNSMPRGPPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKT
ISKAKGQPREPQVCTLPPSRDELTKNQVSLSCAVKGFYPSDIAVEWESNGQPENNYKTTPPVLDSDGSFFLV
SKLTVDKSRWQQGNVFSCSVMHEALHNHYTQKSLSLSPGKGAPDLKLMGRDLSRLPQLVGVSTPLQGGSNSA
AAIGQSSGELRTGGARPPPLGASSQPRPGGDSSPVVDSGPPASNLTSVPVPHTTALSLPACPEESPLLVG
PMLIEFNMPVDLELVAKQNPNVKMGGRYAPRDCVSPHKVAIIPFNRQEHLKYWLYYLHPVLQRQQLDYGI
YVINQAGDTIENRAKLLNVGFQEALKDYDYTCFVFSDVDLIPMNDHNAYRCFSQPRHISVAMDKFGFSLPYV
QYFGGVSALSKQQFLTINGFPNNYWGWGGEDDIFNRLVFRGMSISRPNAVVGRCRMIRHSRDKKNEPNPQR
FDRIAHTKETMLSDGLNSLTYQVLDVQRYPLYTQITVDIGTPS IL2-signal sequence (Amino Acids: 1-20)
hIgGFc (Amino Acids: 26-256)
B4GALT1 (Amino Acids: 262-619)
CH2 (Amino Acids: 41-149)
CH3 (Amino Acids: 151-254)
Glycosyltransferase domain (Amino Acids: 406-611)
Point mutations are indicated by underlines

FIG. 22 (continued)

SEQ ID NO: 43
hIgGFc-ST6GAL1 with S354C/T366W (EU numbering) mutations

MYRMQLLSCIALSLALVTNSMPRGPPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKT
ISKAKGQPREPQVYTLPPCRDELTKNQVSLWCLVKGFYPSDIAVEWESNGQPENNYKTTPPVLDSDGSFFLY
SKLTVDKSRWQQGNVFSCSVMHEALHNHYTQKSLSLSPGKGAPDLKLMEFQVLKSLGKLAMGSDSQSVSSSS
TQDPHRGRQTLGSLRGLAKAKPEASFQVWNKDSSSKNLIPRLQKIWKNYLSMNKYKVSYKGPGPGIKFSAEA
LRCHLRDHVNVSMVEVTDFPFNTSEWEGYLPKESIRTKAGPWGRCAVVSSAGSLKSSQLGREIDDHDAVLRF
NGAPTANFQQDVGTKTTIRLMNSQLVTTEKRFLKDSLYNEGILIVWDPSVYHSDIPKWYQNPDYNFFNNYKT
YRKLHPNQPFYILKPQMPWELWDILQEISPEEIQPNPPSSGMLGIIIMMTLCDQVDIYEFLPSKRKTDVCYY
YQKFFDSACTMGAYHPLLYEKNLVKHLNQGTDEDIYLLGKATLPGFRTIHC

IL2-signal sequence (Amino Acids: 1-20)
hIgGFc (Amino Acids: 26-256)
ST6GAL1 (Amino Acids: 265-627)
CH2 (Amino Acids: 41-149)
CH3 (Amino Acids: 151-254)
Glycosyltransferase domain (Amino Acids: 381-611)
Point mutations are indicated by underlines

FIG. 23

SEQ ID NO: 19

Dog immunoglobulin gamma heavy chain A
>AAL35301.1 immunoglobulin gamma heavy chain A [Canis lupus familiaris]
MESVFCWVFLVLVILKGVQGVQLVESGGDLVKPGGSLRLSCVASGFTFSSYMHWIRQAPGKGLQRVAHI
RGDGRTTHYADAMKGRFTISRDNAKNTLYLQMNSLTVEDTAIYYCVKDIYYGVGDYWGQGTLVTVSSAST
TAPSVFPLAPSCGSTSGSTVALACLVSGYFPEPVTVSWNSGSLTSGVHTFPSVLQSSGLHSLSSMVTVPS
SRWPSETFTCNVHPASNTKVDKPVENECRCTDTPPCPVPEPLGGPSVLIFPPKPKDILRITRTPEVTCV
VLDLGREDPEVQISWFVDGKEVHTAKTQSREQQFNGTYRVVSVLPIEHQDWLTGKEFKCRVNHIDLPSPI
ERTISKARGRAHKPSVYVLPPSPKELSSSDTVSITCLIKDFYPPDIDVEWQSNGQQEPERKHRMTPPQLD
EDGSYFLYSKLSVDKSRWQQGDPFTCAVMHETLQNHYTDLSLSHSPGK

SEQ ID NO: 20

Dog immunoglobulin gamma heavy chain B
>AAL35302.1 immunoglobulin gamma heavy chain B [Canis lupus familiaris]
MESVLFWVFLVTILKGVQGEVRLVESGGTLVKPGGSLKLSCVASGFTFRRYSMDWVRQAPGKSLQWVAGI
NGDGTGTSYSQTVKGRFTISRDNAKNTLYLQINSLRAEDSAVYYCAKSWSRNGDLDYWGQGTLVTVSSAS
TTAPSVFPLAPSCGSTSGSTVALACLVSGYFPEPVTVSWNSGSLTSGVHTFPSVLQSSGLYSLSSMVTVP
SSRWPSETFTCNVAHPASKTKVDKPVPKRENGRVPRPPDCPKCPAPEMLGGPSVFIFPPKPKDTLLIART
PEVTCVVVDLDPEDPEVQISWFVDGKQMTAKTQPREEQFNGTYRVVSVLPIGHQDWLKGKQFTCKVNNK
ALPSPIERTISKARGQAHQPSVYVLPPSREELSKNTVSLTCLIKDFFPPDIDVEWQSNGQQEPESKYRTT
PPQLDEDGSYFLYSKLSVDKSRWQRGDTFICAVMHEALHNHYTQESLSHSPGK FIG. 23 (continued)

SEQ ID NO: 21
Dog immunoglobulin gamma heavy chain C
>AAL35303.1 immunoglobulin gamma heavy chain C [Canis lupus familiaris]
MESVLYWVFLVAILKGVQGDVQLVESGGDLVKPGGSLRLSCVASGFTFSSCAMSWVRQSPGKGPQWVATI
RYDGSDIYYADAVKGRFSISRDNAKNTVYLQMNSLRAEDTAVYYCAKAPPYDSYHYGMDYWGPGTSLFVS
SASTTAPSVFPLAPSCGSQSGSTVALACLVSGYIPEPVTVSWNSVSLTSGVHTFPSVLQSSGLYSLSSMV
TVPSSRWPSETFTCNVAHPATNTKVDKPVAKECECKCNCNNCPCPGCGLLGGPSVFIFPPKPKDILVTAR
TPTVTCVVVDLDPENPEVQISWFVDSKQVQTANTQPREEQSNGTYRVVSVLPIGHQDWLSGKQFKCKVNN
KALSPIEEIISKTPGQAHQPNVYVLPPSRDEMSKNTVTLTCLVKDFFPPEIDVEWQSNGQQEPESKYRM
TPPQLDEDGSYFLYSKLSVDKSRWQRGDTFICAVMHEALHNHYTQISLSHSPGK

FIG. 23 (continued)

SEQ ID NO: 22

Dog immunoglobulin gamma heavy chain D
>AAL35304.1 immunoglobulin gamma heavy chain D [Canis lupus familiaris]
MESVLCWVFLVSILKGVQGEVQLVESGGDLVKPGGSLRLSCVASGFTFSDYGMSWVRQSPGKGLQWVAAV
SNRGDTYYADAVKGRFTISRDNAKNTLYLQMSSLKAEDTAIYHCVTGVWPRHYYGMDHWGNGTSLFVSSA
STTAPSVFPLAPSCGSTSGSTVALACLVSGYFPEPVTVSWNSGSLTSGVHTFPSVLQSSGLYSLSSTVTV
PSSRWPSETFTCNVVHPASNTKVDKPVPKESTCKCISPCPVPESLGGPSVFIFPPKPKDILRITRTPEIT
CVVLDLGREDPEVQISWFVDGKEVHTAKTQPREQQFNSTYRVVSVLPIEHQDWLTGKEFKCRVNHIGLPS
PIERTISKARGQAHQPSVYLPPSPKELSSSDTVTLTCLIKDFFPPEIDVEWQSNGQPEPESKYHTTAPQ
LDEDGSYFLYSKLSVDKSRWQQGDTFTCAVMHEALQNHYTDLSLSHSPGK

SEQ ID NO: 23

Dog ST6GAL1
>tr|E2R2H3|E2R2H3_CANLF Uncharacterized protein OS=Canis lupus
familiaris GN=ST6GAL1 PE=3 SV=1
MIHTNLKKFSCCVLAFLLFAVICVWKEKKGSYYDSLKLQTKEFQMVRGLEKQAATLSS
TQNPPRASQALGSPRGPVKAKSEASFQVWNKDSSSKNLIPRLQKIWRNYLNMNKYKVSYK
GPGPGVKFSAEALHCHLRDHVNVSMVEATDFPFNTSEWEGFLPKENIRTKAGPWGRCAVV
SSAGSLKSSQLGREIDDHDAVLRFNGAPTASFQQDVGTKTTIRLMNSQLVTTEGRFLKDS
LYNEGILIVWDPSVYHSDIPKWYQSPDYSFFENYKSYRKLHPDQPFYILKPQMPWELWDI
IQEVSPEEIQPNPPSSGMLGIIIMMTLCDQVDIYEFLPSKRKTDVCYYQKFFDSACTMG
AYHPLLFEKNLVKHLNQGTDEDIYLLGKATLPGFRRIRC FIG. 23 (continued)

SEQ ID NO: 24
Dog B4GALT1
>tr|F1PGZ1|F1PGZ1_CANLF Uncharacterized protein OS=Canis lupus familiaris GN=B4GALT1 PE=4 SV=2
MVIEFNMPVDLKLVEKQNPEVKVGGRYTPKNCISPHKVAIIPFRNRQEHLKYWLYYLHP
ILQRQQLDYGIYVINQAGETMFNRAKLLNIGFQEALKDYDYNCFVFSDVDLIPMNDHNAY
RCFSQPRHISVAMDKFGFSLPYVQYFGGVSALSKEQFLTINGFPNNYWGWGEDDDIYNR
LVFKGMSVSRPNAMVGKCRMIRHSRDKKNEPNPQRFDRIAHTKETMLSDGLNTLTYKVLD
KERNPLYTKITVDIGTPS

FIG. 24

SEQ ID NO: 25
Cat IgG1a
>BAA32229.1 IgG1 heavy chain, partial [Felis catus]
ASTTAPSVFPLAPSCGTTSGATVALACLVLGYFPEPVTVSWNSGALTSGVHTFPAVLQASGLYSLSSMVT
VPSSRWLSDTFTCNVAHPPSNTKVDKTVRKTDHPPGKPCDCPKCPPPEMLGGPSIFIFPPKPKDTLSIS
RTPEVTCLVVDLGPDDSDVQITWFVDNTQVYTAKTSPREEQFNSTYRVVSVLPILHQDWLKGKEFKCKVN
SKSLPSPIERTISKAKGQPHEPQVYVLPPAQEELSRNKVSVTCLIKSFHPPDIAVEWEITGQPEPENNYR
TTPPQLDSDGTYFVYSKLSVDRSHWQRGNTYTCSVSHEALHSHHTQKSLTQSPGK SEQ ID NO: 26
Cat IgG1b
>BAA32230.1 IgG1 heavy chain, partial [Felis catus]
ASTTAPSVFPLAPSCGTTSGATVALACLVLGYFPEPVTVSWNSGALTSGVHTFPAVLQASGLYSLSSMVT
VPSSRWLSDTFTCNVAHPPSNTKVDKTVRKTDHPPGKPCPPKCPPPEMLGGPSIFIFPPKPKDTLSIS
RTPEVTCLVVDLGPDDSDVQITWFVDNTQVYTAKTSPREEQFNSTYRVVSVLPILHQDWLKGKEFKCKVN
SKSLPSPIERTISKDKGQPHEPQVYVLPPAQEELSRNKVSVTCLIEGFYPSDIAVEWEITGQPEPENNYR
TTPPQLDSDGTYFLYSRLSVDRSRWQRGNTYTCSVSHEALHSHHTQKSLTQSPGK FIG. 24 (continued)

SEQ ID NO: 27
Cat ST6GAL1
>tr|M3WJN7|M3WJN7_FELCA Uncharacterized protein OS=Felis catus GN=ST6GAL1 PE=3 SV=1
MIHANLKKFSCCVLAFLLFAIICVWKEKKGTYDSLKLQSKDFQVLRGLEKQAETSSS
TQDPHRGSQALSSPRGPAKAKPEASFQVWNKDSSSKNLIPRLQKIWRNYLNMNKYKVSYK
GPGPGVKLSAEALHCHLRERVNVSMVEVTDFPFNTSEWEGFLPKENIRTKAGPWGTCAVV
SSAGSLKSSQLGREIDDHDAVLRFNGAPTANFQQDVGTKTTIRLMNSQLVTTEGRFLKDS
LYNEGILIVWDPSVYHSDIPKWYQSPDYSFFENYKSYRKLHPDQPFYILRPQMPWELWDI
IQEVSPEEIQPNPPSSGMLGIIIMMTLCDQVDIYEFLPSKRKTDVCYYQKFFDSACTMG
AYHPLLFEKNLVKHLNQGTDEDIYLLGKATLPGFRRIRC

SEQ ID NO: 28
Cat B4GALT1
>tr|M3WTX2|M3WTX2_FELCA Uncharacterized protein OS=Felis catus GN=B4GALT1 PE=4 SV=1
AVCALHLGVTLVYYLAGRDLNRLPQLVGVPTPLQGGSNGAAAIEQPSAELRPRGAPPLPL
LDASSELRSGRDSSPDADSHPGPGPASNLTSAPVPSTTVLSLLACPEESPLLVGPMVIEF
NMPVDLKLVEKQNPEVKVGGRYTPKNCISPHKVAIIPFRNRQEHLKYWLYLHPILQRQ
QLDYGIYVINQAGETMFNRAKLLNIGFQEALKDYDNCFVFSDVDLIPMNDHNAYRCFSQ
PRHISVAMDKFGSLPYVQYFGGVSALSKQQFLTINGFPNNYWGWGEDDIFNRLVFRG
MSVSRPNAVVGKCRMIRHSRDKKNEPNPQRFDRIAHTKETMLSDGLNTLSYKVLDIERNP
LYTKITVDIGTPS

FIG. 25

SEQ ID NO: 29
Cow IgG1
>S82409.1 Bos taurus IgG1 heavy chain constant region (IgC-gamma) mRNA, partial cds
GCCTCCACCACAGCCCCGAAAGTCTACCCCTCTGAGTTCTTGCTGCTGGGGACAAGTCCAGCTCCACCGTGA
CCCTGGGCTGCCTGGTCTCCAGCTACATGCCCGAGCCGGTGACCGTGAACTCGGGTGCCCTGAA
GAGCGGCGTGCACACCTTCCCGGCCGTCCTCAGTCCTCTACTCTCAGCAGCATGGTGACC
GTGCCCGGCAGCACCTCAGGAACCCAGACCTTCACCTGCAACGTAGCCCGCCAGCAGCACCAAGG
TGGACAAGGCTGTTGATCCCAGATGCAAAACAACCTGTGACTGTTGCCACCCCTGAGCTCCCTGAGG
ACCCTCTGTCTTCATCTTCCCACCGAAACCCCAAGGACACCCTCACAATCTCGGGACGCCCGAGGTCACG
TGTGTGGTGGTGGACGTGGGCCACGAGGACCCCGAGGTGAAGTTCTCCTGGTTCGTGGACGACGTGGAGG
TAAACACAGCCACCAGGACTGGAGGGCAGCCCGAGGAGAGGAGAAAGGGAGTTCAAGTGCAAGGTCACCGTCG
CATCCAGCACCAGGACCATCTCCAGGACCCAAAAGGCCCGAGCCCAGGTGTATGTCCTGGCCCCAC
CCCAGGAAGAGCTCAGCAGAGAAATGGGCAGCCTCACCTGCAGTCAGAGGACAAGTACGGCACCCCCCAGCTG
CGCCGTGGAGTGGCAGAGAAATGGGCAGCCTGAGTCAGGCTCAGCAGGTGGACAACAGCTGGACAAGGAGACA
GACGCCGACGGCTCCTACTTCCTGTACAGCAGGCTCAGGGTGGACAACAGCTGGACAAGGAGACA
CCTACACGTGTGGTGATGCACGAGGCCCTGCACAATCACTACACGCAGAAGTCCACCTCTAAGTCTGC
GGGTAAATGA FIG. 25 (continued)

SEQ ID NO: 30
Cow IgG2
>S82407.1 Ig C gamma =IgG2a heavy chain constant region {CH1-CH3 domains, hinge region} [cattle, Holstein-Friesian, A2/A2 allotype, peripheral blood leukocytes, mRNA Partial, 981 nt]
GCCTCCACCACAGCCCCGAAAGTCTACCCCTCTGGCATCTGCGGAGACACATCCAGCTCCACCGTGA
CCCTGGGCTGCCTGGTGTCCAGCTACATGCCCGAGCCCGTGACCGTGACCTGGAACTCGGGTGCCCTGAA
GAGCGGGCGTGCACACCTTCCCGGCTCCTTCAGTCCCGGCTCTACTCTCAGCAGCAGCATGGTGACC
GTGCCCCCAGCAGTCAGGACCTTCACCTGCAACGTAGCCACCAGCCTTGCGTGAGGGAACCATCTGT
ACAAGGCTGTTGGGGTCTCCATTGACTGTCTCCAAGTGTCATAACCAGCACCCTGATGATCACACCGG
CTTCATCTTCCACCGGAAACCCAGAGTGTGGGGCCACGATAACCCTGAGTTCCTGGTTCGTGGATGACGTGGAGGTGCACACGG
GTGAACGTGGGCCAAGCAGGAGAGCAGTTCAACACAGCACGTACCGCGTGGTCAGCGCCCTGCCCATCCAGCA
CCAGGTCGAAGCTGGACTGGAGGAAAGGAGTTCAAGTGCAAGTGCGGGAGCCAGGTTATGTCCTACCCCAAGGAAG
AGGATCATCTCCAGACAAAGCACGCTCAGCTGCATGGTCACCGGCTTCACCCAGAAGATGTAGCCGTGGA
AGCTCAGCAGCAAAGCACGCTCAGCTGCATGGTCACCGGCTTCACCCAGAAGATGTAGCCGTGGA
GTGGCAGAGAAAACCGGCAGAGTCGAGGAGACAAGTACCCGCCCAGCTGACACCGAC
CGCTCCTACTTCCTGTACAGCAAGCTGACGGTGGACAAGAGCAGGAACAGCTGGCAGGAAGGAAGGCCTACACGT
GTGTGGTGATGCACGAGGCCCTGCACAATCACTACATGCAGAAGTCCACCTCTAAGTCTGCGGGTAAATG A FIG. 25 (continued)

SEQ ID NO: 31
Cow IgG3
>U63638.1 Bos taurus IgG3 heavy chain constant region gene, allotype a, partial cds CCACCATGCCGCGGTCATCAGACCCTGGAAGCAGGCAGTGGCTTGGAAGTGCCCCAGGCTGG
GCTCCTGAGGTCCTGCTGGACCCAGCCATTCACCCAGCCCTCTCTCCACAGCCCTACACAGCCCCGAA
AGTCTACCCTCTGGCATCCAGCTGCGGAGACATCCAGCCGTGACCCTGGGCTGCCTGGTCTCC
AGCTACATGCCCGAGCCGGTGACCGTGAACTCGGGTGCCCTGAAGAGCGGCGTGCACACCTTCC
CGGCCGTCCGGCAGTCCTCTGGGCTGTACTCTCAGCAGCATGGTGCCCGCCAGCAGCTCAGA
AACCCAGACCTTCACCTGCAACGTGAGCCACCCGGCCAGCAGCCAAGGTGACCAAGGCTGTCACTGCA
AGGCGTCCAGTCCCGACGCGCCAAAGACAACTATCCCTGAAAACCCAGTCGTGTCAGGGAGG
TCCCACACTCCTGCCTGCAGGGCCCTCAGCCAGCCTGTGTGAACCCAGGCCAGCCAGCCGTGTCAGGGAGG
CCCTGTCTGTCTCTCCTGAAGTCTCACAGCCTCGGCCCTGAAGCTGGACTTCCACGATGTCCA
GGCTGCCAGGCTGGATGACGCCCCCAGAGACGCCCGAGAGGCGGCCCTCGGACTCGGACTACCAA
AACTTGTCCCTGCCCTAAGCACACCCTGCCAGTGTTCCAAATGCCCAGGTAAGTCCAGTGGCTTCATCCTCT
GAGTCTGAAGTTGAAAAGACACTGGCGAACACTGGAGGCAGCGCGGGTCCAAAGGAGGTTTCCCAGGT
GTCTGACACTGGCGAACACCATGCTTTCTCACCAGAACCTCGGAGGACCTGCGTCGTTCATCTTCCCA
GCAGAACCCCACCAAGACCCCAAGACCCCGAACGCCCGAGTTCACGTGTGGTGCACGCCAGGACGTGGGCC
CCGAAACCCAAGGACACCCTCACAATCTCCTCCTGGTTCGTGCAGTTGCAGTGGAGGTCACTGTTCCTGTGGTGACGTGGACC
AGGATGACCCCGAGGTGCAGTTGCAATCAGCAGCACCTACCGCCCTGTGGTGTCCGTGCTGACCGTGGCCATCCAGCACCAGGACTGGCTG
GAGAGGAGCAGTTCAACAGCACCTTCAGACAGCAGTTCCCATCCAGCACCAGGACTGGCTG FIG. 25 (continued)

```
CAGGGAAAGGAGTTCAAGTGCAAGGTCAACAACAAAGGCCTCCCGGCCCCCATTGTGAGGACCATCTCCA
GGACCAAAGGTGGGCCAGGTGACTGGGCCAATCAGAGTGACCGGGCCAATCAGAGTGACCGCTGTACGG
GACCGGGCCCTGTGGGCCAATCAGAGTGACCGGTGACCGGGAGGTCCCGTGGCCAATCAGAG
TGACCGCTGTGCTAACAGCCTTCCTGTCCCCACAGGGCCAGGCCCGGAGCCCTGATCACCGGTTTCTGGCC
CCACCCCGGAAGAGCTCAGCAGAGAAATGGGCAGCCTGAGTCGAGGACAAGTACCACACGACCGCACCCA
AGATAGACGTGGAGTGGCAGCTCCCTACTTCCTGTACAAGCTCAGGGTGAACAAGAGCAGCTGGCAGGAAGGA
GCTGGATGCTGACGGCTCCCTACTTCCTGTACAAGCTCAGGGTGAACAAGAGCAGCTGGCAGGAAGGA
GACCACTACACGTGCAGTGATGCACGAAGCTTTACGAATCACTACAAAGAGAAGTCCATCTCGAGGT
CTCCGGGTAAATGA
```

SEQ ID NO: 32
Cow Sialyltransferase (ST6GAL1)
>tr|F1MHF1|F1MHF1_BOVIN ST6 beta-galactoside alpha-2,6-sialyltransferase
1 OS=Bos taurus GN=ST6GAL1 PE=3 SV=1
MTRTSLKKKVFSCCVLIFLLFAIICVWKEKKGNYYEFLKLQNKEYQVLQGLEKLAVSSS
SQPVSSSSTHNPQRNIQALGGPKAKLKATFQVWKDSSSKNLAPRLQTIRKNYLNMNKYK
VTYKGPGPGVKFSAEALLCHLRDHVNISMIEATDFPFNTSDWEGYLPQEDIRTKAGPWGR
CAVVSSAGSLKSSRLGREIDDHDAVLRFNGAPTVKFQQDVGTKTTIRLVNSQLVTTEAGF
LKDSLYNEGILIVWDPSVYHSDIPKWYRNPDYSFENNFKSYRKLHPDQPFYILKPQMPWE
LWDIIQEISSELIQPNPPSSGMLGIAIMMSLCDQVDIYEFLPSKRKTDVCYYYQRYFDSA
CTMGAYHPLLFEKNMVKYLNLGTDEDIYLLGKATLPGFRTIRCGA

FIG. 25 (continued)

SEQ ID NO: 33

Cow Galactosyltransferase (B4GALT1)

\>sp|P08037|B4GT1_BOVIN Beta-1,4-galactosyltransferase 1 OS=Bos taurus GN=B4GALT1 PE=1 SV=3

MKFREPLLGGSAAMPGASLQRACRLLVAVCALHLGVTLVYYLAGRDLRRLPQLVGVHPPL
QGSSHGAAAIGQPSGELRLRGVAPPPLQNSSKPRSRAPSNLDAYSHPGPGPGSNLTS
APVPSTTRSLTACPEESPLLVGPMLIEFNIPVDLKLVEQQNPKVKLGGRYTPMDCISPH
KVAIIPFRNRQEHLKYWLYYLHPILQRQQLDYGIYVINQAGESMFNRAKLLNVGFKEAL
KDYDYNCFVFSDVDLIPMNDHNTYRCFSQPRHISVAMDKFGFSLPYVQYFGGVSALSKQQ
FLSINGFPNNYWGWGGEDDIYNRLAFRGMSVSRPNAVIGKCRMIRHSRDKKNEPNPQRF
DRIAHTKETMLSDGLNSLTYMVLEVQRYPLYTKITVDIGTPS

Cytosolic (Amino Acids: 1-24)
TMD (Amino Acids: 25-44)
Luminal (Amino Acids: 45-402)

FIG. 26

SEQ ID NO: 34
Horse IgG₁
>tr|Q95M34|Q95M34_HORSE Immunoglobulin gamma 1 heavy chain constant region (Fragment) OS=Equus caballus GN=IGHC1 PE=2 SV=1
ASTTAPKVFALAPGCGTTSDSTVALGCLVSGYFPEPVKVSWNSGSLTSGVHTFPSVLQSS
GFYSLSSMVTVPASTWTSETYICNVVHAASNFKVDKRIEPIPDNHQKVCDMSKCPKCPAP
ELLGGPSVFIFPPNPKDTLMITRTPEVTCVVVDVSQENPDVKFNWYMDGVEVRTATTRPK
EEQFNSTYRVVSVLRIQHQDWLSGKEFKCKVNNQALPQPIERTITKTKGRSQEPQVVLA
PHPDELSKSKVSVTCLVKDFYPPEINIEWQSNGQPELETKYSTTQAQQDSDGSYFLYSKL
SVDRNRWQQGTTFTCGVMHEALHNHYTQKNVSKNPGK CH1 (Amino Acids: 1-98)
                        CH2 (Amino Acids: 119-228)
                        CH3 (Amino Acids: 229-337)

SEQ ID NO: 35
Horse IgG₂
>CAC44761.1 immunoglobulin gamma 2 heavy chain constant region, partial [Equus caballus]
ASTTAPKYFQLTPSCGITSDATVALGCLVSDYYPEPVTVSWNSGALTSGVHTFPSVLQSSGLYALSSMVT
VPASTWTSETYICNVAHPASSTKVDKRIPPCVLSAEGVIPIPSVPKPQCPPYTHSKFLGGPSVFIFPPNP
KDALMISRTPVVTCVVVNLSDQYPDVQFSWYVDNTEVHSAITKQREAQFNSTYRVVSVLPIQHQDWLSGK
EFKCSVTNVGVPQPISRAISRGKGPSRVPQVYLPPHPDELAKSKVSVTCLVKDFYPPDISVEWQSNRWP
ELEGKYSTTPAQLDGDGSYFLYSKLSLETSRWQQVESFTCAVMHEALHNHFTKTDISESLGK FIG. 26 (continued)

SEQ ID NO: 36
Horse IgG$_3$
>CAC86339.1 immunoglobulin gamma 3 heavy chain constant region, partial
[Equus caballus]
ASTTAPKVFPLAPSCGTTSDSTVALGCLVSSYFPEPVTVSWNSGTLTSGVRTFPSVLQSSGLYSLSSMVT
VPASSLESKTYICNVAHPASSTKVDKRIEPVLPKPTTPAPTVPLTTTVPETTPPCPECPKCPAPELL
GGPSVFIFPPKPKDVLMITRTPEVTCLVVDVSHDSSDVLFTWYVDGTEVKTAKTMPNEEQNNSTYRVVSV
LRIQHQDWLNGKKFKCKVNNQALPAPVERTISKATGQTRVPQVYVLAPHPDELSKNKVSVTCLVKDFLPT
DITVEWQSNEHPEPEGKYRTTEAQKDSDGSYFLYSKLTVETDRWQQGTTFTCVVMHEALHNHVMQKNVSH
SPGK SEQ ID NO: 37
Horse IgG$_4$
>CAC44762.1 immunoglobulin gamma 4 heavy chain constant region, partial
[Equus caballus]
ASTTAPKVFPLASHSAATSGSTVALGCLVSSYFPEPVTVSWNSGALTSGVHTFPSVLQSSGLYSLSSMVT
VPASSLKSQTYICNVAHPASSTKVDKKIHLSVLSAVIKECNGGCPAPECLQVGPSVFIFPPKPKDVLMIS
RTPTVTCVVVDVGHDFEPDVQFNWYVDGVETHTATTEPKQEQFNSTYRVVSVLPIQHKDWLSGKEEFKCKVN
NKALPAPVERTISKPTGQPREPQVYVLAPHRDELXRXNVSVTCLVKDFYPTDIDIEWKSNGQPEPETKYS
TTPAQLDSDGSYFLYSKLTVETNRWQQGTTFTCAVMHEALHNHYTEKSVSKSPGK FIG. 26 (continued)

SEQ ID NO: 38
Horse IgG₅
>CAC86340.1 immunoglobulin gamma 5 heavy chain constant region, partial
[Equus caballus]
ESPKAPDVFPLTICGNTPDPTVPVGCLVSNYFPEPVTVSWNCDALKGDIHTFPLDLSNSAHHSLSSMMAV
PRSSLNQTYICSVAHPASSTKVDKRIVVKGSPCPKCPAPELPGGPSVFIFPPKDVLKISRKPEVTCVV
VDLGHDDPDVQFTWFVDGVETHTATTEPKEEQFNSTYRVVSVLPIQHQDWLSGKEFKCSVTNKALPAPVE
RTTSKAKGQLRVPQVYVLAPHPDELAKNTVSVTCLVKDFYPPEIDVEWQSNEHPEPEGKYSTTPAQLNSD
GSYFLYSKLSVETSRWKQGESFTCGVMHEAVENHYTQKNVSHSPGK SEQ ID NO: 39
Horse IgG₆
>CAC86341.1 immunoglobulin gamma 6 heavy chain constant region, partial
[Equus caballus]
ASTTAPKVFQLASHSAGTSDSTVALGCLVSSYFPEPVTVSWNSGALTSGVHTFPSVRQSSGLYSLSSMVT
VPASSLKSQTYICNVAHPASSTKVDKRIVIKEPCCCPKCPGRPSVFIFPPNPKDTLMISRTPEVTCVVVD
VSQENPDVKFNWYVDGVEAHTATTKAKEKQDNSTYRVVSVLPIQHQDWRRGKEFKCKVNNRALPAPVERT
ITKAKGELQDPKVYILAPHREEVTKNTVSVTCLVKDFYPPDINVEWQSNEEPEPEVKYSTTPAQLDGDGS
YFLYSKLTVETDRWEQGESFTCVVMHEAIRHTYRQKSITNFPGK

FIG. 26 (continued)

SEQ ID NO: 40
Horse Sialyltransferase (ST6GAL1)
>tr|F6SU16|F6SU16_HORSE ST6 beta-galactoside alpha-2,6-sialyltransferase 1 OS=Equus caballus GN=ST6GAL1 PE=3 SV=1
MIHSSLKKKFSFCVLVELLFAVICVWKEKKGSYYESLKLQTKELQMPRSPEKRAIGSGS
KFASSSSTQDPHRNTQGLSNPRSPAKAKPEGSFQVWNKDSSSKNLIPRLQKIWKNYLSMN
KYKVSYKGPGPGVKFSADVLRCRLRDEVNVSMVEATDFPENTSEWEGYLPMEDIRTKAGP
WGKCAVVSSAGSLKSSQLGQEIDDHDAVMRFNGAPTASFQQDVGTKTTIRLMNSQLVTTE
GRFLKDSLYNEGILIVWDPSVYHSDIPKWYKNPDYSFFDNYKSYRKLHPDQPFYILKPQM
PWELWDIIQEISPEEIQPNPPSSGMLGIIIMMTLCDQVDIYEFLPSKRKTDVCYYYQKYF
DTACTMGAYHPLLFEKNMVKHLNQGTDEDIYLFGKATLPGFRSIRC

SEQ ID NO: 41
Horse Galactosyltransferase (B4GALT1)
>tr|F6SRF3|F6SRF3_HORSE Beta-1,4-galactosyltransferase 1 OS=Equus caballus GN=B4GALT1 PE=4 SV=1
SSTSLVGPMMIEFNMAVDLNRVAEENPEVKLGGRYTPKDCISPHKVAIIPFRNRQEHLK
YWLYYLHPILQRQQLDYGIYVINQAGEAMFNRAKLLNVGFQEALKDYDNCFVFSDVDLI
PMNDHNAYRCFSQPRHISVAMDKFGFSLPYVQYFGGVSALSKEQFLTINGFPNNYWGWGG
EDDDIFNRLVFKGMSLSRPNAVIGKCRMIRHSRDKKNEPNPQRFDRIAHTKETMFLDGLN
TLFYNVLDVQRYPLYTKVTVDIGTPS

GLYCOENGINEERING

CLAIM OF PRIORITY

This application is a § 371 National Stage Application of PCT/US2018/066013, filed Dec. 17, 2018, which claims the benefit of U.S. Provisional Application No. 62/607,111, filed on Dec. 18, 2017. The entire contents of the foregoing are incorporated herein by reference.

FEDERALLY SPONSORED RESEARCH OR DEVELOPMENT

This invention was made with Government support under Grant No. AR068272 awarded by the National Institutes of Health (NIH). The Government has certain rights in the invention.

TECHNICAL FIELD

This disclosure relates to glycoengineering, e.g., modulating IgG effector function by engineering antibody glycans in vivo to for various therapeutic effects, e.g., treating IgG-mediated disorders, attenuating autoantibody-mediated inflammation, treating autoimmune diseases, and/or treating antibody-mediated injury during organ transplantation.

BACKGROUND

The proteins and cells that make up the human body are decorated by sugars (Varki, A. Glycobiology 3, 97-130 (1993)). Sugars can be linked to many types of biological molecule to form glycoconjugates. The enzymatic process that links sugars/saccharides to themselves and to other molecules is known as glycosylation. Glycoproteins, proteoglycans, and glycolipids are the most abundant glycoconjugates found in mammalian cells.

It has been determined that aberrant glycosylation is associated with many different diseases. Thus, there is a need to develop tools and methods to engineer glycosylation, and further use such tools or methods to treat various disorders associated with abnormal glycosylation.

SUMMARY

This disclosure relates to glycoengineering.

In one aspect, the disclosure relates to a fusion polypeptide having an antibody heavy chain CH2 region; an antibody heavy chain CH3 region; and a catalytic domain of a sialyltransferase, wherein the catalytic domain of the sialyltransferase catalyzes sialylation of a glycoprotein.

In some embodiments, the sialyltransferase is beta-galactoside alpha-2,6 sialyltransferase 1. In some embodiments, the sialyltransferase is a human sialyltransferase.

In some embodiments, the antibody heavy chain CH2 region is a human IgG heavy chain CH2 region. In some embodiments, the antibody heavy chain CH3 region is a human IgG heavy chain CH3 region.

In another aspect, the disclosure relates to a fusion polypeptide having an antibody heavy chain CH2 region; an antibody heavy chain CH3 region; and a catalytic domain of galactosyltransferase, wherein the catalytic domain of galactosyltransferase catalyzes galactosylation of a glycoprotein.

In some embodiments, the galactosyltransferase is beta-1,4-galactosyltransferase 1. In some embodiments, the galactosyltransferase is a human galactosyltransferase.

In some embodiments, the antibody heavy chain CH2 region is a human IgG heavy chain CH2 region. In some embodiments, the antibody heavy chain CH3 region is a human IgG heavy chain CH3 region.

In one aspect, the disclosure provides a polynucleotide encoding the fusion polypeptide as described herein.

In another aspect, the disclosure also provides a vector that has a polynucleotide sequence encoding the fusion polypeptide as described herein.

In one aspect, the disclosure relates to a cell having the vector as described herein, and the vector optionally expresses the fusion polypeptide as described herein.

In one aspect, the disclosure relates to a heteromultimer that has a first fusion polypeptide having an antibody heavy chain CH2 region, an antibody heavy chain CH3 region, and a catalytic domain of sialyltransferase, wherein the catalytic domain of sialyltransferase catalyzes sialylation of a glycoprotein; and a second fusion polypeptide having an antibody heavy chain CH2 region, an antibody heavy chain CH3 region, and a catalytic domain of galactosyltransferase, wherein the catalytic domain of galactosyltransferase catalyzes galactosylation of a glycoprotein.

In some embodiments, the heteromultimer is a heterodimer, and the first fusion polypeptide associates with the second fusion polypeptide, thereby forming the heterodimer.

In some embodiments, the sialyltransferase is beta-galactoside alpha-2,6 sialyltransferase 1. In some embodiments, the sialyltransferase is a human sialyltransferase.

In some embodiments, the galactosyltransferase is beta-1,4-galactosyltransferase 1. In some embodiments, the galactosyltransferase is a human galactosyltransferase.

In one aspect, the disclosure relates to methods of treating a subject having an IgG-mediated disorder. The methods involve administering to the subject an effective amount of a composition having the heteromultimer as described herein.

In some embodiments, the IgG-mediated disorder is inflammation. In some embodiments, the IgG-mediated disorder is an autoimmune disease.

In some embodiments, the autoimmune disease is arthritis. In some embodiments, the autoimmune disease is Goodpasture's disease. In some embodiments, the autoimmune disease is nephrotoxic nephritis. In some embodiments, the autoimmune disease is celiac disease, diabetes mellitus type 1, Graves disease, inflammatory bowel disease, multiple sclerosis, psoriasis, rheumatoid arthritis, or systemic lupus erythematosus.

In another aspect, the disclosure also relates to methods of treating a subject having an IgG-mediated disorder. The methods involve administering to the subject an effective amount of a first polypeptide having a catalytic domain of sialyltransferase and an effective amount of a second polypeptide having a catalytic domain of galactosyltransferase, wherein the catalytic domain of sialyltransferase catalyzes sialylation of a glycoprotein and the catalytic domain of galactosyltransferase catalyzes galactosylation of a glycoprotein.

In some embodiments, the first polypeptide further has an antibody heavy chain CH2 region, and an antibody heavy chain CH3 region.

In some embodiments, the second polypeptide further has an antibody heavy chain CH2 region, and an antibody heavy chain CH3 region.

In some embodiments, the IgG-mediated disorder is inflammation. In some embodiments, the IgG-mediated disorder is an autoimmune disease.

In some embodiments, the autoimmune disease is arthritis. In some embodiments, the autoimmune disease is Goodpasture's disease. In some embodiments, the autoimmune disease is nephrotoxic nephritis. In some embodiments, the autoimmune disease is celiac disease, diabetes mellitus type 1, Graves disease, inflammatory bowel disease, multiple sclerosis, psoriasis, rheumatoid arthritis, or systemic lupus erythematosus.

In one aspect, the disclosure also relates to methods of treating antibody-mediated injury during organ transplantation in a subject. The methods involve administering to the subject an effective amount of a composition having the heteromultimer as described herein.

In another aspect, the disclosure also relates to methods of treating antibody-mediated injury during organ transplantation in a subject. The methods involve administering to the subject an effective amount of a first polypeptide having a catalytic domain of sialyltransferase and an effective amount of a second polypeptide having a catalytic domain of galactosyltransferase, wherein the catalytic domain of sialyltransferase catalyzes sialylation of a glycoprotein and the catalytic domain of galactosyltransferase catalyzes galactosylation of a glycoprotein.

In one aspect, the disclosure also provides a heteromultimer that has a first fusion polypeptide having a collagen trimerizing domain and a catalytic domain of sialyltransferase; a second fusion polypeptide having a collagen trimerizing domain and a catalytic domain of galactosyltransferase; and a third fusion polypeptide having a collagen trimerizing domain, wherein the first fusion polypeptide, the second fusion polypeptide, and the third fusion polypeptide bind to each other, forming the heteromultimer.

In some embodiments, the third fusion polypeptide further has a catalytic domain of sialyltransferase. In some embodiments, the third fusion polypeptide further has a catalytic domain of galactosyltransferase.

In another aspect, the disclosure also relates to a heteromultimer that has a tetramer having four streptavidin polypeptides; and four polypeptides, wherein each of the four polypeptides is linked with biotin, and one or more of the four polypeptides have a catalytic domain of sialyltransferase or a catalytic domain of galactosyltransferase, wherein each of the four polypeptides binds to the tetramer having the four streptavidin polypeptides.

In some embodiments, each of the four polypeptides has a catalytic domain of sialyltransferase or a catalytic domain of galactosyltransferase.

In some embodiments, each of the four polypeptides has a catalytic domain of sialyltransferase. In some embodiments, each of the four polypeptides has a catalytic domain of galactosyltransferase.

In some embodiments, two of the four polypeptides each has a catalytic domain of sialyltransferase, and two of the four polypeptides each has a catalytic domain of galactosyltransferase.

In one aspect, the disclosure also provides a heteromultimer that has an antibody or antibody fragment thereof; a catalytic domain of sialyltransferase; and a catalytic domain of galactosyltransferase, wherein the catalytic domain of sialyltransferase and the catalytic domain of galactosyltransferase each is linked to the antibody or antibody fragment thereof.

In some embodiments, the heteromultimer has an antibody, and the antibody has two antibody heavy chains, and two antibody light chains. In some embodiments, the catalytic domain of sialyltransferase is linked to C-terminus of the antibody heavy chain. In some embodiments, the catalytic domain of sialyltransferase is linked to C-terminus of the antibody light chain. In some embodiments, the catalytic domain of galactosyltransferase is linked to C-terminus of the antibody heavy chain. In some embodiments, the catalytic domain of galactosyltransferase is linked to C-terminus of the antibody light chain.

As used herein, the term "multimer" refers to a protein having two or more polypeptides or a polypeptide complex formed by two or more polypeptides. The polypeptides can associate with each other, forming a quaternary structure.

As used herein, the term "heteromultimer" refers to a multimer having more than one type of polypeptides.

As used herein, the term "homodimer" refers to a multimer having two identical polypeptides.

As used herein, the term "heterodimer" refers to a multimer having two polypeptides, and the two polypeptides are different.

As used herein, the term "luminal domain" or "enzymatic luminal domain" refers to the portion of a glycosylation enzyme that is located within the lumen of the Golgi apparatus in its native state. The enzymatic luminal domain of a glycosyltransferase is usually the soluble portion of the glycosylation enzyme.

As used herein, the term "soluble portion" or "soluble domain" refers to the portion of glycosylation enzyme that is soluble. For trans-Golgi glycosylation enzymes, the soluble portions are often the enzymatic luminal domains of the glycosylation enzymes. For non-trans-Golgi glycosylation enzymes, the entire glycosylation enzymes can be soluble. Thus, in some embodiments, the soluble portion can be the entire glycosylation enzyme or part of the glycosylation enzyme.

As used herein, the term "catalytic domain" refers to a portion of a protein that has a catalytic activity.

As used herein, the term "IgG-mediated disorder" refers to a disorder caused by or characterized by an increased level or an increased activity of Immunoglobulin G (IgG).

As used herein, the term "linked" refers to being covalently or non-covalently associated, e.g., by a chemical bond (e.g., a peptide bond, or a carbon-carbon bond), by hydrophobic interaction, by Van der Waals interaction, and/or by electrostatic interaction.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-1E. Solubilizing and engineering glycosyltransferase enzymes. (A-C) Schematics of IgG, its complex, biantennary Fc glycan, and enzyme-Fc fusions are shown. (A) IgG Fab and Fc with a single, N-linked glycosylation site at N297. (B) The glycan core structure (within the box) consists of GlcNAc (squares), mannose (green circles), and variable addition of fucose (red triangle), bisecting GlcNAc, galactose (yellow circles), or sialic acid (purple diamonds). (C) The trans-Golgi enzymes B4GALT1 and ST6GAL1 have cytoplasmic (cyto), transmembrane (TMD), and enzymatic luminal domains (Lumen). ST6GAL1 Cleavage site EFQ41-43 resulting in its secretion is in red. Enzymatic luminal domains of B4GALT1 and ST6GAL1 were fused to IgG Fc ($B4^{Fc}$ and $ST6^{Fc}$, respectively). (D, E) Linkage-specific lectin blots assaying for glycosyltransferase activity of $B4^{Fc}$, $ST6^{Fc}$ individually or together. Terminal β1,4 galactose (ECL) or α2,6 sialic acid (SNA) on target glycoproteins fetuin (D), or mouse and human IgG Fcs (E) following incubation with engineered enzymes and sugar-nucleotide donors (UDP-Gal for $B4^{Fc}$, CMP-SA for $ST6^{Fc}$).

FIGS. 2A-2H. Anti-inflammatory activity of in vivo sialylation. (A) Mice were treated with K/B×N sera and PBS (black circles), $ST6^{Fc}$ (pink triangles), $B4^{Fc}$ (orange diamonds), or IVIG (blue squares), and paw swelling monitored over several days. (B) Day 10 clinical scores of individual mice in (A) are plotted. (C) K/B×N treated mice were given PBS (black circles), IVIG (blue squares), or $B4ST6^{Fc}$ (red triangles) and paw swelling monitored over several days. (D) Day 9 clinical scores of individual mice from (C) are shown. (E) H&E of paw sections 7 days after induction of arthritis in mice treated with PBS, WIG, or $B4ST6^{Fc}$. Blood urea nitrogen (BUN) levels on day 7 (F) and survival (G) of mice induced with NTN, and treated with PBS (black circles), IVIG (blue squares), or $B4ST6^{Fc}$ (red triangles). (H) PAS of stained frozen kidney sections from NTN-treated mice 7 days following PBS, IVIG, or $B4ST6^{Fc}$ administration. Means and standard deviation are plotted. Results are representative of at least two independent repeats. *p<0.05, p<0.01, *p<0.005, ****p<0.001, ns (not significant), determined by two-way ANOVA followed by Tukey's posthoc test.

FIGS. 3A-3G. Receptor requirements for in vivo sialylation. (A) FcγRIIB$^{-/-}$ mice were given K/B×N sera and PBS (black circles), IVIG (blue squares), or $B4ST6^{Fc}$ (red triangles) and paw swelling monitored over several days. (B) Day 6 clinical scores of individual mice from (A) are plotted. (C) WT mice were administered TKO SIGN-R1 antibody and K/B×N sera and PBS (black circles), IVIG (blue squares), or $B4ST6^{Fc}$ (red triangles) and paw swelling monitored over several days. (D) Day 6 clinical scores of individual mice from (C) are shown. (E) SIGN-R1$^{-/-}$ and (F) hDC-SIGN$^+$/SIGN-R1$^{-/-}$ mice were given K/B×N sera and PBS (circles), IVIG (squares), or $B4ST6^{Fc}$ (triangles) and paw swelling monitored over several days. (G) Day 6 clinical scores of SIGN-R1$^{-/-}$ and hDC-SIGN$^+$/SIGN-R1$^{-/-}$ mice are shown. Means and standard deviation are plotted. Results are representative of at least two independent repeats. p<0.01, *p<0.005, ****p<0.001, ns (not significant), determined by two-way ANOVA followed by Tukey's posthoc test.

FIG. 20 lists the amino acid sequences of several exemplary glycosylation enzymes.

FIG. 21 lists the amino acid sequences of exemplary fragment crystallizable region (Fc) of several human and mouse immunoglobulin G (IgG).

FIG. 22 lists the amino acid sequences of several exemplary glycosylation enzyme-Fc fusion proteins.

FIG. 23 lists the amino acid sequences of dog IgG heavy chain A, dog IgG heavy chain B, dog IgG heavy chain C, dog IgG heavy chain D, dog ST6GAL1, and dog B4GALT1.

FIG. 24 lists the amino acid sequences of cat IgG1a heavy chain, cat IgG1b heavy chain, cat ST6GAL1, and cat B4GALT1.

FIG. 25 lists the amino acid sequences of cow IgG1 heavy chain constant region, cow IgG2 heavy chain constant region, cow IgG3 heavy chain constant region, cow ST6GAL1, and cow B4GALT1.

FIG. 26 lists the amino acid sequences of horse IgG1 heavy chain constant region, horse IgG2 heavy chain constant region, horse IgG3 heavy chain constant region, horse IgG4 heavy chain constant region, horse IgG5 heavy chain constant region, horse IgG6 heavy chain constant region, horse ST6GAL1, and horse B4GALT1.

DETAILED DESCRIPTION

Immunoglobulin gamma (IgG) antibodies are the preeminent effector proteins of the immune system. They are essential following pathogen exposure or vaccination, bridging the adaptive and innate immune system for clearance of microbes, but can also contribute to the pathogenesis of autoimmune diseases when they are generated against self-antigens (Nimmerjahn and Ravetch, 2008b). The bimodal activity of IgG antibodies allows simultaneous recognition of antigen by the antigen-binding fragment (Fab, FIG. 1A) with high affinity, and recruitment and activation of leukocytes through interactions between the crystallizable fragment (Fc, FIG. 1A) and Fc gamma receptors (FcγRs) expressed by innate immune cells, or the initiator of the complement cascade, C1q (Nimmerjahn et al., 2015). This triggers the canonical inflammatory effector functions of IgG, such as antibody-dependent cytotoxicity (ADCC), uptake of recognized antigens, and complement-dependent cytotoxicity (CDC) (Franklin, 1975, Huber et al., 1976).

Figures 1A, 1B, 1C:
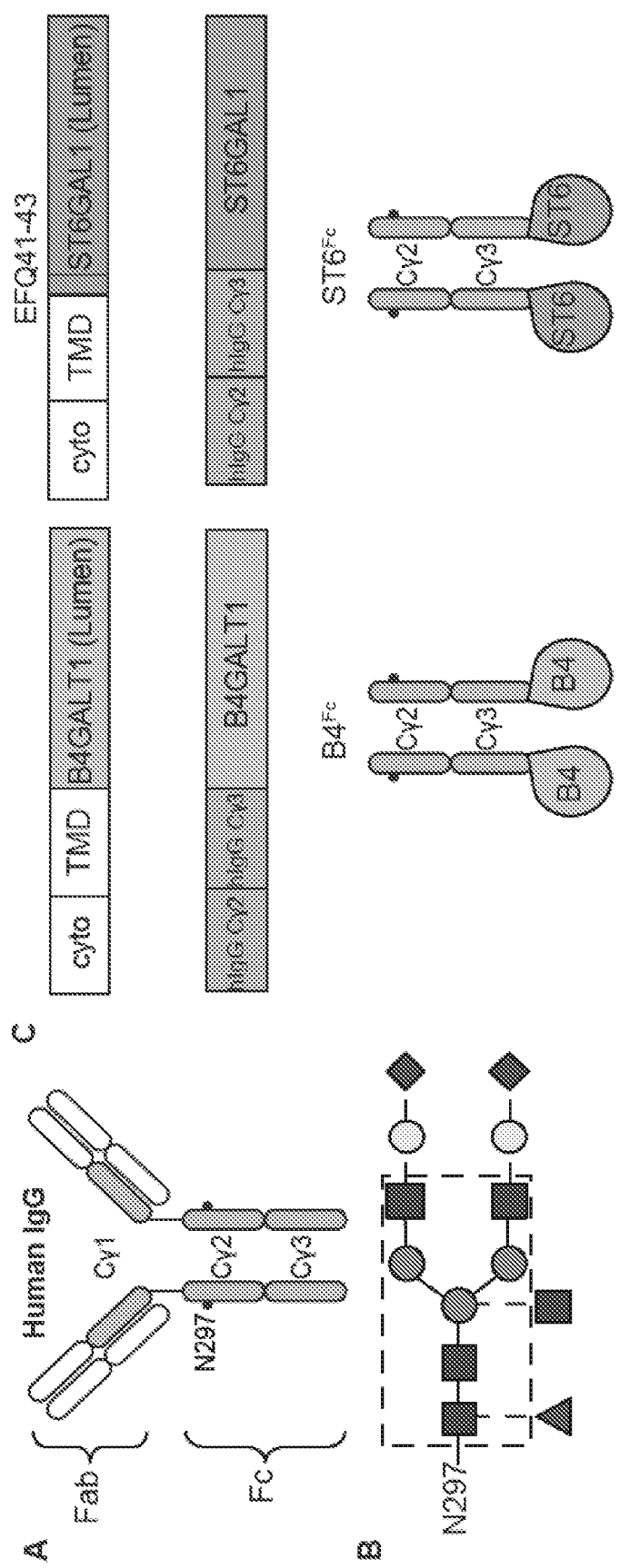

A single N-linked glycan is present on each heavy chain of all IgG, positioned at asparagine-297 in the Fc (N-297, FIGS. 1A-1B) (Arnold et al., 2007). The core heptasaccharide of the glycan has a complex biantennary structure that can vary by the addition of fucose, N-acetylglucosamine (GlcNAc), galactose, or sialic acid (FIG. 1B). These variable additions account for tremendous heterogeneity, with over 30 distinct glycans identified on circulating IgG in healthy individuals (Kaneko et al., 2006b). Importantly, studies over the last decade have demonstrated the composition of the Fc glycan exerts profound influence over IgG effector functions (Jefferis, 2005, Jefferis, 2009a, Jefferis, 2009b). IgG with afucosylated Fc glycans have 50-fold enhanced affinity to the activating FcγR, FcγRIIIA, compared to fucosylated IgG, and exhibit markedly enhanced ADCC in vivo (Ferrara et al., 2011, Natsume et al., 2005, Okazaki et al., 2004, Shields et al., 2002). As a consequence, some next-generation therapeutic IgG intended to elicit ADCC are being engineered to lack fucose (Beck et al., 2010). Indeed, recent studies have extended these findings to infectious diseases, identifying an association of dengue-specific IgG with afucosylated Fc glycans with dengue hemorrhagic fever (Wang et al., 2017), and afucosylated IgG in controlling latent, and not active, TB infections (Lu et al., 2016). The most successful HIV vaccine trial to date resulted in increased levels of bisecting GlcNAc on IgG Fc glycans, a modification that also increased affinity to FcγRIIIA, albeit to a lesser extent than afucosylation (Ackerman et al., 2013, Chung et al., 2014, Davies et al., 2001). Conversely, terminal sialylation of the Fc glycan reduces IgG affinity for type I FcγRs, and sialylated IgG have reduced capacity to initiate ADCC in vivo (Scallon et al., 2007, Anthony et al., 2008a, Li et al., 2017). Enhanced sialylation on IgG following influenza vaccination was attributed to improved affinity maturation through a type II FcγR-CD23, pathway (Wang et al., 2015). Although the regulation of IgG glycosylation is not completely understood, IL-23 has been implicated in regulating expression of ST6GAL1 (Pfeifle et al., 2017).

Paradoxically, IgG is commonly used in the clinic to suppress inflammation (Negi et al., 2007). Intravenous immunoglobulin (IVIG) is a therapeutic preparation of polyclonal, monomeric IgG derived from tens of thousands of healthy donors and has successfully been used in the clinic for almost 40 years at a high dose (1-2 g/kg) for the treatment of inflammatory and autoimmune diseases (Imbach et al., 1981, Nimmerjahn and Ravetch, 2008a). Mechanistic studies revealed that the Fc portion of IVIG was sufficient for anti-inflammatory activity in vivo (Debre et al., 1993, Samuelsson et al., 2001), and that this required inhibitory FcγRIIB (Samuelsson et al., 2001, Schwab et al., 2012, Schwab et al., 2014, Tackenberg et al., 2009, Tackenberg et al., 2010). Further studies demonstrated sialylation of the Fc glycan was essential for this activity (Kaneko et al., 2006b, Anthony et al., 2008a). Instead of binding the activating type I FcγRs, sialylated IgG Fc bound type II FcγRs, human DC-SIGN or murine SIGN-R1, culminating in increased surface expression of the inhibitory FcγRIIB on inflammatory effector cells (Anthony et al., 2011, Anthony et al., 2008b, Samuelsson et al., 2001). Thus, the IgG Fc glycan composition, and specifically terminal sialic acid, along with DC-SIGN and FcγRIIB are responsible for the anti-inflammatory activity of IgG in vivo (Kaneko et al., 2006b, Tackenberg et al., 2009, Anthony et al., 2011, Washburn et al., 2015).

This disclosure relates to methods and compositions comprising a fusion peptide comprising a catalytic domain of a glycosylation enzyme fused to Fc (e.g., glycosylation enzyme-Fc fusion proteins). The methods and compositions described herein can be used to modulate IgG effector function by engineering antibody glycans in vivo for various therapeutic effects. For example, this disclosure relates to modulation of IgG effector function by engineering antibody glycans in vivo as a novel means to attenuate autoantibody-mediated inflammation. It is well established that glycosylation, including sialylation, profoundly affects IgG biology. Indeed, the contribution of IgG glycosylation to infectious diseases is increasingly appreciated, and IgG glycoforms are reported to contribute to the clinical presentation of Dengue fever and Tuberculosis (Lu et al., 2016, Wang et al., 2017).

Afucosylated IgG with enhanced affinity for activating FcγRIIIA were found in patients more likely to suffer from dengue hemorrhagic fever, and also in patients with latent but not active TB infections. Sialylation markedly reduces the affinity of IgG to FcγRs, rendering IgG unable to trIgGer inflammation (Scallon et al., 2007, Kaneko et al., 2006b, Anthony et al., 2008a, Li et al., 2017). Enhanced sialylation on influenza-specific IgG Fc glycans was found following vaccination, and was associated with flu-specific broadly neutralizing antibodies in a CD23-type II FcγR dependent manner (Wang et al., 2015). Also, sialylated IgG Fcs convey anti-inflammatory activity when administered at a sufficiently high dose (Anthony et al., 2008a, Kaneko et al., 2006b, Washburn et al., 2015).

The mechanisms governing the dose-dependent anti-inflammatory actions of IgG have been extensively debated (Clynes, 2007, Schwab and Nimmerjahn, 2013). However, functional tests of IVIG have consistently shown that sialylation of IgG is responsible for this anti-inflammatory activity in vivo (Washburn et al., 2015, Zhang et al., 2016, Fiebiger et al., 2015, Schwab et al., 2012, Schwab et al., 2014, Ohmi et al., 2016). Removal of the Fc glycan from IgG rendered IVIG unable to suppress autoimmune inflammation (Kaneko et al., 2006b). Moreover, IVIG treated with neuraminidase, to removed terminal sialic acid from the Fc glycan, also exhibited no anti-inflammatory activity (Kaneko et al., 2006b). Thus, the IgG Fc glycan composition, and specifically sialic acid, is responsible for the anti-inflammatory activity of IgG in vivo.

Generation of sialylated IgG Fcs is not trivial, and has likely contributed to confusion in the literature. Indeed, contaminating LPS, degradation of Fcs, improper lectin-enrichment (Stadlmann et al., 2009), irrelevant in vitro assays (Bayry et al., 2009), and heterogeneity of Fab-specificity in IVIG have confounded results. Further, characterization of the sialylated material provides an explanation for some of the disparity, as ST6GAL1 can both attach and remove sialic acid (Washburn et al., 2015). Importantly, a number of groups have reported findings similar to original reports that sialylated hIgG1 is in fact anti-inflammatory in experimental models of Guillain-Barré syndrome (Zhang et al., 2016), and collagen-induced arthritis (Ohmi et al., 2016). Of note, through sialylating IgG in vivo, many of the technical issues of generating anti-inflammatory sialylated IgG have been circumvented.

Successful glycoengineering in vivo efforts have used bacterial-derived glycan-modifying enzymes (Albert et al., 2008, Xiao et al., 2016). The Streptococcal endoglycosidase, EndoS, has been demonstrated to attenuate IgG-mediated inflammation (Albert et al., 2008). Also, a *Vibrio cholerae* neurmaminidase was targeted to tumor glycocalixes to improve ADCC (Xiao et al., 2016). These studies demonstrated the power of glycoengineering, however repeated administration of these drugs may prove difficult because of immune responses targeting the bacterial-derived enzymes. While it is possible that B4ST6$^{Fc}$ will be targeted by the immune response, other human IgG Fc fusions have been well tolerated.

The potential applications for in vivo sialylation extend well beyond autoimmune and inflammatory conditions. Indeed, these methods can be applied to conditions currently treated by high dose IVIG. But modulation of IgG sialylation could also be utilized to improve vaccine efficacy, as studies have reported that initial IgG generated following vaccination are sialylated, and these sialylated IgG contribute to improved affinity maturation through a type II FcγR-dependent mechanism (Wang et al., 2015). Furthermore, in vivo sialylation can be effective at truncating the activity of therapeutic IgG at defined intervals after treatment. Also, these glycosyltransferases and the Fc portion of these fusion proteins can be further engineered, including increased FcRn affinity to extended serum half-life or increased/ decreased receptor binding (Schlothauer et al., 2016).

Therefore, this disclosure relates the functions of sialylation on IgG biology by fusing human glycosylation enzymes found in the trans-Golgi to IgG Fcs. Efficient sialylation required both enzymes that attach galactose and sialic acid (Anthony et al., 2008a). Importantly, this combination of glycosylation enzymes is able to attenuate autoantibody-mediated inflammation in two distinct models in vivo, by selectively sialylating IgG deposited at the site of inflammation. Administration of this enzyme combination does not appear to affect sialylation of IgG in circulation, or that of other glycoproteins in circulation. The data show that this is likely because platelets release galactose and sialic acid substrates only at sites of inflammation. Thus, the present disclosure provides a potent approach to attenuate harmful autoantibody-mediated inflammation through glycoengineering endogenous antibodies and converting them to anti-inflammatory mediators.

The methods and compositions (e.g., glycosylation enzyme-Fc fusion proteins) described herein can also be used for various other therapeutic effects, e.g., treating IgG-mediated disorders, treating autoimmune diseases, or treating antibody-mediated injury during organ transplantation. Further, the glycosylation enzyme-Fc fusion proteins as described in the present disclosure are well tolerated, as Complete Blood Count (CBC) and Comprehensive Metabolic Panel (CMP) analysis are within normal levels both one week and two months after administration, making them suitable for clinic use. Thus, this disclosure provides a useful approach to treat IgG-mediated disorders (e.g., inflammation, and autoimmune diseases) and antibody-mediated injury during organ transplantation.

Glycans

Glycans have an important role in the function of many proteins. Glycans are saccharides (i.e., a plurality of monosaccharides linked glycosidically) that form the carbohydrate portion of glycoconjugates (e.g., glycoproteins, glycopeptides, peptidoglycans, glycolipids, glycosides and lipopolysaccharides). They can be added to proteins in the endoplasmic reticulum, and further modified as proteins travel through the Golgi apparatus. Precursor glycan structures can be attached to asparagine (N-linked), serine or threonine (O-linked), phospholipids (GPI), tryptophan (C-linked), or by phosphodiester bonds (phosphoglycosylation). While many biological functions are ascribed to glycans, two general types of functions of glycosylation are (1) maintaining or modifying the structural or functions of glycoproteins, and (2) providing a glycan-based recognition platform for carbohydrate receptors or lectins.

N-Linked Glycosylation

In the lumen of the endoplasmic reticulum, a 14-residue precursor oligosaccharide (glucose$_3$ mannose$_9$ N-acetylglucosamine$_2$, ($Glc_3Man_9GlcNAc_2$)) is transferred to an asparagine residue found in the consensus sequence N-X-S/T by the enzyme oligosaccharyltransferase (Schachter et al., in *Essentials of Glycobiology*, Edn. 2010/03/20, eds. V. A et al., Cold Spring Harbor Laboratory Press, Cold Spring Harbor (N.Y.), 2009). The precursor glycan is trimmed to a high-mannose structure ($Man_{8-9}GlcNAc_2$) by exoglycosidases while the protein being synthesized is assembled and transported to the Golgi. The glycan can then be further processed as a protein progresses through the secretory pathway.

The core complex biantennary glycan structure ($GlcNAc_3Man_3GlcNAc_2$) is generated by the transfer of GlcNAc by β1,2 N-acetylglucosaminyltransferase-II. This structure is found in the constant region of IgG antibodies, and can be further modified. The core GlcNAc is available for fucosylation by a1,6-fucosyltransferase. Bisecting N-acetylglucosamine is attached to the core by N-acetylglucosaminyltransferase-III. As a protein progresses along the secretory pathway, the glycan can be further modified in the trans-Golgi by the addition of galactose and sialic acid to the arms by β1,4 galactosyltransferase and α2,6 sialyltransferase, respectively.

O-Linked Glycosylation

O-linked glycosylation is initiated by the attachment of GlcNAc to serine or threonine (Schachter et al., in *Essentials of Glycobiology*, Edn. 2010 Mar. 20, eds. V. A et al., Cold Spring Harbor Laboratory Press, Cold Spring Harbor (N.Y.), 2009). The pathway responsible for these modifications is less understood than N-linked glycosylation. An estimate suggests at least eight mammalian N-acetylglucosaminyltransferase enzymes exist, which are differentially expressed depending on cell type. Thus, it is not clear whether the ER or Golgi is the initial site for this glycosylation. No known consensus amino acid sequence exists for O-linked glycans, although secondary structural preferences are suggested instead. In fact, most O-glycosylation is found in β turns. Further, enrichment for proline residues is noted at the −1 and +3 positions, while charged residues are not favored at these positions.

Most O-glycans contain a Core 1 subtype structure formed by the addition of galactose in a β1-3 linkage to the GlcNAc by the Core 1 β1-3 galactosyltransferase (Core 1 GalT). Core 2-type O-glycans can be generated by addition of GlcNAc to the GalNAc in a β1-6 linkage. Core 2 O-glycans require the Core 1 structure as a substrate. Generation of the Core 3 O-glycan is controlled by Core 3 GlcNAcT activity, which uses the GlcNAc-serine/threonine substrate. It is possible that competition between Core 1 GalT and Core 3 GalT enzymes in some cell types or among certain glycoproteins regulates Core 1 and Core 3 generation.

GPI-Linked Glycosylation

The de novo biosynthesis of glycosphingolipids begins on the inner leaflet of membranes in the ER-Golgi pathway (Schachter et al., in *Essentials of Glycobiology*, Edn. 2010/03/20, eds. V. A et al., Cold Spring Harbor Laboratory Press, Cold Spring Harbor (N.Y.), 2009). Ceramide is first synthesized, and then glucosylated or galactosylated by specific glycosyltransferases. The addition of a β-linked galactose residue follows. Thereafter, the molecules can be elongated in a stepwise fashion, giving a wide variety of different core structures. The outer extensions of glycosphingolipids, including the addition of sialic acids, fucose, or glucuronic acid residues share much in common with those of N- and O-glycans.

Glycosylation Enzymes

Glycosylation enzymes are responsible for the reaction in which a carbohydrate, i.e. a glycosyl donor, is attached to a hydroxyl or other functional group of another molecule (a glycosyl acceptor, e.g., proteins, lipids, and glycans). The soluble portions (or the enzymatic luminal domains) or the catalytic domains of these glycosylation enzymes can be fused with Fc, or other appropriate peptides to form multimers, and can be used in any methods described herein.

α-2,6 Sialyltransferase (ST6GAL1)

Attachment of sialic acid to galactose on IgG Fc glycans is catalyzed by the enzyme α-2,6 sialyltransferase (ST6GAL1; NP 003023.1; SEQ ID NO: 1). Sialylation of IgG by ST6GAL1 typically occurs in the trans-Golgi where ST6GAL1 is found anchored in the Golgi by a transmembrane domain (TMD, FIG. 1C). This trans-Golgi enzyme can attach terminal sialic acid to complex biantennary glycans. As shown in FIG. 1C, the trans-Golgi enzyme ST6GAL1 has a cytoplasmic domain (cyto), a transmembrane domain (TMD), and an enzymatic luminal domain (Lumen) (amino acids 24-406 of SEQ ID NO:1, amino acids 29-406 of SEQ ID NO:1, amino acids 34-406 of SEQ ID NO:1, or amino acids 41-406 of SEQ ID NO:1). The catalytic domain (amino acids: 160-390 of SEQ ID NO: 1) is located within the enzymatic luminal domain.

Several distinct promoters regulate the cellular and tissue specific expression of this transferase (Kalcheva et al. Mammalian genome: official journal of the International Mammalian Genome Society 8, 619-620 (1997); Wang et al. The Journal of biological chemistry 268, 4355-4361 (1993)). For example, promoter 1 is used exclusively to express ST6GAL1 by hepatocytes, while B cells use promoter 2 (Appenheimer, M. M. et al. Glycobiology 13, 591-600 (2003)). Hepatocytes are responsible exclusively for production of soluble ST6GAL1 (sST6GAL1), which is cleaved and secreted into the circulation. Importantly, genetic disruption of liver-specific promoter 1 resulted in markedly reduced levels of circulating sialylated IgG, compared to wild type controls. However, B cells from both mouse strains were able to express the enzyme, implicating the hepatic soluble form of this enzyme in IgG sialylation.

β-1,4-Galactosyltransferase 1 (B4GALT1)

Beta-1,4-galactosyltransferase 1 is an enzyme that is encoded by the B4GALT1 gene in humans. B4GALT1 (NP 001488.2; SEQ ID NO: 2) is a type II membrane-bound glycoprotein that appear to have exclusive specificity for the donor substrate UDP-galactose. It transfers galactose in a beta1,4 linkage to similar acceptor sugars (e.g., N-Acetylglucosamine (GlcNAc)) that are either monosaccharides or the non-reducing ends of glycoprotein carbohydrate chains. The catalytic domain (amino acids: 185-390 of SEQ ID NO: 2) is located within the luminal domain (amino acids 79-398 of SEQ ID NO: 2, or amino acids 106-398 of SEQ ID NO: 2) of B4GALT1.

Soluble Glycosylation Enzymes

Many glycosylation enzymes are secreted. The soluble forms can be derived, e.g., from their membrane-associated forms by proteolytic cleavage near the transmembrane (TM) region, in the carboxyl-terminal direction.

As shown in FIG. 1C, the trans-Golgi enzymes B4GALT1 and ST6GAL1 include cytoplasmic domains (cyto), transmembrane domains (TMD), and enzymatic luminal domains (Lumen). The single hydrophobic segment serves as a signal-anchor sequence. This transmembrane segment (TMD) spans the lipid bilayers of the secretory pathway, including the membrane of the Golgi apparatus. The enzymatic luminal domain of a glycosyltransferase is located within the lumen of the Golgi apparatus. Membrane-tethered transferases are susceptible to proteolytic cleavages within its "stem" region. Proteolysis liberates a catalytically active, soluble form of the enzyme that may be released from the cell. As a consequence, many glycosylation enzymes are found in soluble form in the circulation and in various body fluids. Intriguingly, the production of these soluble enzymes in hepatocytes and endothelium can also be dramatically increased under certain inflammatory conditions.

ST6GAL1 has a β-Secretase (BACE1) cleavage site in its luminal domain at EFQ41-43, which can result in its secretion (FIG. 1C, FIGS. 8A-8D). The soluble ST6GAL1 is enzymatically active in the circulation, and can contribute to sialylation of IgG Fc glycans.

The cleavage site for B4GALT1 is L79 and S106. A subpopulation of this enzyme is secreted following proteolytic cleavage in its stem domain, and the soluble form of this enzyme is enzymatically active.

Thus, in one aspect, this disclosure provides a fusion protein or a peptide comprising or consisting of the enzymatic luminal domain of sialyltransferase or the catalytic domain of sialyltransferase. In some embodiments, the enzymatic luminal domain of sialyltransferase does not have BACE1 cleavage site. In some embodiments, the enzymatic luminal domain of sialyltransferase comprises or consists of amino acids 24-406 of SEQ ID NO:1, amino acids 29-406 of SEQ ID NO:1, amino acids 34-406 of SEQ ID NO:1, or amino acids 41-406 of SEQ ID NO:1. The catalytic domain of sialyltransferase catalyzes sialylation of a glycoprotein. In some embodiments, the catalytic domain of sialyltransferase comprises or consists of amino acids 160-390 of SEQ ID NO: 1.

This disclosure also provides a fusion protein or a peptide comprising or consisting of the enzymatic luminal domain of galactosyltransferase or the catalytic domain of galactosyltransferase. In some embodiments, the enzymatic luminal domain of galactosyltransferase comprises or consists of amino acids 79-398 of SEQ ID NO: 2, or amino acids 106-398 of SEQ ID NO: 2. The catalytic domain of galactosyltransferase catalyzes galactosylation of a glycoprotein. In some embodiments, the catalytic domain of galactosyltransferase comprises or consists of amino acids 185-390 of SEQ ID NO: 2.

Nucleic Acid Sequences and Amino Acid Sequences

This disclosure provides various nucleic acid sequences and amino acid sequences.

In some embodiments, the nucleic acid sequence is at least 60%, 65%, 70%, 75%, 80%, 85%, 90%, 91%, 92%, 93%, 94%, 95%, 96%, 97%, 98%, 99% identical to any of the nucleic acid sequences disclosed herein. In some embodiments, the nucleic acid sequence is identical to any of the sequences described in this disclosure.

In some embodiments, the amino acid sequence is at least 60%, 65%, 70%, 75%, 80%, 85%, 90%, 91%, 92%, 93%, 94%, 95%, 96%, 97%, 98%, 99% identical to any of the amino acid sequences disclosed herein. In some embodiments, the amino acid sequence is identical to any of the sequences described in this disclosure.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

FcB4, FcST6, and FcChm

Golgi enzymes, including ST6GAL1 and B4GALT1, are Golgi type II membrane proteins. The enzymatic transferase activity is located in the C-terminus of the protein (FIG. 1C).

The glycosylation enzyme, enzymatic luminal domain, soluble domain, or the catalytic domain thereof can be fused to IgG (e.g., IgG1, IgG2, IgG3, IgG4) or a part thereof. In some embodiments, the glycosylation enzyme, enzymatic luminal domain, soluble domain, or the catalytic domain thereof can be used to the Fc portions of IgG (e.g., IgG1, IgG2, IgG3, IgG4). Fc fusions have a number of advantageous: the soluble protein will have an extended serum half-life (e.g., more than 5 days, 10 days, 14 days, or 20 days), and also will form a dimer. In some embodiments, these fusion polypeptides can form homodimers or heterodimers, depending on the glycosylation target.

The IgG Fc can be the Fc region of any IgG known in the art. For example, the IgG Fc can be a human IgG1-Fc (e.g., comprising amino acids 26-256 of SEQ ID NO: 3), a human IgG2-Fc (e.g., comprising amino acids 52-266 of SEQ ID NO: 4), a human IgG3-Fc (e.g., comprising amino acids 41-318 of SEQ ID NO: 5), a human IgG4-Fc (e.g., comprising amino acids 53-268 of SEQ ID NO: 6), a mouse IgG1-Fc (e.g., comprising amino acids 26-252 of SEQ ID NO: 7), a mouse IgG2a-Fc (e.g., comprising amino acids 21-253 of SEQ ID NO: 8), a mouse IgG2b-Fc (e.g., comprising amino acids 21-259 of SEQ ID NO: 9), a mouse IgG3-Fc (e.g., comprising amino acids 21-253 of SEQ ID NO: 10), a canine IgG-A Fc (e.g., comprising amino acids 21-244 of SEQ ID NO: 15), or a feline IgG1 Fc (e.g., comprising amino acids 21-243 of SEQ ID NO: 17). Preferably, the species of the immunoglobulins is chosen to correspond with the species of the subject to whom the fusion protein will be administered.

In some embodiments, the peptides comprise an IgG antibody heavy chain CH2 region, an IgG antibody heavy chain CH3 region, and an enzymatic luminal domain or a catalytic domain of sialyltransferase. In some embodiments, the peptide has the amino acid sequence that is set forth in SEQ ID NO: 11. The disclosure also provides polypeptides comprising an IgG antibody heavy chain CH2 region, an IgG antibody heavy chain CH3 region, and an enzymatic luminal domains or a catalytic domain of galactosyltransferase. In some embodiments, the peptide has the amino acid sequence that is set forth in SEQ ID NO: 12. In some embodiments, these polypeptides can form a homodimer. The homodimer can have two enzymatic luminal domains (or catalytic domains) of sialyltransferase (e.g., FcST6 or ST6$^{Fc}$). In some other cases, the homodimer can have two enzymatic luminal domains (or catalytic domains) of galactosyltransferase (e.g., FcB4 or B4$^{Fc}$). In some embodiments, these polypeptides can form a heterodimer (FcChm or FcB4/FcST6), which has one enzymatic luminal domain (or catalytic domain) of sialyltransferase and one enzymatic luminal domain (or catalytic domain) of galactosyltransferase.

FIG. 22 shows some examples of glycosylation enzyme—Fc fusion proteins, including human IgG Fc-B4GALT1 fusion protein (SEQ ID NO: 11), human IgG1 Fc-ST6GAL1 fusion protein (SEQ ID NO: 12), mouse IgG1 Fc-B4GALT1 fusion protein (SEQ ID NO: 13), mouse IgG1 Fc-ST6GAL1 fusion protein (SEQ ID NO: 14), canine IgG-A (IgG1) Fc-ST6GAL1 fusion protein (SEQ ID NO: 15), canine IgG-A(IgG1) Fc-B4GALT1 fusion protein (SEQ ID NO: 16), feline IgG1 Fc-ST6GAL1 fusion protein (SEQ ID NO: 17), feline IgG1 Fc-B4GALT1 fusion protein (SEQ ID NO: 18).

In some embodiments, these peptides can additionally have signal sequences, e.g., IL2-signal sequence (amino acids 1-20 of SEQ ID NO: 3), or x-signal sequence (amino acids 1-39 of SEQ ID NO: 4). These signal sequences usually present at the N-terminus of the peptides.

In some embodiments, the Fc regions can have "knobs-into-holes" (KIH) mutations. The KIH mutations can be used for facilitating the formation of heterodimers. In some embodiments, one Fc has one or more of mutations selected from the group consisting of Y349C, T366S, L368A, and Y407V (all in EU numbering). The other Fc can have one or both mutations selected from the group consisting of S354C and T366W (all in EU numbering). In some embodiments, Fc-B4GALT1 fusion protein has a sequence set forth in SEQ ID NO: 42. In some embodiments, Fc-ST6GAL1 fusion protein has a sequence set forth in SEQ ID NO: 43.

In some embodiments, the enzymatic luminal domain, soluble domain or the catalytic domain of glycosylation enzymes can be fused to a part or the entire part of IgG1, IgG2, IgG3, or IgG4. In some embodiments, the enzymatic luminal domain, soluble domain or the catalytic domain of glycosylation enzymes can be fused to Fc portions of IgG1, IgG2, IgG3, or IgG4. In some embodiments, the Fc portion is the Fc of IgG3.

Intact antibodies with desired specificity can be fused to glycosylation enzymes, enabling specific targeting of the enzymes. Further, similar protein fusions can be generated using dog/cat/horse/cow equivalent/homologous antibodies or glycosylation enzymes, enabling treatment of non-human animals (e.g., pets and livestock).

Monomers, Dimers, Trimers, and Tetramers

Figures 15A, 15B, 15C, 15D:
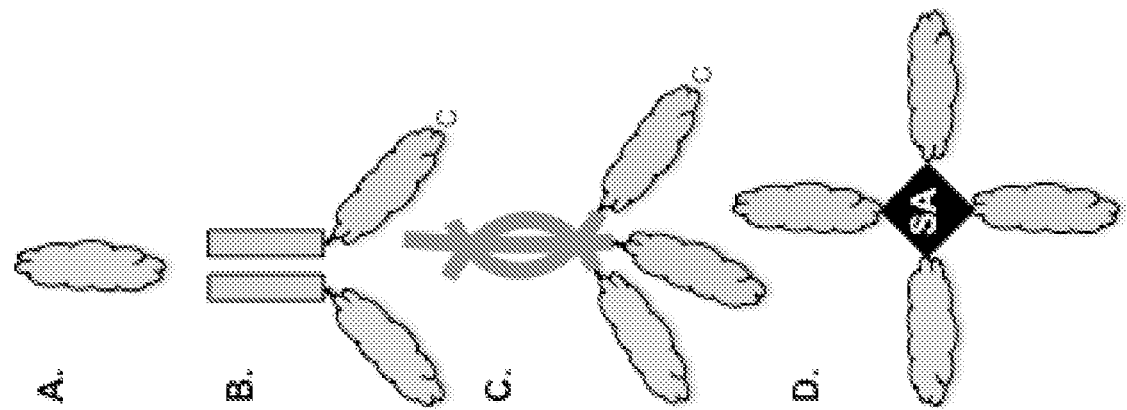
FIG. 15A is a diagram showing a soluble portion of a glycosylation enzyme.
FIG. 15B is a diagram showing a dimer formed by soluble portions of glycosylation enzymes that are fused to IgG Fcs.
FIG. 15C is a diagram showing a trimer formed by soluble portions of glycosylation enzymes that are fused to collagen trimerizing domains.
FIG. 15D is a diagram showing a tetramer formed by soluble portions of glycosylation enzymes that are biotinylated by biotin ligase and subsequently incubated with streptavidin (SA).
Figure 17:
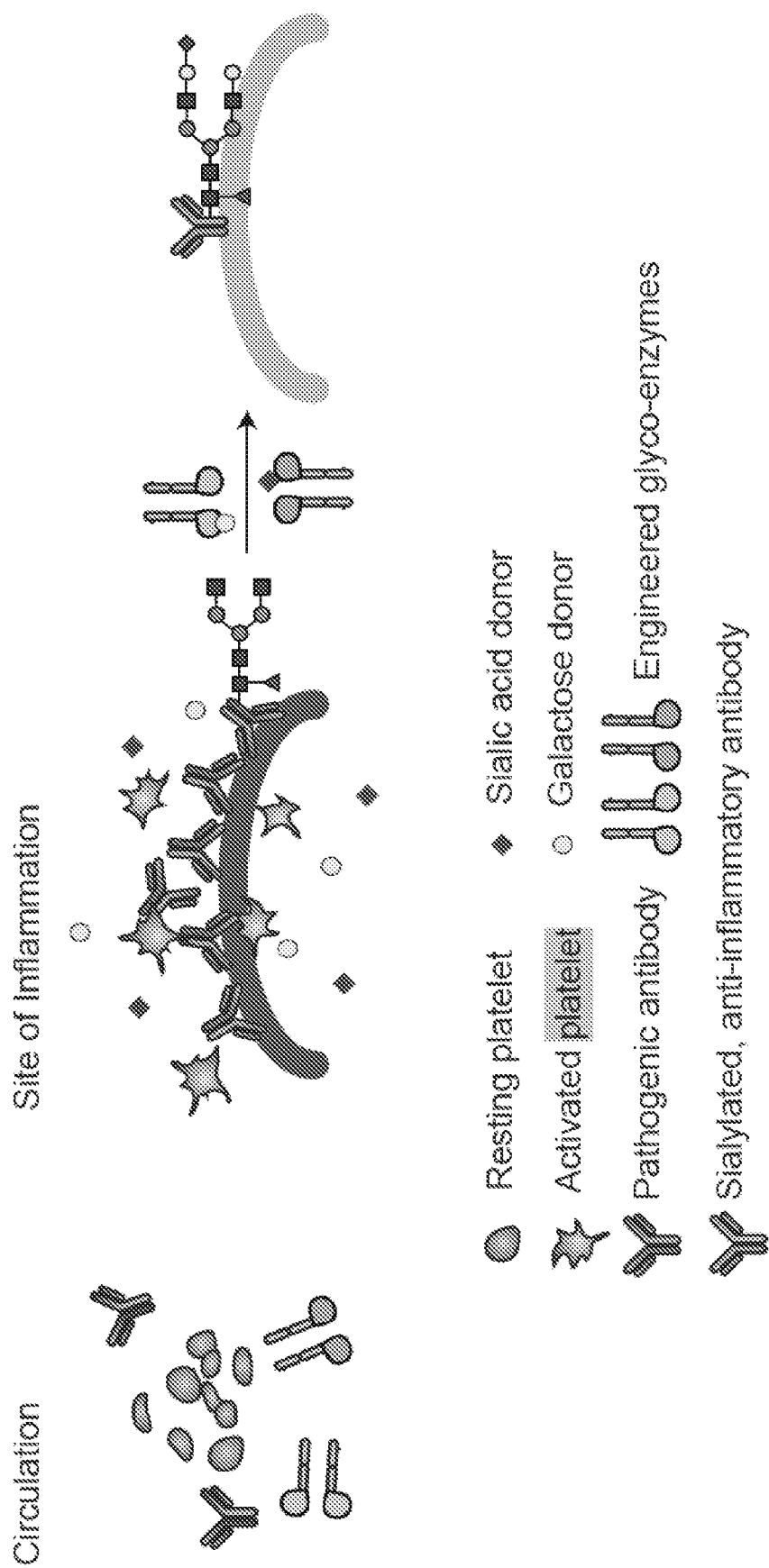
FIG. 17 is a diagram showing engineered glycol-enzymes can be used to treat inflammation.

Exemplary monomers are shown in FIG. 15A. As shown in FIG. 15A, a monomer can be the enzymatic luminal domain, the soluble domain, or the catalytic domain of a glycosylation enzyme (e.g., sialyltransferase or galactosyltransferase). Multimers can be generated by any methods known in the art. In some embodiments, the multimer can have one, two, three, four, or more than four enzymatic luminal domains, soluble domains, or catalytic domains of glycosylation enzymes. In some embodiments, the multimer can have one, two, three, four, or more than four enzymatic luminal domains (or catalytic domains) of sialyltransferase. In some embodiments, the multimer can have one, two, three, four, or more than four enzymatic luminal domains (or catalytic domains) of galactosyltransferase.

In some embodiments, the multimers can be dimers (e.g., FcB4, FcST6, and FcChm).

The multimers can also be trimers, or tetramers. Trimers, and tetramers can be generated by fusing the luminal enzymatic portion or the soluble portion to, e.g., a collagen-like peptide scaffold (Gly-Pro-Pro)×10, or biotinylation sites, respectively. As shown in FIGS. 15C-15D, soluble portions of glycosylation enzymes can be engineered as trimers by fusing to collagen trimerizing domains (FIG. 15C), or tetrameters by including biotin-ligase recognitions sites, biotinylating the fusion with biotin ligase, and subsequently incubating with streptavidin (FIG. 15D). In FIGS. 15C-15D, the multimers are drawn as heteromultimers, but can also be made as homomultimers, as needed. The detailed method of producing multivalent protein binders is described, e.g., in Fan, Chia-Yu, et al. "Production of multivalent protein binders using a self-trimerizing collagen-like peptide scaffold." The FASEB Journal 22.11 (2008): 3795-3804, which is incorporated by reference in its entirety.

Site-Specific Glycoengineering

Although soluble Golgi enzymes are found throughout the body, there are applications and circumstances where the ability to selectively target these enzymes to defined anatomical locations is more desirable. In some appropriate cases, the enzymatic luminal domain or the catalytic domain can be linked to immunoglobulin (e.g., antibody, or single-chain variable fragment) to yield full length antibody-enzyme conjugates.

A single native IgG antibody comprises two identical copies of a light chain and two identical copies of a heavy chain. The heavy chains, which each contain one variable domain (or variable region, VH) and three constant domains (or constant regions, CH1, CH2, CH3), bind to one another via disulfide bonding within their constant domains to form the "stem" of the antibody. The light chains, which each contain one variable domain (or variable region, VL) and one constant domain (or constant region, CL), each bind to one heavy chain via disulfide binding. The variable region of each light chain is aligned with the variable region of the heavy chain to which it is bound. The fragment antigen-binding (Fab) fragment is a region on an antibody that binds to antigens. It is composed of one constant and one variable region of each of the heavy and the light chain. The fragment crystallizable region (Fc region) is the tail region of an antibody that interacts with cell surface receptors called Fc receptors and some proteins of the complement system. This property allows antibodies to activate the immune system.

In IgG, the Fc region is composed of two identical protein fragments, derived from the second and third constant regions of the antibody's two heavy chains.

Figures 16A, 16B:
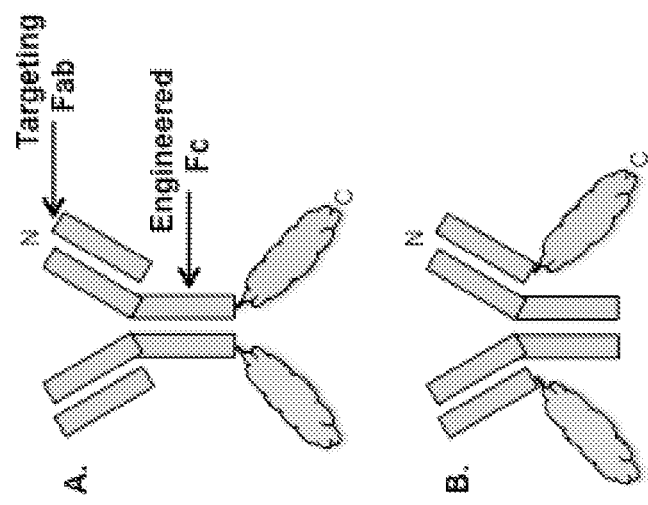
FIG. 16A is a diagram showing soluble portions of glycosylation enzymes that are fused to the C-terminus of the heavy chains of an antibody.
FIG. 16B is a diagram showing soluble portions of glycosylation enzymes that are fused to the C-terminus of the light chains of an antibody.

Fusion to the Fc or constant C-terminus of the Fab will depend on the specific application (FIGS. 16A-16B). Similarly, the variable region sequence used in the full-length immunoglobulin will be selected by the ability to localize the immunoglobulin-attached glycosylation enzymes. Criteria for variable region sequences will include recognition of a motif located adjacent to a glycosylation site of interest, such that a fused enzyme will be in close proximity to modify the target glycan. Also, variable region sequences that bind directly to the glycan or block the accessibility of the glycan will be avoided. Finally, the Fc portion can be engineered to elicit desired antibody-dependent effector functions (FIG. 16A). For example, for glycosylation enzymes that target infectious agents, Fcs that exhibit enhance antibody-dependent cytotoxicity (ADCC) can be effective. In contrast, glycosylation enzymes-fusions for other applications, including xenograft transplantation, would contain Fcs incapable of ADCC.

As shown in FIGS. 16A-16B, enzyme fusions can be generated using immunoglobulin variable chains and constant chains of interest. Enzymes can be fused to the C-terminus of the Fc or constant Fab, depending on the application. Fabs are selected for their specificity, ability to bring glycosylation enzyme near enough to the intended glycan. The Fc can be engineered to elicit, or not elicit, desired immunoglobulin effector functions.

In some embodiments, the disclosure provides a hetero-multimer. The heteromultimer includes an antibody or antibody fragment thereof, an enzymatic luminal domain (or catalytic domain) of sialyltransferase, and/or an enzymatic luminal domain (or catalytic domain) of galactosyltransferase. In some embodiments, the antibody or antibody fragment thereof has two heavy chains, and two light chains. The enzymatic luminal domain (or catalytic domain) of sialyltransferase can be fused to the C-terminus of the heavy chain or the light chain. Similarly, the enzymatic luminal domain (or catalytic domain) of galactosyltransferase can also be fused to the C-terminus of the heavy chain or the light chain.

Methods of Treatment

The methods described herein include methods for the treatment of IgG-mediated disorders (e.g., inflammation, autoimmune diseases) and antibody-mediated injury in organ transplantation. In some embodiments, the disorder is an autoimmune disease such as idiopathic thrombocytopenic purpura (ITP), multiple sclerosis, systemic lupus erythematosus, rheumatoid arthritis, chronic inflammatory demyelinating neuropathy, Sjogren's syndrome, and Granulomatosis with Polyangitis (Wegner's), etc. These autoimmune diseases are described, e.g., in Dal, Mehmet Sinan, et al. "Assessment of the underlying causes of the immune thrombocytopenia: Ten years experience." JPMA. The Journal of the Pakistan Medical Association 67.7 (2017): 1004; Prineas, John W., and John D E Parratt. "Multiple sclerosis: Serum anti-CNS autoantibodies." Multiple Sclerosis Journal (2017): 1352458517706037; Bai, Yunqiang, et al. "Self-dsDNA in the pathogenesis of systemic lupus erythematosus." Clinical & Experimental Immunology (2017); Hughes, Graham R V "Frequency of anti-DNA antibodies in SLE, RA and other diseases: experience with the ammonium sulphate precipitation technique." Scandinavian Journal of Rheumatology 4.sup11 (1975): 42-51; Fu, S. M., et al. "Autoantibodies and glomerulonephritis in systemic lupus erythematosus." Lupus 12.3 (2003): 175-180; Tan, Eng M. "Autoantibodies and autoimmunity: A three-decade perspective. A tribute to Henry G Kunkel." Annals of the New York Academy of Sciences 815.1 (1997): 1-14; Querol et al., "Autoantibodies in chronic inflammatory neuropathies: diagnostic and therapeutic implications." Nat Rev Neurol. 2017 September; 13(9):533-547; each of which is incorporated by reference herein in its entirety.

Generally, the methods include administering a therapeutically effective amount of agents (e.g., fusion proteins or peptides) comprising or consisting of the enzymatic luminal domain or the catalytic domain of glycosylation enzymes, multimers (e.g., FcB4, FcST6, FcChm), or compositions as described herein, to a subject who is in need of, or who has been determined to be in need of, such treatment.

As used in this context, to "treat" means to ameliorate at least one symptom of the disorders or the diseases. Often, the treatment results in an improvement in the symptoms. In some embodiments, the treatment can result in a reduction of inflammation. In some embodiments, one or more of the clinical symptoms are ameliorated or reduced, the duration is shortened, the frequency of the occurrence of the symptoms is reduced, or the clinical symptoms are prevented from manifesting (i.e., the risk of the symptoms is reduced).

As used herein, the terms "subject" and "patient" are used interchangeably throughout the specification and describe an animal, human or non-human, e.g., a mammal, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals. Thus, the glycosylation enzymes, the antibodies, or the parts thereof (e.g., Fc regions of the antibodies or the catalytic domain of the glycosylation enzymes) as described herein can also derive from these non-human animals. The present disclosure further provides the amino acid sequences of the glycosylation enzymes, and the antibodies or the parts thereof that derive from some of these non-human animals. For example, FIG. 23 lists the amino acid sequences of dog IgG heavy chain A, dog IgG heavy chain B, dog IgG heavy chain C, dog IgG heavy chain D, dog ST6GAL1, and dog B4GALT1. FIG. 24 lists the amino acid sequences of cat IgG1a heavy chain, cat IgG1b heavy chain, cat ST6GAL1, and cat B4GALT1. FIG. 25 lists the amino acid sequences of cow IgG1 heavy chain constant region, cow IgG2 heavy chain constant region, cow IgG3 heavy chain constant region, cow ST6GAL1, and cow B4GALT1. FIG. 26 lists the amino acid sequences of horse IgG1 heavy chain constant region, horse IgG2 heavy chain constant region, horse IgG3 heavy chain constant region, horse IgG4 heavy chain constant region, horse IgG5 heavy chain constant region, horse IgG6 heavy chain constant region, horse ST6GAL1, and horse B4GALT1.

In some embodiments, the subject is a human (e.g., male human or female human) with an age over 25 years old, 30 years old, 40 years old, 50 years old, 60 years old, 70 years old, or 80 years old.

As used herein, the terms "therapeutically effective" and "effective amount", used interchangeably, applied to a dose or amount refers to a quantity of a composition, compound or pharmaceutical formulation that is sufficient to result in a desired activity upon administration to a subject in need thereof. Within the context of the present disclosure, the term "therapeutically effective" refers to that the composition, compound or pharmaceutical formulation, in a sufficient amount, can reduce or eliminate at least one symptom or one condition of the disorders as described herein.

IgG-Mediated Disorder

As used herein, the term "IgG-mediated disorder" refers to any disorder caused by or characterized by an increased level or an increased activity of IgG. Therefore, inhibiting the activity of IgG is often the treatment for a IgG-mediated disorder. The IgG-mediated disorder can include, but are not limited to, inflammation, and various auto-immune diseases.

In fact, IgG is widely used in the clinic to suppress inflammation. Intravenous immunoglobulin (IVIG) is a therapeutic preparation of polyclonal, monomeric IgG derived from tens of thousands of healthy donors. It is given to immunocompromised patients at 400-600 mg/kg as an antibody replacement therapy. In 1981, IVIG was administered at a high dose (1-2 g/kg) to pediatric patients suffering from an autoimmune disease in which autoantibodies target platelets (immune-mediated thrombocytopenia, ITP). The treatment restored platelet counts to normal, offering temporary relief to the patients (Imbach, P. et al. Lancet 1, 1228-1231 (1981)). Since then, IVIG is routinely used as an anti-inflammatory therapy for the treatment of many diseases, including the autoimmune diseases ITP, multiple sclerosis, systemic lupus erythematosus, and for solid organ transplantation (see, e.g., Fillit, H. Lancet Neurol 3, 704 (2004); Fillit, H., Hess, G., Hill, J., Bonnet, P. & Toso, C. Neurology 73, 180-185 (2009); Hack, C. E. & Scheltens, P. J Neurol Neurosurg Psychiatry 75, 1374-1375 (2004); Ishii, N., Hashimoto, T., Zillikens, D. & Ludwig, R. J. Clin Rev Allergy Immunol 38, 186-195 (2010); Nimmerjahn, F. & Ravetch, J. V. Annu Rev Immunol 26, 513-533 (2008)).

The mechanisms governing the dose-dependent pro- and anti-inflammatory actions of IgG have been extensively studied (Clynes, R. Curr Opin Immunol 19, 646-651 (2007); Schwab, I. & Nimmerjahn, F. Nat Rev Immunol 13, 176-189 (2013)). Removal of the Fc glycan from IgG has shed light on the mechanism driving the anti-inflammatory activity of IgG (Kaneko, Y., Nimmerjahn, F. & Ravetch, J. V. Science 313, 670-673 (2006)). De-glycosylated IVIG was unable to suppress inflammation in a model of rheumatoid arthritis. Further, IVIG treated with neuraminidase, to removed terminal sialic acid from the Fc glycan, also exhibited no anti-inflammatory activity. Thus, the IgG Fc glycan composition, and specifically terminal sialic acid, is responsible for the anti-inflammatory activity of IgG. Further, sialylated IgG Fc exhibited anti-inflammatory activity at a 30-fold lower dose than IVIG.

Therefore, the methods described in this disclosure can be used to treat various IgG-mediated disorder (e.g., inflammation, autoimmune diseases).

In another aspect, the methods described in this disclosure can be used to treat any diseases or disorders that can be treated by IVIG. These disease or disorders include, but not limited to, inflammation, autoimmune diseases, idiopathic thrombocytopenic purpura (ITP), multiple sclerosis, systemic lupus erythematosus, and Alzheimer's Disease.

In some embodiments, the methods include the steps of identifying a subject having an IgG-mediated disorder, and administering to the subject any polypeptides, multimers, or compositions as described in this disclosure to the subject.

Inflammation

Inflammation is part of the complex biological response of body tissues to harmful stimuli. The function of inflammation is to eliminate the initial cause of cell injury, clear out necrotic cells and tissues damaged from the original insult and the inflammatory process, and to initiate tissue repair. However, in some cases, inflammation can cause harm to the body. As discussed above, inflammation is often mediated by antibodies. Therefore, the methods described herein can be used to treat, inhibit, reduce, or control inflammation.

Autoimmune Diseases

An autoimmune disease is a condition arising from an abnormal immune response to a normal body part. As auto-immune diseases are often mediated by abnormal function of IgG, thus the methods described in this disclosure can be used to treat various autoimmune diseases. The autoimmune diseases can affect major organ (e.g., heart, kidney, liver, lung, skin, and reproductive organs), gland (e.g., adrenal gland, pancreas, thyroid gland, and salivary gland), digestive system, blood, connective tissue, muscle, nervous system, eye, ear, vascular system, etc. Some common auto-immune diseases include celiac disease, diabetes mellitus type 1, Graves disease, inflammatory bowel disease, multiple sclerosis, psoriasis, rheumatoid arthritis, and systemic lupus erythematosus.

A list of autoimmune diseases that can be treated by the methods described in this disclosure includes, but are not limited to, Addison's disease, agammaglobulinemia, alopecia areata, amyloidosis, ankylosing spondylitis, anti-gbm/anti-tbm nephritis, antiphospholipid syndrome, autoimmune hepatitis, autoimmune inner ear disease, axonal & neuronal neuropathy, Behcet's disease, bullous pemphigoid, Castleman disease, celiac disease, chagas disease, chronic inflammatory demyelinating polyneuropathy, chronic recurrent multifocal osteomyelitis, Churg-Strauss, cicatricial pemphigoid/benign mucosal pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, systemic lupus erythematosus, Dressler's syndrome, endometriosis, eosinophilic esophagitis (EoE), eosinophilic fasciitis, erythema nodosum, essential mixed cryoglobulinemia, evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves disease, Guillain-Barre syndrome, Hashimoto's thyroiditis, hemolytic anemia, Henoch-Schonlein purpura, herpes gestationis or pemphigoid gestationis, hypogammalglobulinemia, IgA nephropathy, IgG4-related sclerosing disease, inclusion body myositis, interstitial cystitis, juvenile arthritis, juvenile diabetes (Type 1 diabetes), juvenile myositis, kawasaki disease, lambert-eaton syndrome, leukocytoclastic vasculitis, lichen planus, lichen sclerosus, ligneous conjunctivitis, linear IgA disease, lupus, lyme disease chronic, Meniere's disease, microscopic polyangiitis, mixed connective tissue disease, Mooren's ulcer, Mucha-Habermann disease, multiple sclerosis, myasthenia gravis, myositis, narcolepsy, neuromyelitis optica, neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria, Parry Romberg syndrome, pars planitis (peripheral uveitis), Parsonnage-Turner syndrome, pemphigus, peripheral neuropathy, perivenous encephalomyelitis, pernicious anemia, POEMS syndrome (polyneuropathy, organomegaly, endocrinopathy, monoclonal gammopathy, skin changes), polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, Rheumatoid Arthritis, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis, Susac's syndrome, sympathetic ophthalmia, Takayasu's arteritis, temporal arteritis/giant cell arteritis, thrombocytopenic purpura (e.g., idiopathic thrombocytopenic purpura), Tolosa-Hunt syndrome, transverse myelitis, type 1 diabetes, ulcerative colitis, undifferentiated connective tissue disease, uveitis, vasculitis, vitiligo, Wegener's granulomatosis (now termed Granulomatosis with Polyangiitis).

In some cases, the autoimmune disease is an acquired autoimmune disorder. For example, infection with HIV can cause destruction of the immune system leading to damage to several organ systems and tissues. Thus, in one aspect, the methods described in this disclosure can be used to treat an acquired autoimmune disorder.

Solid Organ Transplantation

Transplant rejection occurs when transplanted tissue is rejected by the recipient's immune system, which destroys the transplanted tissue. The transplant rejection often involves antibody-mediated injury. The role of antibodies in transplantation is described, e.g., in Hourmant et al. "Frequency and clinical implications of development of donor-specific and non-donor-specific HLA antibodies after kidney transplantation." Journal of the American Society of Nephrology 16.9 (2005): 2804-2812, which is incorporated by reference in its entirety. Thus, in one aspect, the methods described in this disclosure can be used to treat or control transplant rejection (e.g., reduce or minimize antibody-mediated injury), or treat graft-versus-host disease. In some embodiments, the transplanted organ is heart, kidneys, liver, lungs, pancreas, intestine, skin, or thymus.

Vaccination Improvement

Vaccines can stimulate the immune system to generate antibodies that are specific for pathogen antigens. Studies have demonstrated that sialylated antibodies specific for vaccine antigens, through a feed-forward mechanism, result in generation of highly-specific and high affinity antibodies. This mechanism is described, e.g., in Wang, Taia T., et al. "Anti-HA glycoforms drive B cell affinity selection and determine influenza vaccine efficacy." Cell 162.1 (2015): 160-169. Thus, the methods described herein can also be used in conjunction with standard vaccinations to generate sialylated antibodies specific for vaccine antigens, ultimately yielding highly-specific and high affinity antibodies for pathogen antigens.

In some embodiments, the methods include administering a therapeutically effective amount of polypeptides, multimers (e.g., FcB4, FcST6, and/or FcChm), or compositions as described herein, to a subject, before, during, or after the subject is administered with vaccines. In some embodiments, a composition comprising a vaccine and the polypeptides, multimers (e.g., FcB4, FcST6, and/or FcChm), or compositions as described herein is administered to the subject.

Expression Systems

To use the fusion proteins or peptides as described herein, it may be desirable to express them from a nucleic acid that encodes them. This can be performed in a variety of ways. For example, the nucleic acid encoding the fusion proteins or peptides can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion proteins or peptides for production. The nucleic acid encoding the fusion proteins or peptides can also be cloned into an expression vector, for administration to a plant cell, animal cell, preferably a mammalian cell or a human cell, fungal cell, bacterial cell, or protozoan cell.

To obtain expression, a sequence encoding a fusion protein or peptide is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available. In some embodiments, the fusion proteins and peptides are expressed by transfection of HEK-293T cells, Expi293 cells, or CHO cells with vectors comprising the polynucleotides encoding fusion proteins and peptides as described in this disclosure.

The promoter used to direct expression of a nucleic acid depends on the particular application. For example, a strong constitutive promoter is typically used for expression and purification of fusion proteins. In contrast, when a vector encoding the fusion protein or peptide is to be administered in vivo, either a constitutive or an inducible promoter can be used, depending on the particular need. In some embodiments, the promoter for administration of the vector encoding the fusion protein or peptide can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein or peptide, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the fusion protein or peptide can include RNA Pol III promoters to drive expression of the guide RNAs, e.g., the H1, U6 or 7SK promoters. These human promoters allow for expression of fusion protein or peptide in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the fusion protein or peptide.

The present disclosure also includes the vectors and cells comprising the vectors, as well as kits comprising the proteins and nucleic acids described herein, e.g., for use in various methods as described herein.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of polypeptides, multimers (e.g., FcB4, FcST6, FcChm), or compositions (i.e., an effective dosage) depends on the polypeptides, multimers, or compositions that are selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the polypeptides, multimers, or compositions described herein can include a single treatment or a series of treatments.

Dosage, toxicity and therapeutic efficacy of the polypeptides, multimers, or compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Polypeptides, multimers, or compositions which exhibit high therapeutic indices are preferred. While polypeptides, multimers, or compositions that exhibit toxic side effects may be used, care should be taken to design a delivery system that targets polypeptides, multimers, or compositions to the site of affected tissue in order to minimize potential damage to uninfected cells and, thereby, reduce side effects.

The data obtained from cell culture assays and animal studies can be used in formulating a range of dosage for use in humans. The dosage of polypeptides, multimers, or compositions lies preferably within a range of circulating concentrations that include the ED50 with little or no toxicity. The dosage may vary within this range depending upon the dosage form employed and the route of administration utilized. For any polypeptides, multimers, or compositions used in the methods as described in this disclosure, the therapeutically effective dose can be estimated initially from cell culture assays. A dose may be formulated in animal models to achieve a circulating plasma concentration range that includes the IC50 (i.e., the concentration of the test polypeptide, multimer, or composition which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the use of pharmaceutical compositions comprising any polypeptides or multimers (e.g., FcB4, FcST6, and/or FcChm) as described in this disclosure as an active ingredient, as well as the compositions themselves. In some embodiments, the composition comprises FcB4, FcST6, and FcChm.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating polypeptides, multimers, or compositions as described in this disclosure in the required amount in an appropriate solvent with one or a combination of ingredients enumerated above, as required, followed by filtered sterilization. Generally, dispersions are prepared by incorporating the polypeptides, multimers, or compositions into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active agents can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or agents of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the composition can be delivered in the form of an aerosol spray from a pressured container or dispenser that contains a suitable propellant, e.g., a gas such as carbon dioxide, or a nebulizer. Such methods include those described in U.S. Pat. No. 6,468,798.

In some embodiments, the polypeptides or multimers are prepared with carriers that will protect the polypeptides or multimers against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1: In Vivo Sialylation of IgG Antibodies Attenuates Autoimmune Disease Experiments were performed to determine therapeutic effects of modulating IgG-mediated inflammation through glycoengineering of endogenous IgG in vivo.

Materials and Methods:

Construction and production of the glycosylation enzyme-Fc fusions. Human IgG Fc, preceded by IL2 secretion signal sequence, and soluble domains of ST6GAL1 (Beta-galactoside alpha-2,6 sialyltransferase 1) or B4GALT1 (Beta-1,4-galactosyltransferase 1) were joined by overlapping PCR, such that human IgG Fc is fused to 5' end of the enzymes. A list of the primers used in this study is provided in Table 2. Restriction sites for HindIII (AAGCTT), XhoI (CTCGAG) were indicated in the table. The Fc-enzyme fusion genes were then TOPO cloned into a mammalian expression vector, pcDNA3.4, according to the manufacturer's protocol (Life Technologies). Recombinant Fc-enzymes were generated by transient transfection of the plasmids to Expi293 cells using Expi293 Expression System Kit (Life Technologies) according to the manufacturer's protocol. B4ST6$^{Fc}$ enzyme was produced by co-transfecting pcDNA3.4/ST6$^{Fc}$ and pcDNA3.4/B4$^{Fc}$ at a 1:1 ratio. The enzymes were purified from the culture supernatant using Protein G agarose beads (Thermo Scientific) and dialyzed in PBS for in vivo injections.

In vivo Animal Studies. 7-8 weeks old C57BL/6 and NOD mice were purchased from the Jackson Laboratory and maintained in the animal facility at Massachusetts General Hospital (MGH) under specific pathogen free conditions according to the National Institutes of Health (NIH) guidelines. KRN TCR transgenic mice on a C57BL/6 background (KB) were gifts from D. Mathis and C. Benoist (Harvard Medical School, Boston, Mass.) and were bred to NOD mice to generate K/BxN mice (Korganow et al., 1999). K/BxN serum was prepared as described previously (Kaneko et al., 2006). Inflammatory arthritis was induced by intravenous injection of K/BxN sera (200 μL of pooled K/BxN serum per mouse). For therapeutic intervention experiments, IVIG (1 g/kg), B4$^{Fc}$ (1.25 mg/kg or 2.5 mg/kg), ST6$^{Fc}$ (1.25 mg/kg or 2.5 mg/kg), B4ST6$^{Fc}$ (2.5 mg/kg), or saline was injected day 0 or day 3 after K/BxN serum. Arthritis was scored by clinical examination, and the index of all four paws was added (0=unaffected, 1=swelling of one joint, 2=swelling of more than one joint, 3=severe swelling of the entire paw) as described (Kaneko et al., 2006). PBS, IVIG (1 g/kg) or B4ST6$^{Fc}$ (50 μg) was injected 1 hr. prior to K/BxN serum injection. For nephrotoxic nephritis experiments, mice were pre-immunized with 200 μg of sheep IgG (BioRad) in CFA via intraperitoneal route, followed by intravenous injection of sheep NTS (Probetex, Inc.) (2 μl of serum per gram of mouse) 4 days later. IVIG (1 g/kg), B4ST6$^{Fc}$ (50 μg) or its vehicle alone was injected 1 hour before sheep NTS injection. Urea nitrogen (BUN) in sera was measured by the enzyme coupled equilibrium method using a modified urease kit (Stanbio Laboratory). All animal experiments were conducted in compliance with the Institutional Animal Care and Use Committee of MGH.

Clopidogrel Treatment. Platelet inhibition was performed by daily injections of 10 mg/kg clopidogrel (Selleckchem) as previously described (Pucci et al., 2016). Treatment was initiated 2 days before K/BxN sera in the inflammatory arthritis model. In the nephrotoxic nephritis model, treatment was initiated 2 days after pre-immunization with sheep IgG. Treatment was continued for duration of 3 weeks.

In vitro glycosylation. Enzymatic activity of fusion enzymes was examined in vitro as previously described (Anthony et al., 2008). Briefly, glycan-acceptor protein (fetuin, human or mouse IgG Fc) was treated with Sialidase A (ProZyme) and β1,4-galactosidase-S(New England Biolabs, Inc.) overnight at 37° C. to remove sialic acid and galactose. To assess the galactosyltransferase activity of B4$^{Fc}$ or B4ST6$^{Fc}$, asialylated, agalactosylated glycan-acceptor protein was incubated with 5 mM UDP-galactose (Calbiochem) in 2× galactosylation buffer (50 mM MOPS, 20 mM MnCl$_2$, pH7.2) overnight at 37° C. To assess the sialyltransferase activity of ST6$^{Fc}$ or B4ST6$^{Fc}$, asialylated glycoprotein was incubated with 5 mM CMP-sialic acid (Nacalai tesque) in the sialylation buffer (150 mM NaCl, 20 mM HEPES, pH7.4) overnight at 37° C.

Western and Lectin Blots. Western and lectin blots were performed as described previously (Anthony et al., 2008). Briefly, equal amounts of protein were resolved on 4-12% Bis-Tris SDS-PAGE gel (Life Technologies) and then transferred to polyvinylidene difluoride membranes. After blocking the membranes with 5% dry milk in PBST (0.05% Tween 20) for western blot, proteins were detected using either anti-human IgG-HRP (20 ng/ml, Promega); anti-human B4GALT1 (100 ng/ml, Sigma-Aldrich) followed by anti-rabbit IgG-HRP (50 ng/ml, Promega); or anti-human ST6GAL1 sera (1:100, generous gift from Dr. J. Paulson) followed by anti-rabbit IgG-HRP. For lectin blots, the membranes were blocked in Protein Free Blocking Buffer (Thermo Fisher Scientific), and probed with either biotinylated Sambucus Nigra Lectin (SNA; 5 μg/ml, Vector Laboratories) or with biotinylated Erythrina Cristagalli Lectin (ECL; 5 μg/ml, Vector Laboratories) to detect terminal sialic acid or galactose, respectively.

HPLC Glycan Analysis. Total or Fc specific N-linked glycan was released from glycoproteins using PNGaseF or Endo S (New England Biolabs, Inc.), respectively, according to manufacturer's instruction. Deglycosylation reactions were carried out at 37° C. overnight to ensure effective release of glycans. Glycans were purified from the reaction using GlykoClean™ G Cartridges (Prozyme), dried, and fluorescently labeled with 2-AB (2-aminobenzamide) (Sigma-Aldrich). Labeled glycans were cleaned with GlykoClean™ S-plus Cartridges (Prozyme), dried, and subjected to HPLC analysis. Glycan samples were dissolved in 100 mM ammonium formate (pH4.5) and separated using Agilent 1260 Infinity Quaternary LC system, outfitted with AdvanceBio Glycan Mapping column 2.1×150 mm, 2.7 μm and a fluorescent detector. Resulting peaks were analyzed in OpenLAB software (Agilent) and assigned glycoforms by comparing peaks of commercially available human IgG N-linked glycan library.

Measurement of sheep IgG-specific circulating IgG levels. 96-well ELISA plates coated with 5 μg/mL of sheep IgG were incubated with 1:500 diluted sera after blocking with 5% bovine serum albumin. After washing with PBS containing 0.05% Tween 20, the plates were incubated with HRP conjugated anti-mouse IgG-Fc (Bethyl Laboratories). The amount of IgG bound was assessed by 3,3', 5,5$^{Fc}$-tetramethylbensidine (TMB; Biolegend) and the absorbance measured at 450 nm after 2M sulfuric acid addition.

Preparation of kidney and joint homogenate for IgG purification. Mice were bled on days 4, and 7 after anti- GBM antiserum injection. The serum was separated from the blood by serum gel tubes (BD) and incubated with Protein G high-capacity agarose beads (Thermo Fisher Scientific) for IgG purification. Paws cut above joints and kidneys were dissected, suspended in 1 mL PBS supplemented with protease inhibitor and 2 mM EDTA and cut into small pieces before being mechanically homogenized with stainless steel beads and TissueLyser II (Qiagen) for two minutes at 3 Hz/s. Homogenate was then diluted 5-fold the volume (PBS with Protein Inhibitor (Thermo) and 2 mM EDTA), filtered through 70 µm mesh, and centrifuged at 1000×g for 5 min. Supernatant was used to purify IgG with Protein G high-capacity agarose beads.

Histology. Ankle joints were dissected and incubated in the fixative and decalcifier solution Cal-Ex II for 48 hrs-72 hrs (Fisher Chemical), and embedded in paraffin. 4 µm sections were stained with hematoxylin/eosin for histological analysis. Kidneys were dissected, fixed in 10% buffered formalin and embedded in paraffin. 4 µm paraffin sections were stained with periodic acid-schiff (PAS), and hematoxylin/eosin for analysis by light microscope. 4 µm OCT (Tissue-Tek) frozen kidneys sections were fixed in acetone and stained, where indicated, with DAPI (Biolegend) or rabbit anti-mouse IgG-Fc specific-DyLight405 (Jackson ImmunoResearch) in combination with rat anti-mouse CD41-APC (Biolegend), rat anti-mouse CD62P-PE (Biolegend), and goat anti-mouse Nephrin (R&D Systems) followed by donkey anti-goat IgG-AF488 (Jackson ImmunoResearch) according to manufacturer's instructions. Slides were examined using a fluorescence microscope (Carl Zeiss).

Platelet preparation. Platelet isolation, activation and inhibition were adapted from past studies (Boilard et al., 2010, Lee et al., 2014). Healthy individuals gave informed consent and whole blood was collected in sodium citrate buffered blood collection tubes (BD) and centrifuged for 10 min at 200×g. The platelet rich plasma (PRP) in supernatant was collected and further centrifuged for 5 min at 900×g. After removing the platelet poor plasma in supernatant the pelleted platelets are resuspended in 140 mM NaCl, 3 mM KCl, 0.5 mM $MgCl_2$, 5 mM $NaHCO_3$, 10 mM D-glucose, 10 mM HEPES, pH 7.4. Platelet activation was achieved using 0.2 U of Thrombin (Roche) for 5 min at 37° C. Platelet activation was inhibited using 0.25 mg of Clopidogrel for 15 min at room temperature. Platelets were pelleted by centrifugation at 1000×g for 5 min, and platelet supernatant was quantified for UDP-Galactose and CMP-SA.

Quantification of galactose and sialic acid donor in human serum. Quantitation of the glycan donor was performed on human platelet supernatant using sialyltransferase and glycosyltransferase activity kit as indicated by the manufacturer (R & D systems), with one exception. Standard curves were generated using a range of UDP-Gal and CMP-SA in order to more accurately report the concentration.

Serum Half-life Experiments. 50 µg of IVIG or $B4ST6^{Fc}$ was intravenously administered to C57BL/6 female mice. The mice they were bled daily up to 4 days after the injection and every other day until day 10. IVIG or $B4ST6^{Fc}$ in mice sera was detected by ELISA. Briefly, 96-well plates were coated with 5 µg/ml of anti-human IgG Fc (Bethyl Laboratories), blocked with 2% BSA in PBS, and probed with anti-human IgG-HRP (20 ng/ml, Promega). 3,3,5,5-tetramethylbenzidine (TMB; Thermo Fisher Scientific) was used for the detection, and 2M sulfuric acid was used to stop the reaction.

Blood testing. 50 µg of $B4ST6^{Fc}$ was intravenously injected to mice. After 1 week or 2 months of the administration of the enzyme the mice were bled, and whole blood and sera were sent to MGH Histopathology Research Core for complete blood count and comprehensive metabolic panel tests.

Quantification and Statistical Analysis. Data were analyzed in GraphPad Prism: *$p<0.05$, $p<0.01$, *$p<0.005$, ****$p<0.001$ as determined by two-way ANOVA followed by Tukey's posthoc.

TABLE 1

Materials and Resources

| REAGENT or RESOURCE | SOURCE | IDENTIFIER |
|---|---|---|
| Antibodies | | |
| Anti-human IgG-HRP | Promega | Cat#: W4031 |
| Anti-human B4GALT1 | Sigma-Aldrich | Cat#: HPA010807 |
| Anti-rabbit IgG-HRP | Promega | Cat#: W4011 |
| Anti-mouse IgG-Fc-HRP | Bethyl Laboratories | Cat#: A90-131A |
| Anti-human ST6GAL1 | Dr. J. Paulson | n/a |
| Anti-human IgG-Fc | Bethyl Laboratories | Cat#: A80-104A |
| Sheep IgG | BioRad | Cat#: PSPOl |
| PE anti-mouse/rat CD62P | Biolegend | Cat#: 148305 |
| APC anti-mouse CD41 Antibody | Biolegend | Cat#: 133913 |
| Mouse nephrin antibody | R & D systems | Cat#: AF3159 |
| DyLight ™ 405 AffiniPure Rabbit Anti-Mouse IgG, Fcγ fragment specific | Jackson ImmunoResearch | Cat#: 315-475-008 |
| Alexa Fluor ® 488 AffiniPure Donkey Anti-Goat IgG (H + L) | Jackson ImmunoResearch | Cat#: 705-545-003 |
| Chemicals, Peptides, and Recombinant Proteins | | |
| pcDNA ™3.4 TOPO ™ TA Cloning Kit | Thermo Fisher | Cat#: A14697 |
| Expi293 ™ Expression System Kit | Thermo Fisher | Cat#: A14635 |
| Pierce ™ Protein G Plus Agarose | Thermo Fisher | Cat#: 22852B |
| Sialidase A | ProZyme | Cat#: GK80040 |
| β1-4 Galactosidase S | New England Biolab | Cat#: P0745L |
| UDP-α-D-Galactose, Disodium Salt | Millipre Sigma | Cat#: 670111<br>CAS#: 137868-52-1 |
| CMP-Sialic acid (Cytidine-5'-monophospho-N-acetylneuraminic Acid Disodium Salt) | Nacalai USA, Inc. | Cat#: 10432-24 |

TABLE 1-continued

Materials and Resources

| REAGENT or RESOURCE | SOURCE | IDENTIFIER |
|---|---|---|
| Pierce ™ Protein-Free (TBS) Blocking Buffer | Thermo Fisher | Cat#: 37570 |
| Biotinylated Sambucus Nigra Lectin (SNA) | Vector Laboratories | Cat#: B-1305 |
| Biotinylated Erythrina Cristagalli Lectin (ECL) | Vector Laboratories | Cat#: B-1145 |
| PNGase F | New England Biolab | Cat#: P0704L |
| Endo S | New England Biolab | Cat#: P0741L |
| GlykoClean ™ G Cartridges | ProZyme | Cat#: GC250 |
| GlykoClean ™ S-plus Cartridges | ProZyme | Cat#: GC210 |
| Anthranilamide (2-AB) | Sigma-Aldrich | Cat#: A89804 |
| NTS (Sheep Anti-Rat Glomeruli (Anti-GBM) Serum) | Probetex | Cat#: PTX001-S |
| TMB Substrate | Biolegend | Cat#: 421101 |
| Protease Inhibitor Mini Tablets | Thermo Fisher | Cat#: 88665 |
| Cal-Ex ™ II Fixative/Decalcifier | Fisher Chemical | Cat#: CS511-1D |
| QuikChange II XL Site-Directed Mutagenesis Kit | Agilent | Cat#: 200521 |
| Clopidogrel | Selleck Chemicals | Cat#: S1415 |
| DAPI (4',6-Diamidino-2-Phenylindole, Dilactate) | Biolegend | Cat#: 422801 |
| Critical Commercial Assays | | |
| Urea Nitrogen (BUN) Liqui-UV Test | Stanbio Laboratory | Cat#: 2020-430 |
| Sialyltransferase Activity Kit | R & D systems | Cat#: EA002 |
| Glycosyltransferase Activity Kit | R & D systems | Cat#: EA001 |
| Experimental Models: Cell Lines | | |
| Expi293F ™ Cells | Thermo Fisher | RRID:CVCL_D615 Cat#: A14527 |
| Experimental Models: Organisms/Strains | | |
| Mouse: C57BL/6J | The Jackson Laboratory | RRID: IMSR_JAX:000664 |
| Agilent AdvanceBio Glycan Mapping column (120 Å, 2.1 × 150 mm, 2.7 μm) | Agilent | Cat#: 683775-913 |

TABLE 2

Oligonucleotides

Primers: target gene/primer name/sequence (5'→3')

Human ST6GAL1/hST6:EFQ_Fwd
AAA(AAGCTT)ATGGAATTCCAGGTGTTAAAGAGTCTGGGG

Human ST6GAL1/hST6GAL1(K24)
GGCGCGCCAATGAAGGAAAAGAAGAAAGGGAGTTACTATGATTCC

Human ST6GAL1/hST6GAL1(K27)
AAGCTTATGAAGAAAGGGAGTTACTATGATTCCTTTAAATTGC

Human ST6GAL1/hST6GAL1(Y32)
AAGCTTATGTATGATTCCTTTAAATTGCAAACCAAGGAATTCC

Human ST6GAL1/hST6_Rev
AAA(CTCGAG)TTAGCAGTGAATGGTCCGGAAGCC

Human B4GALT1/hB4:ECD_Fwd
AAA(AAGCTT)ATGGGCCGCGACCTGAGCCGCC

Human B4GALT1/hB4_Rev
AAA(CTCGAG)CTAGCTCGGTGTCCCGATGTCC

Human ST6GAL1/hST6_SDM_C353A_F
CAAGCGCAAGACTGACGTGGCCTACTACTACCAGAAGTTC

Human ST6GAL1/hST6_SDM_C353A_R
GAACTTCTGGTAGTAGTAGGCCACGTCAGTCTTGCGCTTG

Human ST6GAL1/hST6_SDM_C364A_F
GTTCTTCGATAGTGCCGCCACGATGGGTGCCTAC

TABLE 2-continued

Oligonucleotides

Human ST6GAL1/hST6_SDM_C364A_R
GTAGGCACCCATCGTGGCGGCACTATCGAAGAAC

IL2 signal sequence/Kozac_Il2ss_Fwd
AAACTCGAGGCCACCATGTACAGGATGCAACTCCTGTC

Restriction sites for HindIII (AAGCTT) and XhoI (CTCGAG) are indicated by brackets.

Example 2: Engineering Soluble Glycosyltransferases

ST6GAL1 catalyzes attachment of α2,6 sialic acid to galactose on N-linked glycans (Meng et al., 2013). Sialylation by ST6GAL1 typically occurs in the trans-Golgi where the glycosyltransferase is anchored by a transmembrane domain (TMD, FIG. 1C). A β-Secretase (BACE1) cleavage site is present in the luminal domain of ST6GAL1 at EFQ41-43, which results in ST6GAL1 secretion (FIGS. 1C and 8) (Woodard-Grice et al., 2008). Remarkably, recent studies have suggested a soluble ST6GAL1 contributes to sialylation of IgG Fc glycans (Jones et al., 2012, Sugimoto et al., 2007, Jones et al., 2016). The extraordinary effects of sialylation on IgG biology prompted us to explore the therapeutic potential of glycoengineering IgG in vivo.

Figures 8A, 8B, 8C:
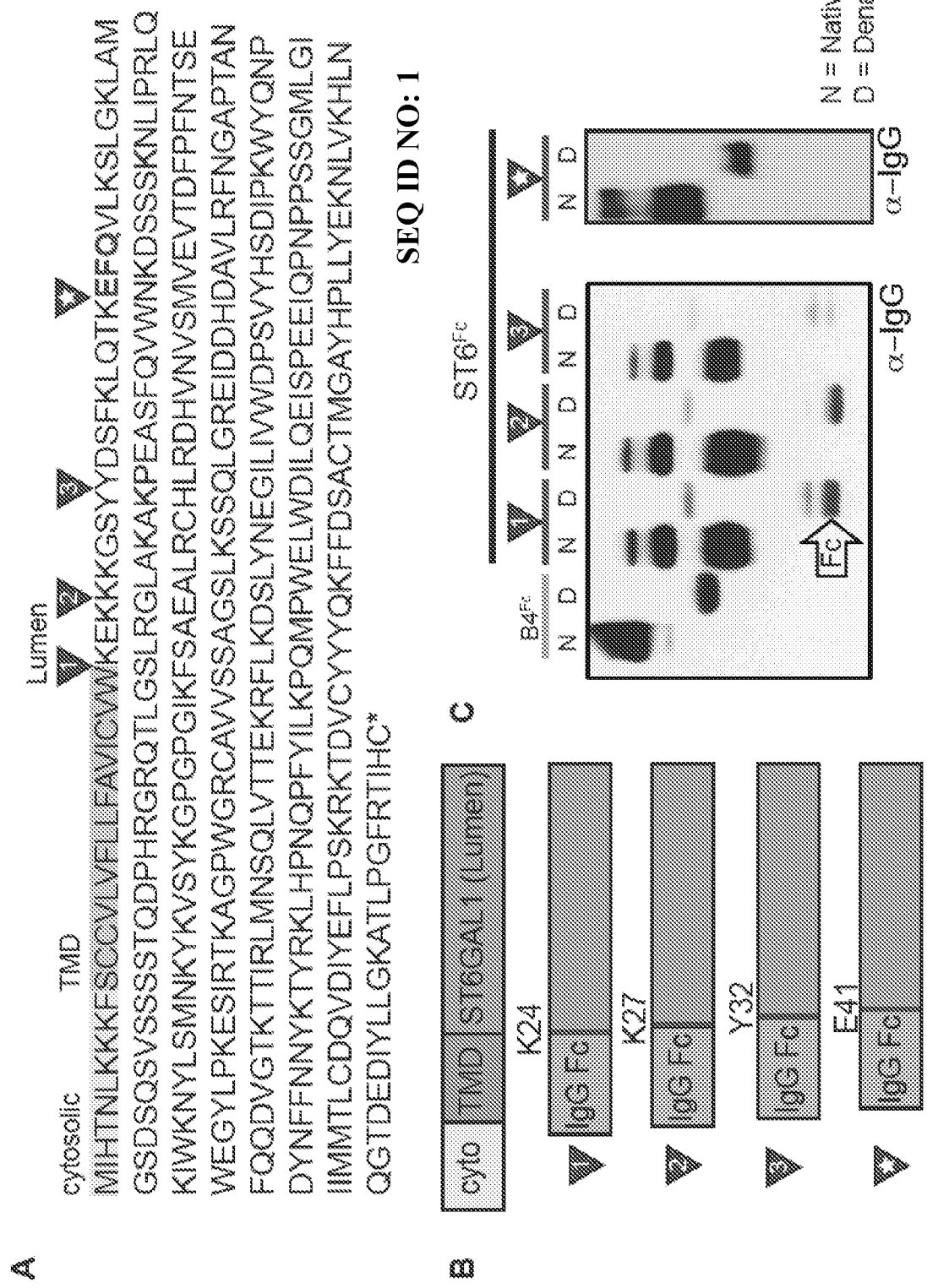
FIGS. 8A-8D. Engineering and characterization of soluble galactosyl- and sialyltransferase proteins. (A) Protein sequence of human ST6GAL1. Yellow and light blue shaded sequences represent cytosolic and transmembrane domain (TMD), respectively. Numbered red triangles indicate the start site of the sialyltransferase which was fused to IgG Fc. The triangle with a star indicates the start site of the soluble ST6GAL1 that was used in all experiments in this manuscript. (B) Schematic representations of each ST6GAL1 are shown. (C) Immunoblots of Fc-enzyme proteins for reactivity to IgG (N, native protein; D, denatured protein). ST6Fcs were cleaved to Fc and ST6GAL1 upon denaturation when fused upstream of EFQ41-43. (D) Immunoblots of ST6$^{Fc}$, B4$^{Fc}$, and B4ST6$^{Fc}$ for reactivity to B4GALT1, ST6GAL1, or IgG.
Figure 8D:
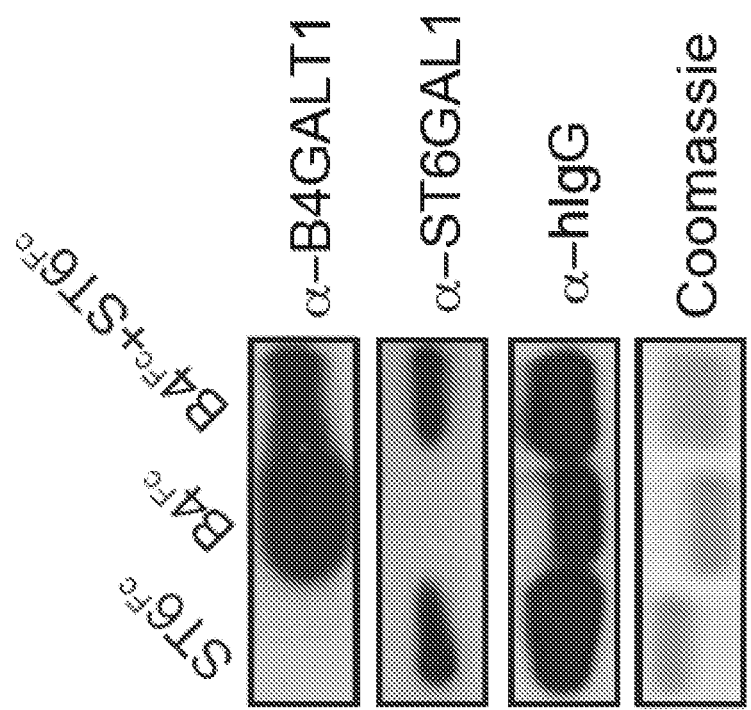

To this end, glycosylation enzymes were fused to human IgG1 Fc, a common approach to generate soluble forms of membrane proteins. Expression constructs with fusions of Fc and ST6GAL1 that included the region upstream of EFQ41-43 in the amino acid sequence resulted in multiple protein products, consistent with BACE1 activity (FIG. 8). However, when the Fc was linked directly to E41, omitting the first 40 amino acids of ST6GAL1, a single product was generated (ST6$^{Fc}$, FIGS. 1C and 8B). Because sialylation efficiency improves with increased galactose content (Anthony et al., 2008a), a similar approach was used for the B4GALT1 enzyme responsible for attachment of galactose to the IgG Fc glycan. The engineered fusions of B4GALT1 luminal domains with human IgG1 Fc resulted in a single protein product (B4$^{Fc}$, FIGS. 1C and 8B). The engineered glycosyltransferases were determined to be of the correct molecular weight, and were recognized by antibodies specific for B4GALT1, ST6GAL1, and human IgG by immunoblotting (FIG. 8D).

Figures 1D, 1E:
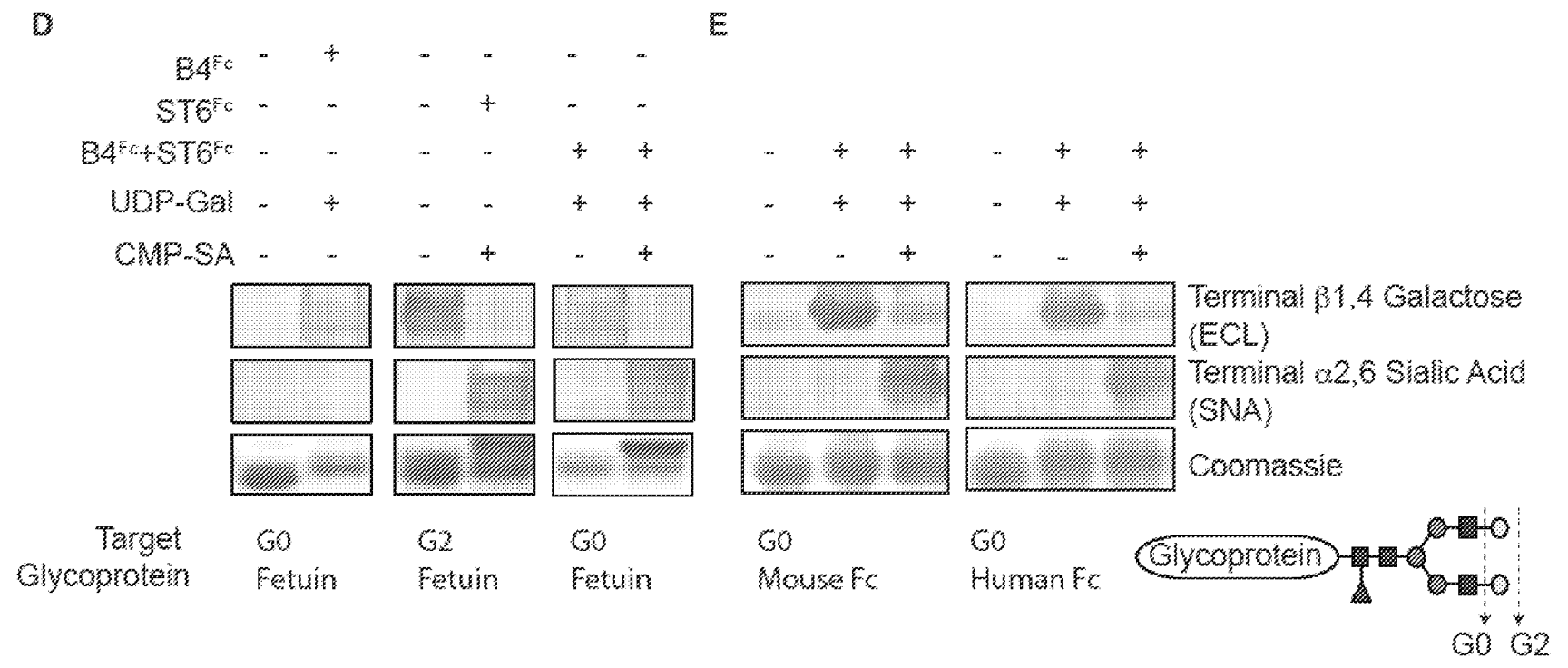

The activity of engineered enzymes in vitro using fetuin, a highly glycosylated protein, as a target for glycoengineering was examined. Fetuin was first treated with glycosidases that remove sialic acid and galactose residues, generating asialylated, galactosylated (G2) and agalactosylated (G0) fetuin (FIG. 1D). The G0 and G2 fetuin was incubated with B4$^{Fc}$, ST6$^{Fc}$, or with both enzymes (B4ST6$^{Fc}$) and sugar-nucleotide donors (UDP-Galactose (UDP-Gal) and CMP-Sialic Acid (CMP-SA) for galactose and sialic acid, respectively). Linkage-specific glycosylation was examined by lectin blotting, and revealed that B4$^{Fc}$ efficiently attached terminal galactose in β1,4 linkages, and ST6$^{Fc}$ attached α2,6 terminal sialic acid (FIG. 1D). B4ST6$^{Fc}$ attached β1,4 galactose when incubated with a galactose donor (UDP-Gal, FIG. 1D). As mentioned above, studies demonstrated galactosylation increases efficiency of sialylation, presumably by increasing the number of potential sialylation sites (Anthony et al., 2008a), and B4ST6$^{Fc}$ efficiently sialylated fetuin when incubated with both galactose and sialic acid donors (FIG. 1D). Further, B4ST6$^{Fc}$ transferred galactose and sialic acid to both mouse and human IgG (FIG. 1E).

Example 3: Anti-Inflammatory Activity of In Vivo Sialylation

Figures 2C, 2D, 2E:
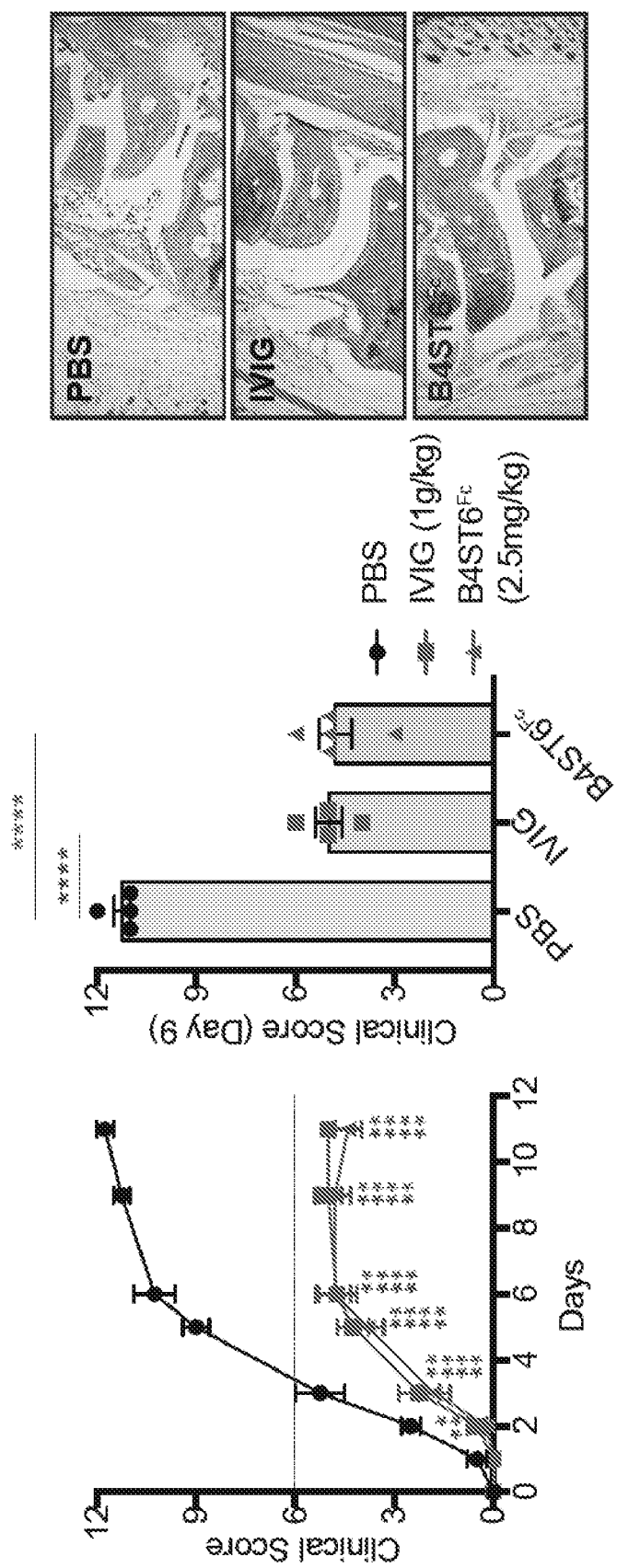

The ability of these engineered glycosylation enzymes to attenuate inflammation in vivo was tested. Mice were given arthritogenic K/BxN sera, which initiates joint inflammation mediated primarily by IgG1-autoantibodies that presents with edema and inflammatory cell infiltration within days after treatment (Korganow et al., 1999). Animals also received PBS, high dose IVIG (1 g/kg), B4$^{Fc}$ (2.5 mg/kg), ST6$^{Fc}$ (2.5 mg/kg), or both B4$^{Fc}$ and ST6$^{Fc}$ (B4ST6', 2.5 mg/kg, FIGS. 2A-2D). The arthritogenic sera induced robust inflammation in PBS-treated animals as measured by clinical score, while inflammation was attenuated by IVIG (FIGS. 2A-2B). Neither B4$^{Fc}$ nor ST6$^{Fc}$ individually was able to reduce induced inflammation. However, when the engineered enzymes were co-administered (B4ST6', 2.5 mg/kg), inflammation was significantly attenuated to a similar level achieved by IVIG (FIGS. 2C-2D). The inflammatory infiltrate to the joint, and tissue destruction 7 days after treatment was markedly reduced in IVIG and B4ST6$^{Fc}$-treated animals compared to PBS-treated controls (FIG. 2E). Together, these results demonstrate that administration of enzymes that attach both galactose and sialic acid are effective at attenuating passive autoimmune arthritic inflammation in vivo.

Figure 2H:
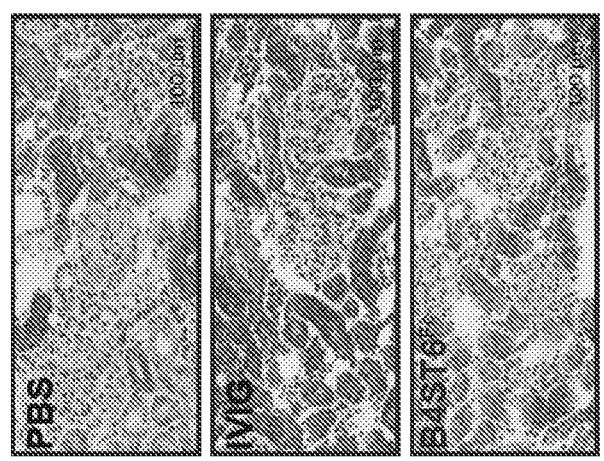
Figure 2G:
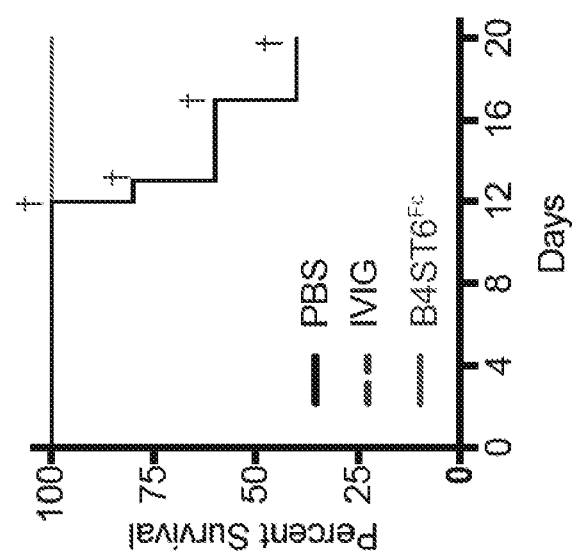
Figure 2F:
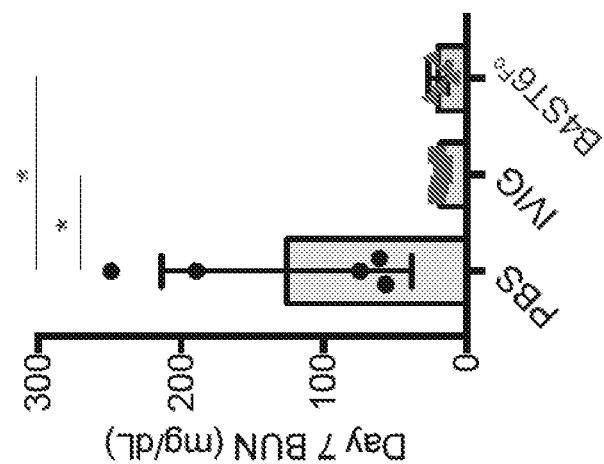
Figure 9B:
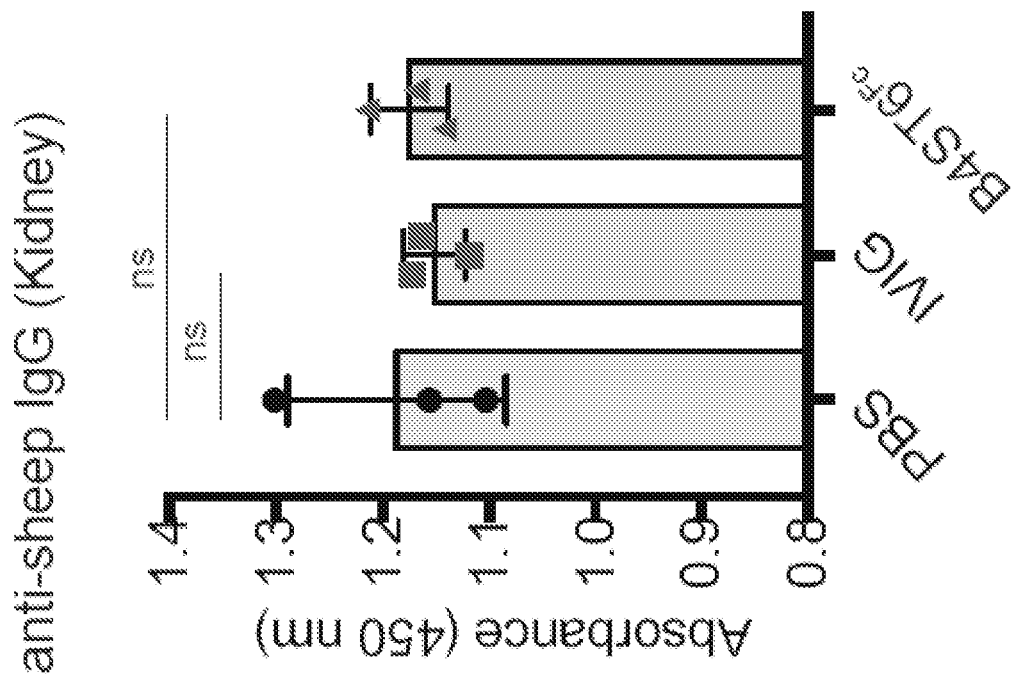
FIGS. 9A-9B. Anti-sheep response after NTN-induction. (A, B) NTN-induced mice were treated with PBS (black circles), high dose IVIG (blue squares), or B4ST6$^{Fc}$ (2.5 mg/kg) (red triangles). Day 7 anti-sheep IgG titers were determined by ELISA.
Figure 9A:
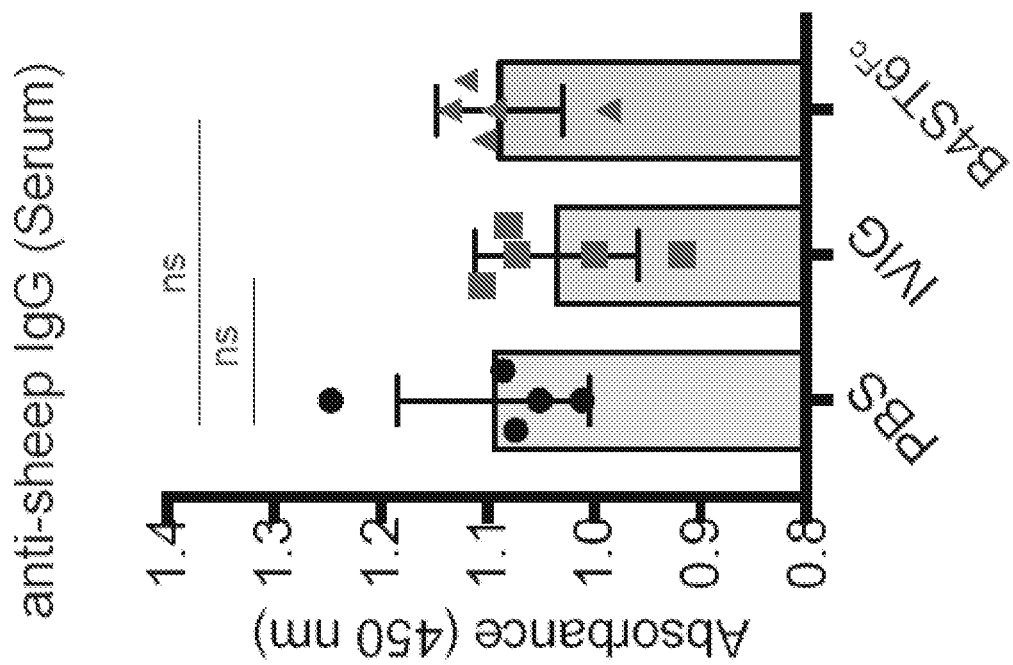

To extend these findings to an active model of autoimmune disease, a model of Goodpasture's disease that results in nephrotoxic nephritis (NTN), driven predominantly by IgG2b-based immune complexes deposited in the kidneys resulting in kidney damage (Lerner et al., 1967, Schrijver et al., 1990, Kaneko et al., 2006a) was used. Administration of B4ST6$^{Fc}$ suppressed kidney pathology as effectively as IVIG, as measured by blood urea nitrogen (BUN) levels at day 7 (FIG. 2F), and extended survival (FIG. 2G). Indeed, inflammatory cell infiltration into the kidneys at day 7 was reduced by B4ST6$^{Fc}$ and IVIG, compared to PBS controls (FIG. 2H). Neither IVIG nor B4ST6$^{Fc}$ affected the induced pathogenic antibody response, as measured by serum or kidney IgG titers (FIGS. 9A-9B). Together, these results demonstrate that in vivo sialylation by B4ST6$^{Fc}$ effectively ameliorates autoantibody-mediated kidney destruction at a dose that is 400-fold lower than immunomodulatory high dose IVIG.

Example 4: Requirements for In Vivo Sialylation

Figure 3D:
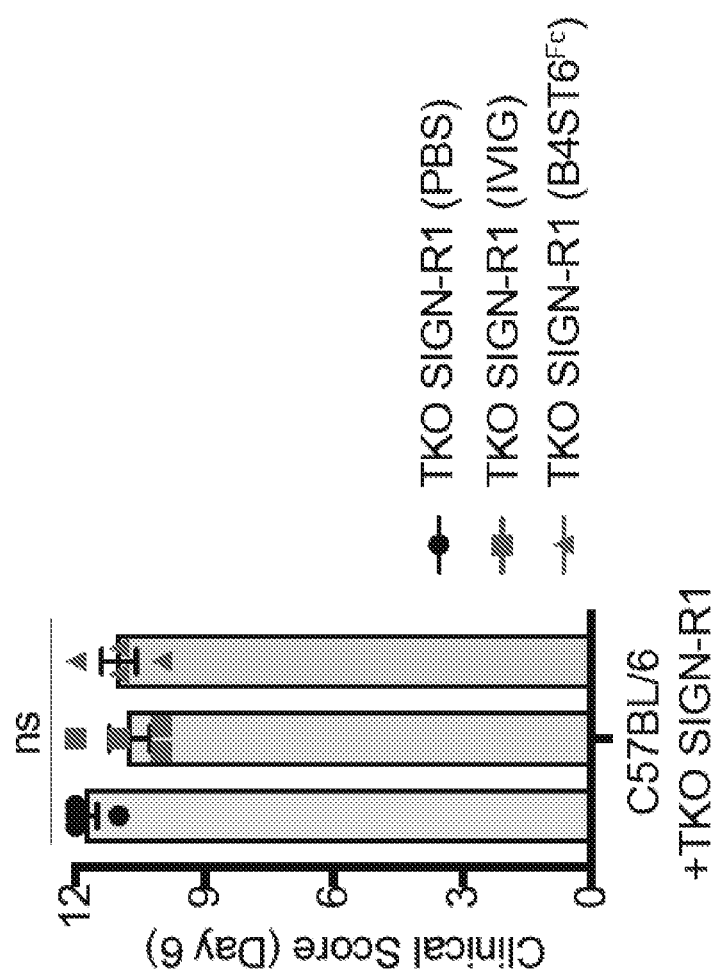
Figure 3C:
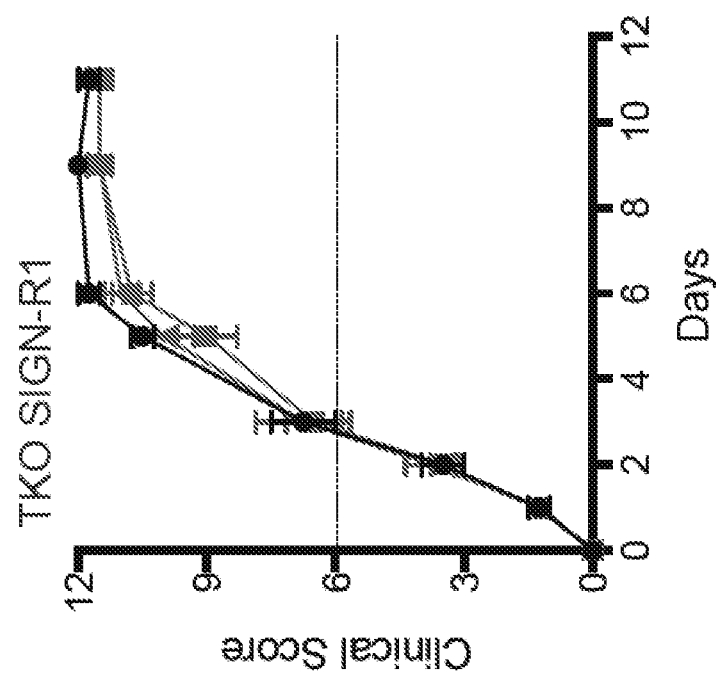
Figure 10B:
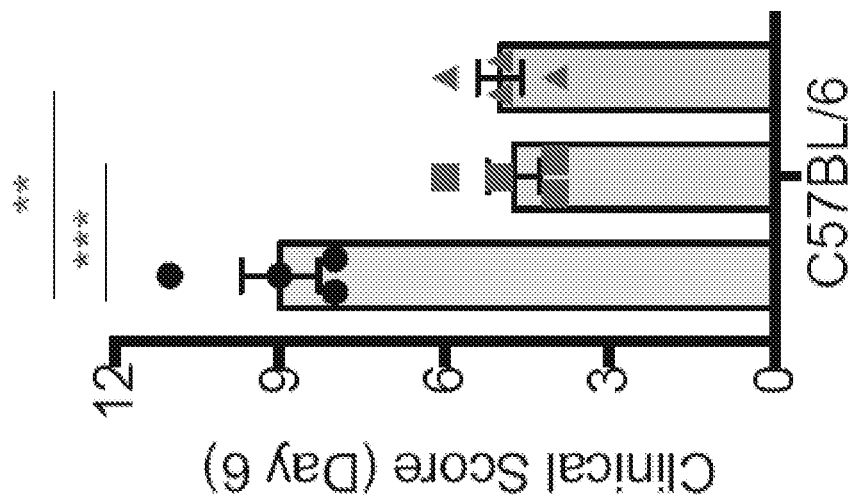
FIGS. 10A-10B. Receptor requirements of in vivo sialylation control groups. (A, B) Day 6 clinical scores of untreated C57BL/6 mice after K/BxN injection for FIGS. 2B and 2D, respectively. These are from control groups for FcγRIIB$^{-/-}$ (A) and TKO-SIGN-R1 (B) treatments shown in FIGS. 3A-3D. Results are representative of at least two independent repeats. *p<0.05, p<0.01, *p<0.005, ****p<0.001, ns (not significant), determined by two-way ANOVA followed by Tukey's posthoc.
Figure 10A:
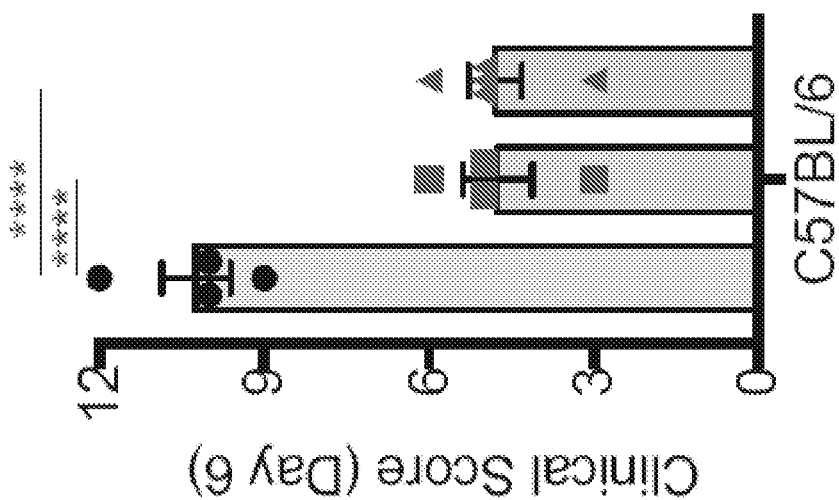

The requirements of the inhibitory FcγRIIB for the anti-inflammatory activity of IVIG and sialylated IgG Fc have been supported by functional studies using murine models (Samuelsson et al., 2001, Bruhns et al., 2003, Anthony et al., 2011, Schwab et al., 2014), and increased surface expression of FcγRIIB on leukocytes as been observed following administration of high dose IVIG to chronic inflammatory demyelinating polyneuropathy patients (Tackenberg et al., 2009). Further, sialylated IgG Fc were shown to require murine SIGN-R1 or human DC-SIGN to suppress inflammation (Anthony et al., 2011, Anthony et al., 2008b, Schwab et al., 2012). Thus, sialylation of IgG converts receptor preference to type II FcγRs, and ligation of these receptors by sialylated IgG culminates in the upregulation of the inhibitory FcγRIIB on inflammatory cells (Pincetic et al., 2014). Experiments were also performed to determine whether in vivo sialylation suppressed inflammation through a pathway similar to IVIG. K/BxN sera along with PBS, IVIG, or B4ST6$^{Fc}$ was administered to wild type or FcγRIIB$^{-/-}$ mice, and paw inflammation over the next several days was tracked. Neither IVIG nor B4ST6$^{Fc}$ suppressed inflammation relative to PBS (FIGS. 3A, 3B and 10A) in FcγRIIB$^{-/-}$ mice demonstrating a requirement for this receptor for their anti-inflammatory activity. Next, an antibody was administered to mice that results in transient knockdown of SIGN-R1 (TKO SIGN-R1 (Kang et al., 2004)), which has been shown to attenuate IVIG and sialylated IgG anti-inflammatory activity in vivo (Anthony et al., 2008b). This resulted in no observed differences in mice treated with K/BxN and PBS, IVIG, or B4ST6$^{Fc}$, indicating SIGN-R1 perturbation inhibited the anti-inflammatory activity of both IVIG and in vivo sialylation (FIGS. 3C, 3D, and 10B).

Figures 3E, 3F, 3G:
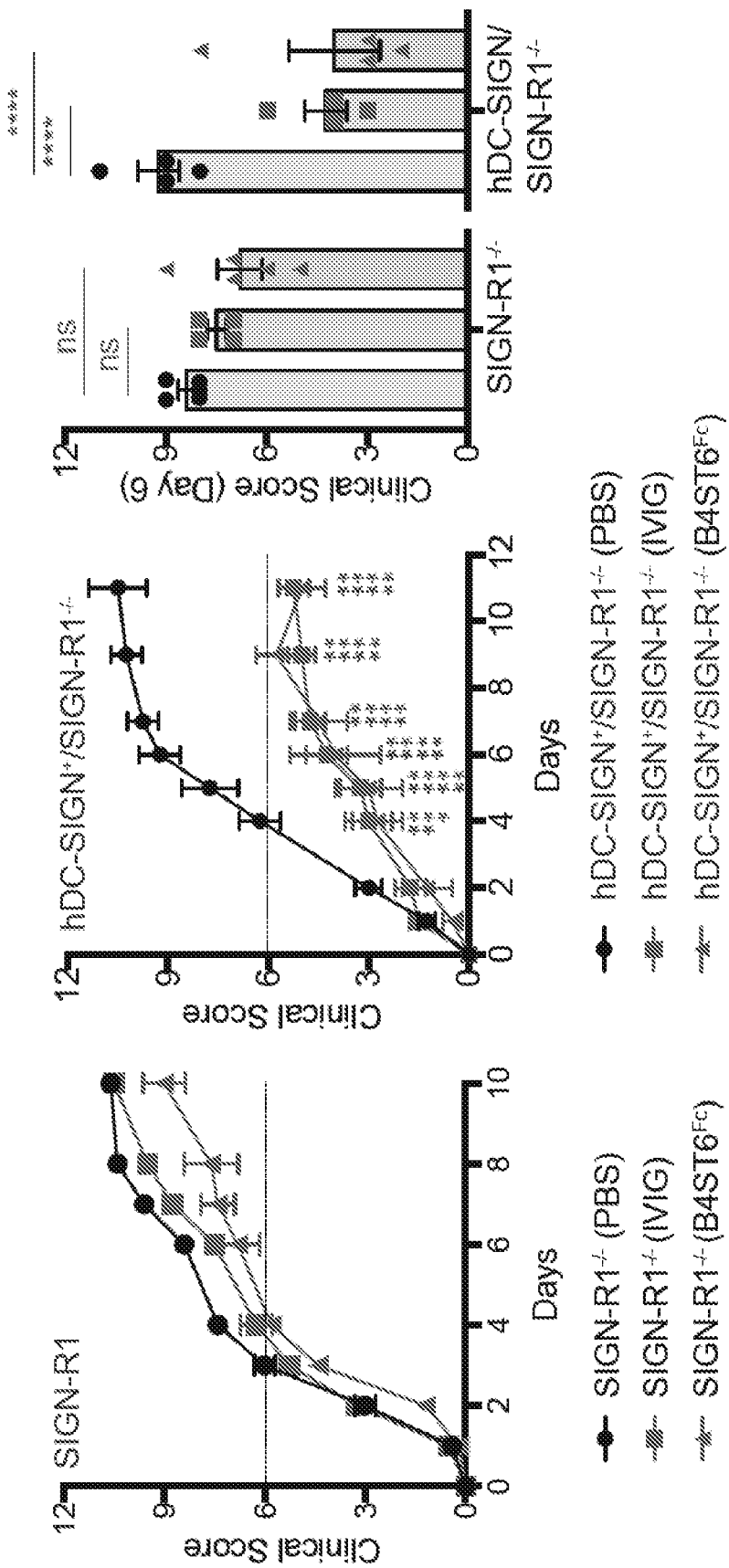

Next, K/BxN sera was administered to SIGN-R1$^{-/-}$ and human DC-SIGN transgenic mice that were crossed to a SIGN-R1$^{-/-}$ background (hDC-SIGN$^+$/SIGN-R1$^{-/-}$, FIGS. 3E, 3F, 3G). The mice also received PBS, IVIG, or B4ST6$^{Fc}$, and inflammation was monitored over the next several days. Transfer of K/BxN sera along with PBS treatment resulted in robust inflammation in both genotypes (FIG. 3E, 3F). SIGN-R1$^{-/-}$ animals were not protected from induced arthritis by IVIG or B4ST6$^{Fc}$ (FIG. 3E). However, both IVIG and B4ST6$^{Fc}$ attenuated induced-inflammation in hDC-SIGN$^+$/SIGN-R1$^{-/-}$ mice (FIG. 3F). Together, these results suggest that IVIG and in vivo sialylation by engineered galactosyl- and sialyltransferases suppress inflammation through similar pathways.

Figure 4A:
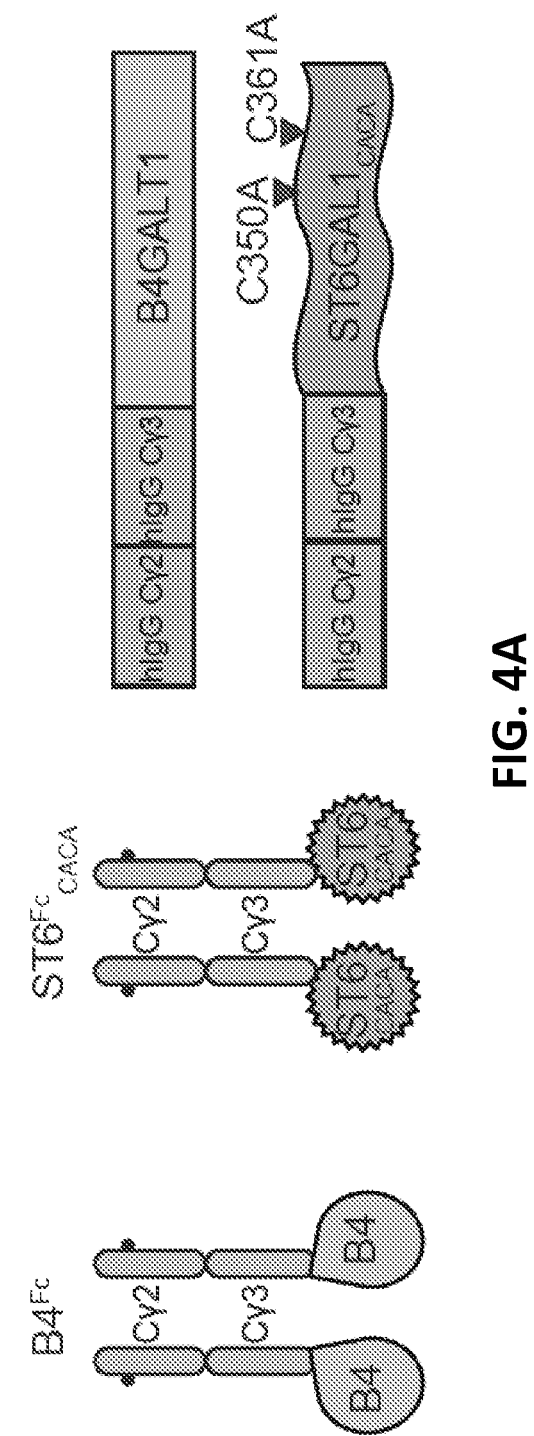
FIGS. 4A-4E. Enzymatic requirements for in vivo sialylation. (A) Schematics of B4GALT1 and enzymatically dead ST6GAL1 (C350A, C361A) and the resulting $B4ST6^{Fc}_{CACA}$. (B) Schematic of removal of the Fc glycan on $B4^{Fc}$ and $ST6^{Fc}$ following EndoS-treatment resulting in $B4ST6^{Fc}$-Endo. (C) Linkage-specific lectin blots assaying for terminal β1,4 galactose (ECL) or α2,6 sialic acid (SNA) on human IgG Fcs following incubation with $B4ST6^{Fc}$, $B4ST6^{Fc}_{CACA}$, or $B4ST6^{Fc}$-Endo. Galactosylation was assayed by incubation with UDP-Gal on (G0) IgG Fc. Sialyltransferase activity was evaluated by incubation with CMP-SA on (G2) IgG Fc. (D) WT mice were administered K/B×N sera and PBS (black circles), IVIG (blue squares), or $B4ST6^{Fc}$ (red triangles), $B4ST6^{Fc}_{CACA}$ (black crosses, red dotted line), or $B4ST6^{Fc}$-Endo (red triangle with black edge, red dotted line) and paw swelling monitored over several days. (E) Day 6 clinical scores of mice from (D) are shown. Means and standard deviation are plotted. Results are representative of at least two independent repeats. *p<0.05, p<0.005, **p<0.001, ns (not significant), determined by two-way ANOVA followed by Tukey's posthoc test.
Figures 4B, 4C:
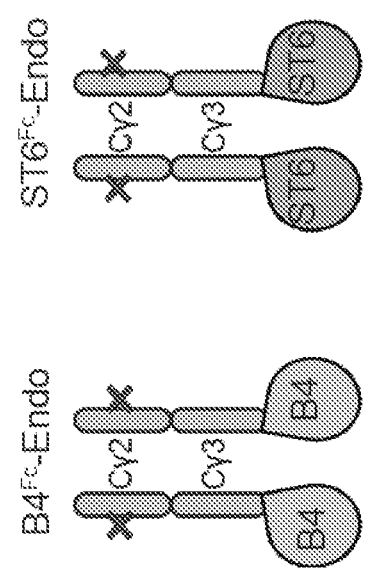
Figure 4E:
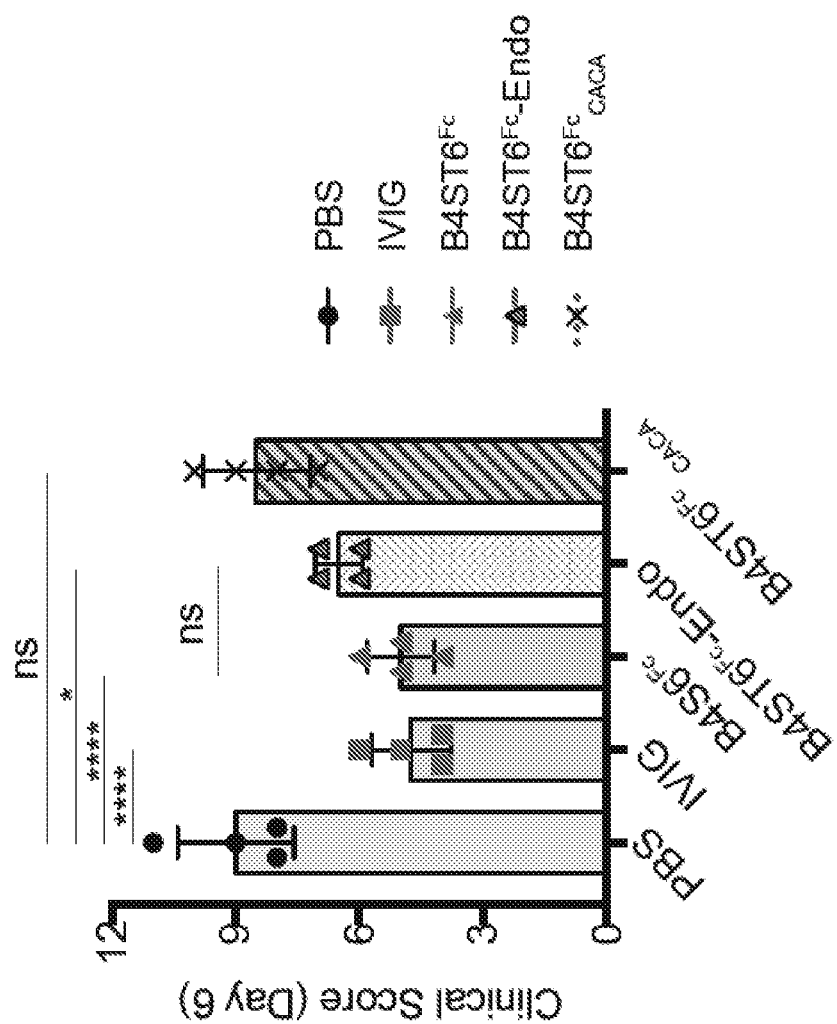
Figure 4D:
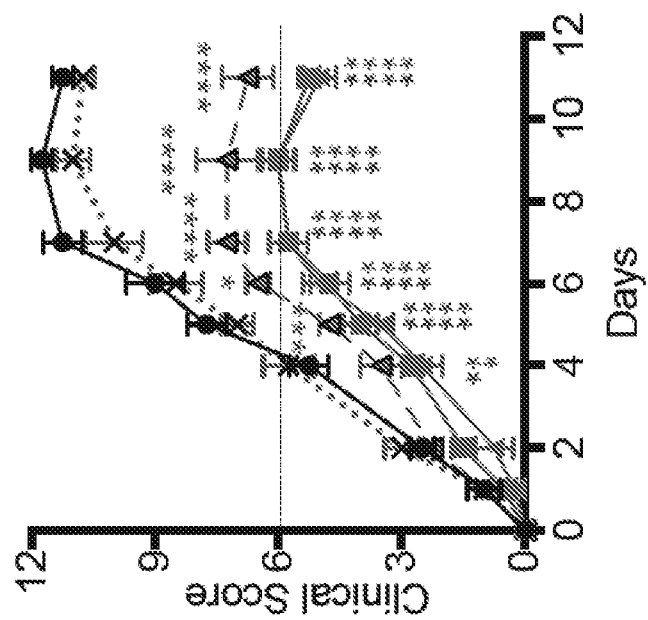

The shared receptors and pathways between IVIG and in vivo sialylation raised the possibility that the Fc glycan on the engineered enzymes, and not enzymatic activity, were responsible for the in vivo anti-inflammatory activity. Therefore, an enzymatically inactive ST6$^{Fc}$ by mutating two enzymatic-domain cysteine residues to alanine was generated (C350A, C361A, ST6$^{Fc}_{CACA}$, FIG. 4A (Meng et al., 2013)). In parallel, B4$^{Fc}$ and ST6$^{Fc}$ were treated with the IgG Fc-specific endoglycosidase, EndoS to remove the Fc glycan (B4ST6$^{Fc}$-Endo, FIG. 4B) (Collin and Olsen, 2001). Enzymatic removal of the Fc glycan has been shown to ablate interactions of IgG and FcγRs (Allhorn et al., 2010, Benkhoucha et al., 2012, Yang et al., 2010). Importantly, B4ST6$^{Fc}_{CACA}$ was unable to transfer sialic acid to human IgG Fc in vitro, although galactosyltransferase activity remained intact (FIG. 4C). However, B4ST6$^{Fc}$-Endo retained galactosyl- and sialyltransferase activity (FIG. 4C). These enzymes were tested for anti-inflammatory activity in vivo. K/BxN sera was administered to mice, which also received PBS, IVIG, B4ST6$^{Fc}$, B4ST6$^{Fc}_{CACA}$, or B4ST6$^{Fc}$-Endo. K/BxN transfer induced robust inflammation, which was attenuated by IVIG, B4ST6$^{Fc}$, and B4ST6$^{Fc}$-Endo (FIGS. 4D, 4E). However, B4ST6$^{Fc}_{CACA}$ was unable to suppress induced inflammation (FIGS. 4D, 4E). These results demonstrate that transferase activity, and not Fc glycans on engineered enzymes are required for suppression of inflammation in vivo.

Example 5: Site-Specific Sialylation In Vivo

Figure 11A:
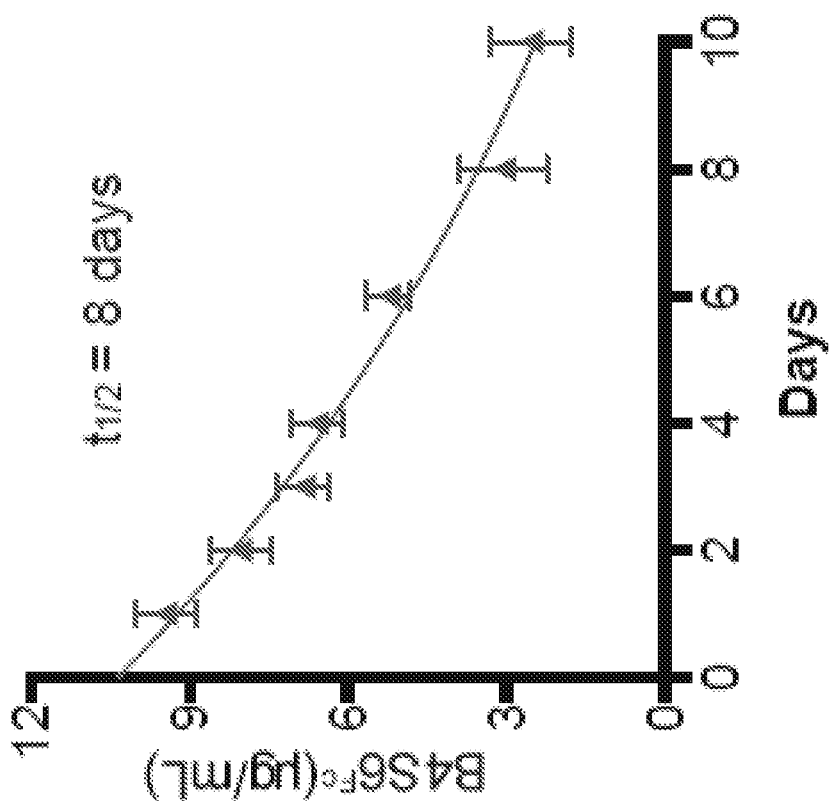
FIGS. 11A-11D. In vivo sialylation during homeostasis. Serum concentrations of IVIG (A) and B4ST6$^{Fc}$ (B) at defined intervals after administration are plotted with half-lives inset. (C) Blood test values following administration of PBS (black circles), B4ST6$^{Fc}$ one week earlier (red triangles), or B4ST6$^{Fc}$ two months earlier (open red triangles). WBC, white blood cell; LYM, lymphocytes; MONO, monocytes; GRAN, granulocytes; HCT, hematocrit; MCV, mean corpuscular volume; RDW, red blood cell distribution width; HGB, hemoglobin; MCHC, mean corpuscular hemoglobin concentration; MCH, mean corpuscular hemoglobin; RBC, red blood cell (erythrocyte) count; PLT, platelet; MPV, mean platelet volume; BUN, blood urea nitrogen; ALT (GPT), Alanine Amino Transferase; ALP, alkaline phosphatase; GGT, Gamma-Glutamyl Transferase (D) Ratios of monosialylated and agalactosylated glycans (S1/G0) are plotted following administration of PBS, B4ST6$^{Fc}$ one week earlier, or B4ST6$^{Fc}$ two months earlier.
Figure 11B:
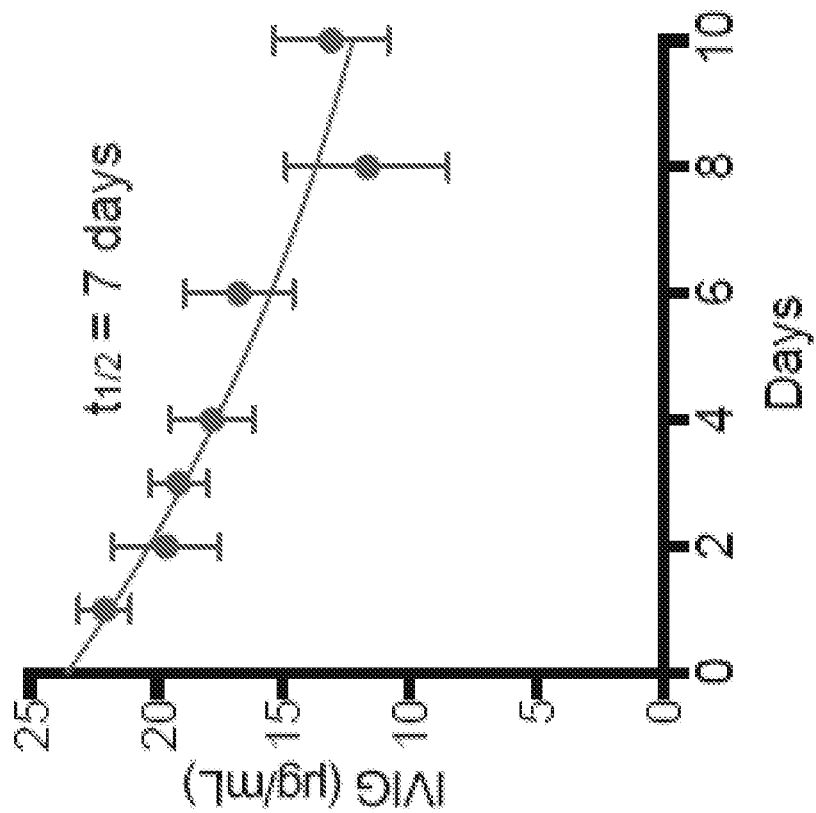
Figure 11C:
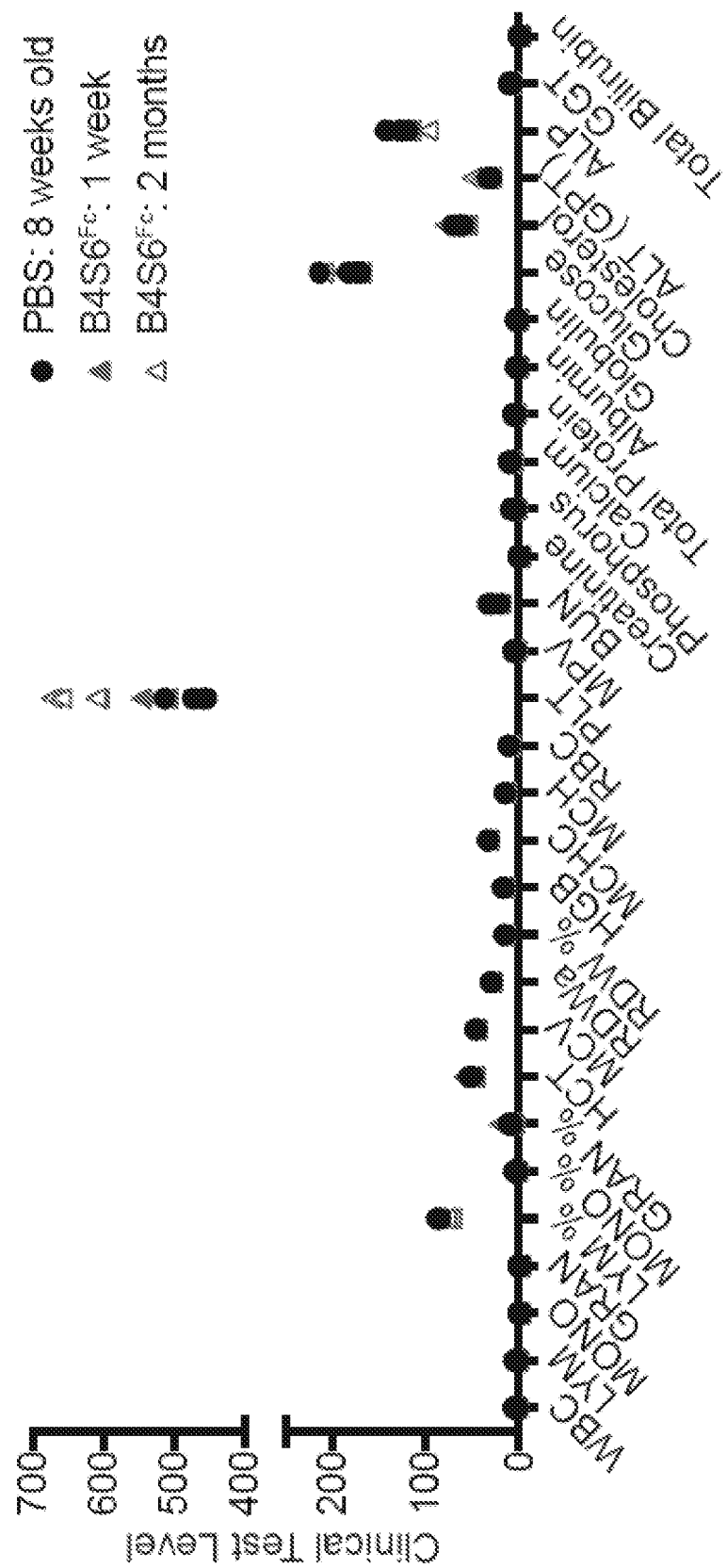
Figure 11D:
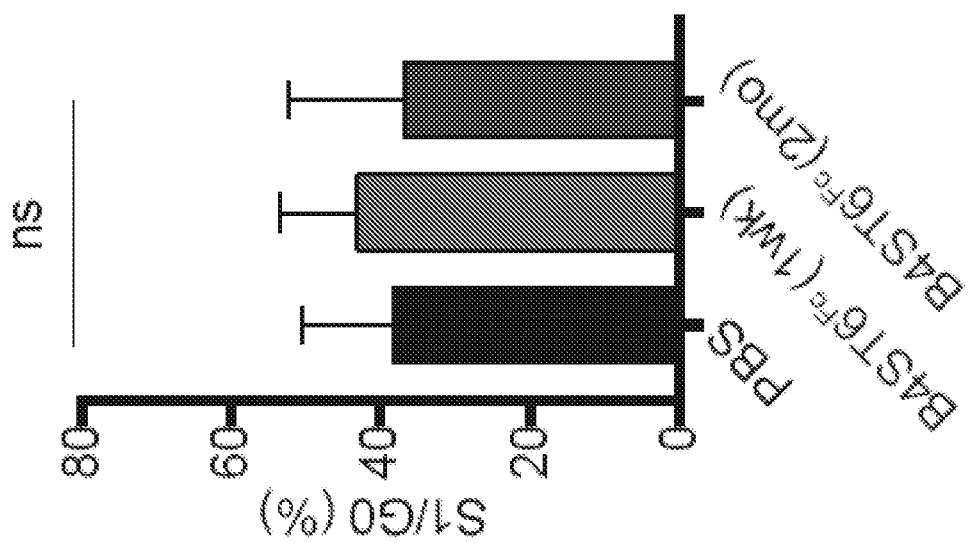

While administration of the engineered glycosyltransferases potently suppressed autoimmune inflammation, a potential undesirable side effect may be off-target glycan modification. In general, low levels of sialic acid are found on IgG Fc glycans, as 5-10% of total IgG in healthy individuals have sialylated Fc glycans. Most complex antennary glycans on cellular and soluble glycoproteins are highly sialylated limiting potential off-target effects of in vivo sialylation (Kaneko et al., 2006b, Youings et al., 1996). Nonetheless, experiments were performed to examine toxicity and systemic glycosylation following B4ST6$^{Fc}$ administration in vivo. The half-life of B4ST6$^{Fc}$ in circulation was similar to WIG (8 and 7 days, respectively, FIGS. 11A, 11B), suggesting that the Fc portion of these molecules similarly controls serum half-life in vivo. Experiments were also performed to examine the homeostatic impact of B4ST6$^{Fc}$ one week and two months after administration (FIG. 11C). No detrimental effect was noted on complete blood count (CBC) analysis of red blood cells (RBC), white blood cells (WBC) and platelets. Serum glucose and calcium levels remained within normal range, while kidney and liver function was unaltered on comprehensive metabolic panel (CMP) analysis. The analyses revealed little differences between PBS-treatment and either B4ST6$^{Fc}$-treatment group, and suggested that administration of B4ST6$^{Fc}$ is not toxic (FIG. 11C). Further experiments were performed to examine the glycosylation of IgG and total serum proteins one week and two months following administration of B4ST6$^{Fc}$ (FIG. 11D). Minimal changes in glycosylation were observed in B4ST6$^{Fc}$ treated animals compared to PBS-treated controls, suggesting that minimal off-target effects result from in vivo sialylation.

Figures 5A, 5B:
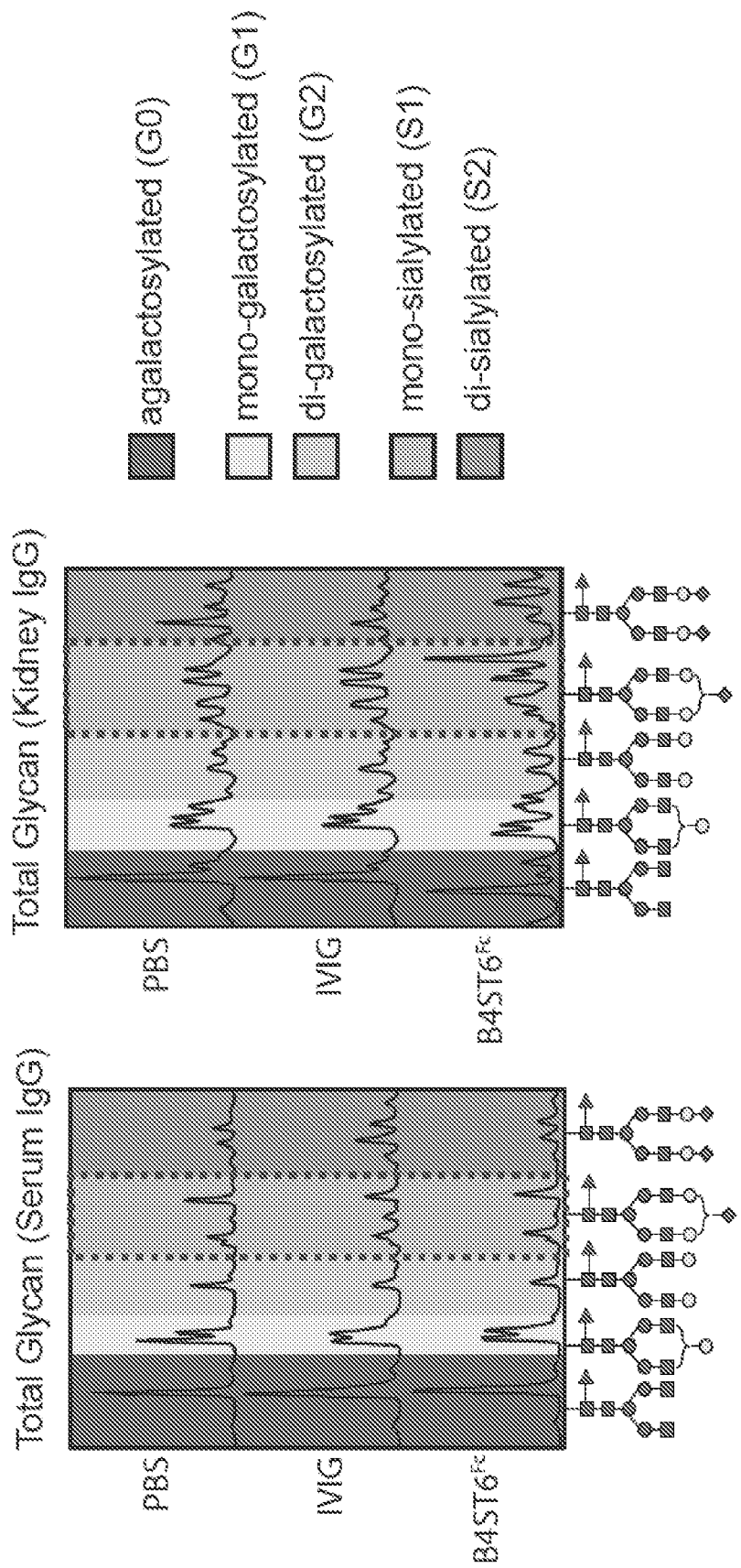
FIGS. 5A-5E. Characterizing in vivo sialylation during autoimmune inflammation. (A, B) HPLC traces of total glycans recovered from serum or kidney IgG in day 7 NTN-treated mice following administration of PBS, IVIG, or $B4ST6^{Fc}$. Shading corresponds to retention time of terminal sugar (blue, G0; yellow, G1; orange, two G2; pink, one 51; purple, S2). (C, D) Ratios of mono-sialylated and agalactosylated glycans (S1/G0) from IgG described in (A, B). (E) Total IgG purified from serum and kidney of NTN-treated mice received PBS, IVIG, or $B4ST6^{Fc}$ was probed by immunoblotting for mouse and human IgG. Means and standard deviation are plotted. Results are representative of at least two independent repeats. **p<0.01, ns (not significant), as determined by two-way ANOVA followed by Tukey's posthoc test.
Figure 5D:
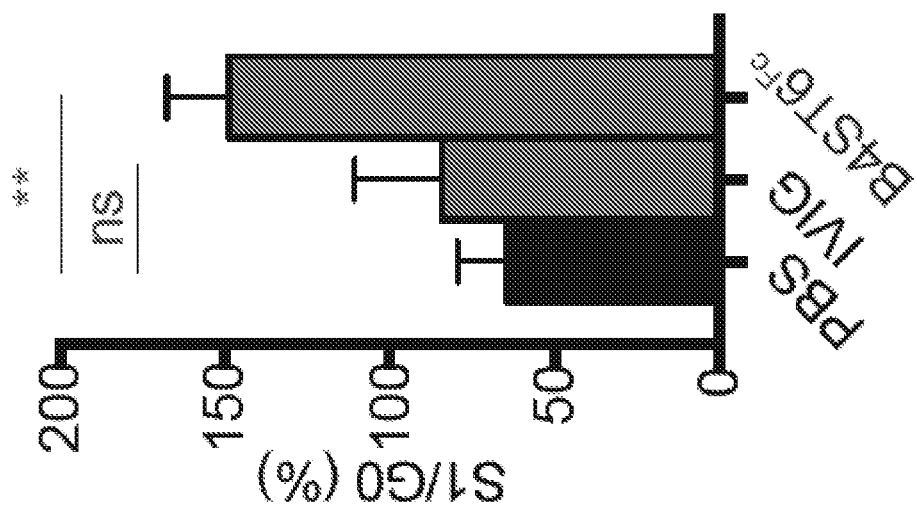
Figure 5C:
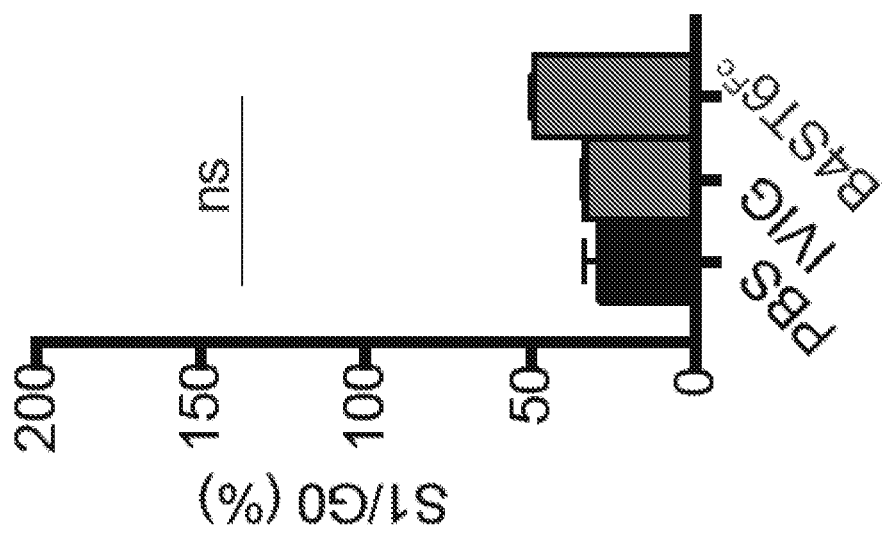
Figure 5E:
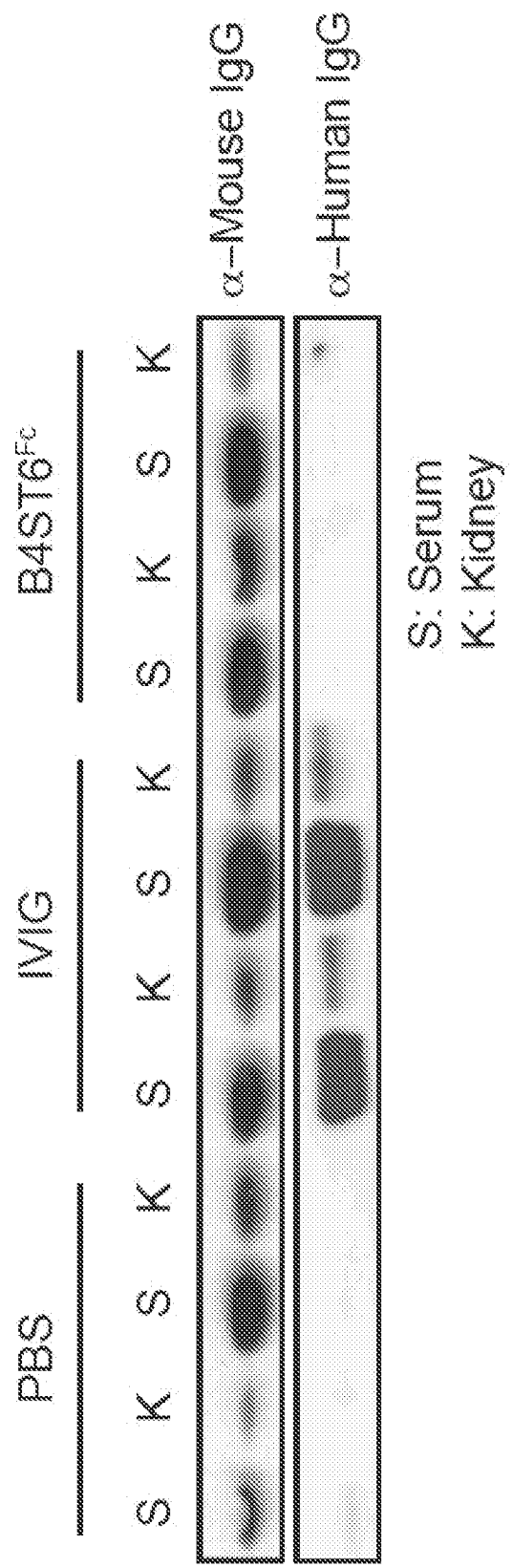
Figure 12:
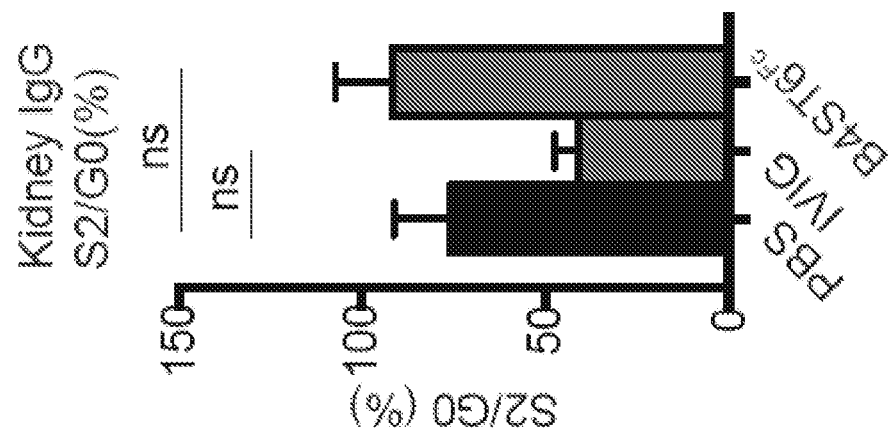
FIG. 12. Site-specific in vivo sialylation during inflammation. Ratios of disialylated and agalactosylated glycans (S2/G0) IgG recovered from kidney of NTN-induced mice.

Because administration of both engineered enzymes was anti-inflammatory in vivo, but did not notably alter serum IgG or protein glycosylation during homeostatic conditions, experiments were performed to examine glycosylation during an inflammatory response. NTN was induced in a panel of mice that received PBS, IVIG, or B4ST6$^{Fc}$, and the total N-linked glycosylation was examined. Seven days after disease induction, no differences in circulating IgG in PBS, IVIG, or B4ST6$^{Fc}$-treated mice were observed, consistent with the findings where B4ST6$^{Fc}$ does not affect glycosylation of circulating glycoproteins (FIG. 5A). Intriguingly, it has been observed that there was an increase in sialylation of IgG recovered from the kidneys of B4ST6$^{Fc}$-treated animals, compared to IgG recovered from kidneys of PBS or IVIG treated mice (FIG. 5B). The ratio of anti-inflammatory monosialylated to inflammatory agalactosylated IgG Fc glycans (S1/G0%) of serum revealed no differences in sialic acid content on serum IgG, while IgG recovered from the kidney had significant increases in sialylation, but no change in disialylated to agalactosylated kidney IgG Fc glycans (FIGS. 5C, 5D, 12). Immunoblot analysis of IgG purified from the serum (S) and kidney (K) of PBS, IVIG, or B4ST6$^{Fc}$ treated animals revealed measurable levels of mouse IgG in all samples, while human IgG Fc were only detectable in mice treated with IVIG (FIG. 5E). This indicates that the analysis of IgG glycans on PBS and B4ST6$^{Fc}$ treatment group was restricted to endogenous mouse IgG Fc, and not the Fc of the engineered glycosyltransferases. Together, these results demonstrate that endogenous IgG at the site of inflammation is sialylated selectively by B4ST6'.

Example 6: In Vivo Sialylation Requires Platelet Activation

Figure 6A:
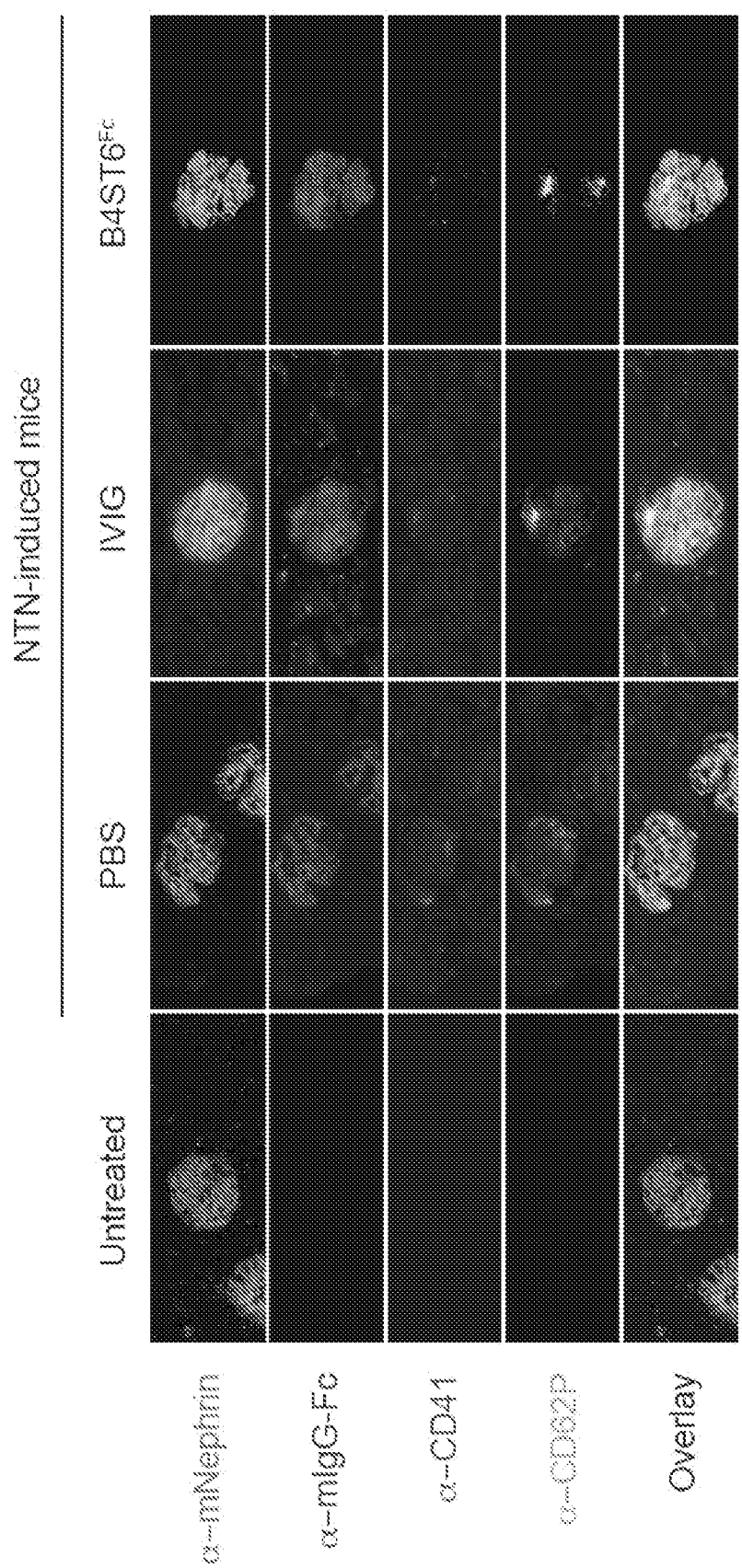
FIGS. 6A-6H. Platelet activation and in vivo sialylation. (A) Kidneys of untreated and day 7 NTN-treated mice following treatment with PBS, IVIG and $B4ST6^{Fc}$ were examined for glomeruli (mNephrin, green), mouse IgG (blue), platelets (CD41, red), activated platelets (CD62, yellow). Representative individual and overlaid images are shown. (B, C) Untreated and clopidogrel-treated mice were given K/B×N sera and PBS (black circles), IVIG (blue squares), or $B4ST6^{Fc}$ (red triangles) and paw swelling monitored over several days. (D) Day 6 clinical scores of untreated and clopidogrel-treated mice are shown. NTN was induced in untreated (E, F) and clopidogrel-treated (G, H) animals, and day 7 BUN levels (mg/dL) and survival was monitored. Means and standard deviation are plotted. Results are representative of at least two independent repeats. *p<0.05, *p<0.005, **p<0.001, ns (not significant), determined by two-way ANOVA followed by Tukey's posthoc test.
Figure 13A:
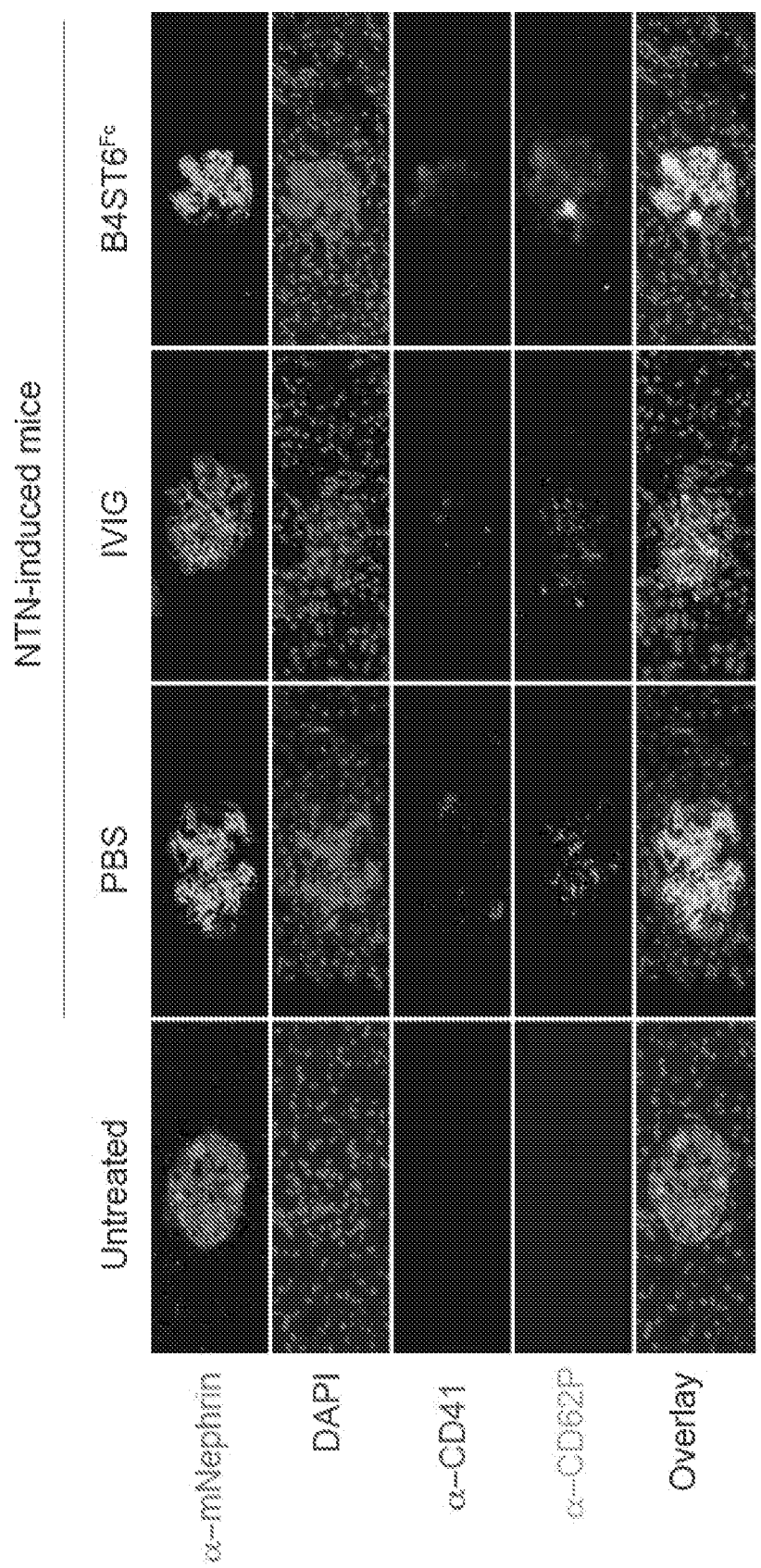
FIGS. 13A-13B. Platelets during in vivo sialylation of NTN. (A) Kidneys of untreated and 7 days after NTN induction in PBS, IVIG and B4ST6$^{Fc}$ treated animals were examined for glomeruli (mNephrin, green), DAPI (blue), platelets (CD41), activated platelets (CD62). Representative individual and overlayed images are shown. (B) Day 7 anti-sheep IgG titers of NTN-induced mice were treated with PBS (black circles), high dose IVIG (blue squares), or B4ST6$^{Fc}$ (2.5 mg/kg) (red triangles) some of which also received clopidogrel.

Studies that have examined the activity of soluble ST6GAL1 implicated platelets as donors of CMP-sialic acid (CMP-SA), which is required for sialylation reactions (Jones et al., 2016, Jones et al., 2012, Lee et al., 2014). Therefore, experiments were performed to determine whether platelets provided sugar-nucleotide donors for B4ST6$^{Fc}$. Indeed, CD41$^+$ platelets were detected in the glomeruli of mouse kidneys in which NTN had been induced, but not in the glomeruli of untreated kidneys, consistent with previous studies demonstrating platelet recruitment to sites of inflammation (FIGS. 6A and 13A) (Devi et al., 2010, Boilard et al., 2010). Further, CD41$^+$ platelets in NTN-inflamed kidneys also expressed the platelet activation marker, CD62P (FIGS. 6A, 13A). Treatment with PBS, WIG, or B4ST6$^{Fc}$ during NTN-inflammation did not affect accumulation and activation of platelets (FIGS. 6A, 13A).

Figure 6C:
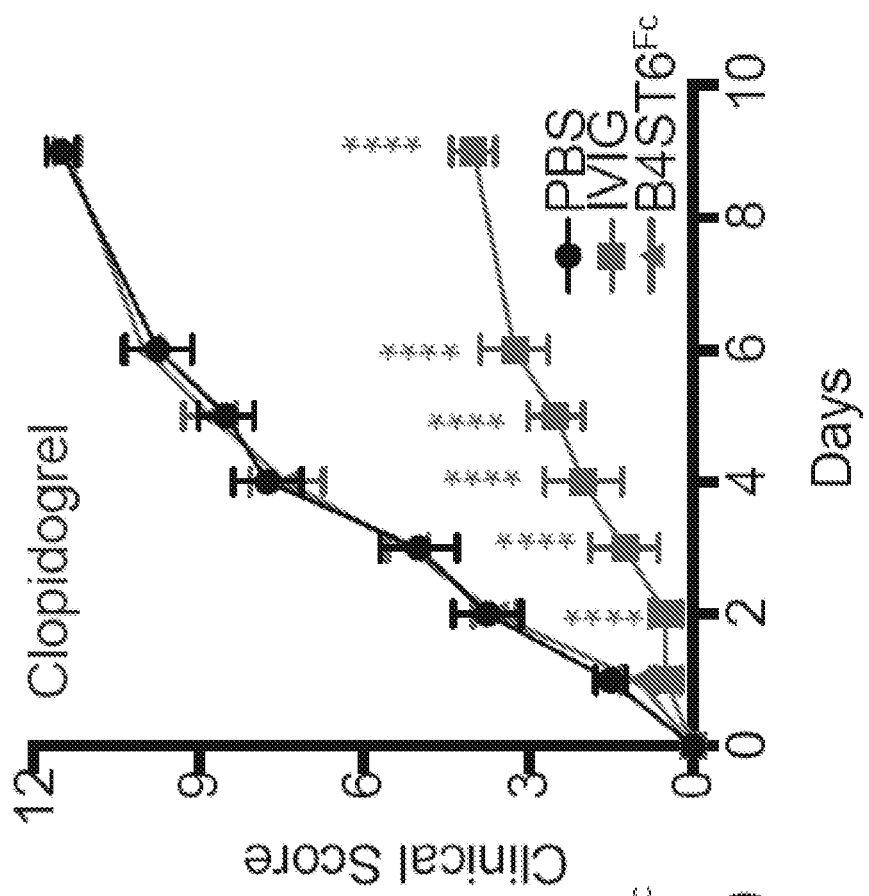
Figure 6B:
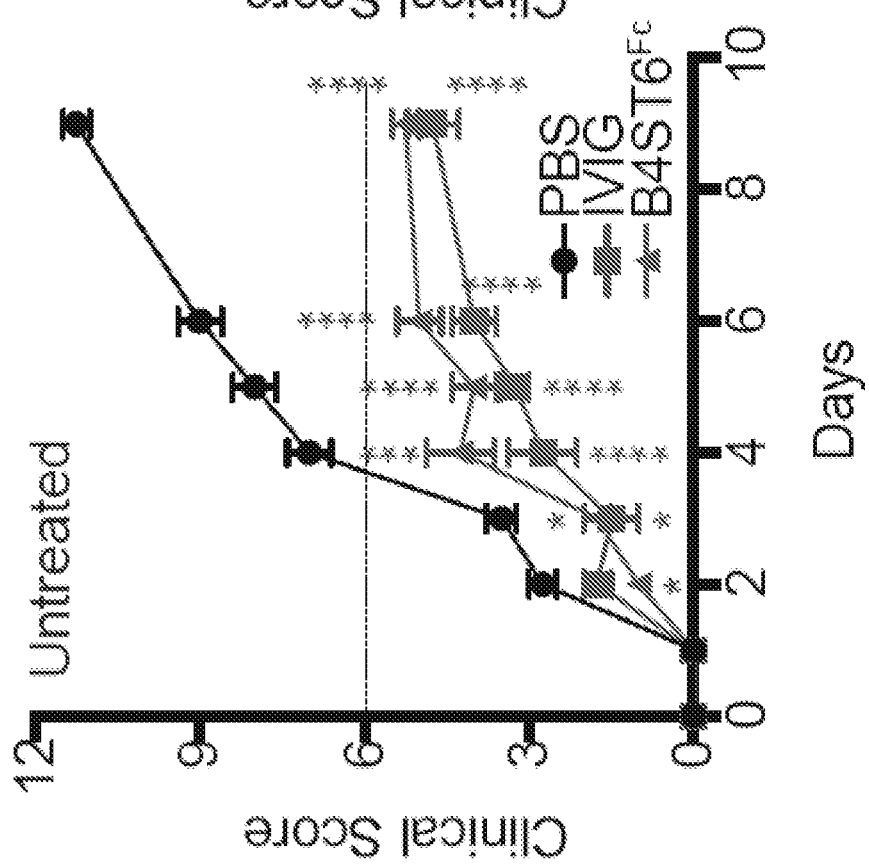
Figures 6D, 6E:
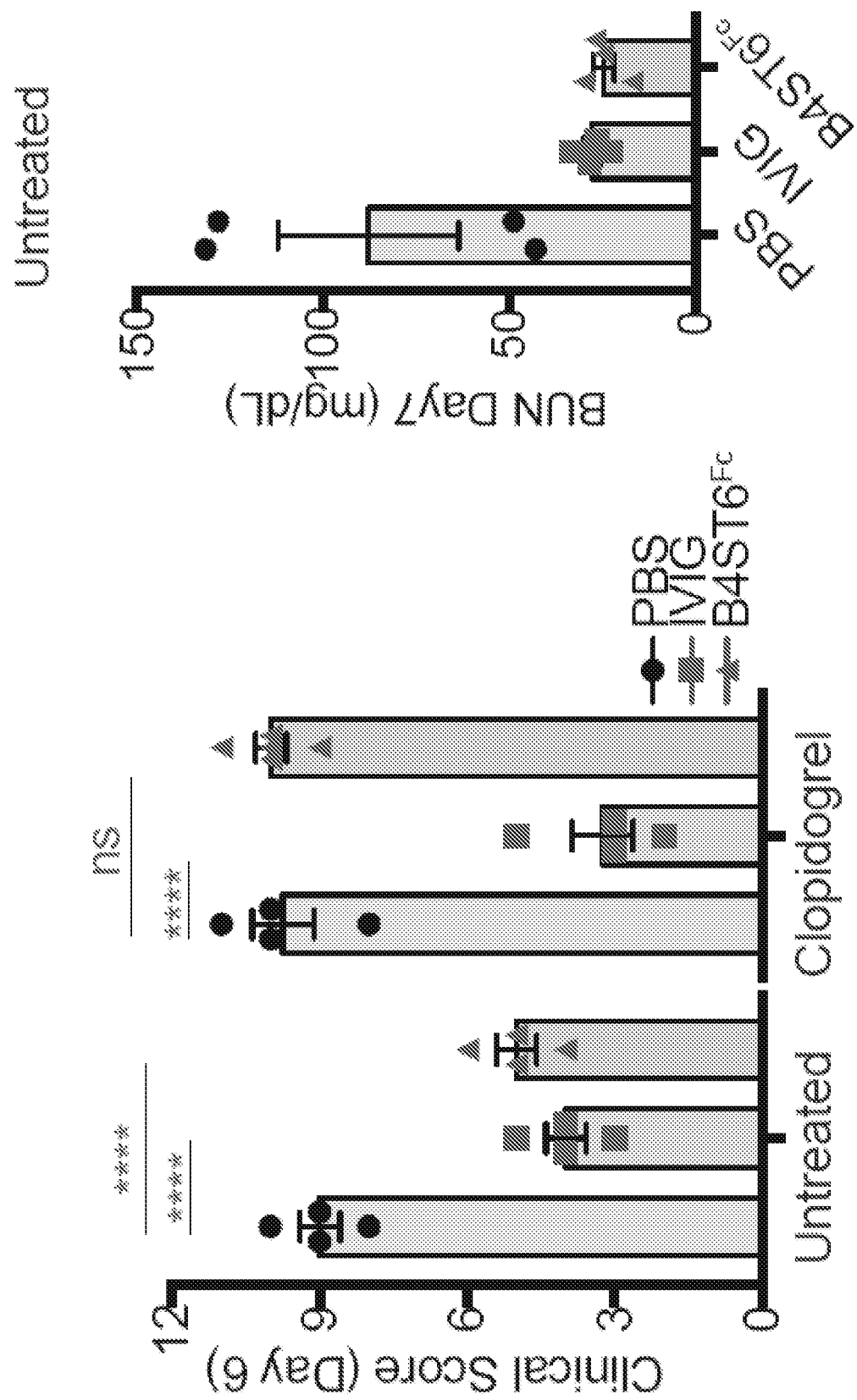

Experiments were also performed to determine whether platelet activation was required for the anti-inflammatory activity of in vivo sialylation. Mice were given clopidogrel (10 mg/kg) daily two days prior to administration of K/BxN sera to prevent platelet activation (Pucci et al., 2016). The mice also received PBS, IVIG, or B4ST6$^{Fc}$ and inflammation was monitored over the next several days. Clopidogrel treatment did not affect induced-inflammation of PBS-treated animals (FIGS. 6B-6D). IVIG suppressed inflammation in the presence of clopidogrel (FIGS. 6B-6D). However, B4ST6$^{Fc}$ was unable to attenuate inflammation when given coordinately with Clopidogrel (FIGS. 6C, 6D).

Figures 6F, 6G, 6H:
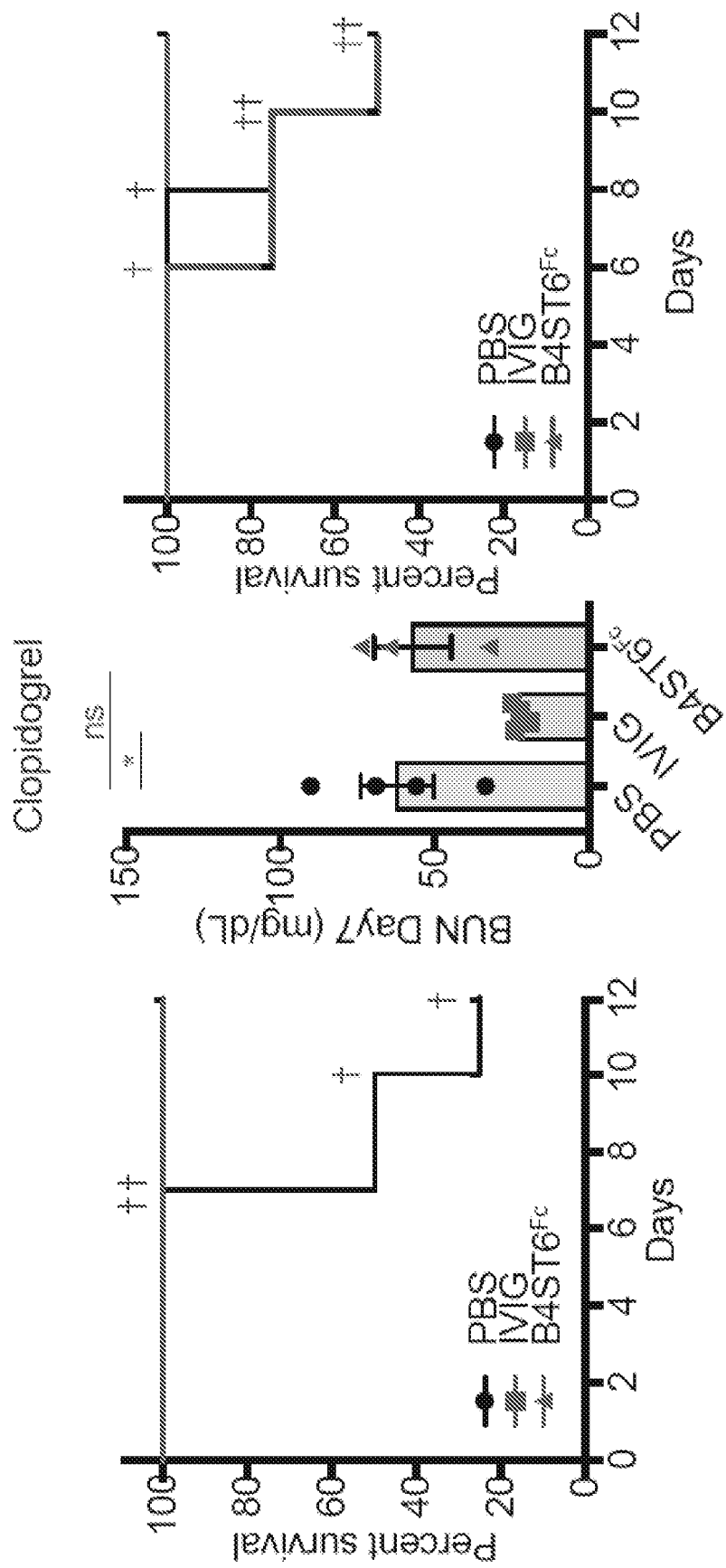
Figure 13B:
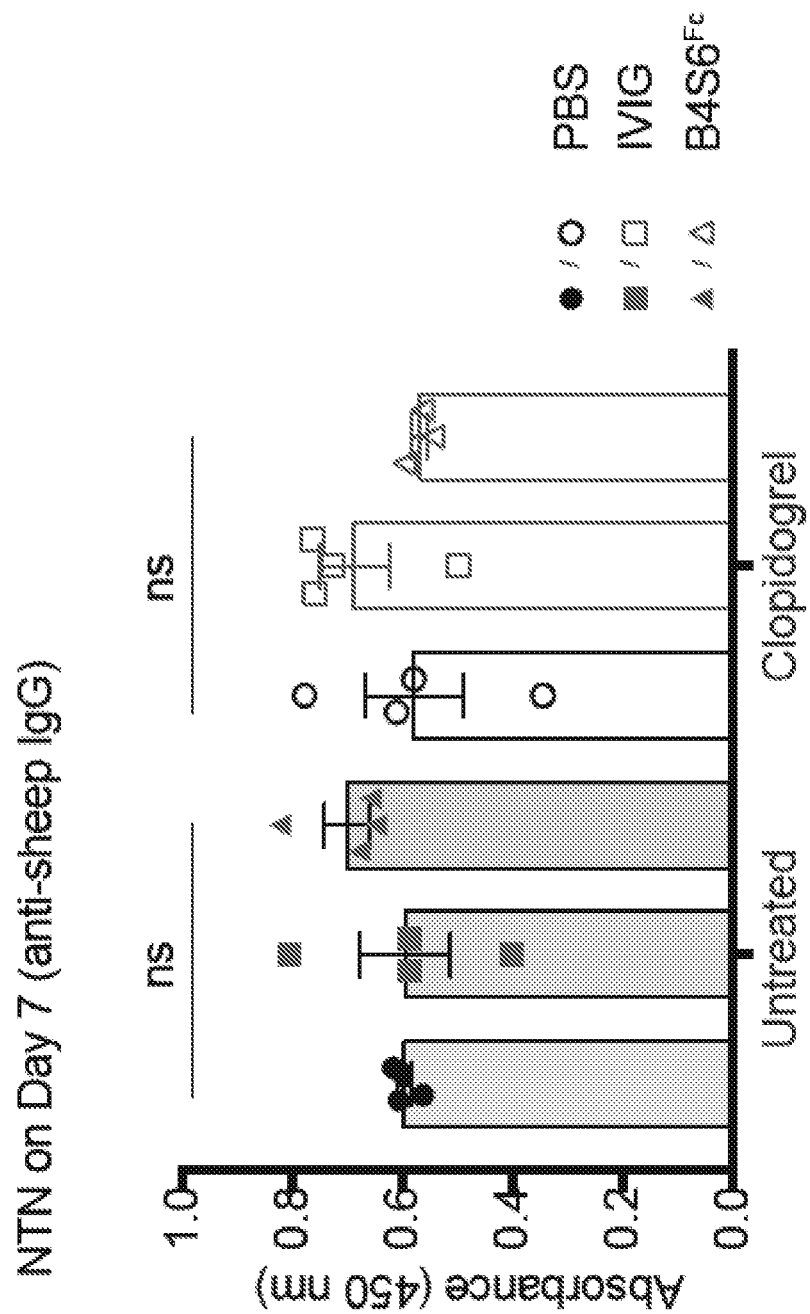

In an effort to extend these results, NTN was induced in mice that were administered clopidogrel (FIGS. 6E-6H) that then received PBS, IVIG, or B4ST6$^{Fc}$. Importantly, these treatments did not affect the anti-sheep IgG titers in the treated mice (FIG. 13B). Induction of NTN caused kidney damage in clopidogrel and PBS-treated animals, as measured by blood urea nitrogen levels and survival (FIGS. 6G, 6H). IVIG protected treated mice from kidney disease, regardless of clopidogrel treatment (FIGS. 6E-H). However, B4ST6$^{Fc}$ was ineffective at attenuating disease when given along with clopidogrel (FIGS. 6G, 6H). Together, these results demonstrate that the anti-inflammatory activity of B4ST6$^{Fc}$, but not WIG, is dependent on platelet activation in vivo.

Figure 7A:
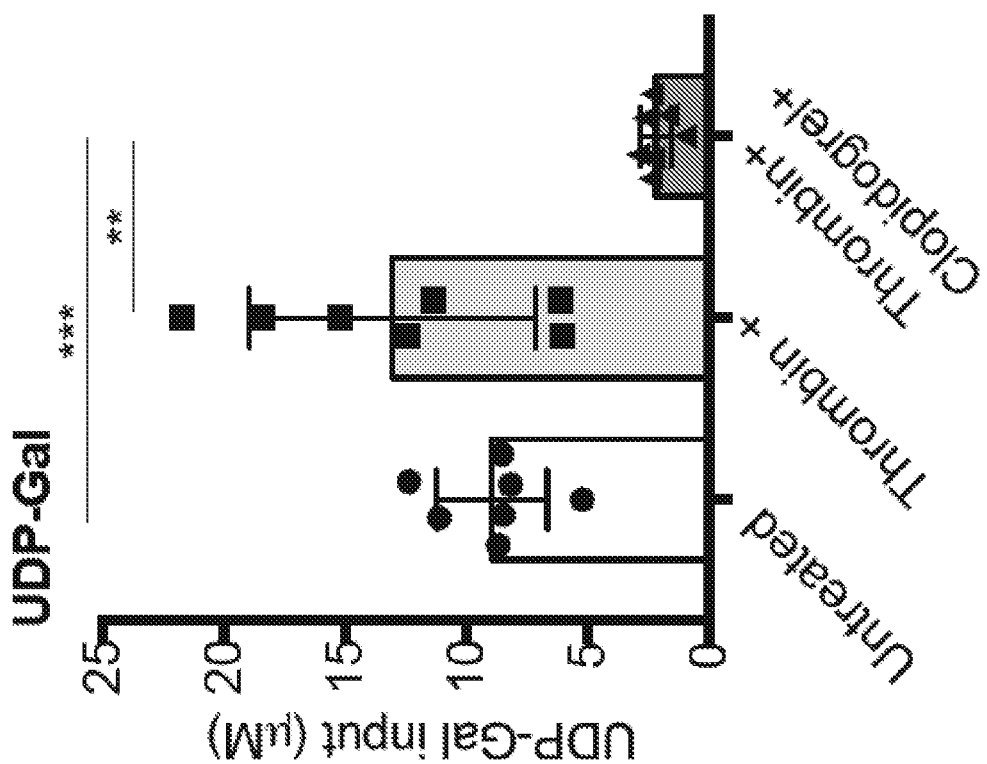
FIGS. 7A-7D. Therapeutic in vivo sialylation. (A, B) Human platelets plasma were untreated, activated (Thrombin+), or activated after clopidogrel treatment (Thrombin+, Clopidogrel+), and assayed for UPD-Gal (A) and CMP-SA (B). (C-D) Mice were treated with K/B×N sera on day 0 and PBS (black circles), IVIG (blue squares), or $B4ST6^{Fc}$ (red triangles), or day 3 and paw swelling monitored (C) over several days. (D) Day 7 clinical scores of individual mice from (C) are shown. Means and standard deviation are plotted. Results are representative of at least two independent repeats. p<0.01, *p<0.005, ****p<0.001, ns (not significant), determined by two ANOVA followed by Tukey's posthoc test.
Figure 7B:
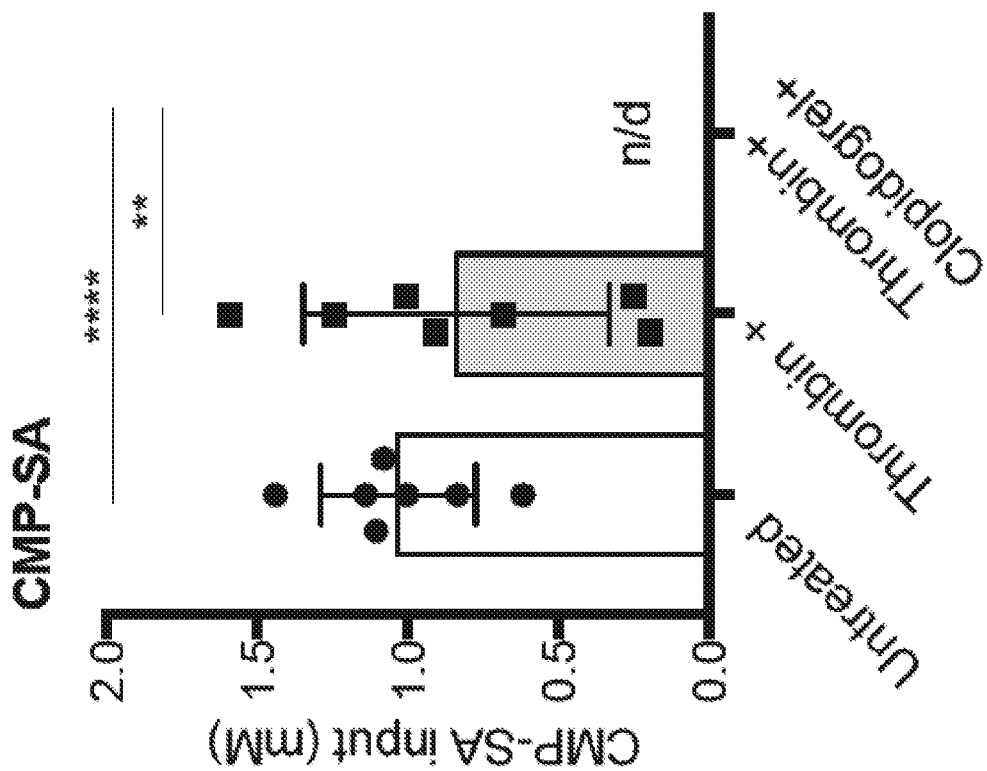

Further experiments were performed to determine whether human platelets released sugar-nucleotide donors required for sialylation, and generated platelet-enriched plasma (PRP) from healthy donors (Lee et al., 2014, Jones et al., 2016, Tan et al., 2016). Platelets was left untreated, activated (Thrombin+), or activated following clopridogrel treatment (Clopridogrel+/Thrombin+), and assayed for release of sialic acid- and galactose-nucleotide donors (CMP-SA, UDP-Gal). Indeed, human platelets released both sialic acid- and galactose-nucleotide donors upon activation, and the release was significantly inhibited by clopidogrel (FIGS. 7A, 7B). Intriguingly, activation increased galactose-nucleotide donor release, but not sialic acid-donor release.

Figure 7D:
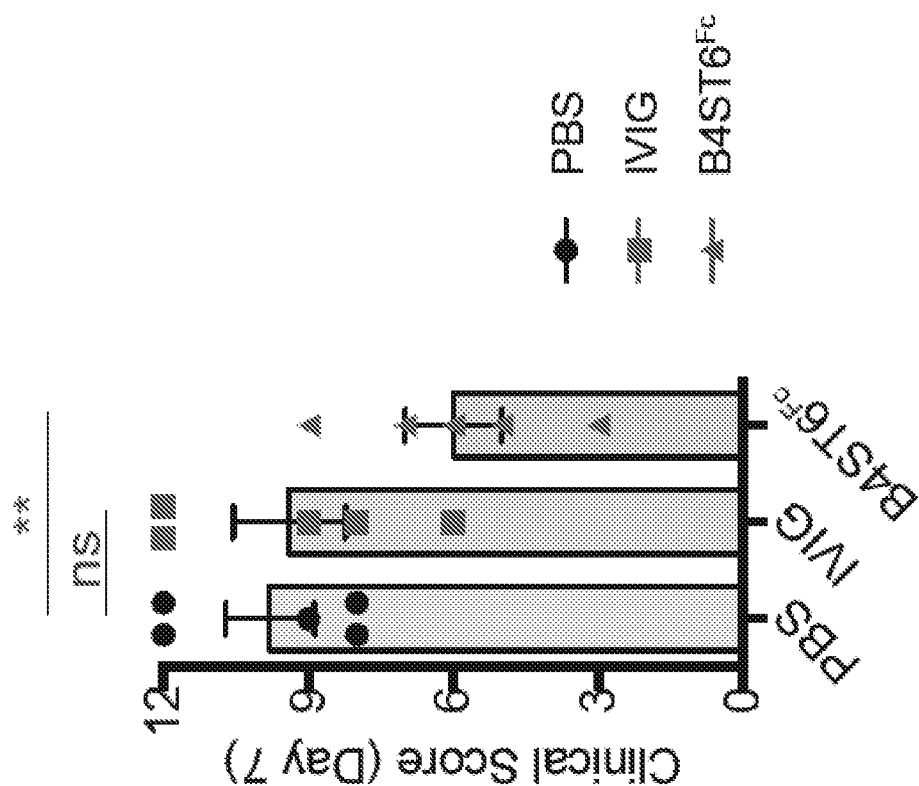
Figure 7C:
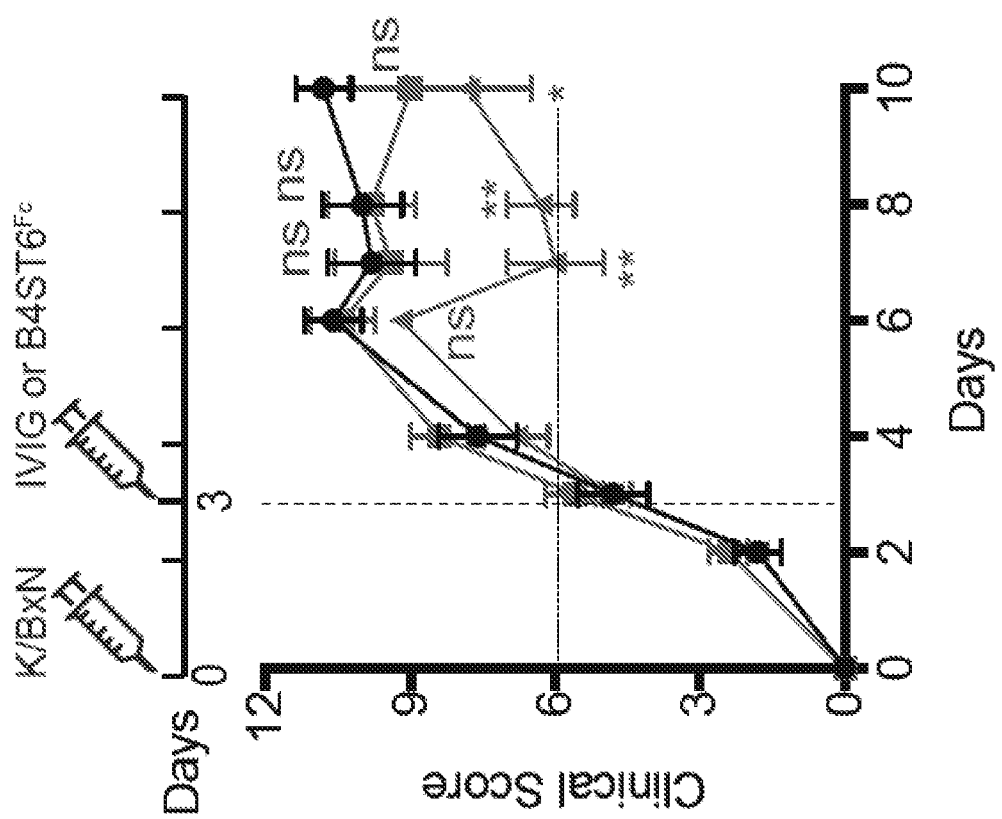
Figure 14B:
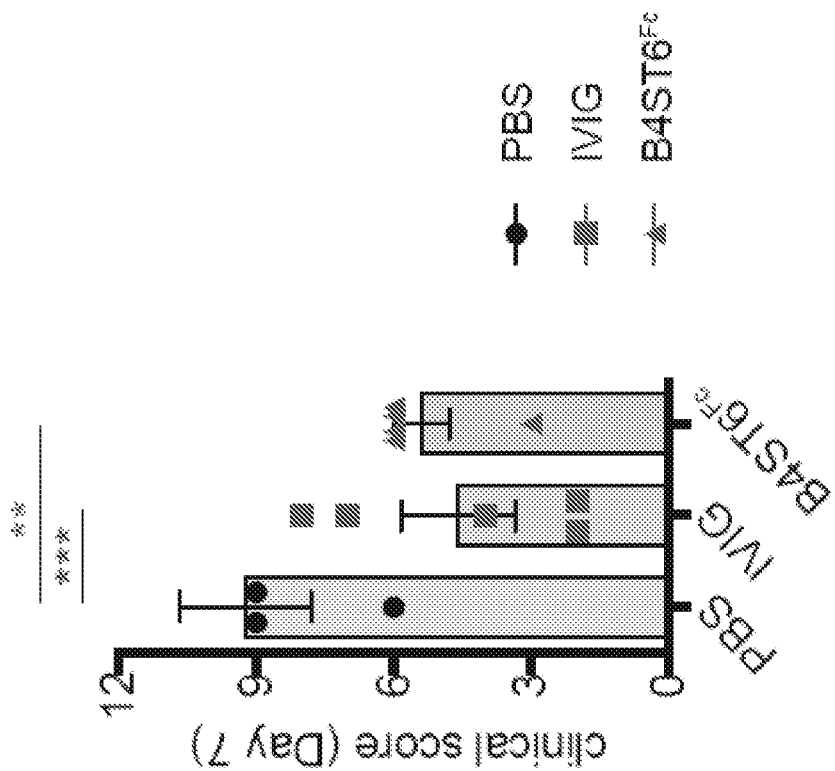
FIGS. 14A-14B. Preventative and therapeutic in vivo sialylation. (A) K/BxN treated mice were given PBS (black circles), IVIG (blue squares), or B4ST6$^{Fc}$ (red triangles) on day 0 and paw swelling monitored over several days. (B) Day 7 clinical scores of individual mice are shown. These are control groups for data shown in FIGS. 7C and 7D.
Figure 14A:
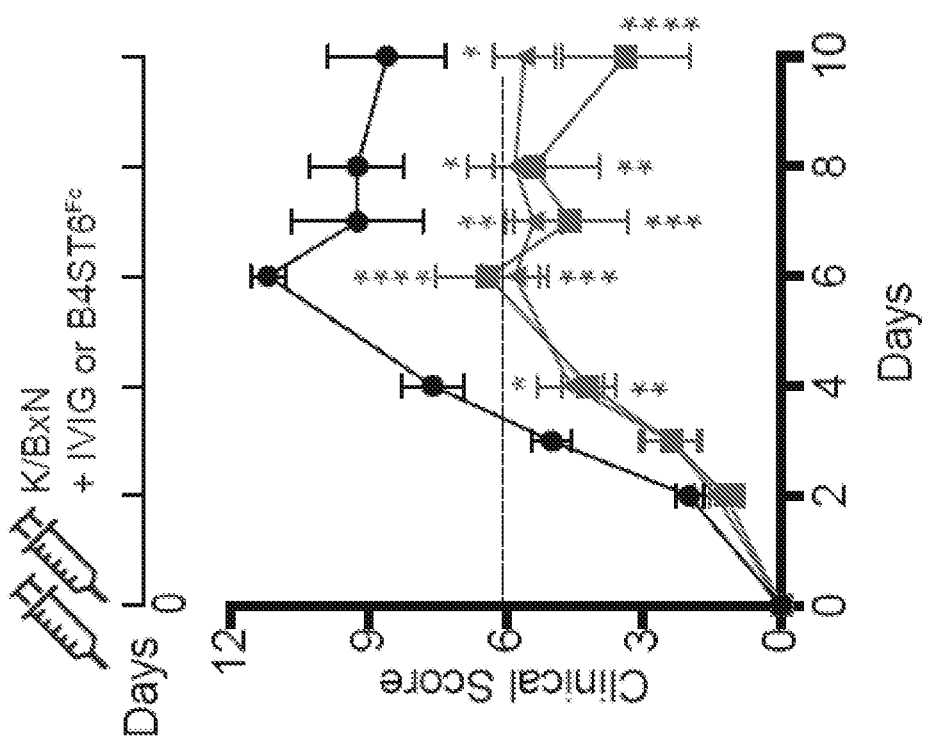

A successful anti-inflammatory therapeutic is required to suppress ongoing inflammation. To determine whether in vivo sialylation was effective therapeutically, mice were treated with arthritis-inducing sera and then given PBS, IVIG, or B4ST6$^{Fc}$ on day 0 or day 3 after induction of arthritis. IVIG and B4ST6$^{Fc}$, but not PBS, were effective at reducing induced arthritis when administered on day 0 (FIGS. 14A, 14B). However, IVIG was unable to suppress induced arthritis when administered day 3 after disease induction (FIGS. 7C, 7D). Importantly, mice treated with arthritogenic sera and B4ST6$^{Fc}$ on day 3 exhibited significantly reduced inflammation on day 7 and 8 compared to IVIG- and PBS-treated groups (FIGS. 7C, 7D). These results reveal that B4ST6$^{Fc}$ is able to effectively attenuate autoantibody-induced inflammation in a therapeutic fashion, which was unachievable with IVIG in this model, consistent with previous results (Bruhns et al., 2003).

Example 7: Heterodimerization of B4$^{Fc}$ and ST6$^{Fc}$

In order to achieve heterodimerization of B4$^{Fc}$ and ST6$^{Fc}$, "knobs-into-holes" (KIH) mutations were introduced in each heavy chain, CH3 domains. Specifically, Y349C/T366S/L368A/Y407V and S354C/T366W point mutations were introduced in B4$^{Fc}$ (SEQ ID NO: 42) and ST6$^{Fc}$ (SEQ ID NO: 43), respectively.

Figure 18:
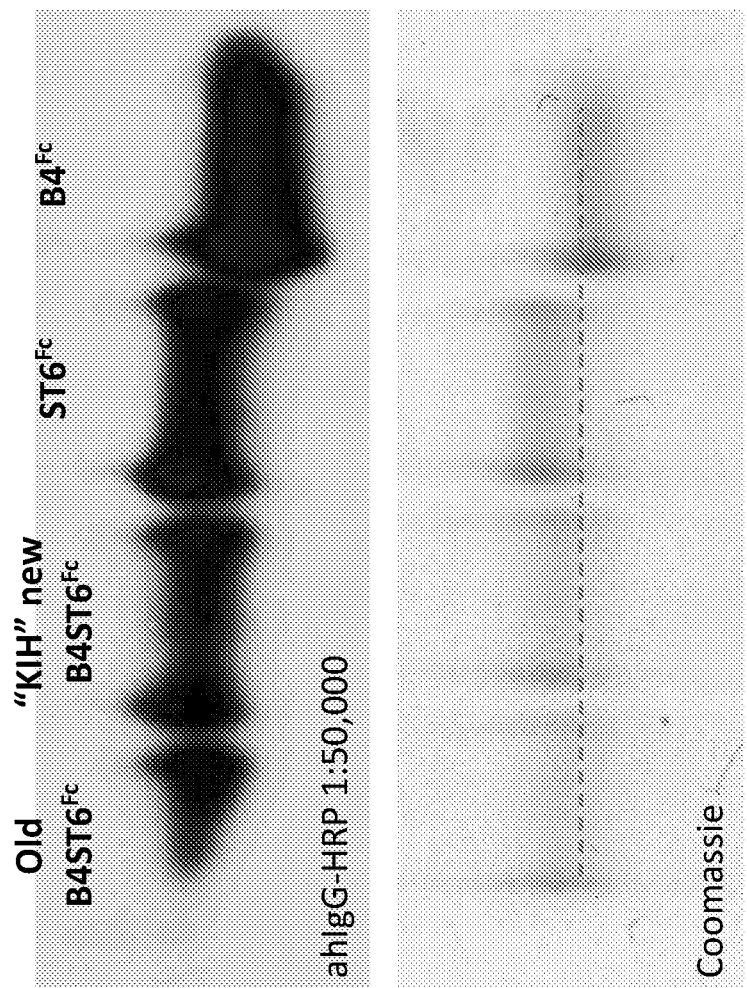
FIG. 18 shows western blot results (with anti-human IgG) and Coomassie Gel stain of the B4ST6$^{Fc}$ with and without "knobs-into-holes" mutations, ST6$^{Fc}$ homodimers, and B4$^{Fc}$ homodimers.

FIG. 18 shows western blot results (with anti-human IgG) and Coomassie Gel stain of the original B4ST6$^{Fc}$ and new "knobs-into-holes" B4ST6$^{Fc}$. In the figure, ST6$^{Fc}$ stands for ST6$^{Fc}$ homodimers. B4$^{Fc}$ stands for B4$^{Fc}$ homodimers. The original B4ST6$^{Fc}$ does not have the knobs-into-holes mutations, thus it is likely it is a mixture of ST6$^{Fc}$ homodimers, B4$^{Fc}$ homodimers, and B4$^{Fc}$ST6$^{Fc}$ heterodimers. The "KIH" B4ST6$^{Fc}$ are B4$^{Fc}$ST6$^{Fc}$ heterodimers and ran slightly higher in a gel as shown in Coomassie gel.

Example 8: Testing B4$^{Fc}$ST6$^{Fc}$ Heterodimers in Arthritis Model

Figure 19:
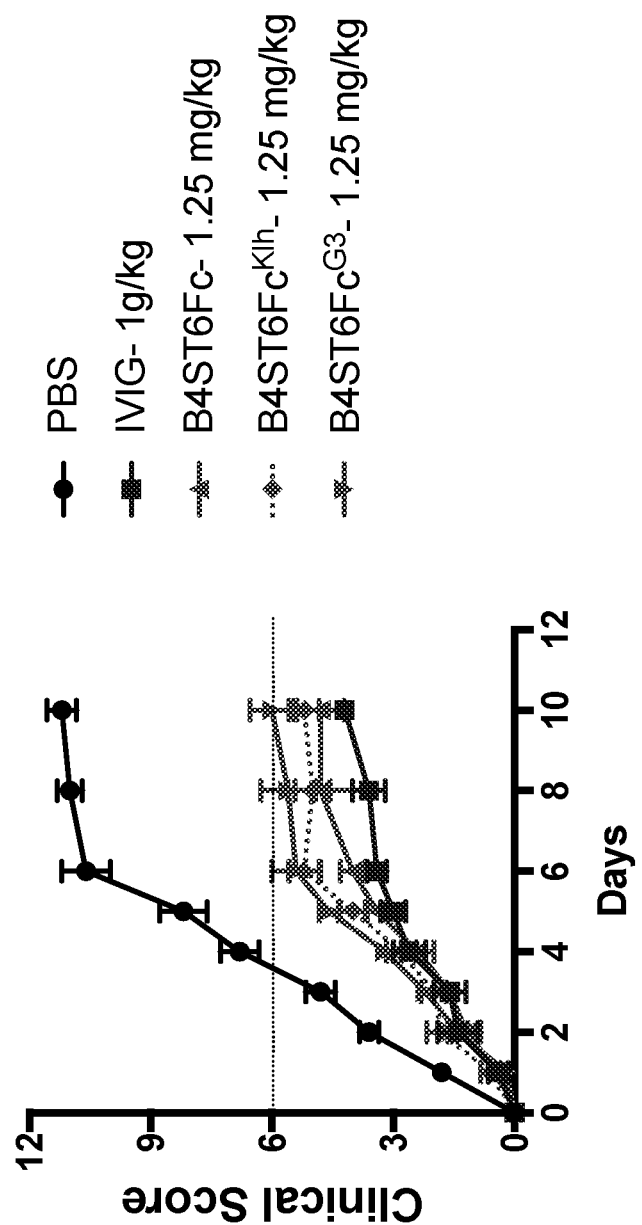
FIG. 19 shows the effects of original B4ST6$^{Fc}$, heterodimeric B4ST6Fc$^{KIh}$, and B4ST6Fc$^{G3}$ in arthritis models.

To test the in vivo activity, mice were administered with K/BxN sera and then high dose of IVIG, the original B4ST6$^{Fc}$, heterodimeric B4ST6Fc$^{KIn}$ ("knobs-into-holes" B4ST6$^{Fc}$), and B4ST6Fc$^{G3}$ (which has an IgG3 Fc domain without KIH mutations) were administered to the mice. Paw swelling was monitored over the next several days. As shown in FIG. 19, in the PBS-treated controls (circle), K/BxN sera induced robust inflammation in the paw. In contrast, high dose of IVIG (square), B4ST6$^{Fc}$ (solid triangles), heterodimeric B4ST6Fc$^{KIn}$ (dotted line and diamonds), and B4ST6Fc$^{G3}$ (inverted triangles) all attenuated inflammation. The results indicate that the original B4ST6$^{Fc}$, heterodimeric B4ST6Fc$^{KIn}$, and B4ST6Fc$^{G3}$ can attenuate inflammation in arthritis models, and thus can be used to treat autoimmune disorders.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Ackerman, M. E., Crispin, M., Yu, X., Baruah, K., Boesch, A. W., Harvey, D. J., Dugast, A. S., Heizen, E. L., Ercan, A., Choi, I., Streeck, H., Nigrovic, P. A., Bailey-Kellogg, C., Scanlan, C. & Alter, G. 2013. Natural variation in Fc glycosylation of HIV-specific antibodies impacts antiviral activity. J Clin Invest, 123, 2183-92.

Albert, H., Collin, M., Dudziak, D., Ravetch, J. V. & Nimmerjahn, F. 2008. In vivo enzymatic modulation of IgG glycosylation inhibits autoimmune disease in an IgG subclass-dependent manner. Proc Natl Acad Sci USA, 105, 15005-9.

Allhorn, M., Briceno, J. G., Baudino, L., Lood, C., Olsson, M. L., Izui, S. & Collin, M. 2010. The IgG-specific endoglycosidase EndoS inhibits both cellular and complement-mediated autoimmune hemolysis. Blood, 115, 5080-8.

Anthony, R. M., Kobayashi, T., Wermeling, F. & Ravetch, J. V. 2011. Intravenous gammaglobulin suppresses inflammation through a novel T(H)2 pathway. Nature, 475, 110-3.

Anthony, R. M., Nimmerjahn, F., Ashline, D. J., Reinhold, V. N., Paulson, J. C. & Ravetch, J. V. 2008a. Recapitulation of IVIG anti-inflammatory activity with a recombinant IgG Fc. Science, 320, 373-6.

Anthony, R. M., Wermeling, F., Karlsson, M. C. & Ravetch, J. V. 2008b. Identification of a receptor required for the anti-inflammatory activity of IVIG. Proc Natl Acad Sci USA, 105, 19571-8.

Arnold, J. N., Wormald, M. R., Sim, R. B., Rudd, P. M. & Dwek, R. A. 2007. The impact of glycosylation on the biological function and structure of human immunoglobulins. Annu Rev Immunol, 25, 21-50.

Bayry, J., Bansal, K., Kazatchkine, M. D. & Kaveri, S. V. 2009. DC-SIGN and alpha2,6-sialylated IgG Fc interaction is dispensable for the anti-inflammatory activity of IVIg on human dendritic cells. Proc Natl Acad Sci USA, 106, E24; author reply E25.

Beck, A., Wurch, T., Bailly, C. & Corvaia, N. 2010. Strategies and challenges for the next generation of therapeutic antibodies. Nat Rev Immunol, 10, 345-52.

Benkhoucha, M., Molnarfi, N., Santiago-Raber, M. L., Weber, M. S., Merkler, D., Collin, M. & Lalive, P. H. 2012. IgG glycan hydrolysis by EndoS inhibits experimental autoimmune encephalomyelitis. J Neuroinflammation, 9, 209.

Boilard, E., Nigrovic, P. A., Larabee, K., Watts, G. F., Coblyn, J. S., Weinblatt, M. E., Massarotti, E. M., Remold-O'donnell, E., Farndale, R. W., Ware, J. & Lee, D. M. 2010. Platelets amplify inflammation in arthritis via collagen-dependent microparticle production. Science, 327, 580-3.

Bruhns, P., Samuelsson, A., Pollard, J. W. & Ravetch, J. V. 2003. Colony-stimulating factor-1-dependent macrophages are responsible for IVIG protection in antibody-induced autoimmune disease. Immunity, 18, 573-81.

Chung, A. W., Ghebremichael, M., Robinson, H., Brown, E., Choi, I., Lane, S., Dugast, A. S., Schoen, M. K., Rolland, M., Suscovich, T. J., Mahan, A. E., Liao, L., Streeck, H., Andrews, C., Rerks-Ngarm, S., Nitayaphan, S., De Souza, M. S., Kaewkungwal, J., Pitisuttithum, P., Francis, D., Michael, N. L., Kim, J. H., Bailey-Kellogg, C., Ackerman, M. E. & Alter, G. 2014. Polyfunctional Fc-effector profiles mediated by IgG subclass selection distinguish RV144 and VAX003 vaccines. Sci Transl Med, 6, 228ra38.

Clynes, R. 2007. Protective mechanisms of IVIG. Curr Opin Immunol, 19, 646-51.

Collin, M. & Olsen, A. 2001. EndoS, a novel secreted protein from Streptococcus pyogenes with endoglycosidase activity on human IgG. EMBO J, 20, 3046-55.

Davies, J., Jiang, L., Pan, L. Z., Labarre, M. J., Anderson, D. & Reff, M. 2001. Expression of GnTIII in a recombinant anti-CD20 CHO production cell line: Expression of antibodies with altered glycoforms leads to an increase in ADCC through higher affinity for FC gamma RIII Biotechnol Bioeng, 74, 288-94.

Debre, M., Bonnet, M. C., Fridman, W. H., Carosella, E., Philippe, N., Reinert, P., Vilmer, E., Kaplan, C., Teillaud, J. L. & Griscelli, C. 1993. Infusion of Fc gamma fragments for treatment of children with acute immune thrombocytopenic purpura. Lancet, 342, 945-9.

Devi, S., Kuligowski, M. P., Kwan, R. Y., Westein, E., Jackson, S. P., Kitching, A. R. & Hickey, M. J. 2010. Platelet recruitment to the inflamed glomerulus occurs via an alphaIIbbeta3/GPVI-dependent pathway. Am J Pathol, 177, 1131-42.

Ferrara, C., Grau, S., Jager, C., Sondermann, P., Brunker, P., Waldhauer, I., Hennig, M., Ruf, A., Rufer, A. C., Stihle, M., Umana, P. & Benz, J. 2011. Unique carbohydrate-carbohydrate interactions are required for high affinity binding between Fc{gamma}RIII and antibodies lacking core fucose. Proc Natl Acad Sci USA, 108, 12669-74.

Fiebiger, B. M., Maamary, J., Pincetic, A. & Ravetch, J. V. 2015. Protection in antibody- and T cell-mediated autoimmune diseases by antiinflammatory IgG Fcs requires type II FcRs. Proc Natl Acad Sci USA, 112, E2385-94.

Franklin, E. C. 1975. Structure and function of immunoglobulins. Acta Endocrinol Suppl (Copenh), 194, 77-95.

Huber, R., Deisenhofer, J., Colman, P. M., Matsushima, M. & Palm, W. 1976. Crystallographic structure studies of an IgG molecule and an Fc fragment. Nature, 264, 415-20.

Imbach, P., Barandun, S., D'apuzzo, V., Baumgartner, C., Hirt, A., Morell, A., Rossi, E., Schoni, M., Vest, M. & Wagner, H. P. 1981. High-dose intravenous gammaglobulin for idiopathic thrombocytopenic purpura in childhood. Lancet, 1, 1228-31.

Jefferis, R. 2005. Glycosylation of recombinant antibody therapeutics. Biotechnol Prog, 21, 11-6.

Jefferis, R. 2009a. Glycosylation as a strategy to improve antibody-based therapeutics. Nat Rev Drug Discov, 8, 226-34.

Jefferis, R. 2009b. Glycosylation of antibody therapeutics: optimisation for purpose. Methods Mol Biol, 483, 223-38.

Jones, M. B., Nasirikenari, M., Lugade, A. A., Thanavala, Y. & Lau, J. T. 2012. Anti-inflammatory IgG production requires functional P1 promoter in beta-galactoside alpha2,6-sialyltransferase 1 (ST6Gal-1) gene. J Biol Chem, 287, 15365-70.

Jones, M. B., Oswald, D. M., Joshi, S., Whiteheart, S. W., Orlando, R. & Cobb, B. A. 2016. B-cell-independent sialylation of IgG. Proc Natl Acad Sci USA, 113, 7207-12.

Kalcheva, I., Elliott, R. W., Dalziel, M. & Lau, J. T. 1997. The gene encoding beta-galactoside alpha2,6-sialyltransferase maps to mouse chromosome 16. Mamm Genome, 8, 619-20.

Kaneko, Y., Nimmerjahn, F., Madaio, M. P. & Ravetch, J. V. 2006a. Pathology and protection in nephrotoxic nephritis is determined by selective engagement of specific Fc receptors. J Exp Med, 203, 789-97.

Kaneko, Y., Nimmerjahn, F. & Ravetch, J. V. 2006b. Anti-inflammatory activity of immunoglobulin G resulting from Fc sialylation. Science, 313, 670-3.

Kang, Y. S., Kim, J. Y., Bruening, S. A., Pack, M., Charalambous, A., Pritsker, A., Moran, T. M., Loeffler, J. M., Steinman, R. M. & Park, C. G. 2004. The C-type lectin SIGN-R1 mediates uptake of the capsular polysaccharide of Streptococcus pneumoniae in the marginal zone of mouse spleen. Proc Natl Acad Sci USA, 101, 215-20.

Korganow, A. S., Ji, H., Mangialaio, S., Duchatelle, V., Pelanda, R., Martin, T., Degott, C., Kikutani, H., Rajewsky, K., Pasquali, J. L., Benoist, C. & Mathis, D. 1999. From systemic T cell self-reactivity to organ-specific autoimmune disease via immunoglobulins. Immunity, 10, 451-61.

Lee, M. M., Nasirikenari, M., Manhardt, C. T., Ashline, D. J., Hanneman, A. J., Reinhold, V. N. & Lau, J. T. 2014. Platelets support extracellular sialylation by supplying the sugar donor substrate. J Biol Chem, 289, 8742-8.

Lerner, R. A., Glassock, R. J. & Dixon, F. J. 1967. The role of anti-glomerular basement membrane antibody in the pathogenesis of human glomerulonephritis. J Exp Med, 126, 989-1004.

Li, T., Dilillo, D. J., Bournazos, S., Giddens, J. P., Ravetch, J. V. & Wang, L. X. 2017. Modulating IgG effector function by Fc glycan engineering. Proc Natl Acad Sci USA, 114, 3485-3490.

Lu, L. L., Chung, A. W., Rosebrock, T. R., Ghebremichael, M., Yu, W. H., Grace, P. S., Schoen, M. K., Tafesse, F., Martin, C., Leung, V., Mahan, A. E., Sips, M., Kumar, M. P., Tedesco, J., Robinson, H., Tkachenko, E., Draghi, M., Freedberg, K. J., Streeck, H., Suscovich, T. J., Lauffenburger, D. A., Restrepo, B. I., Day, C., Fortune, S. M. & Alter, G. 2016. A Functional Role for Antibodies in Tuberculosis. Cell, 167, 433-443 e14.

Meng, L., Forouhar, F., Thieker, D., Gao, Z., Ramiah, A., Moniz, H., Xiang, Y., Seetharaman, J., Milaninia, S., Su, M., Bridger, R., Veillon, L., Azadi, P., Kornhaber, G., Wells, L., Montelione, G. T., Woods, R. J., Tong, L. & Moremen, K. W. 2013. Enzymatic basis for N-glycan sialylation: structure of rat alpha2,6-sialyltransferase (ST6GAL1) reveals conserved and unique features for glycan sialylation. J Biol Chem, 288, 34680-98.

Natsume, A., Wakitani, M., Yamane-Ohnuki, N., Shoji-Hosaka, E., Niwa, R., Uchida, K., Satoh, M. & Shitara, K. 2005. Fucose removal from complex-type oligosaccharide enhances the antibody-dependent cellular cytotoxicity of single-gene-encoded antibody comprising a single-chain antibody linked the antibody constant region. J Immunol Methods, 306, 93-103.

Negi, V. S., Elluru, S., Siberil, S., Graff-Dubois, S., Mouthon, L., Kazatchkine, M. D., Lacroix-Desmazes, S., Bayry, J. & Kaveri, S. V. 2007. Intravenous immunoglobulin: an update on the clinical use and mechanisms of action. J Clin Immunol, 27, 233-45.

Nimmerjahn, F., Gordan, S. & Lux, A. 2015. FcgammaR dependent mechanisms of cytotoxic, agonistic, and neutralizing antibody activities. Trends Immunol, 36, 325-36.

Nimmerjahn, F. & Ravetch, J. V. 2008a. Anti-inflammatory actions of intravenous immunoglobulin. Annu Rev Immunol, 26, 513-33.

Nimmerjahn, F. & Ravetch, J. V. 2008b. Fcgamma receptors as regulators of immune responses. Nat Rev Immunol, 8, 34-47.

Ohmi, Y., Ise, W., Harazono, A., Takakura, D., Fukuyama, H., Baba, Y., Narazaki, M., Shoda, H., Takahashi, N., Ohkawa, Y., Ji, S., Sugiyama, F., Fujio, K., Kumanogoh, A., Yamamoto, K., Kawasaki, N., Kurosaki, T., Takahashi, Y. & Furukawa, K. 2016. Sialylation converts arthritogenic IgG into inhibitors of collagen-induced arthritis. Nat Commun, 7, 11205.

Okazaki, A., Shoji-Hosaka, E., Nakamura, K., Wakitani, M., Uchida, K., Kakita, S., Tsumoto, K., Kumagai, I. & Shitara, K. 2004. Fucose depletion from human IgG1 oligosaccharide enhances binding enthalpy and association rate between IgG1 and FcgammaRIIIa. J Mol Biol, 336, 1239-49.

Pfeifle, R., Rothe, T., Ipseiz, N., Scherer, H. U., Culemann, S., Harre, U., Ackermann, J. A., Seefried, M., Kleyer, A., Uderhardt, S., Haugg, B., Hueber, A. J., Daum, P., Heidkamp, G. F., Ge, C., Bohm, S., Lux, A., Schuh, W., Magorivska, I., Nandakumar, K. S., Lonnblom, E., Becker, C., Dudziak, D., Wuhrer, M., Rombouts, Y., Koeleman, C. A., Toes, R., Winkler, T. H., Holmdahl, R., Herrmann, M., Bluml, S., Nimmerjahn, F., Schett, G. & Kronke, G. 2017. Regulation of autoantibody activity by the IL-23-TH17 axis determines the onset of autoimmune disease. Nat Immunol, 18, 104-113.

Pincetic, A., Bournazos, S., Dilillo, D. J., Maamary, J., Wang, T. T., Dahan, R., Fiebiger, B. M. & Ravetch, J. V. 2014. Type I and type II Fc receptors regulate innate and adaptive immunity. Nat Immunol, 15, 707-16.

Pucci, F., Rickelt, S., Newton, A. P., Garris, C., Nunes, E., Evavold, C., Pfirschke, C., Engblom, C., Mino-Kenudson, M., Hynes, R. O., Weissleder, R. & Pittet, M. J. 2016. PF4 Promotes Platelet Production and Lung Cancer Growth. Cell Rep, 17, 1764-1772.

Samuelsson, A., Towers, T. L. & Ravetch, J. V. 2001. Anti-inflammatory activity of IVIG mediated through the inhibitory Fc receptor. Science, 291, 484-6.

Scallon, B. J., Tam, S. H., Mccarthy, S. G., Cai, A. N. & Raju, T. S. 2007. Higher levels of sialylated Fc glycans in immunoglobulin G molecules can adversely impact functionality. Mol Immunol, 44, 1524-34.

Schlothauer, T., Herter, S., Koller, C. F., Grau-Richards, S., Steinhart, V., Spick, C., Kubbies, M., Klein, C., Umana, P. & Mossner, E. 2016. Novel human IgG1 and IgG4 Fc-engineered antibodies with completely abolished immune effector functions. Protein Eng Des Sel, 29, 457-466.

Schrijver, G., Bogman, M. J., Assmann, K. J., De Waal, R. M., Robben, H. C., Van Gasteren, H. & Koene, R. A. 1990. Anti-GBM nephritis in the mouse: role of granulocytes in the heterologous phase. Kidney Int, 38, 86-95.

Schwab, I., Biburger, M., Kronke, G., Schett, G. & Nimmerjahn, F. 2012. IVIg-mediated amelioration of ITP in mice is dependent on sialic acid and SIGNR1. Eur J Immunol, 42, 826-30.

Schwab, I., Mihai, S., Seeling, M., Kasperkiewicz, M., Ludwig, R. J. & Nimmerjahn, F. 2014. Broad requirement for terminal sialic acid residues and FcgammaRIIB for the preventive and therapeutic activity of intravenous immunoglobulins in vivo. Eur J Immunol, 44, 1444-53.

Schwab, I. & Nimmerjahn, F. 2013. Intravenous immunoglobulin therapy: how does IgG modulate the immune system? Nat Rev Immunol, 13, 176-89.

Shields, R. L., Lai, J., Keck, R., O'connell, L. Y., Hong, K., Meng, Y. G., Weikert, S. H. & Presta, L. G. 2002. Lack of fucose on human IgG1 N-linked oligosaccharide improves binding to human Fcgamma RIII and antibody-dependent cellular toxicity. J Biol Chem, 277, 26733-40.

Stadlmann, J., Weber, A., Pabst, M., Anderle, H., Kunert, R., Ehrlich, H. J., Peter Schwarz, H. & Altmann, F. 2009. A close look at human IgG sialylation and subclass distribution after lectin fractionation. Proteomics, 9, 4143-53.

Sugimoto, I., Futakawa, S., Oka, R., Ogawa, K., Marth, J. D., Miyoshi, E., Taniguchi, N., Hashimoto, Y. & Kitazume, S. 2007. Beta-galactoside alpha2,6-sialyltransferase I cleavage by BACE1 enhances the sialylation of soluble glycoproteins. A novel regulatory mechanism for alpha2,6-sialylation. J Biol Chem, 282, 34896-903.

Tackenberg, B., Jelcic, I., Baerenwaldt, A., Oertel, W. H., Sommer, N., Nimmerjahn, F. & Lunemann, J. D. 2009. Impaired inhibitory Fcgamma receptor IIB expression on B cells in chronic inflammatory demyelinating polyneuropathy. Proc Natl Acad Sci USA, 106, 4788-92.

Tackenberg, B., Nimmerjahn, F. & Lunemann, J. D. 2010. Mechanisms of IVIG efficacy in chronic inflammatory demyelinating polyneuropathy. J Clin Immunol, 30 Suppl 1, S65-9.

Tan, M., Yan, H. B., Li, J. N., Li, W. K., Fu, Y. Y., Chen, W. & Zhou, Z. 2016. Thrombin Stimulated Platelet-Derived Exosomes Inhibit Platelet-Derived Growth Factor Receptor-Beta Expression in Vascular Smooth Muscle Cells. Cell Physiol Biochem, 38, 2348-65.

Wang, T. T., Maamary, J., Tan, G. S., Bournazos, S., Davis, C. W., Krammer, F., Schlesinger, S. J., Palese, P., Ahmed, R. & Ravetch, J. V. 2015. Anti-HA Glycoforms Drive B Cell Affinity Selection and Determine Influenza Vaccine Efficacy. Cell, 162, 160-9.

Wang, T. T., Sewatanon, J., Memoli, M. J., Wrammert, J., Bournazos, S., Bhaumik, S. K., Pinsky, B. A., Chokephaibulkit, K., Onlamoon, N., Pattanapanyasat, K., Taubenberger, J. K., Ahmed, R. & Ravetch, J. V. 2017. IgG antibodies to dengue enhanced for FcgammaRIIIA binding determine disease severity. Science, 355, 395-398.

Wang, X., Vertino, A., Eddy, R. L., Byers, M. G., Jani-Sait, S. N., Shows, T. B. & Lau, J. T. 1993. Chromosome mapping and organization of the human beta-galactoside alpha 2,6-sialyltransferase gene. Differential and cell-type specific usage of upstream exon sequences in B-lymphoblastoid cells. J Biol Chem, 268, 4355-61.

Washburn, N., Schwab, I., Ortiz, D., Bhatnagar, N., Lansing, J. C., Medeiros, A., Tyler, S., Mekala, D., Cochran, E., Sarvaiya, H., Garofalo, K., Meccariello, R., Meador, J. W., 3rd, Rutitzky, L., Schultes, B. C., Ling, L., Avery, W., Nimmerjahn, F., Manning, A. M., Kaundinya, G. V. & Bosques, C. J. 2015. Controlled tetra-Fc sialylation of IVIg results in a drug candidate with consistent enhanced anti-inflammatory activity. Proc Natl Acad Sci USA, 112, E1297-306.

Woodard-Grice, A. V., Mcbrayer, A. C., Wakefield, J. K., Zhuo, Y. & Bellis, S. L. 2008. Proteolytic shedding of ST6Gal-I by BACE1 regulates the glycosylation and function of alpha4beta1 integrins. J Biol Chem, 283, 26364-73.

Xiao, H., Woods, E. C., Vukojicic, P. & Bertozzi, C. R. 2016. Precision glycocalyx editing as a strategy for cancer immunotherapy. Proc Natl Acad Sci USA, 113, 10304-9.

Yang, R., Otten, M. A., Hellmark, T., Collin, M., Bjorck, L., Zhao, M. H., Daha, M. R. & Segelmark, M. 2010. Successful treatment of experimental glomerulonephritis with IdeS and EndoS, IgG-degrading streptococcal enzymes. Nephrol Dial Transplant, 25, 2479-86.

Youings, A., Chang, S. C., Dwek, R. A. & Scragg, I. G. 1996. Site-specific glycosylation of human immunoglobulin G is altered in four rheumatoid arthritis patients. Biochem J, 314 (Pt 2), 621-30.

Zhang, G., Massaad, C. A., Gao, T., Pillai, L., Bogdanova, N., Ghauri, S. & Sheikh, K. A. 2016. Sialylated intravenous immunoglobulin suppress anti-ganglioside antibody mediated nerve injury. Exp Neurol, 282, 49-55.

---

What is claimed is:

1. A fusion polypeptide comprising:
   an antibody heavy chain CH2 region;
   an antibody heavy chain CH3 region; and
   a catalytic domain of a sialyltransferase, wherein the catalytic domain of the sialyltransferase catalyzes sialylation of a glycoprotein.

2. The fusion polypeptide of claim 1, wherein the sialyltransferase is beta-galactoside alpha-2,6 sialyltransferase 1.

3. The fusion polypeptide of claim 1, wherein the sialyltransferase is a human sialyltransferase.

4. The fusion polypeptide of claim 1, wherein the antibody heavy chain CH2 region is a human IgG heavy chain CH2 region.

5. The fusion polypeptide of claim 1, wherein the antibody heavy chain CH3 region is a human IgG heavy chain CH3 region.

6. A fusion polypeptide comprising:
   an antibody heavy chain CH2 region;
   an antibody heavy chain CH3 region; and
   a catalytic domain of a galactosyltransferase, wherein the catalytic domain of the galactosyltransferase catalyzes galactosylation of a glycoprotein.

7. The fusion polypeptide of claim 6, wherein the galactosyltransferase is beta-1,4-galactosyltransferase 1.

8. The fusion polypeptide of claim 6, wherein the galactosyltransferase is a human galactosyltransferase.

9. The fusion polypeptide of claim 6, wherein the antibody heavy chain CH2 region is a human IgG heavy chain CH2 region.

10. The fusion polypeptide of claim 6, wherein the antibody heavy chain CH3 region is a human IgG heavy chain CH3 region.

11. A polynucleotide encoding the fusion polypeptide of claim 1.

12. A vector comprising a polynucleotide encoding the fusion polypeptide of claim 1.

13. A cell comprising the vector of claim 12, and optionally expressing the fusion polypeptide of claim 1.

14. A multimer comprising
   a first fusion polypeptide comprising an antibody heavy chain CH2 region, an antibody heavy chain CH3 region, and a catalytic domain of sialyltransferase, wherein the catalytic domain of sialyltransferase catalyzes sialylation of a glycoprotein; and
   a second fusion polypeptide comprising an antibody heavy chain CH2 region, an antibody heavy chain CH3 region, and a catalytic domain of galactosyltransferase, wherein the catalytic domain of galactosyltransferase catalyzes galactosylation of a glycoprotein.

15. The multimer of claim 14, wherein the multimer is a dimer, and the first fusion polypeptide associates with the second fusion polypeptide, thereby forming the dimer.

16. The multimer of claim 14, wherein the sialyltransferase is beta-galactoside alpha-2,6 sialyltransferase 1.

17. The multimer of claim 14, wherein the sialyltransferase is a human sialyltransferase.

18. The multimer of claim 14, wherein the galactosyltransferase is beta-1,4-galactosyltransferase 1.

19. The multimer of claim 14, wherein the galactosyltransferase is a human galactosyltransferase.

20. A method of treating a subject having inflammation or autoimmune disease, the method comprising:
   administering to the subject an effective amount of a composition comprising the multimer of claim 14.

21. The method of claim 20, wherein the subject has inflammation.

22. The method of claim 20, wherein the subject has an autoimmune disease.

23. The method of claim 22, wherein the autoimmune disease is arthritis.

24. The method of claim 22, wherein the autoimmune disease is Goodpasture's disease.

25. The method of claim 22, wherein the autoimmune disease is nephrotoxic nephritis.

26. The method of claim 22, wherein the autoimmune disease is celiac disease, diabetes mellitus type 1, Graves disease, inflammatory bowel disease, multiple sclerosis, psoriasis, rheumatoid arthritis, or systemic lupus erythematosus.

27. A method of treating antibody-mediated injury during organ transplantation in a subject, the method comprising
   administering to the subject an effective amount of a composition comprising the multimer of claim 14.

28. The fusion protein of claim 1, wherein the catalytic domain of the sialyltransferase is fused to the C-terminus of the antibody heavy chain CH3 region.

29. The fusion protein of claim 6, wherein the catalytic domain of the galactosyltransferase is fused to the C-terminus of the antibody heavy chain CH3 region.

30. The multimer of claim 14, wherein the catalytic domain of the sialyltransferase is fused to the C-terminus of the antibody heavy chain CH3 region of the first fusion polypeptide, and the catalytic domain of the galactosyltransferase is fused to the C-terminus of the antibody heavy chain CH3 region of the second fusion polypeptide.

31. The multimer of claim 15, wherein the antibody heavy chain CH3 region of the first fusion polypeptide and the antibody heavy chain CH3 region of the second fusion polypeptide comprise one or more knobs-into-holes mutations.

* * * * *

UNITED STATES PATENT AND TRADEMARK OFFICE
CERTIFICATE OF CORRECTION

| | | |
|---|---|---|
| PATENT NO. | : 11,674,125 B2 | Page 1 of 1 |
| APPLICATION NO. | : 16/954814 | |
| DATED | : June 13, 2023 | |
| INVENTOR(S) | : Robert M. Anthony and Maya Kitaoka | |

It is certified that error appears in the above-identified patent and that said Letters Patent is hereby corrected as shown below:

In the Claims

In Column 152, Line 6, Claim 28, delete "protein" and insert -- polypeptide --

In Column 152, Line 9, Claim 29, delete "protein" and insert -- polypeptide --

Signed and Sealed this
Twenty-second Day of August, 2023

Katherine Kelly Vidal
Director of the United States Patent and Trademark Office

SEQUENCE LISTING

```
<160> NUMBER OF SEQ ID NOS: 43

<210> SEQ ID NO 1
<211> LENGTH: 406
<212> TYPE: PRT
<213> ORGANISM: Homo sapiens

<400> SEQUENCE: 1

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
                20                  25                  30

Ser Tyr Tyr Asp Ser Phe Lys Leu Gln Thr Lys Glu Phe Gln Val Leu
            35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
            115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
    195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
    275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
```

```
                    305                 310                 315                 320

Pro Ser Ser Gly Met Leu Gly Ile Ile Met Met Thr Leu Cys Asp
                        325                 330                 335

Gln Val Asp Ile Tyr Glu Phe Leu Pro Ser Lys Arg Lys Thr Asp Val
                        340                 345                 350

Cys Tyr Tyr Tyr Gln Lys Phe Phe Asp Ser Ala Cys Thr Met Gly Ala
                        355                 360                 365

Tyr His Pro Leu Leu Tyr Glu Lys Asn Leu Val Lys His Leu Asn Gln
                        370                 375                 380

Gly Thr Asp Glu Asp Ile Tyr Leu Leu Gly Lys Ala Thr Leu Pro Gly
        385                 390                 395                 400

Phe Arg Thr Ile His Cys
                        405

<210> SEQ ID NO 2
<211> LENGTH: 398
<212> TYPE: PRT
<213> ORGANISM: Homo sapiens

<400> SEQUENCE: 2

Met Arg Leu Arg Glu Pro Leu Leu Ser Gly Ser Ala Ala Met Pro Gly
        1               5                   10                  15

Ala Ser Leu Gln Arg Ala Cys Arg Leu Leu Val Ala Val Cys Ala Leu
                        20                  25                  30

His Leu Gly Val Thr Leu Val Tyr Tyr Leu Ala Gly Arg Asp Leu Ser
                        35                  40                  45

Arg Leu Pro Gln Leu Val Gly Val Ser Thr Pro Leu Gln Gly Gly Ser
        50                  55                  60

Asn Ser Ala Ala Ala Ile Gly Gln Ser Ser Gly Glu Leu Arg Thr Gly
        65                  70                  75                  80

Gly Ala Arg Pro Pro Pro Leu Gly Ala Ser Ser Gln Pro Arg Pro
                        85                  90                  95

Gly Gly Asp Ser Ser Pro Val Val Asp Ser Gly Pro Gly Pro Ala Ser
                        100                 105                 110

Asn Leu Thr Ser Val Pro Val Pro His Thr Thr Ala Leu Ser Leu Pro
                        115                 120                 125

Ala Cys Pro Glu Glu Ser Pro Leu Leu Val Gly Pro Met Leu Ile Glu
                        130                 135                 140

Phe Asn Met Pro Val Asp Leu Glu Leu Val Ala Lys Gln Asn Pro Asn
        145                 150                 155                 160

Val Lys Met Gly Gly Arg Tyr Ala Pro Arg Asp Cys Val Ser Pro His
                        165                 170                 175

Lys Val Ala Ile Ile Ile Pro Phe Arg Asn Arg Gln Glu His Leu Lys
                        180                 185                 190

Tyr Trp Leu Tyr Tyr Leu His Pro Val Leu Gln Arg Gln Gln Leu Asp
                        195                 200                 205

Tyr Gly Ile Tyr Val Ile Asn Gln Ala Gly Asp Thr Ile Phe Asn Arg
                        210                 215                 220

Ala Lys Leu Leu Asn Val Gly Phe Gln Glu Ala Leu Lys Asp Tyr Asp
        225                 230                 235                 240

Tyr Thr Cys Phe Val Phe Ser Asp Val Asp Leu Ile Pro Met Asn Asp
                        245                 250                 255

His Asn Ala Tyr Arg Cys Phe Ser Gln Pro Arg His Ile Ser Val Ala
                        260                 265                 270
```

```
Met Asp Lys Phe Gly Phe Ser Leu Pro Tyr Val Gln Tyr Phe Gly
            275                 280                 285

Val Ser Ala Leu Ser Lys Gln Gln Phe Leu Thr Ile Asn Gly Phe Pro
        290                 295                 300

Asn Asn Tyr Trp Gly Trp Gly Gly Glu Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
370                 375                 380

Pro Leu Tyr Thr Gln Ile Thr Val Asp Ile Gly Thr Pro Ser
385                 390                 395

<210> SEQ ID NO 3
<211> LENGTH: 256
<212> TYPE: PRT
<213> ORGANISM: Homo sapiens

<400> SEQUENCE: 3

Met Tyr Arg Met Gln Leu Leu Ser Cys Ile Ala Leu Ser Leu Ala Leu
1               5                   10                  15

Val Thr Asn Ser Met Pro Arg Gly Pro Pro Lys Ser Cys Asp Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Tyr Ser Lys Leu Thr Val Asp Lys Ser
    210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255
```

<210> SEQ ID NO 4
<211> LENGTH: 266
<212> TYPE: PRT
<213> ORGANISM: Homo sapiens

<400> SEQUENCE: 4

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ser Ser Asp Pro Arg Lys Cys Cys Val Glu Cys Pro Pro
        35                  40                  45

Cys Pro Ala Pro Pro Val Ala Gly Pro Ser Val Phe Leu Phe Pro Pro
    50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Gln Phe Asn Trp
                85                  90                  95

Tyr Val Asp Gly Val Glu Val His Asn Ala Lys Thr Lys Pro Arg Glu
            100                 105                 110

Glu Gln Phe Asn Ser Thr Phe Arg Val Val Ser Val Leu Thr Val Val
        115                 120                 125

His Gln Asp Trp Leu Asn Gly Lys Glu Tyr Lys Cys Lys Val Ser Asn
    130                 135                 140

Lys Gly Leu Pro Ala Pro Ile Glu Lys Thr Ile Ser Lys Thr Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Met Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
            260                 265

<210> SEQ ID NO 5
<211> LENGTH: 318
<212> TYPE: PRT
<213> ORGANISM: Homo sapiens

<400> SEQUENCE: 5

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ser Ser Asp Pro Glu Leu Lys Thr Pro Leu Gly Asp Thr
        35                  40                  45

Thr His Thr Cys Pro Arg Cys Pro Glu Pro Lys Ser Cys Asp Thr Pro
    50                  55                  60

Pro Pro Cys Pro Arg Cys Pro Glu Pro Lys Ser Cys Asp Thr Pro Pro
65                  70                  75                  80

Pro Cys Pro Arg Cys Pro Glu Pro Lys Ser Cys Asp Thr Pro Pro Pro
            85                  90                  95

Cys Pro Arg Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
        130                 135                 140

Gln Phe Lys Trp Tyr Val Asp Gly Val Glu Val His Asn Ala Lys Thr
145                 150                 155                 160

Lys Pro Arg Glu Glu Gln Tyr Asn Ser Thr Phe Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
            195                 200                 205

Lys Thr Lys Gly Gln Pro Arg Glu Pro Gln Val Tyr Thr Leu Pro Pro
    210                 215                 220

Ser Arg Glu Glu Met Thr Lys Asn Gln Val Ser Leu Thr Cys Leu Val
225                 230                 235                 240

Lys Gly Phe Tyr Pro Ser Asp Ile Ala Val Glu Trp Glu Ser Ser Gly
                245                 250                 255

Gln Pro Glu Asn Asn Tyr Asn Thr Thr Pro Pro Met Leu Asp Ser Asp
            260                 265                 270

Gly Ser Phe Phe Leu Tyr Ser Lys Leu Thr Val Asp Lys Ser Arg Trp
            275                 280                 285

Gln Gln Gly Asn Ile Phe Ser Cys Ser Val Met His Glu Ala Leu His
    290                 295                 300

Asn Arg Phe Thr Gln Lys Ser Leu Ser Leu Ser Pro Gly Lys
305                 310                 315

<210> SEQ ID NO 6
<211> LENGTH: 268
<212> TYPE: PRT
<213> ORGANISM: Homo sapiens

<400> SEQUENCE: 6

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ser Ser Asp Pro Glu Ser Lys Tyr Gly Pro Pro Cys Pro
        35                  40                  45

Ser Cys Pro Ala Pro Glu Phe Leu Gly Gly Pro Ser Val Phe Leu Phe
    50                  55                  60

Pro Pro Lys Pro Lys Asp Thr Leu Met Ile Ser Arg Thr Pro Glu Val
65                  70                  75                  80

Thr Cys Val Val Val Asp Val Ser Gln Glu Asp Pro Glu Val Gln Phe
            85                  90                  95

Asn Trp Tyr Val Asp Gly Val Glu Val His Asn Ala Lys Thr Lys Pro
            100                 105                 110

Arg Glu Glu Gln Phe Asn Ser Thr Tyr Arg Val Val Ser Val Leu Thr

```
            115                 120                 125
Val Leu His Gln Asp Trp Leu Asn Gly Lys Glu Tyr Lys Cys Lys Val
    130                 135                 140

Ser Asn Lys Gly Leu Pro Ser Ser Ile Glu Lys Thr Ile Ser Lys Ala
145                 150                 155                 160

Lys Gly Gln Pro Arg Glu Pro Gln Val Tyr Thr Leu Pro Pro Ser Gln
                165                 170                 175

Glu Glu Met Thr Lys Asn Gln Val Ser Leu Thr Cys Leu Val Lys Gly
            180                 185                 190

Phe Tyr Pro Ser Asp Ile Ala Val Glu Trp Glu Ser Asn Gly Gln Pro
        195                 200                 205

Glu Asn Asn Tyr Lys Thr Thr Pro Pro Val Leu Asp Ser Asp Gly Ser
    210                 215                 220

Phe Phe Leu Tyr Ser Arg Leu Thr Val Asp Lys Ser Arg Trp Gln Glu
225                 230                 235                 240

Gly Asn Val Phe Ser Cys Ser Val Met His Glu Ala Leu His Asn His
                245                 250                 255

Tyr Thr Gln Lys Ser Leu Ser Leu Ser Pro Gly Lys
            260                 265

<210> SEQ ID NO 7
<211> LENGTH: 252
<212> TYPE: PRT
<213> ORGANISM: Mus musculus

<400> SEQUENCE: 7

Met Tyr Arg Met Gln Leu Leu Ser Cys Ile Ala Leu Ser Leu Ala Leu
1               5                   10                  15

Val Thr Asn Ser Met Pro Arg Gly Pro Val Pro Arg Asp Cys Gly Cys
            20                  25                  30

Lys Pro Cys Ile Cys Thr Val Pro Glu Val Ser Ser Val Phe Ile Phe
        35                  40                  45

Pro Pro Lys Pro Lys Asp Val Leu Thr Ile Thr Leu Thr Pro Lys Val
    50                  55                  60

Thr Cys Val Val Val Asp Ile Ser Lys Asp Asp Pro Glu Val Gln Phe
65                  70                  75                  80

Ser Trp Phe Val Asp Asp Val Glu Val His Thr Ala Gln Thr Lys Pro
                85                  90                  95

Arg Glu Glu Gln Ile Asn Ser Thr Phe Arg Ser Val Ser Glu Leu Pro
            100                 105                 110

Ile Met His Gln Asp Trp Leu Asn Gly Lys Glu Phe Lys Cys Arg Val
        115                 120                 125

Asn Ser Ala Ala Phe Pro Ala Pro Ile Glu Lys Thr Ile Ser Lys Thr
    130                 135                 140

Lys Gly Arg Pro Lys Ala Pro Gln Val Tyr Thr Ile Pro Pro Pro Lys
145                 150                 155                 160

Glu Gln Met Ala Lys Asp Lys Val Ser Leu Thr Cys Met Ile Thr Asn
                165                 170                 175

Phe Phe Pro Glu Asp Ile Thr Val Glu Trp Gln Trp Asn Gly Gln Pro
            180                 185                 190

Ala Glu Asn Tyr Lys Asn Thr Gln Pro Ile Met Asp Thr Asp Gly Ser
        195                 200                 205

Tyr Phe Val Tyr Ser Lys Leu Asn Val Gln Lys Ser Asn Trp Glu Ala
    210                 215                 220
```

```
Gly Asn Thr Phe Thr Cys Ser Val Leu His Glu Gly Leu His Asn His
225                 230                 235                 240

His Thr Glu Lys Ser Leu Ser His Ser Pro Gly Lys
            245                 250
```

<210> SEQ ID NO 8
<211> LENGTH: 253
<212> TYPE: PRT
<213> ORGANISM: Mus musculus

<400> SEQUENCE: 8

```
Met Tyr Arg Met Gln Leu Leu Ser Cys Ile Ala Leu Ser Leu Ala Leu
1               5                   10                  15

Val Thr Asn Ser Met Pro Arg Gly Pro Thr Ile Lys Pro Cys Pro Pro
            20                  25                  30

Cys Lys Cys Pro Ala Pro Asn Leu Leu Gly Gly Pro Ser Val Phe Ile
        35                  40                  45

Phe Pro Pro Lys Ile Lys Asp Val Leu Met Ile Ser Leu Ser Pro Ile
    50                  55                  60

Val Thr Cys Val Val Val Asp Val Ser Glu Asp Asp Pro Asp Val Gln
65                  70                  75                  80

Ile Ser Trp Phe Val Asn Asn Val Glu Val His Thr Ala Gln Thr Gln
                85                  90                  95

Thr His Arg Glu Asp Tyr Asn Ser Thr Leu Arg Val Val Ser Ala Leu
            100                 105                 110

Pro Ile Gln His Gln Asp Trp Met Ser Gly Lys Glu Phe Lys Cys Lys
        115                 120                 125

Val Asn Asn Lys Asp Leu Pro Ala Pro Ile Glu Arg Thr Ile Ser Lys
    130                 135                 140

Pro Lys Gly Ser Val Arg Ala Pro Gln Val Tyr Val Leu Pro Pro Pro
145                 150                 155                 160

Glu Glu Glu Met Thr Lys Lys Gln Val Thr Leu Thr Cys Met Val Thr
                165                 170                 175

Asp Phe Met Pro Glu Asp Ile Tyr Val Glu Trp Thr Asn Asn Gly Lys
            180                 185                 190

Thr Glu Leu Asn Tyr Lys Asn Thr Glu Pro Val Leu Asp Ser Asp Gly
        195                 200                 205

Ser Tyr Phe Met Tyr Ser Lys Leu Arg Val Glu Lys Lys Asn Trp Val
    210                 215                 220

Glu Arg Asn Ser Tyr Ser Cys Ser Val Val His Glu Gly Leu His Asn
225                 230                 235                 240

His His Thr Thr Lys Ser Phe Ser Arg Thr Pro Gly Lys
                245                 250
```

<210> SEQ ID NO 9
<211> LENGTH: 259
<212> TYPE: PRT
<213> ORGANISM: Mus musculus

<400> SEQUENCE: 9

```
Met Tyr Arg Met Gln Leu Leu Ser Cys Ile Ala Leu Ser Leu Ala Leu
1               5                   10                  15

Val Thr Asn Ser Glu Pro Ser Gly Pro Ile Ser Thr Ile Asn Pro Cys
            20                  25                  30

Pro Pro Cys Lys Glu Cys His Lys Cys Pro Ala Pro Asn Leu Glu Gly
        35                  40                  45
```

-continued

```
Gly Pro Ser Val Phe Ile Phe Pro Pro Asn Ile Lys Asp Val Leu Met
     50                  55                  60

Ile Ser Leu Thr Pro Lys Val Thr Cys Val Val Val Asp Val Ser Glu
 65                  70                  75                  80

Asp Asp Pro Asp Val Arg Ile Ser Trp Phe Val Asn Asn Val Glu Val
                 85                  90                  95

His Thr Ala Gln Thr Gln Thr His Arg Glu Asp Tyr Asn Ser Thr Ile
            100                 105                 110

Arg Val Val Ser Ala Leu Pro Ile Gln His Gln Asp Trp Met Ser Gly
        115                 120                 125

Lys Glu Phe Lys Cys Lys Val Asn Asn Lys Asp Leu Pro Ser Pro Ile
130                 135                 140

Glu Arg Thr Ile Ser Lys Ile Lys Gly Leu Val Arg Ala Pro Gln Val
145                 150                 155                 160

Tyr Ile Leu Pro Pro Pro Ala Glu Gln Leu Ser Arg Lys Asp Val Ser
                165                 170                 175

Leu Thr Cys Leu Val Val Gly Phe Asn Pro Gly Asp Ile Ser Val Glu
            180                 185                 190

Trp Thr Ser Asn Gly His Thr Glu Glu Asn Tyr Lys Asp Thr Ala Pro
        195                 200                 205

Val Leu Asp Ser Asp Gly Ser Tyr Phe Ile Tyr Ser Lys Leu Asp Ile
210                 215                 220

Lys Thr Ser Lys Trp Glu Lys Thr Asp Ser Phe Ser Cys Asn Val Arg
225                 230                 235                 240

His Glu Gly Leu Lys Asn Tyr Tyr Leu Lys Lys Thr Ile Ser Arg Ser
                245                 250                 255

Pro Gly Lys
```

<210> SEQ ID NO 10
<211> LENGTH: 253
<212> TYPE: PRT
<213> ORGANISM: Mus musculus

<400> SEQUENCE: 10

```
Met Tyr Arg Met Gln Leu Leu Ser Cys Ile Ala Leu Ser Leu Ala Leu
  1               5                  10                  15

Val Thr Asn Ser Glu Pro Arg Ile Pro Lys Pro Ser Thr Pro Pro Gly
             20                  25                  30

Ser Ser Cys Pro Pro Gly Asn Ile Leu Gly Gly Pro Ser Val Phe Ile
         35                  40                  45

Phe Pro Pro Lys Pro Lys Asp Ala Leu Met Ile Ser Leu Thr Pro Lys
 50                  55                  60

Val Thr Cys Val Val Val Asp Val Ser Glu Asp Asp Pro Asp Val His
 65                  70                  75                  80

Val Ser Trp Phe Val Asp Asn Lys Glu Val His Thr Ala Trp Thr Gln
                 85                  90                  95

Pro Arg Glu Ala Gln Tyr Asn Ser Thr Phe Arg Val Val Ser Ala Leu
            100                 105                 110

Pro Ile Gln His Gln Asp Trp Met Arg Gly Lys Glu Phe Lys Cys Lys
        115                 120                 125

Val Asn Asn Lys Ala Leu Pro Ala Pro Ile Glu Arg Thr Ile Ser Lys
130                 135                 140

Pro Lys Gly Arg Ala Gln Thr Pro Gln Val Tyr Thr Ile Pro Pro Pro
145                 150                 155                 160
```

```
Arg Glu Gln Met Ser Lys Lys Val Ser Leu Thr Cys Leu Val Thr
            165                 170                 175
Asn Phe Phe Ser Glu Ala Ile Ser Val Glu Trp Glu Arg Asn Gly Glu
        180                 185                 190
Leu Glu Gln Asp Tyr Lys Asn Thr Pro Pro Ile Leu Asp Ser Asp Gly
            195                 200                 205
Thr Tyr Phe Leu Tyr Ser Lys Leu Thr Val Asp Thr Asp Ser Trp Leu
210                 215                 220
Gln Gly Glu Ile Phe Thr Cys Ser Val Val His Glu Ala Leu His Asn
225                 230                 235                 240
His His Thr Gln Lys Asn Leu Ser Arg Ser Pro Gly Lys
            245                 250

<210> SEQ ID NO 11
<211> LENGTH: 619
<212> TYPE: PRT
<213> ORGANISM: Artificial Sequence
<220> FEATURE:
<223> OTHER INFORMATION: human IgG Fc - B4GALT1 fusion protein

<400> SEQUENCE: 11

Met Tyr Arg Met Gln Leu Leu Ser Cys Ile Ala Leu Ser Leu Ala Leu
1               5                   10                  15
Val Thr Asn Ser Met Pro Arg Gly Pro Pro Lys Ser Cys Asp Lys Thr
            20                  25                  30
His Thr Cys Pro Pro Cys Pro Ala Pro Glu Leu Leu Gly Gly Pro Ser
        35                  40                  45
Val Phe Leu Phe Pro Pro Lys Pro Lys Asp Thr Leu Met Ile Ser Arg
    50                  55                  60
Thr Pro Glu Val Thr Cys Val Val Val Asp Val Ser His Glu Asp Pro
65                  70                  75                  80
Glu Val Lys Phe Asn Trp Tyr Val Asp Gly Val Glu Val His Asn Ala
                85                  90                  95
Lys Thr Lys Pro Arg Glu Glu Gln Tyr Asn Ser Thr Tyr Arg Val Val
            100                 105                 110
Ser Val Leu Thr Val Leu His Gln Asp Trp Leu Asn Gly Lys Glu Tyr
        115                 120                 125
Lys Cys Lys Val Ser Asn Lys Ala Leu Pro Ala Pro Ile Glu Lys Thr
    130                 135                 140
Ile Ser Lys Ala Lys Gly Gln Pro Arg Glu Pro Gln Val Tyr Thr Leu
145                 150                 155                 160
Pro Pro Ser Arg Asp Glu Leu Thr Lys Asn Gln Val Ser Leu Thr Cys
                165                 170                 175
Leu Val Lys Gly Phe Tyr Pro Ser Asp Ile Ala Val Glu Trp Glu Ser
            180                 185                 190
Asn Gly Gln Pro Glu Asn Asn Tyr Lys Thr Thr Pro Pro Val Leu Asp
        195                 200                 205
Ser Asp Gly Ser Phe Phe Leu Tyr Ser Lys Leu Thr Val Asp Lys Ser
    210                 215                 220
Arg Trp Gln Gln Gly Asn Val Phe Ser Cys Ser Val Met His Glu Ala
225                 230                 235                 240
Leu His Asn His Tyr Thr Gln Lys Ser Leu Ser Leu Ser Pro Gly Lys
                245                 250                 255
Gly Ala Pro Asp Leu Lys Leu Met Gly Arg Asp Leu Ser Arg Leu Pro
            260                 265                 270
```

Gln Leu Val Gly Val Ser Thr Pro Leu Gln Gly Gly Ser Asn Ser Ala
                275                 280                 285

Ala Ala Ile Gly Gln Ser Ser Gly Glu Leu Arg Thr Gly Gly Ala Arg
            290                 295                 300

Pro Pro Pro Pro Leu Gly Ala Ser Ser Gln Pro Arg Pro Gly Gly Asp
305                 310                 315                 320

Ser Ser Pro Val Val Asp Ser Gly Pro Gly Pro Ala Ser Asn Leu Thr
                325                 330                 335

Ser Val Pro Val Pro His Thr Thr Ala Leu Ser Leu Pro Ala Cys Pro
                340                 345                 350

Glu Glu Ser Pro Leu Leu Val Gly Pro Met Leu Ile Glu Phe Asn Met
                355                 360                 365

Pro Val Asp Leu Glu Leu Val Ala Lys Gln Asn Pro Asn Val Lys Met
            370                 375                 380

Gly Gly Arg Tyr Ala Pro Arg Asp Cys Val Ser Pro His Lys Val Ala
385                 390                 395                 400

Ile Ile Ile Pro Phe Arg Asn Arg Gln Glu His Leu Lys Tyr Trp Leu
                405                 410                 415

Tyr Tyr Leu His Pro Val Leu Gln Arg Gln Gln Leu Asp Tyr Gly Ile
                420                 425                 430

Tyr Val Ile Asn Gln Ala Gly Asp Thr Ile Phe Asn Arg Ala Lys Leu
            435                 440                 445

Leu Asn Val Gly Phe Gln Glu Ala Leu Lys Asp Tyr Asp Tyr Thr Cys
            450                 455                 460

Phe Val Phe Ser Asp Val Asp Leu Ile Pro Met Asn Asp His Asn Ala
465                 470                 475                 480

Tyr Arg Cys Phe Ser Gln Pro Arg His Ile Ser Val Ala Met Asp Lys
                485                 490                 495

Phe Gly Phe Ser Leu Pro Tyr Val Gln Tyr Phe Gly Gly Val Ser Ala
                500                 505                 510

Leu Ser Lys Gln Gln Phe Leu Thr Ile Asn Gly Phe Pro Asn Asn Tyr
            515                 520                 525

Trp Gly Trp Gly Gly Glu Asp Asp Asp Ile Phe Asn Arg Leu Val Phe
530                 535                 540

Arg Gly Met Ser Ile Ser Arg Pro Asn Ala Val Val Gly Arg Cys Arg
545                 550                 555                 560

Met Ile Arg His Ser Arg Asp Lys Lys Asn Glu Pro Asn Pro Gln Arg
                565                 570                 575

Phe Asp Arg Ile Ala His Thr Lys Glu Thr Met Leu Ser Asp Gly Leu
            580                 585                 590

Asn Ser Leu Thr Tyr Gln Val Leu Asp Val Gln Arg Tyr Pro Leu Tyr
            595                 600                 605

Thr Gln Ile Thr Val Asp Ile Gly Thr Pro Ser
            610                 615

<210> SEQ ID NO 12
<211> LENGTH: 627
<212> TYPE: PRT
<213> ORGANISM: Artificial Sequence
<220> FEATURE:
<223> OTHER INFORMATION: human IgG1 Fc - ST6GAL1 fusion protein

<400> SEQUENCE: 12

Met Tyr Arg Met Gln Leu Leu Ser Cys Ile Ala Leu Ser Leu Ala Leu
1               5                   10                  15

```
Val Thr Asn Ser Met Pro Arg Gly Pro Pro Lys Ser Cys Asp Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
                100                 105                 110

Ser Val Leu Thr Val Leu His Gln Asp Trp Leu Asn Gly Lys Glu Tyr
            115                 120                 125

Lys Cys Lys Val Ser Asn Lys Ala Leu Pro Ala Pro Ile Glu Lys Thr
        130                 135                 140

Ile Ser Lys Ala Lys Gly Gln Pro Arg Glu Pro Gln Val Tyr Thr Leu
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Tyr Ser Lys Leu Thr Val Asp Lys Ser
210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255

Gly Ala Pro Asp Leu Lys Leu Met Glu Phe Gln Val Leu Lys Ser Leu
            260                 265                 270

Gly Lys Leu Ala Met Gly Ser Asp Ser Gln Ser Val Ser Ser Ser Ser
        275                 280                 285

Thr Gln Asp Pro His Arg Gly Arg Gln Thr Leu Gly Ser Leu Arg Gly
    290                 295                 300

Leu Ala Lys Ala Lys Pro Glu Ala Ser Phe Gln Val Trp Asn Lys Asp
305                 310                 315                 320

Ser Ser Ser Lys Asn Leu Ile Pro Arg Leu Gln Lys Ile Trp Lys Asn
                325                 330                 335

Tyr Leu Ser Met Asn Lys Tyr Lys Val Ser Tyr Lys Gly Pro Gly Pro
                340                 345                 350

Gly Ile Lys Phe Ser Ala Glu Ala Leu Arg Cys His Leu Arg Asp His
        355                 360                 365

Val Asn Val Ser Met Val Glu Val Thr Asp Phe Pro Phe Asn Thr Ser
    370                 375                 380

Glu Trp Glu Gly Tyr Leu Pro Lys Glu Ser Ile Arg Thr Lys Ala Gly
385                 390                 395                 400

Pro Trp Gly Arg Cys Ala Val Val Ser Ala Gly Ser Leu Lys Ser
                405                 410                 415

Ser Gln Leu Gly Arg Glu Ile Asp Asp His Asp Ala Val Leu Arg Phe
        420                 425                 430

Asn Gly Ala Pro Thr Ala Asn Phe Gln Gln Asp Val Gly Thr Lys Thr
```

-continued

```
                435                 440                 445
Thr Ile Arg Leu Met Asn Ser Gln Leu Val Thr Thr Glu Lys Arg Phe
450                 455                 460
Leu Lys Asp Ser Leu Tyr Asn Glu Gly Ile Leu Ile Val Trp Asp Pro
465                 470                 475                 480
Ser Val Tyr His Ser Asp Ile Pro Lys Trp Tyr Gln Asn Pro Asp Tyr
                485                 490                 495
Asn Phe Phe Asn Asn Tyr Lys Thr Tyr Arg Lys Leu His Pro Asn Gln
                500                 505                 510
Pro Phe Tyr Ile Leu Lys Pro Gln Met Pro Trp Glu Leu Trp Asp Ile
                515                 520                 525
Leu Gln Glu Ile Ser Pro Glu Glu Ile Gln Pro Asn Pro Pro Ser Ser
530                 535                 540
Gly Met Leu Gly Ile Ile Ile Met Met Thr Leu Cys Asp Gln Val Asp
545                 550                 555                 560
Ile Tyr Glu Phe Leu Pro Ser Lys Arg Lys Thr Asp Val Cys Tyr Tyr
                565                 570                 575
Tyr Gln Lys Phe Phe Asp Ser Ala Cys Thr Met Gly Ala Tyr His Pro
                580                 585                 590
Leu Leu Tyr Glu Lys Asn Leu Val Lys His Leu Asn Gln Gly Thr Asp
                595                 600                 605
Glu Asp Ile Tyr Leu Leu Gly Lys Ala Thr Leu Pro Gly Phe Arg Thr
610                 615                 620
Ile His Cys
625

<210> SEQ ID NO 13
<211> LENGTH: 611
<212> TYPE: PRT
<213> ORGANISM: Artificial Sequence
<220> FEATURE:
<223> OTHER INFORMATION: mouse IgG1 Fc - B4GALT1 fusion protein

<400> SEQUENCE: 13

Met Tyr Arg Met Gln Leu Leu Ser Cys Ile Ala Leu Ser Leu Ala Leu
1               5                   10                  15
Val Thr Asn Ser Met Val Pro Arg Asp Cys Gly Cys Lys Pro Cys Ile
                20                  25                  30
Cys Thr Val Pro Glu Val Ser Ser Val Phe Ile Phe Pro Pro Lys Pro
                35                  40                  45
Lys Asp Val Leu Thr Ile Thr Leu Thr Pro Lys Val Thr Cys Val Val
50                  55                  60
Val Asp Ile Ser Lys Asp Asp Pro Glu Val Gln Phe Ser Trp Phe Val
65                  70                  75                  80
Asp Asp Val Glu Val His Thr Ala Gln Thr Lys Pro Arg Glu Glu Gln
                85                  90                  95
Ile Asn Ser Thr Phe Arg Ser Val Ser Glu Leu Pro Ile Met His Gln
                100                 105                 110
Asp Trp Leu Asn Gly Lys Glu Phe Lys Cys Arg Val Asn Ser Ala Ala
                115                 120                 125
Phe Pro Ala Pro Ile Glu Lys Thr Ile Ser Lys Thr Lys Gly Arg Pro
                130                 135                 140
Lys Ala Pro Gln Val Tyr Thr Ile Pro Pro Lys Glu Gln Met Ala
145                 150                 155                 160
Lys Asp Lys Val Ser Leu Thr Cys Met Ile Thr Asn Phe Phe Pro Glu
```

```
                165                 170                 175
Asp Ile Thr Val Glu Trp Gln Trp Asn Gly Gln Pro Ala Glu Asn Tyr
                180                 185                 190

Lys Asn Thr Gln Pro Ile Met Asp Thr Asp Gly Ser Tyr Phe Val Tyr
                195                 200                 205

Ser Lys Leu Asn Val Gln Lys Ser Asn Trp Glu Ala Gly Asn Thr Phe
            210                 215                 220

Thr Cys Ser Val Leu His Glu Gly Leu His Asn His Thr Glu Lys
225                 230                 235                 240

Ser Leu Ser His Ser Pro Gly Lys Gly Ala Pro Asp Leu Lys Leu Met
                245                 250                 255

Gly Arg Asp Leu Ser Arg Leu Pro Gln Leu Val Gly Val Ser Thr Pro
                260                 265                 270

Leu Gln Gly Gly Ser Asn Ser Ala Ala Ile Gly Gln Ser Ser Gly
            275                 280                 285

Glu Leu Arg Thr Gly Gly Ala Arg Pro Pro Pro Leu Gly Ala Ser
            290                 295                 300

Ser Gln Pro Arg Pro Gly Gly Asp Ser Ser Pro Val Val Asp Ser Gly
305                 310                 315                 320

Pro Gly Pro Ala Ser Asn Leu Thr Ser Val Pro Val Pro His Thr Thr
                325                 330                 335

Ala Leu Ser Leu Pro Ala Cys Pro Glu Glu Ser Pro Leu Leu Val Gly
                340                 345                 350

Pro Met Leu Ile Glu Phe Asn Met Pro Val Asp Leu Glu Leu Val Ala
                355                 360                 365

Lys Gln Asn Pro Asn Val Lys Met Gly Gly Arg Tyr Ala Pro Arg Asp
                370                 375                 380

Cys Val Ser Pro His Lys Val Ala Ile Ile Pro Phe Arg Asn Arg
385                 390                 395                 400

Gln Glu His Leu Lys Tyr Trp Leu Tyr Tyr Leu His Pro Val Leu Gln
                405                 410                 415

Arg Gln Gln Leu Asp Tyr Gly Ile Tyr Val Ile Asn Gln Ala Gly Asp
                420                 425                 430

Thr Ile Phe Asn Arg Ala Lys Leu Leu Asn Val Gly Phe Gln Glu Ala
            435                 440                 445

Leu Lys Asp Tyr Asp Tyr Thr Cys Phe Val Phe Ser Asp Val Asp Leu
            450                 455                 460

Ile Pro Met Asn Asp His Asn Ala Tyr Arg Cys Phe Ser Gln Pro Arg
465                 470                 475                 480

His Ile Ser Val Ala Met Asp Lys Phe Gly Phe Ser Leu Pro Tyr Val
                485                 490                 495

Gln Tyr Phe Gly Gly Val Ser Ala Leu Ser Lys Gln Gln Phe Leu Thr
                500                 505                 510

Ile Asn Gly Phe Pro Asn Asn Tyr Trp Gly Trp Gly Gly Glu Asp Asp
            515                 520                 525

Asp Ile Phe Asn Arg Leu Val Phe Arg Gly Met Ser Ile Ser Arg Pro
            530                 535                 540

Asn Ala Val Val Gly Arg Cys Arg Met Ile Arg His Ser Arg Asp Lys
545                 550                 555                 560

Lys Asn Glu Pro Asn Pro Gln Arg Phe Asp Arg Ile Ala His Thr Lys
                565                 570                 575

Glu Thr Met Leu Ser Asp Gly Leu Asn Ser Leu Thr Tyr Gln Val Leu
                580                 585                 590
```

```
Asp Val Gln Arg Tyr Pro Leu Tyr Thr Gln Ile Thr Val Asp Ile Gly
        595                 600                 605

Thr Pro Ser
    610

<210> SEQ ID NO 14
<211> LENGTH: 623
<212> TYPE: PRT
<213> ORGANISM: Artificial Sequence
<220> FEATURE:
<223> OTHER INFORMATION: mouse IgG1 Fc - ST6GAL1 fusion protein

<400> SEQUENCE: 14

Met Tyr Arg Met Gln Leu Leu Ser Cys Ile Ala Leu Ser Leu Ala Leu
1               5                   10                  15

Val Thr Asn Ser Met Pro Arg Gly Pro Val Pro Arg Asp Cys Gly Cys
            20                  25                  30

Lys Pro Cys Ile Cys Thr Val Pro Glu Val Ser Ser Val Phe Ile Phe
            35                  40                  45

Pro Pro Lys Pro Lys Asp Val Leu Thr Ile Thr Leu Thr Pro Lys Val
    50                  55                  60

Thr Cys Val Val Val Asp Ile Ser Lys Asp Asp Pro Glu Val Gln Phe
65                  70                  75                  80

Ser Trp Phe Val Asp Asp Val Glu Val His Thr Ala Gln Thr Lys Pro
                85                  90                  95

Arg Glu Glu Gln Ile Asn Ser Thr Phe Arg Ser Val Ser Glu Leu Pro
            100                 105                 110

Ile Met His Gln Asp Trp Leu Asn Gly Lys Glu Phe Lys Cys Arg Val
        115                 120                 125

Asn Ser Ala Ala Phe Pro Ala Pro Ile Glu Lys Thr Ile Ser Lys Thr
    130                 135                 140

Lys Gly Arg Pro Lys Ala Pro Gln Val Tyr Thr Ile Pro Pro Pro Lys
145                 150                 155                 160

Glu Gln Met Ala Lys Asp Lys Val Ser Leu Thr Cys Met Ile Thr Asn
                165                 170                 175

Phe Phe Pro Glu Asp Ile Thr Val Glu Trp Gln Trp Asn Gly Gln Pro
            180                 185                 190

Ala Glu Asn Tyr Lys Asn Thr Gln Pro Ile Met Asp Thr Asp Gly Ser
        195                 200                 205

Tyr Phe Val Tyr Ser Lys Leu Asn Val Gln Lys Ser Asn Trp Glu Ala
    210                 215                 220

Gly Asn Thr Phe Thr Cys Ser Val Leu His Glu Gly Leu His Asn His
225                 230                 235                 240

His Thr Glu Lys Ser Leu Ser His Ser Pro Gly Lys Gly Ala Pro Asp
                245                 250                 255

Leu Lys Leu Met Glu Phe Gln Val Leu Lys Ser Leu Gly Lys Leu Ala
            260                 265                 270

Met Gly Ser Asp Ser Gln Ser Val Ser Ser Ser Thr Gln Asp Pro
        275                 280                 285

His Arg Gly Arg Gln Thr Leu Gly Ser Leu Arg Gly Leu Ala Lys Ala
    290                 295                 300

Lys Pro Glu Ala Ser Phe Gln Val Trp Asn Lys Asp Ser Ser Ser Lys
305                 310                 315                 320

Asn Leu Ile Pro Arg Leu Gln Lys Ile Trp Lys Asn Tyr Leu Ser Met
                325                 330                 335
```

```
Asn Lys Tyr Lys Val Ser Tyr Lys Gly Pro Gly Pro Gly Ile Lys Phe
            340                 345                 350

Ser Ala Glu Ala Leu Arg Cys His Leu Arg Asp His Val Asn Val Ser
        355                 360                 365

Met Val Glu Val Thr Asp Phe Pro Phe Asn Thr Ser Glu Trp Glu Gly
    370                 375                 380

Tyr Leu Pro Lys Glu Ser Ile Arg Thr Lys Ala Gly Pro Trp Gly Arg
385                 390                 395                 400

Cys Ala Val Val Ser Ser Ala Gly Ser Leu Lys Ser Ser Gln Leu Gly
                405                 410                 415

Arg Glu Ile Asp Asp His Asp Ala Val Leu Arg Phe Asn Gly Ala Pro
            420                 425                 430

Thr Ala Asn Phe Gln Gln Asp Val Gly Thr Lys Thr Thr Ile Arg Leu
        435                 440                 445

Met Asn Ser Gln Leu Val Thr Thr Glu Lys Arg Phe Leu Lys Asp Ser
    450                 455                 460

Leu Tyr Asn Glu Gly Ile Leu Ile Val Trp Asp Pro Ser Val Tyr His
465                 470                 475                 480

Ser Asp Ile Pro Lys Trp Tyr Gln Asn Pro Asp Tyr Asn Phe Phe Asn
                485                 490                 495

Asn Tyr Lys Thr Tyr Arg Lys Leu His Pro Asn Gln Pro Phe Tyr Ile
            500                 505                 510

Leu Lys Pro Gln Met Pro Trp Glu Leu Trp Asp Ile Leu Gln Glu Ile
        515                 520                 525

Ser Pro Glu Glu Ile Gln Pro Asn Pro Pro Ser Ser Gly Met Leu Gly
    530                 535                 540

Ile Ile Ile Met Met Thr Leu Cys Asp Gln Val Asp Ile Tyr Glu Phe
545                 550                 555                 560

Leu Pro Ser Lys Arg Lys Thr Asp Val Cys Tyr Tyr Gln Lys Phe
                565                 570                 575

Phe Asp Ser Ala Cys Thr Met Gly Ala Tyr His Pro Leu Leu Tyr Glu
            580                 585                 590

Lys Asn Leu Val Lys His Leu Asn Gln Gly Thr Asp Glu Asp Ile Tyr
        595                 600                 605

Leu Leu Gly Lys Ala Thr Leu Pro Gly Phe Arg Thr Ile His Cys
    610                 615                 620

<210> SEQ ID NO 15
<211> LENGTH: 600
<212> TYPE: PRT
<213> ORGANISM: Artificial Sequence
<220> FEATURE:
<223> OTHER INFORMATION: canine IgG-A (IgG1) Fc - ST6GAL1 fusion protein

<400> SEQUENCE: 15

Met Tyr Arg Met Gln Leu Leu Ser Cys Ile Ala Leu Ser Leu Ala Leu
1               5                   10                  15

Val Thr Asn Ser Pro Pro Cys Pro Val Pro Glu Pro Leu Gly Gly Pro
            20                  25                  30

Ser Val Leu Ile Phe Pro Pro Lys Pro Lys Asp Ile Leu Arg Ile Thr
        35                  40                  45

Arg Thr Pro Glu Val Thr Cys Val Val Leu Asp Leu Gly Arg Glu Asp
    50                  55                  60

Pro Glu Val Gln Ile Ser Trp Phe Val Asp Gly Lys Glu Val His Thr
65                  70                  75                  80
```

-continued

```
Ala Lys Thr Gln Ser Arg Glu Gln Gln Phe Asn Gly Thr Tyr Arg Val
                85                  90                  95

Val Ser Val Leu Pro Ile Glu His Gln Asp Trp Leu Thr Gly Lys Glu
            100                 105                 110

Phe Lys Cys Arg Val Asn His Ile Asp Leu Pro Ser Pro Ile Glu Arg
        115                 120                 125

Thr Ile Ser Lys Ala Arg Gly Arg Ala His Lys Pro Ser Val Tyr Val
    130                 135                 140

Leu Pro Pro Ser Pro Lys Glu Leu Ser Ser Ser Asp Thr Val Ser Ile
145                 150                 155                 160

Thr Cys Leu Ile Lys Asp Phe Tyr Pro Pro Asp Ile Asp Val Glu Trp
                165                 170                 175

Gln Ser Asn Gly Gln Gln Glu Pro Glu Arg Lys His Arg Met Thr Pro
            180                 185                 190

Pro Gln Leu Asp Glu Asp Gly Ser Tyr Phe Leu Tyr Ser Lys Leu Ser
        195                 200                 205

Val Asp Lys Ser Arg Trp Gln Gln Gly Asp Pro Phe Thr Cys Ala Val
    210                 215                 220

Met His Glu Thr Leu Gln Asn His Tyr Thr Asp Leu Ser Leu Ser His
225                 230                 235                 240

Ser Pro Gly Lys Glu Phe Gln Met Val Arg Gly Leu Glu Lys Gln Ala
                245                 250                 255

Ala Thr Leu Ser Ser Thr Gln Asn Pro Pro Arg Ala Ser Gln Ala Leu
            260                 265                 270

Gly Ser Pro Arg Gly Pro Val Lys Ala Lys Ser Glu Ala Ser Phe Gln
        275                 280                 285

Val Trp Asn Lys Asp Ser Ser Ser Lys Asn Leu Ile Pro Arg Leu Gln
    290                 295                 300

Lys Ile Trp Arg Asn Tyr Leu Asn Met Asn Lys Tyr Lys Val Ser Tyr
305                 310                 315                 320

Lys Gly Pro Gly Pro Gly Val Lys Phe Ser Ala Glu Ala Leu His Cys
                325                 330                 335

His Leu Arg Asp His Val Asn Val Ser Met Val Glu Ala Thr Asp Phe
            340                 345                 350

Pro Phe Asn Thr Ser Glu Trp Glu Gly Phe Leu Pro Lys Glu Asn Ile
        355                 360                 365

Arg Thr Lys Ala Gly Pro Trp Gly Arg Cys Ala Val Val Ser Ser Ala
    370                 375                 380

Gly Ser Leu Lys Ser Ser Gln Leu Gly Arg Glu Ile Asp Asp His Asp
385                 390                 395                 400

Ala Val Leu Arg Phe Asn Gly Ala Pro Thr Ala Ser Phe Gln Gln Asp
                405                 410                 415

Val Gly Thr Lys Thr Thr Ile Arg Leu Met Asn Ser Gln Leu Val Thr
            420                 425                 430

Thr Glu Gly Arg Phe Leu Lys Asp Ser Leu Tyr Asn Glu Gly Ile Leu
        435                 440                 445

Ile Val Trp Asp Pro Ser Val Tyr His Ser Asp Ile Pro Lys Trp Tyr
    450                 455                 460

Gln Ser Pro Asp Tyr Ser Phe Phe Glu Asn Tyr Lys Ser Tyr Arg Lys
465                 470                 475                 480

Leu His Pro Asp Gln Pro Phe Tyr Ile Leu Lys Pro Gln Met Pro Trp
                485                 490                 495
```

```
Glu Leu Trp Asp Ile Ile Gln Glu Val Ser Pro Glu Ile Gln Pro
                500                 505                 510

Asn Pro Pro Ser Ser Gly Met Leu Gly Ile Ile Ile Met Met Thr Leu
            515                 520                 525

Cys Asp Gln Val Asp Ile Tyr Glu Phe Leu Pro Ser Lys Arg Lys Thr
    530                 535                 540

Asp Val Cys Tyr Tyr Tyr Gln Lys Phe Phe Asp Ser Ala Cys Thr Met
545                 550                 555                 560

Gly Ala Tyr His Pro Leu Leu Phe Glu Lys Asn Leu Val Lys His Leu
                565                 570                 575

Asn Gln Gly Thr Asp Glu Asp Ile Tyr Leu Leu Gly Lys Ala Thr Leu
            580                 585                 590

Pro Gly Phe Arg Arg Ile Arg Cys
        595                 600

<210> SEQ ID NO 16
<211> LENGTH: 502
<212> TYPE: PRT
<213> ORGANISM: Artificial Sequence
<220> FEATURE:
<223> OTHER INFORMATION: canine IgG-A(IgG1) Fc - B4GALT1 fusion protein

<400> SEQUENCE: 16

Met Tyr Arg Met Gln Leu Leu Ser Cys Ile Ala Leu Ser Leu Ala Leu
1               5                   10                  15

Val Thr Asn Ser Pro Pro Cys Pro Val Pro Glu Pro Leu Gly Gly Pro
            20                  25                  30

Ser Val Leu Ile Phe Pro Pro Lys Pro Lys Asp Ile Leu Arg Ile Thr
        35                  40                  45

Arg Thr Pro Glu Val Thr Cys Val Val Leu Asp Leu Gly Arg Glu Asp
50                  55                  60

Pro Glu Val Gln Ile Ser Trp Phe Val Asp Gly Lys Glu Val His Thr
65                  70                  75                  80

Ala Lys Thr Gln Ser Arg Glu Gln Gln Phe Asn Gly Thr Tyr Arg Val
                85                  90                  95

Val Ser Val Leu Pro Ile Glu His Gln Asp Trp Leu Thr Gly Lys Glu
            100                 105                 110

Phe Lys Cys Arg Val Asn His Ile Asp Leu Pro Ser Pro Ile Glu Arg
        115                 120                 125

Thr Ile Ser Lys Ala Arg Gly Arg Ala His Lys Pro Ser Val Tyr Val
130                 135                 140

Leu Pro Pro Ser Pro Lys Glu Leu Ser Ser Ser Asp Thr Val Ser Ile
145                 150                 155                 160

Thr Cys Leu Ile Lys Asp Phe Tyr Pro Pro Asp Ile Asp Val Glu Trp
                165                 170                 175

Gln Ser Asn Gly Gln Gln Glu Pro Glu Arg Lys His Arg Met Thr Pro
            180                 185                 190

Pro Gln Leu Asp Glu Asp Gly Ser Tyr Phe Leu Tyr Ser Lys Leu Ser
        195                 200                 205

Val Asp Lys Ser Arg Trp Gln Gln Gly Asp Pro Phe Thr Cys Ala Val
    210                 215                 220

Met His Glu Thr Leu Gln Asn His Tyr Thr Asp Leu Ser Leu Ser His
225                 230                 235                 240

Ser Pro Gly Lys Met Val Ile Glu Phe Asn Met Pro Val Asp Leu Lys
                245                 250                 255
```

```
Leu Val Glu Lys Gln Asn Pro Glu Val Lys Val Gly Gly Arg Tyr Thr
            260                 265                 270

Pro Lys Asn Cys Ile Ser Pro His Lys Val Ala Ile Ile Pro Phe
        275                 280                 285

Arg Asn Arg Gln Glu His Leu Lys Tyr Trp Leu Tyr Tyr Leu His Pro
    290                 295                 300

Ile Leu Gln Arg Gln Leu Asp Tyr Gly Ile Tyr Val Ile Asn Gln
305                 310                 315                 320

Ala Gly Glu Thr Met Phe Asn Arg Ala Lys Leu Leu Asn Ile Gly Phe
                325                 330                 335

Gln Glu Ala Leu Lys Asp Tyr Asp Tyr Asn Cys Phe Val Phe Ser Asp
                340                 345                 350

Val Asp Leu Ile Pro Met Asn Asp His Asn Ala Tyr Arg Cys Phe Ser
            355                 360                 365

Gln Pro Arg His Ile Ser Val Ala Met Asp Lys Phe Gly Phe Ser Leu
    370                 375                 380

Pro Tyr Val Gln Tyr Phe Gly Gly Val Ser Ala Leu Ser Lys Glu Gln
385                 390                 395                 400

Phe Leu Thr Ile Asn Gly Phe Pro Asn Asn Tyr Trp Gly Trp Gly Gly
                405                 410                 415

Glu Asp Asp Asp Ile Tyr Asn Arg Leu Val Phe Lys Gly Met Ser Val
                420                 425                 430

Ser Arg Pro Asn Ala Met Val Gly Lys Cys Arg Met Ile Arg His Ser
            435                 440                 445

Arg Asp Lys Lys Asn Glu Pro Asn Pro Gln Arg Phe Asp Arg Ile Ala
    450                 455                 460

His Thr Lys Glu Thr Met Leu Ser Asp Gly Leu Asn Thr Leu Thr Tyr
465                 470                 475                 480

Lys Val Leu Asp Lys Glu Arg Asn Pro Leu Tyr Thr Lys Ile Thr Val
                485                 490                 495

Asp Ile Gly Thr Pro Ser
            500

<210> SEQ ID NO 17
<211> LENGTH: 599
<212> TYPE: PRT
<213> ORGANISM: Artificial Sequence
<220> FEATURE:
<223> OTHER INFORMATION: feline IgG1 Fc-ST6GAL1 fusion protein

<400> SEQUENCE: 17

Met Tyr Arg Met Gln Leu Leu Ser Cys Ile Ala Leu Ser Leu Ala Leu
1               5                   10                  15

Val Thr Asn Ser Pro Lys Cys Pro Pro Pro Glu Met Leu Gly Gly Pro
                20                  25                  30

Ser Ile Phe Ile Phe Pro Pro Lys Pro Lys Asp Thr Leu Ser Ile Ser
            35                  40                  45

Arg Thr Pro Glu Val Thr Cys Leu Val Val Asp Leu Gly Pro Asp Asp
    50                  55                  60

Ser Asp Val Gln Ile Thr Trp Phe Val Asp Asn Thr Gln Val Tyr Thr
65                  70                  75                  80

Ala Lys Thr Ser Pro Arg Glu Glu Gln Phe Asn Ser Thr Tyr Arg Val
                85                  90                  95

Val Ser Val Leu Pro Ile Leu His Gln Asp Trp Leu Lys Gly Lys Glu
            100                 105                 110
```

```
Phe Lys Cys Lys Val Asn Ser Lys Ser Leu Pro Ser Pro Ile Glu Arg
            115                 120                 125
Thr Ile Ser Lys Ala Lys Gly Gln Pro His Glu Pro Gln Val Tyr Val
130                 135                 140
Leu Pro Pro Ala Gln Glu Leu Ser Arg Asn Lys Val Ser Val Thr
145                 150                 155                 160
Cys Leu Ile Lys Ser Phe His Pro Pro Asp Ile Ala Val Glu Trp Glu
                165                 170                 175
Ile Thr Gly Gln Pro Glu Pro Glu Asn Asn Tyr Arg Thr Thr Pro Pro
            180                 185                 190
Gln Leu Asp Ser Asp Gly Thr Tyr Phe Val Tyr Ser Lys Leu Ser Val
                195                 200                 205
Asp Arg Ser His Trp Gln Arg Gly Asn Thr Tyr Thr Cys Ser Val Ser
210                 215                 220
His Glu Ala Leu His Ser His His Thr Gln Lys Ser Leu Thr Gln Ser
225                 230                 235                 240
Pro Gly Lys Asp Phe Gln Val Leu Arg Gly Leu Glu Lys Gln Ala Glu
                245                 250                 255
Thr Ser Ser Ser Thr Gln Asp Pro His Arg Gly Ser Gln Ala Leu Ser
            260                 265                 270
Ser Pro Arg Gly Pro Ala Lys Ala Lys Pro Glu Ala Ser Phe Gln Val
            275                 280                 285
Trp Asn Lys Asp Ser Ser Ser Lys Asn Leu Ile Pro Arg Leu Gln Lys
            290                 295                 300
Ile Trp Arg Asn Tyr Leu Asn Met Asn Lys Tyr Lys Val Ser Tyr Lys
305                 310                 315                 320
Gly Pro Gly Pro Gly Val Lys Leu Ser Ala Glu Ala Leu His Cys His
                325                 330                 335
Leu Arg Glu Arg Val Asn Val Ser Met Val Glu Val Thr Asp Phe Pro
            340                 345                 350
Phe Asn Thr Ser Glu Trp Glu Gly Phe Leu Pro Lys Glu Asn Ile Arg
            355                 360                 365
Thr Lys Ala Gly Pro Trp Gly Thr Cys Ala Val Val Ser Ser Ala Gly
            370                 375                 380
Ser Leu Lys Ser Ser Gln Leu Gly Arg Glu Ile Asp Asp His Asp Ala
385                 390                 395                 400
Val Leu Arg Phe Asn Gly Ala Pro Thr Ala Asn Phe Gln Gln Asp Val
                405                 410                 415
Gly Thr Lys Thr Thr Ile Arg Leu Met Asn Ser Gln Leu Val Thr Thr
            420                 425                 430
Glu Gly Arg Phe Leu Lys Asp Ser Leu Tyr Asn Glu Gly Ile Leu Ile
            435                 440                 445
Val Trp Asp Pro Ser Val Tyr His Ser Asp Ile Pro Lys Trp Tyr Gln
450                 455                 460
Ser Pro Asp Tyr Ser Phe Phe Glu Asn Tyr Lys Ser Tyr Arg Lys Leu
465                 470                 475                 480
His Pro Asp Gln Pro Phe Tyr Ile Leu Arg Pro Gln Met Pro Trp Glu
                485                 490                 495
Leu Trp Asp Ile Ile Gln Glu Val Ser Pro Glu Glu Ile Gln Pro Asn
            500                 505                 510
Pro Pro Ser Ser Gly Met Leu Gly Ile Ile Ile Met Met Thr Leu Cys
            515                 520                 525
Asp Gln Val Asp Ile Tyr Glu Phe Leu Pro Ser Lys Arg Lys Thr Asp
```

-continued

```
             530                 535                 540
Val Cys Tyr Tyr Gln Lys Phe Phe Asp Ser Ala Cys Thr Met Gly
545                 550                 555                 560

Ala Tyr His Pro Leu Leu Phe Glu Lys Asn Leu Val Lys His Leu Asn
                565                 570                 575

Gln Gly Thr Asp Glu Asp Ile Tyr Leu Leu Gly Lys Ala Thr Leu Pro
                580                 585                 590

Gly Phe Arg Arg Ile Arg Cys
        595

<210> SEQ ID NO 18
<211> LENGTH: 603
<212> TYPE: PRT
<213> ORGANISM: Artificial Sequence
<220> FEATURE:
<223> OTHER INFORMATION: feline IgG1 Fc - B4GALT1 fusion protein

<400> SEQUENCE: 18

Met Tyr Arg Met Gln Leu Leu Ser Cys Ile Ala Leu Ser Leu Ala Leu
1               5                   10                  15

Val Thr Asn Ser Pro Lys Cys Pro Pro Glu Met Leu Gly Gly Pro
                20                  25                  30

Ser Ile Phe Ile Phe Pro Pro Lys Pro Lys Asp Thr Leu Ser Ile Ser
            35                  40                  45

Arg Thr Pro Glu Val Thr Cys Leu Val Val Asp Leu Gly Pro Asp Asp
    50                  55                  60

Ser Asp Val Gln Ile Thr Trp Phe Val Asp Asn Thr Gln Val Tyr Thr
65                  70                  75                  80

Ala Lys Thr Ser Pro Arg Glu Glu Gln Phe Asn Ser Thr Tyr Arg Val
                85                  90                  95

Val Ser Val Leu Pro Ile Leu His Gln Asp Trp Leu Lys Gly Lys Glu
            100                 105                 110

Phe Lys Cys Lys Val Asn Ser Lys Ser Leu Pro Ser Pro Ile Glu Arg
        115                 120                 125

Thr Ile Ser Lys Ala Lys Gly Gln Pro His Glu Pro Gln Val Tyr Val
    130                 135                 140

Leu Pro Pro Ala Gln Glu Glu Leu Ser Arg Asn Lys Val Ser Val Thr
145                 150                 155                 160

Cys Leu Ile Lys Ser Phe His Pro Pro Asp Ile Ala Val Glu Trp Glu
                165                 170                 175

Ile Thr Gly Gln Pro Glu Pro Glu Asn Asn Tyr Arg Thr Thr Pro Pro
            180                 185                 190

Gln Leu Asp Ser Asp Gly Thr Tyr Phe Val Tyr Ser Lys Leu Ser Val
        195                 200                 205

Asp Arg Ser His Trp Gln Arg Gly Asn Thr Tyr Thr Cys Ser Val Ser
    210                 215                 220

His Glu Ala Leu His Ser His His Thr Gln Lys Ser Leu Thr Gln Ser
225                 230                 235                 240

Pro Gly Lys Tyr Leu Ala Gly Arg Asp Leu Asn Arg Leu Pro Gln Leu
                245                 250                 255

Val Gly Val Pro Thr Pro Leu Gln Gly Gly Ser Asn Gly Ala Ala Ala
            260                 265                 270

Ile Glu Gln Pro Ser Ala Glu Leu Arg Pro Arg Gly Ala Pro Pro Leu
        275                 280                 285

Pro Leu Leu Asp Ala Ser Ser Glu Leu Arg Ser Gly Arg Asp Ser Ser
```

```
        290                 295                 300
Pro Asp Ala Asp Ser His Pro Gly Pro Gly Pro Ala Ser Asn Leu Thr
305                 310                 315                 320

Ser Ala Pro Val Pro Ser Thr Thr Val Leu Ser Leu Ala Cys Pro
                325                 330                 335

Glu Glu Ser Pro Leu Leu Val Gly Pro Met Val Ile Glu Phe Asn Met
            340                 345                 350

Pro Val Asp Leu Lys Leu Val Glu Lys Gln Asn Pro Glu Val Lys Val
                355                 360                 365

Gly Gly Arg Tyr Thr Pro Lys Asn Cys Ile Ser Pro His Lys Val Ala
            370                 375                 380

Ile Ile Ile Pro Phe Arg Asn Arg Gln Glu His Leu Lys Tyr Trp Leu
385                 390                 395                 400

Tyr Tyr Leu His Pro Ile Leu Gln Arg Gln Leu Asp Tyr Gly Ile
                405                 410                 415

Tyr Val Ile Asn Gln Ala Gly Glu Thr Met Phe Asn Arg Ala Lys Leu
                420                 425                 430

Leu Asn Ile Gly Phe Gln Glu Ala Leu Lys Asp Tyr Asp Tyr Asn Cys
            435                 440                 445

Phe Val Phe Ser Asp Val Asp Leu Ile Pro Met Asn Asp His Asn Ala
450                 455                 460

Tyr Arg Cys Phe Ser Gln Pro Arg His Ile Ser Val Ala Met Asp Lys
465                 470                 475                 480

Phe Gly Phe Ser Leu Pro Tyr Val Gln Tyr Phe Gly Gly Val Ser Ala
                485                 490                 495

Leu Ser Lys Gln Gln Phe Leu Thr Ile Asn Gly Phe Pro Asn Asn Tyr
            500                 505                 510

Trp Gly Trp Gly Gly Glu Asp Asp Ile Phe Asn Arg Leu Val Phe
            515                 520                 525

Arg Gly Met Ser Val Ser Arg Pro Asn Ala Val Val Gly Lys Cys Arg
            530                 535                 540

Met Ile Arg His Ser Arg Asp Lys Lys Asn Glu Pro Asn Pro Gln Arg
545                 550                 555                 560

Phe Asp Arg Ile Ala His Thr Lys Glu Thr Met Leu Ser Asp Gly Leu
                565                 570                 575

Asn Thr Leu Ser Tyr Lys Val Leu Asp Ile Glu Arg Asn Pro Leu Tyr
            580                 585                 590

Thr Lys Ile Thr Val Asp Ile Gly Thr Pro Ser
            595                 600

<210> SEQ ID NO 19
<211> LENGTH: 468
<212> TYPE: PRT
<213> ORGANISM: Canis familiaris

<400> SEQUENCE: 19

Met Glu Ser Val Phe Cys Trp Val Phe Leu Val Val Ile Leu Lys Gly
1               5                   10                  15

Val Gln Gly Glu Val Gln Leu Val Glu Ser Gly Gly Asp Leu Val Lys
                20                  25                  30

Pro Gly Gly Ser Leu Arg Leu Ser Cys Val Ala Ser Gly Phe Thr Phe
            35                  40                  45

Ser Ser Tyr Tyr Met His Trp Ile Arg Gln Ala Pro Gly Lys Gly Leu
        50                  55                  60
```

```
Gln Arg Val Ala His Ile Arg Gly Asp Gly Arg Thr Thr His Tyr Ala
 65                  70                  75                  80

Asp Ala Met Lys Gly Arg Phe Thr Ile Ser Arg Asp Asn Ala Lys Asn
                 85                  90                  95

Thr Leu Tyr Leu Gln Met Asn Ser Leu Thr Val Glu Asp Thr Ala Ile
            100                 105                 110

Tyr Tyr Cys Val Lys Asp Ile Tyr Tyr Gly Val Gly Asp Tyr Trp Gly
        115                 120                 125

Gln Gly Thr Leu Val Thr Val Ser Ser Ala Ser Thr Thr Ala Pro Ser
130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
            165                 170                 175

Ser Trp Asn Ser Gly Ser Leu Thr Ser Gly Val His Thr Phe Pro Ser
            180                 185                 190

Val Leu Gln Ser Ser Gly Leu His Ser Leu Ser Ser Met Val Thr Val
            195                 200                 205

Pro Ser Ser Arg Trp Pro Ser Glu Thr Phe Thr Cys Asn Val Val His
210                 215                 220

Pro Ala Ser Asn Thr Lys Val Asp Lys Pro Val Phe Asn Glu Cys Arg
225                 230                 235                 240

Cys Thr Asp Thr Pro Pro Cys Pro Val Pro Glu Pro Leu Gly Gly Pro
                245                 250                 255

Ser Val Leu Ile Phe Pro Pro Lys Pro Lys Asp Ile Leu Arg Ile Thr
            260                 265                 270

Arg Thr Pro Glu Val Thr Cys Val Val Leu Asp Leu Gly Arg Glu Asp
            275                 280                 285

Pro Glu Val Gln Ile Ser Trp Phe Val Asp Gly Lys Glu Val His Thr
            290                 295                 300

Ala Lys Thr Gln Ser Arg Glu Gln Gln Phe Asn Gly Thr Tyr Arg Val
305                 310                 315                 320

Val Ser Val Leu Pro Ile Glu His Gln Asp Trp Leu Thr Gly Lys Glu
                325                 330                 335

Phe Lys Cys Arg Val Asn His Ile Asp Leu Pro Ser Pro Ile Glu Arg
            340                 345                 350

Thr Ile Ser Lys Ala Arg Gly Arg Ala His Lys Pro Ser Val Tyr Val
            355                 360                 365

Leu Pro Pro Ser Pro Lys Glu Leu Ser Ser Ser Asp Thr Val Ser Ile
            370                 375                 380

Thr Cys Leu Ile Lys Asp Phe Tyr Pro Pro Asp Ile Asp Val Glu Trp
385                 390                 395                 400

Gln Ser Asn Gly Gln Gln Glu Pro Glu Arg Lys His Arg Met Thr Pro
                405                 410                 415

Pro Gln Leu Asp Glu Asp Gly Ser Tyr Phe Leu Tyr Ser Lys Leu Ser
            420                 425                 430

Val Asp Lys Ser Arg Trp Gln Gln Gly Asp Pro Phe Thr Cys Ala Val
            435                 440                 445

Met His Glu Thr Leu Gln Asn His Tyr Thr Asp Leu Ser Leu Ser His
            450                 455                 460

Ser Pro Gly Lys
465
```

```
<210> SEQ ID NO 20
<211> LENGTH: 473
<212> TYPE: PRT
<213> ORGANISM: Canis familiaris

<400> SEQUENCE: 20

Met Glu Ser Val Leu Phe Trp Val Phe Leu Val Thr Ile Leu Lys Gly
1               5                   10                  15

Val Gln Gly Glu Val Arg Leu Val Glu Ser Gly Gly Thr Leu Val Lys
            20                  25                  30

Pro Gly Gly Ser Leu Lys Leu Ser Cys Val Ala Ser Gly Phe Thr Phe
        35                  40                  45

Arg Arg Tyr Ser Met Asp Trp Val Arg Gln Ala Pro Gly Lys Ser Leu
    50                  55                  60

Gln Trp Val Ala Gly Ile Asn Gly Asp Gly Thr Gly Thr Ser Tyr Ser
65                  70                  75                  80

Gln Thr Val Lys Gly Arg Phe Thr Ile Ser Arg Asp Asn Ala Lys Asn
                85                  90                  95

Thr Leu Tyr Leu Gln Ile Asn Ser Leu Arg Ala Glu Asp Ser Ala Val
            100                 105                 110

Tyr Tyr Cys Ala Lys Ser Trp Ser Arg Asn Gly Asp Leu Asp Tyr Trp
        115                 120                 125

Gly Gln Gly Thr Leu Val Thr Val Ser Ser Ala Ser Thr Thr Ala Pro
    130                 135                 140

Ser Val Phe Pro Leu Ala Pro Ser Cys Gly Ser Thr Ser Gly Ser Thr
145                 150                 155                 160

Val Ala Leu Ala Cys Leu Val Ser Gly Tyr Phe Pro Glu Pro Val Thr
                165                 170                 175

Val Ser Trp Asn Ser Gly Ser Leu Thr Ser Gly Val His Thr Phe Pro
            180                 185                 190

Ser Val Leu Gln Ser Ser Gly Leu Tyr Ser Leu Ser Ser Met Val Thr
        195                 200                 205

Val Pro Ser Ser Arg Trp Pro Ser Glu Thr Phe Thr Cys Asn Val Ala
    210                 215                 220

His Pro Ala Ser Lys Thr Lys Val Asp Lys Pro Val Pro Lys Arg Glu
225                 230                 235                 240

Asn Gly Arg Val Pro Arg Pro Asp Cys Pro Lys Cys Pro Ala Pro
                245                 250                 255

Glu Met Leu Gly Gly Pro Ser Val Phe Ile Phe Pro Pro Lys Pro Lys
            260                 265                 270

Asp Thr Leu Leu Ile Ala Arg Thr Pro Glu Val Thr Cys Val Val Val
        275                 280                 285

Asp Leu Asp Pro Glu Asp Pro Glu Val Gln Ile Ser Trp Phe Val Asp
    290                 295                 300

Gly Lys Gln Met Gln Thr Ala Lys Thr Gln Pro Arg Glu Glu Gln Phe
305                 310                 315                 320

Asn Gly Thr Tyr Arg Val Val Ser Val Leu Pro Ile Gly His Gln Asp
                325                 330                 335

Trp Leu Lys Gly Lys Gln Phe Thr Cys Lys Val Asn Asn Lys Ala Leu
            340                 345                 350

Pro Ser Pro Ile Glu Arg Thr Ile Ser Lys Ala Arg Gly Gln Ala His
        355                 360                 365

Gln Pro Ser Val Tyr Val Leu Pro Pro Ser Arg Glu Glu Leu Ser Lys
    370                 375                 380
```

```
Asn Thr Val Ser Leu Thr Cys Leu Ile Lys Asp Phe Phe Pro Pro Asp
385                 390                 395                 400

Ile Asp Val Glu Trp Gln Ser Asn Gly Gln Gln Glu Pro Glu Ser Lys
                405                 410                 415

Tyr Arg Thr Thr Pro Pro Gln Leu Asp Glu Asp Gly Ser Tyr Phe Leu
            420                 425                 430

Tyr Ser Lys Leu Ser Val Asp Lys Ser Arg Trp Gln Arg Gly Asp Thr
        435                 440                 445

Phe Ile Cys Ala Val Met His Glu Ala Leu His Asn His Tyr Thr Gln
450                 455                 460

Glu Ser Leu Ser His Ser Pro Gly Lys
465                 470
```

<210> SEQ ID NO 21
<211> LENGTH: 474
<212> TYPE: PRT
<213> ORGANISM: Canis familiaris

<400> SEQUENCE: 21

```
Met Glu Ser Val Leu Tyr Trp Val Phe Leu Val Ala Ile Leu Lys Gly
1               5                   10                  15

Val Gln Gly Asp Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Ser Cys Ala Met Ser Trp Val Arg Gln Ser Pro Gly Lys Gly Pro
50                  55                  60

Gln Trp Val Ala Thr Ile Arg Tyr Asp Gly Ser Asp Ile Tyr Tyr Ala
65                  70                  75                  80

Asp Ala Val Lys Gly Arg Phe Ser Ile Ser Arg Asp Asn Ala Lys Asn
                85                  90                  95

Thr Val Tyr Leu Gln Met Asn Ser Leu Arg Ala Glu Asp Thr Ala Val
            100                 105                 110

Tyr Tyr Cys Ala Lys Ala Pro Pro Tyr Asp Ser Tyr His Tyr Gly Met
        115                 120                 125

Asp Tyr Trp Gly Pro Gly Thr Ser Leu Phe Val Ser Ser Ala Ser Thr
130                 135                 140

Thr Ala Pro Ser Val Phe Pro Leu Ala Pro Ser Cys Gly Ser Gln Ser
145                 150                 155                 160

Gly Ser Thr Val Ala Leu Ala Cys Leu Val Ser Gly Tyr Ile Pro Glu
                165                 170                 175

Pro Val Thr Val Ser Trp Asn Ser Val Ser Leu Thr Ser Gly Val His
            180                 185                 190

Thr Phe Pro Ser Val Leu Gln Ser Ser Gly Leu Tyr Ser Leu Ser Ser
        195                 200                 205

Met Val Thr Val Pro Ser Ser Arg Trp Pro Ser Glu Thr Phe Thr Cys
210                 215                 220

Asn Val Ala His Pro Ala Thr Asn Thr Lys Val Asp Lys Pro Val Ala
225                 230                 235                 240

Lys Glu Cys Glu Cys Lys Cys Asn Cys Asn Asn Cys Pro Cys Pro Gly
                245                 250                 255

Cys Gly Leu Leu Gly Gly Pro Ser Val Phe Ile Phe Pro Pro Lys Pro
            260                 265                 270

Lys Asp Ile Leu Val Thr Ala Arg Thr Pro Thr Val Thr Cys Val Val
        275                 280                 285
```

```
Val Asp Leu Asp Pro Glu Asn Pro Glu Val Gln Ile Ser Trp Phe Val
    290                 295                 300

Asp Ser Lys Gln Val Gln Thr Ala Asn Thr Gln Pro Arg Glu Glu Gln
305                 310                 315                 320

Ser Asn Gly Thr Tyr Arg Val Ser Val Leu Pro Ile Gly His Gln
                325                 330                 335

Asp Trp Leu Ser Gly Lys Gln Phe Lys Cys Lys Val Asn Asn Lys Ala
                340                 345                 350

Leu Pro Ser Pro Ile Glu Glu Ile Ser Lys Thr Pro Gly Gln Ala
                355                 360                 365

His Gln Pro Asn Val Tyr Val Leu Pro Pro Ser Arg Asp Glu Met Ser
    370                 375                 380

Lys Asn Thr Val Thr Leu Thr Cys Leu Val Lys Asp Phe Phe Pro Pro
385                 390                 395                 400

Glu Ile Asp Val Glu Trp Gln Ser Asn Gly Gln Gln Glu Pro Glu Ser
                405                 410                 415

Lys Tyr Arg Met Thr Pro Pro Gln Leu Asp Glu Asp Gly Ser Tyr Phe
                420                 425                 430

Leu Tyr Ser Lys Leu Ser Val Asp Lys Ser Arg Trp Gln Arg Gly Asp
                435                 440                 445

Thr Phe Ile Cys Ala Val Met His Glu Ala Leu His Asn His Tyr Thr
    450                 455                 460

Gln Ile Ser Leu Ser His Ser Pro Gly Lys
465                 470
```

<210> SEQ ID NO 22
<211> LENGTH: 470
<212> TYPE: PRT
<213> ORGANISM: Canis familiaris

<400> SEQUENCE: 22

```
Met Glu Ser Val Leu Cys Trp Val Phe Leu Val Ser Ile Leu Lys Gly
1               5                   10                  15

Val Gln Gly Glu Val Gln Leu Val Glu Ser Gly Gly Asp Leu Val Lys
                20                  25                  30

Pro Gly Gly Ser Leu Arg Leu Ser Cys Val Ala Ser Gly Phe Thr Phe
            35                  40                  45

Ser Asp Tyr Gly Met Ser Trp Val Arg Gln Ser Pro Gly Lys Gly Leu
    50                  55                  60

Gln Trp Val Ala Ala Val Ser Asn Arg Gly Asp Thr Tyr Tyr Ala Asp
65                  70                  75                  80

Ala Val Lys Gly Arg Phe Thr Ile Ser Arg Asp Asn Ala Lys Asn Thr
                85                  90                  95

Leu Tyr Leu Gln Met Ser Ser Leu Lys Ala Glu Asp Thr Ala Ile Tyr
                100                 105                 110

His Cys Val Thr Gly Val Trp Pro Arg His Tyr Gly Met Asp His
            115                 120                 125

Trp Gly Asn Gly Thr Ser Leu Phe Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
```

```
                180             185                 190
Pro Ser Val Leu Gln Ser Ser Gly Leu Tyr Ser Leu Ser Ser Thr Val
            195                 200             205

Thr Val Pro Ser Ser Arg Trp Pro Ser Glu Thr Phe Thr Cys Asn Val
    210                 215             220

Val His Pro Ala Ser Asn Thr Lys Val Asp Lys Pro Val Pro Lys Glu
225                 230                 235                 240

Ser Thr Cys Lys Cys Ile Ser Pro Cys Pro Val Pro Glu Ser Leu Gly
                245                 250             255

Gly Pro Ser Val Phe Ile Phe Pro Pro Lys Pro Lys Asp Ile Leu Arg
            260                 265             270

Ile Thr Arg Thr Pro Glu Ile Thr Cys Val Val Leu Asp Leu Gly Arg
        275                 280             285

Glu Asp Pro Glu Val Gln Ile Ser Trp Phe Val Asp Gly Lys Glu Val
        290                 295             300

His Thr Ala Lys Thr Gln Pro Arg Glu Gln Gln Phe Asn Ser Thr Tyr
305                 310                 315                 320

Arg Val Val Ser Val Leu Pro Ile Glu His Gln Asp Trp Leu Thr Gly
                325                 330             335

Lys Glu Phe Lys Cys Arg Val Asn His Ile Gly Leu Pro Ser Pro Ile
            340                 345             350

Glu Arg Thr Ile Ser Lys Ala Arg Gly Gln Ala His Gln Pro Ser Val
        355                 360             365

Tyr Val Leu Pro Pro Ser Pro Lys Glu Leu Ser Ser Ser Asp Thr Val
        370                 375             380

Thr Leu Thr Cys Leu Ile Lys Asp Phe Phe Pro Pro Glu Ile Asp Val
385                 390                 395                 400

Glu Trp Gln Ser Asn Gly Gln Pro Glu Pro Glu Ser Lys Tyr His Thr
                405                 410             415

Thr Ala Pro Gln Leu Asp Glu Asp Gly Ser Tyr Phe Leu Tyr Ser Lys
            420                 425             430

Leu Ser Val Asp Lys Ser Arg Trp Gln Gln Gly Asp Thr Phe Thr Cys
        435                 440             445

Ala Val Met His Glu Ala Leu Gln Asn His Tyr Thr Asp Leu Ser Leu
        450                 455             460

Ser His Ser Pro Gly Lys
465                 470

<210> SEQ ID NO 23
<211> LENGTH: 399
<212> TYPE: PRT
<213> ORGANISM: Canis familiaris

<400> SEQUENCE: 23

Met Ile His Thr Asn Leu Lys Lys Phe Ser Cys Cys Val Leu Ala
1               5                   10                  15

Phe Leu Leu Phe Ala Val Ile Cys Val Trp Lys Glu Lys Lys Gly
            20                  25                  30

Ser Tyr Tyr Asp Ser Leu Lys Leu Gln Thr Lys Glu Phe Gln Met Val
            35                  40                  45

Arg Gly Leu Glu Lys Gln Ala Ala Thr Leu Ser Ser Thr Gln Asn Pro
        50                  55                  60

Pro Arg Ala Ser Gln Ala Leu Gly Ser Pro Arg Gly Pro Val Lys Ala
65                  70                  75                  80
```

```
Lys Ser Glu Ala Ser Phe Gln Val Trp Asn Lys Asp Ser Ser Lys
                85                  90                  95

Asn Leu Ile Pro Arg Leu Gln Lys Ile Trp Arg Asn Tyr Leu Asn Met
            100                 105                 110

Asn Lys Tyr Lys Val Ser Tyr Lys Gly Pro Gly Pro Gly Val Lys Phe
        115                 120                 125

Ser Ala Glu Ala Leu His Cys His Leu Arg Asp His Val Asn Val Ser
    130                 135                 140

Met Val Glu Ala Thr Asp Phe Pro Phe Asn Thr Ser Glu Trp Glu Gly
145                 150                 155                 160

Phe Leu Pro Lys Glu Asn Ile Arg Thr Lys Ala Gly Pro Trp Gly Arg
                165                 170                 175

Cys Ala Val Val Ser Ser Ala Gly Ser Leu Lys Ser Ser Gln Leu Gly
            180                 185                 190

Arg Glu Ile Asp Asp His Asp Ala Val Leu Arg Phe Asn Gly Ala Pro
        195                 200                 205

Thr Ala Ser Phe Gln Gln Asp Val Gly Thr Lys Thr Thr Ile Arg Leu
    210                 215                 220

Met Asn Ser Gln Leu Val Thr Thr Glu Gly Arg Phe Leu Lys Asp Ser
225                 230                 235                 240

Leu Tyr Asn Glu Gly Ile Leu Ile Val Trp Asp Pro Ser Val Tyr His
                245                 250                 255

Ser Asp Ile Pro Lys Trp Tyr Gln Ser Pro Asp Tyr Ser Phe Phe Glu
            260                 265                 270

Asn Tyr Lys Ser Tyr Arg Lys Leu His Pro Asp Gln Pro Phe Tyr Ile
        275                 280                 285

Leu Lys Pro Gln Met Pro Trp Glu Leu Trp Asp Ile Ile Gln Glu Val
    290                 295                 300

Ser Pro Glu Glu Ile Gln Pro Asn Pro Pro Ser Ser Gly Met Leu Gly
305                 310                 315                 320

Ile Ile Ile Met Met Thr Leu Cys Asp Gln Val Asp Ile Tyr Glu Phe
                325                 330                 335

Leu Pro Ser Lys Arg Lys Thr Asp Val Cys Tyr Tyr Tyr Gln Lys Phe
            340                 345                 350

Phe Asp Ser Ala Cys Thr Met Gly Ala Tyr His Pro Leu Leu Phe Glu
        355                 360                 365

Lys Asn Leu Val Lys His Leu Asn Gln Gly Thr Asp Glu Asp Ile Tyr
    370                 375                 380

Leu Leu Gly Lys Ala Thr Leu Pro Gly Phe Arg Arg Ile Arg Cys
385                 390                 395

<210> SEQ ID NO 24
<211> LENGTH: 258
<212> TYPE: PRT
<213> ORGANISM: Canis familiaris

<400> SEQUENCE: 24

Met Val Ile Glu Phe Asn Met Pro Val Asp Leu Lys Leu Val Glu Lys
1               5                   10                  15

Gln Asn Pro Glu Val Lys Val Gly Gly Arg Tyr Thr Pro Lys Asn Cys
            20                  25                  30

Ile Ser Pro His Lys Val Ala Ile Ile Pro Phe Arg Asn Arg Gln
        35                  40                  45

Glu His Leu Lys Tyr Trp Leu Tyr Tyr Leu His Pro Ile Leu Gln Arg
    50                  55                  60
```

```
Gln Gln Leu Asp Tyr Gly Ile Tyr Val Ile Asn Gln Ala Gly Glu Thr
 65                  70                  75                  80

Met Phe Asn Arg Ala Lys Leu Leu Asn Ile Gly Phe Gln Glu Ala Leu
                 85                  90                  95

Lys Asp Tyr Asp Tyr Asn Cys Phe Val Phe Ser Asp Val Asp Leu Ile
            100                 105                 110

Pro Met Asn Asp His Asn Ala Tyr Arg Cys Phe Ser Gln Pro Arg His
        115                 120                 125

Ile Ser Val Ala Met Asp Lys Phe Gly Phe Ser Leu Pro Tyr Val Gln
130                 135                 140

Tyr Phe Gly Gly Val Ser Ala Leu Ser Lys Glu Gln Phe Leu Thr Ile
145                 150                 155                 160

Asn Gly Phe Pro Asn Asn Tyr Trp Gly Trp Gly Gly Glu Asp Asp Asp
                165                 170                 175

Ile Tyr Asn Arg Leu Val Phe Lys Gly Met Ser Val Ser Arg Pro Asn
            180                 185                 190

Ala Met Val Gly Lys Cys Arg Met Ile Arg His Ser Arg Asp Lys Lys
        195                 200                 205

Asn Glu Pro Asn Pro Gln Arg Phe Asp Arg Ile Ala His Thr Lys Glu
210                 215                 220

Thr Met Leu Ser Asp Gly Leu Asn Thr Leu Thr Tyr Lys Val Leu Asp
225                 230                 235                 240

Lys Glu Arg Asn Pro Leu Tyr Thr Lys Ile Thr Val Asp Ile Gly Thr
                245                 250                 255

Pro Ser

<210> SEQ ID NO 25
<211> LENGTH: 335
<212> TYPE: PRT
<213> ORGANISM: Felis catus

<400> SEQUENCE: 25

Ala Ser Thr Thr Ala Pro Ser Val Phe Pro Leu Ala Pro Ser Cys Gly
 1               5                  10                  15

Thr Thr Ser Gly Ala Thr Val Ala Leu Ala Cys Leu Val Leu Gly Tyr
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ala Ser Gly Leu Tyr Ser
        50                  55                  60

Leu Ser Ser Met Val Thr Val Pro Ser Ser Arg Trp Leu Ser Asp Thr
 65                  70                  75                  80

Phe Thr Cys Asn Val Ala His Pro Pro Ser Asn Thr Lys Val Asp Lys
                 85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175
```

```
Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
            245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285

Asp Gly Thr Tyr Phe Val Tyr Ser Lys Leu Ser Val Asp Arg Ser His
            290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
            325                 330                 335

<210> SEQ ID NO 26
<211> LENGTH: 335
<212> TYPE: PRT
<213> ORGANISM: Felis catus

<400> SEQUENCE: 26

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ala Ser Gly Leu Tyr Ser
50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
```

```
                210                 215                 220
Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
            245                 250                 255

Gly Phe Tyr Pro Ser Asp Ile Ala Val Glu Trp Glu Ile Thr Gly Gln
                260                 265                 270

Pro Glu Pro Glu Asn Asn Tyr Arg Thr Thr Pro Pro Gln Leu Asp Ser
            275                 280                 285

Asp Gly Thr Tyr Phe Leu Tyr Ser Arg Leu Ser Val Asp Arg Ser Arg
290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 27
<211> LENGTH: 399
<212> TYPE: PRT
<213> ORGANISM: Felis catus

<400> SEQUENCE: 27

```
Met Ile His Ala Asn Leu Lys Lys Phe Ser Cys Cys Val Leu Ala
1               5                   10                  15

Phe Leu Leu Phe Ala Ile Ile Cys Val Trp Lys Glu Lys Lys Gly
            20                  25                  30

Thr Tyr Tyr Asp Ser Leu Lys Leu Gln Ser Lys Asp Phe Gln Val Leu
            35                  40                  45

Arg Gly Leu Glu Lys Gln Ala Glu Thr Ser Ser Ser Thr Gln Asp Pro
50                  55                  60

His Arg Gly Ser Gln Ala Leu Ser Ser Pro Arg Gly Pro Ala Lys Ala
65                  70                  75                  80

Lys Pro Glu Ala Ser Phe Gln Val Trp Asn Lys Asp Ser Ser Lys
            85                  90                  95

Asn Leu Ile Pro Arg Leu Gln Lys Ile Trp Arg Asn Tyr Leu Asn Met
                100                 105                 110

Asn Lys Tyr Lys Val Ser Tyr Lys Gly Pro Gly Pro Gly Val Lys Leu
            115                 120                 125

Ser Ala Glu Ala Leu His Cys His Leu Arg Glu Arg Val Asn Val Ser
130                 135                 140

Met Val Glu Val Thr Asp Phe Pro Phe Asn Thr Ser Glu Trp Glu Gly
145                 150                 155                 160

Phe Leu Pro Lys Glu Asn Ile Arg Thr Lys Ala Gly Pro Trp Gly Thr
                165                 170                 175

Cys Ala Val Val Ser Ser Ala Gly Ser Leu Lys Ser Ser Gln Leu Gly
            180                 185                 190

Arg Glu Ile Asp Asp His Asp Ala Val Leu Arg Phe Asn Gly Ala Pro
        195                 200                 205

Thr Ala Asn Phe Gln Gln Asp Val Gly Thr Lys Thr Thr Ile Arg Leu
    210                 215                 220

Met Asn Ser Gln Leu Val Thr Thr Glu Gly Arg Phe Leu Lys Asp Ser
225                 230                 235                 240

Leu Tyr Asn Glu Gly Ile Leu Ile Val Trp Asp Pro Ser Val Tyr His
                245                 250                 255
```

```
Ser Asp Ile Pro Lys Trp Tyr Gln Ser Pro Asp Tyr Ser Phe Phe Glu
            260                 265                 270

Asn Tyr Lys Ser Tyr Arg Lys Leu His Pro Asp Gln Pro Phe Tyr Ile
        275                 280                 285

Leu Arg Pro Gln Met Pro Trp Glu Leu Trp Asp Ile Ile Gln Glu Val
    290                 295                 300

Ser Pro Glu Glu Ile Gln Pro Asn Pro Pro Ser Ser Gly Met Leu Gly
305                 310                 315                 320

Ile Ile Ile Met Met Thr Leu Cys Asp Gln Val Asp Ile Tyr Glu Phe
                325                 330                 335

Leu Pro Ser Lys Arg Lys Thr Asp Val Cys Tyr Tyr Gln Lys Phe
            340                 345                 350

Phe Asp Ser Ala Cys Thr Met Gly Ala Tyr His Pro Leu Leu Phe Glu
            355                 360                 365

Lys Asn Leu Val Lys His Leu Asn Gln Gly Thr Asp Glu Asp Ile Tyr
            370                 375                 380

Leu Leu Gly Lys Ala Thr Leu Pro Gly Phe Arg Arg Ile Arg Cys
385                 390                 395
```

<210> SEQ ID NO 28
<211> LENGTH: 373
<212> TYPE: PRT
<213> ORGANISM: Felis catus

<400> SEQUENCE: 28

```
Ala Val Cys Ala Leu His Leu Gly Val Thr Leu Val Tyr Tyr Leu Ala
1               5                   10                  15

Gly Arg Asp Leu Asn Arg Leu Pro Gln Leu Val Gly Val Pro Thr Pro
            20                  25                  30

Leu Gln Gly Gly Ser Asn Gly Ala Ala Ile Glu Gln Pro Ser Ala
            35                  40                  45

Glu Leu Arg Pro Arg Gly Ala Pro Pro Leu Pro Leu Leu Asp Ala Ser
    50                  55                  60

Ser Glu Leu Arg Ser Gly Arg Asp Ser Ser Pro Asp Ala Asp Ser His
65                  70                  75                  80

Pro Gly Pro Gly Pro Ala Ser Asn Leu Thr Ser Ala Pro Val Pro Ser
                85                  90                  95

Thr Thr Val Leu Ser Leu Leu Ala Cys Pro Glu Glu Ser Pro Leu Leu
            100                 105                 110

Val Gly Pro Met Val Ile Glu Phe Asn Met Pro Val Asp Leu Lys Leu
        115                 120                 125

Val Glu Lys Gln Asn Pro Glu Val Lys Val Gly Gly Arg Tyr Thr Pro
130                 135                 140

Lys Asn Cys Ile Ser Pro His Lys Val Ala Ile Ile Pro Phe Arg
145                 150                 155                 160

Asn Arg Gln Glu His Leu Lys Tyr Trp Leu Tyr Tyr Leu His Pro Ile
                165                 170                 175

Leu Gln Arg Gln Gln Leu Asp Tyr Gly Ile Tyr Val Ile Asn Gln Ala
            180                 185                 190

Gly Glu Thr Met Phe Asn Arg Ala Lys Leu Leu Asn Ile Gly Phe Gln
        195                 200                 205

Glu Ala Leu Lys Asp Tyr Asp Tyr Asn Cys Phe Val Phe Ser Asp Val
    210                 215                 220

Asp Leu Ile Pro Met Asn Asp His Asn Ala Tyr Arg Cys Phe Ser Gln
225                 230                 235                 240
```

```
Pro Arg His Ile Ser Val Ala Met Asp Lys Phe Gly Phe Ser Leu Pro
                245                 250                 255

Tyr Val Gln Tyr Phe Gly Gly Val Ser Ala Leu Ser Lys Gln Gln Phe
            260                 265                 270

Leu Thr Ile Asn Gly Phe Pro Asn Asn Tyr Trp Gly Trp Gly Gly Glu
            275                 280                 285

Asp Asp Asp Ile Phe Asn Arg Leu Val Phe Arg Gly Met Ser Val Ser
290                 295                 300

Arg Pro Asn Ala Val Val Gly Lys Cys Arg Met Ile Arg His Ser Arg
305                 310                 315                 320

Asp Lys Lys Asn Glu Pro Asn Pro Gln Arg Phe Asp Arg Ile Ala His
                325                 330                 335

Thr Lys Glu Thr Met Leu Ser Asp Gly Leu Asn Thr Leu Ser Tyr Lys
            340                 345                 350

Val Leu Asp Ile Glu Arg Asn Pro Leu Tyr Thr Lys Ile Thr Val Asp
            355                 360                 365

Ile Gly Thr Pro Ser
    370

<210> SEQ ID NO 29
<211> LENGTH: 990
<212> TYPE: PRT
<213> ORGANISM: Bos taurus

<400> SEQUENCE: 29

Gly Cys Cys Thr Cys Cys Ala Cys Cys Ala Gly Cys Cys Cys Cys Cys
1               5                   10                  15

Cys Gly Ala Ala Ala Gly Thr Cys Thr Ala Cys Cys Thr Cys Thr
            20                  25                  30

Gly Ala Gly Thr Thr Cys Thr Thr Gly Cys Thr Gly Cys Gly Gly Gly
            35                  40                  45

Gly Ala Cys Ala Ala Gly Thr Cys Cys Ala Gly Cys Thr Cys Cys Ala
            50                  55                  60

Cys Cys Gly Thr Gly Ala Cys Cys Cys Thr Gly Gly Gly Cys Thr Gly
65                  70                  75                  80

Cys Cys Thr Gly Gly Thr Cys Thr Cys Ala Gly Cys Thr Ala Cys
                85                  90                  95

Ala Thr Gly Cys Cys Gly Ala Gly Cys Cys Gly Gly Thr Gly Ala
            100                 105                 110

Cys Cys Gly Thr Gly Ala Cys Cys Thr Gly Gly Ala Ala Cys Thr Cys
            115                 120                 125

Gly Gly Gly Thr Gly Cys Cys Cys Thr Gly Ala Ala Gly Ala Gly Cys
            130                 135                 140

Gly Gly Cys Gly Thr Gly Cys Ala Cys Ala Cys Cys Thr Cys Cys
145                 150                 155                 160

Cys Gly Gly Cys Cys Gly Thr Cys Cys Thr Thr Cys Ala Gly Thr Cys
                165                 170                 175

Cys Thr Cys Cys Gly Gly Gly Cys Thr Cys Ala Cys Thr Cys Thr
            180                 185                 190

Cys Thr Cys Ala Gly Cys Ala Gly Cys Ala Thr Gly Thr Gly Ala
            195                 200                 205

Cys Cys Gly Thr Gly Cys Cys Cys Gly Gly Cys Ala Gly Cys Ala Cys
            210                 215                 220

Cys Thr Cys Ala Gly Gly Ala Ala Cys Cys Cys Ala Gly Ala Cys Cys
```

-continued

```
225                 230                 235                 240

Thr Thr Cys Ala Cys Cys Thr Gly Cys Ala Ala Cys Gly Thr Ala Gly
                245                 250                 255

Cys Cys Cys Ala Cys Cys Cys Gly Gly Cys Cys Ala Gly Cys Ala Gly
            260                 265                 270

Cys Ala Cys Cys Ala Ala Gly Gly Thr Gly Gly Ala Cys Ala Ala Gly
        275                 280                 285

Gly Cys Thr Gly Thr Thr Gly Ala Thr Cys Cys Cys Ala Gly Ala Thr
    290                 295                 300

Gly Cys Ala Ala Ala Ala Cys Ala Ala Cys Cys Thr Gly Thr Gly Ala
305                 310                 315                 320

Cys Thr Gly Thr Thr Gly Cys Cys Cys Ala Cys Cys Gly Cys Cys Thr
                325                 330                 335

Gly Ala Gly Cys Thr Cys Cys Cys Thr Gly Gly Ala Gly Gly Ala Cys
            340                 345                 350

Cys Cys Thr Cys Thr Gly Thr Cys Thr Thr Cys Ala Thr Cys Thr Thr
        355                 360                 365

Cys Cys Cys Ala Cys Cys Gly Ala Ala Ala Cys Cys Cys Ala Ala Gly
    370                 375                 380

Gly Ala Cys Ala Cys Cys Cys Thr Cys Ala Cys Ala Ala Thr Cys Thr
385                 390                 395                 400

Cys Gly Gly Gly Ala Ala Cys Gly Cys Cys Cys Gly Ala Gly Gly Thr
                405                 410                 415

Cys Ala Cys Gly Thr Gly Thr Gly Thr Gly Gly Thr Gly Gly Thr Gly
            420                 425                 430

Gly Ala Cys Gly Thr Gly Gly Gly Cys Cys Ala Cys Gly Ala Thr Gly
        435                 440                 445

Ala Cys Cys Cys Cys Gly Ala Gly Gly Thr Gly Ala Ala Gly Thr Thr
    450                 455                 460

Cys Thr Cys Cys Thr Gly Gly Thr Thr Cys Gly Thr Gly Gly Ala Cys
465                 470                 475                 480

Gly Ala Cys Gly Thr Gly Gly Ala Gly Gly Thr Ala Ala Ala Cys Ala
                485                 490                 495

Cys Ala Gly Cys Cys Ala Cys Gly Ala Cys Gly Ala Ala Gly Cys Cys
            500                 505                 510

Gly Ala Gly Ala Gly Ala Gly Gly Ala Gly Cys Ala Gly Thr Thr Cys
        515                 520                 525

Ala Ala Cys Ala Gly Cys Ala Cys Cys Thr Ala Cys Cys Gly Cys Gly
    530                 535                 540

Thr Gly Gly Thr Cys Ala Gly Cys Gly Cys Cys Cys Thr Gly Cys Gly
545                 550                 555                 560

Cys Ala Thr Cys Cys Ala Gly Cys Ala Cys Cys Ala Gly Gly Ala Cys
                565                 570                 575

Thr Gly Gly Ala Cys Thr Gly Gly Ala Gly Gly Ala Ala Ala Gly Gly
            580                 585                 590

Ala Gly Thr Thr Cys Ala Ala Gly Thr Gly Cys Ala Ala Gly Gly Thr
        595                 600                 605

Cys Cys Ala Cys Ala Ala Cys Gly Ala Ala Gly Gly Cys Cys Thr Cys
    610                 615                 620

Cys Cys Ala Gly Cys Cys Cys Cys Cys Ala Thr Cys Gly Thr Gly Ala
625                 630                 635                 640

Gly Gly Ala Cys Cys Ala Thr Cys Thr Cys Cys Ala Gly Gly Ala Cys
                645                 650                 655
```

Cys Ala Ala Gly Gly Gly Cys Gly Cys Cys Gly Gly
         660             665             670

Gly Ala Gly Cys Cys Gly Cys Ala Gly Gly Thr Gly Thr Ala Thr Gly
            675             680             685

Thr Cys Cys Thr Gly Gly Cys Cys Cys Ala Cys Cys Cys Cys Ala
        690             695             700

Gly Gly Ala Ala Gly Ala Gly Cys Thr Cys Ala Gly Cys Ala Ala Ala
705             710             715             720

Ala Gly Cys Ala Cys Gly Gly Thr Cys Ala Gly Cys Thr Cys Ala
            725             730             735

Cys Cys Thr Gly Cys Ala Thr Gly Thr Cys Ala Cys Ala Gly
            740             745             750

Cys Thr Thr Cys Thr Ala Cys Cys Ala Gly Ala Cys Thr Ala Cys
            755             760             765

Ala Thr Cys Gly Cys Cys Gly Thr Gly Ala Gly Thr Gly Gly Cys
            770             775             780

Ala Gly Ala Gly Ala Ala Ala Thr Gly Gly Cys Ala Gly Cys Cys
785             790             795             800

Thr Gly Ala Gly Thr Cys Ala Gly Ala Gly Gly Ala Cys Ala Ala Gly
            805             810             815

Thr Ala Cys Gly Gly Cys Ala Cys Gly Ala Cys Cys Cys Thr Cys
            820             825             830

Cys Cys Cys Ala Gly Cys Thr Gly Gly Ala Cys Gly Cys Gly Ala
            835             840             845

Cys Gly Gly Cys Thr Cys Thr Ala Cys Thr Cys Cys Thr Gly
            850             855             860

Thr Ala Cys Ala Gly Cys Ala Gly Gly Cys Thr Cys Ala Gly Gly
865             870             875             880

Thr Gly Gly Ala Cys Ala Gly Gly Ala Ala Cys Ala Gly Cys Thr Gly
            885             890             895

Gly Cys Ala Gly Gly Ala Ala Gly Gly Ala Cys Ala Cys Cys
            900             905             910

Thr Ala Cys Ala Cys Gly Thr Gly Thr Gly Thr Gly Thr Gly Ala
            915             920             925

Thr Gly Cys Ala Cys Gly Ala Gly Gly Cys Cys Thr Gly Cys Ala
            930             935             940

Cys Ala Ala Thr Cys Ala Cys Thr Ala Cys Ala Cys Gly Cys Ala Gly
945             950             955             960

Ala Ala Gly Thr Cys Cys Ala Cys Cys Thr Cys Thr Ala Gly Thr
            965             970             975

Cys Thr Gly Cys Gly Gly Thr Ala Ala Thr Gly Ala
            980             985             990

<210> SEQ ID NO 30
<211> LENGTH: 981
<212> TYPE: PRT
<213> ORGANISM: Bos taurus

<400> SEQUENCE: 30

Gly Cys Cys Thr Cys Cys Ala Cys Ala Cys Ala Gly Cys Cys Cys
1               5               10              15

Cys Gly Ala Ala Ala Gly Thr Cys Thr Ala Cys Cys Thr Cys Thr
            20              25              30

Gly Gly Cys Ala Thr Cys Cys Ala Gly Cys Thr Gly Cys Gly Gly Ala

```
                35                  40                  45
Gly Ala Cys Ala Cys Ala Thr Cys Cys Ala Gly Cys Thr Cys Cys Ala
 50                  55                  60
Cys Cys Gly Thr Gly Ala Cys Cys Cys Thr Gly Gly Gly Cys Thr Gly
 65                  70                  75                  80
Cys Cys Thr Gly Gly Thr Gly Thr Cys Cys Ala Gly Cys Thr Ala Cys
                 85                  90                  95
Ala Thr Gly Cys Cys Cys Gly Ala Gly Cys Cys Gly Gly Thr Gly Ala
                100                 105                 110
Cys Cys Gly Thr Gly Ala Cys Cys Thr Gly Gly Ala Ala Cys Thr Cys
                115                 120                 125
Gly Gly Gly Thr Gly Cys Cys Thr Gly Ala Ala Gly Ala Gly Ala Cys
                130                 135                 140
Gly Gly Cys Gly Thr Gly Cys Ala Cys Ala Cys Cys Thr Thr Cys Cys
145                 150                 155                 160
Cys Gly Gly Cys Thr Gly Thr Cys Cys Thr Cys Ala Gly Thr Cys
                165                 170                 175
Cys Thr Cys Cys Gly Gly Cys Thr Cys Thr Ala Cys Thr Cys Thr
                180                 185                 190
Cys Thr Cys Ala Gly Cys Ala Gly Cys Ala Thr Gly Gly Thr Gly Ala
                195                 200                 205
Cys Cys Gly Thr Gly Cys Cys Cys Gly Cys Cys Ala Gly Cys Ala Gly
                210                 215                 220
Cys Thr Cys Ala Gly Gly Ala Cys Ala Gly Ala Cys Cys Thr Thr Cys
225                 230                 235                 240
Ala Cys Cys Thr Gly Cys Ala Ala Cys Gly Thr Ala Gly Cys Cys Cys
                245                 250                 255
Ala Cys Cys Cys Gly Gly Cys Cys Ala Gly Cys Ala Gly Cys Ala Cys
                260                 265                 270
Cys Ala Ala Gly Gly Thr Gly Gly Ala Cys Ala Ala Gly Gly Cys Thr
                275                 280                 285
Gly Thr Thr Gly Gly Gly Thr Cys Thr Cys Cys Ala Thr Thr Gly
                290                 295                 300
Ala Cys Thr Gly Cys Thr Cys Cys Ala Ala Gly Thr Gly Thr Cys Ala
305                 310                 315                 320
Thr Ala Ala Cys Cys Ala Gly Cys Cys Thr Thr Gly Cys Gly Thr Gly
                325                 330                 335
Ala Gly Gly Ala Cys Cys Ala Thr Cys Thr Gly Thr Cys Thr
                340                 345                 350
Thr Cys Ala Thr Cys Thr Thr Cys Cys Cys Ala Cys Cys Gly Ala Ala
                355                 360                 365
Ala Cys Cys Ala Ala Gly Ala Cys Ala Cys Cys Thr Gly
                370                 375                 380
Ala Thr Gly Ala Thr Cys Ala Cys Ala Gly Ala Ala Cys Gly Cys
385                 390                 395                 400
Cys Cys Gly Ala Gly Gly Thr Cys Ala Cys Gly Thr Gly Thr
                405                 410                 415
Gly Gly Thr Gly Gly Thr Gly Ala Ala Cys Gly Thr Gly Gly Gly Cys
                420                 425                 430
Cys Ala Cys Gly Ala Thr Ala Ala Cys Cys Cys Gly Ala Gly Gly
                435                 440                 445
Thr Gly Cys Ala Gly Thr Thr Cys Thr Cys Cys Thr Gly Gly Thr Thr
                450                 455                 460
```

```
Cys Gly Thr Gly Gly Ala Thr Gly Ala Cys Gly Gly Ala Gly
465                 470                 475                 480

Gly Thr Gly Cys Ala Cys Ala Cys Gly Gly Cys Ala Gly Thr
                485                 490                 495

Cys Gly Ala Ala Gly Cys Cys Ala Ala Gly Ala Gly Gly Ala
                500                 505                 510

Gly Cys Ala Gly Thr Thr Cys Ala Ala Cys Ala Gly Cys Ala Cys Gly
            515                 520                 525

Thr Ala Cys Cys Gly Cys Gly Thr Gly Thr Cys Ala Gly Cys Gly
530                 535                 540

Cys Cys Cys Thr Gly Cys Cys Ala Thr Cys Cys Ala Gly Cys Ala
545                 550                 555                 560

Cys Cys Ala Gly Gly Ala Cys Thr Gly Gly Ala Cys Thr Gly Gly Ala
                565                 570                 575

Gly Gly Ala Ala Ala Gly Gly Ala Gly Thr Thr Cys Ala Ala Gly Thr
                580                 585                 590

Gly Cys Ala Ala Gly Gly Thr Cys Ala Ala Cys Ala Ala Cys Ala Ala
            595                 600                 605

Ala Gly Gly Cys Cys Thr Cys Thr Cys Gly Gly Cys Cys Cys Cys
610                 615                 620

Ala Thr Cys Gly Thr Gly Ala Gly Gly Ala Thr Cys Ala Thr Cys Thr
625                 630                 635                 640

Cys Cys Ala Gly Gly Ala Gly Cys Ala Ala Gly Gly Gly Cys Cys
                645                 650                 655

Gly Gly Cys Cys Cys Gly Gly Gly Ala Gly Cys Cys Gly Cys Ala Gly
                660                 665                 670

Gly Thr Gly Thr Ala Thr Gly Thr Cys Cys Thr Gly Ala Cys Cys
            675                 680                 685

Cys Ala Cys Cys Cys Ala Ala Gly Gly Ala Ala Gly Ala Gly Cys Thr
690                 695                 700

Cys Ala Gly Cys Ala Ala Ala Gly Cys Ala Cys Gly Cys Thr Cys
705                 710                 715                 720

Ala Gly Cys Gly Thr Cys Ala Cys Cys Thr Gly Cys Ala Thr Gly Gly
                725                 730                 735

Thr Cys Ala Cys Cys Gly Gly Cys Thr Thr Cys Thr Ala Cys Cys Cys
                740                 745                 750

Ala Gly Ala Ala Gly Ala Thr Gly Thr Ala Gly Cys Cys Gly Thr Gly
            755                 760                 765

Gly Ala Gly Thr Gly Gly Cys Ala Gly Ala Ala Ala Cys Cys
770                 775                 780

Gly Gly Cys Ala Gly Ala Cys Thr Gly Ala Gly Thr Cys Gly Gly Ala
785                 790                 795                 800

Gly Gly Ala Cys Ala Ala Gly Thr Ala Cys Cys Gly Cys Ala Cys Gly
                805                 810                 815

Ala Cys Cys Cys Cys Gly Cys Cys Cys Ala Gly Cys Thr Gly Gly
                820                 825                 830

Ala Cys Ala Cys Cys Gly Ala Cys Cys Gly Thr Cys Cys Thr Ala
            835                 840                 845

Cys Thr Thr Cys Cys Thr Gly Thr Ala Cys Ala Gly Cys Ala Ala Gly
                850                 855                 860

Cys Thr Cys Ala Gly Gly Gly Thr Gly Gly Ala Cys Ala Gly Gly Ala
865                 870                 875                 880
```

```
Ala Cys Ala Gly Cys Thr Gly Gly Cys Ala Gly Ala Gly Gly
                885                 890                 895

Ala Gly Ala Cys Gly Cys Cys Thr Ala Cys Ala Cys Gly Thr Gly Thr
            900                 905                 910

Gly Thr Gly Gly Thr Gly Ala Thr Gly Cys Ala Cys Gly Ala Gly Gly
        915                 920                 925

Cys Cys Cys Thr Gly Cys Ala Cys Ala Ala Thr Cys Ala Cys Thr Ala
        930                 935                 940

Cys Ala Thr Gly Cys Ala Gly Ala Ala Gly Thr Cys Cys Ala Cys Cys
945                 950                 955                 960

Thr Cys Thr Ala Ala Gly Thr Cys Thr Gly Cys Gly Gly Thr Ala
            965                 970                 975

Ala Ala Thr Gly Ala
        980

<210> SEQ ID NO 31
<211> LENGTH: 1764
<212> TYPE: PRT
<213> ORGANISM: Bos taurus

<400> SEQUENCE: 31

Cys Cys Ala Cys Cys Ala Thr Gly Cys Cys Gly Gly Cys Cys Gly Gly
1               5                   10                  15

Thr Cys Ala Thr Cys Ala Gly Ala Cys Cys Thr Gly Gly Ala Ala
            20                  25                  30

Gly Cys Ala Gly Gly Cys Ala Gly Thr Gly Gly Cys Thr Gly Gly Gly
        35                  40                  45

Cys Thr Thr Gly Gly Ala Ala Gly Thr Gly Cys Cys Cys Cys Ala Gly
        50                  55                  60

Gly Cys Cys Thr Gly Gly Gly Cys Thr Cys Cys Thr Ala Gly Gly
65                  70                  75                  80

Thr Cys Cys Thr Gly Cys Thr Gly Gly Ala Cys Cys Cys Ala Gly Cys
            85                  90                  95

Ala Thr Thr Cys Ala Cys Cys Cys Ala Gly Cys Cys Thr Cys Cys Thr
            100                 105                 110

Cys Thr Cys Thr Cys Ala Cys Ala Gly Cys Cys Thr Cys Cys Ala Cys
        115                 120                 125

Cys Ala Cys Ala Gly Cys Cys Cys Gly Ala Ala Ala Gly Thr Cys
        130                 135                 140

Thr Ala Cys Cys Cys Thr Cys Thr Gly Gly Cys Ala Thr Cys Ala
145                 150                 155                 160

Gly Cys Thr Gly Cys Gly Gly Ala Gly Ala Cys Ala Cys Ala Thr Cys
            165                 170                 175

Cys Ala Gly Cys Thr Cys Cys Ala Cys Cys Gly Thr Ala Cys Cys
        180                 185                 190

Cys Thr Gly Gly Gly Cys Thr Gly Cys Cys Thr Gly Gly Thr Cys Thr
        195                 200                 205

Cys Cys Ala Gly Cys Thr Ala Cys Ala Thr Gly Cys Cys Cys Gly Ala
        210                 215                 220

Gly Cys Cys Gly Gly Thr Gly Ala Cys Cys Gly Thr Gly Cys Cys
225                 230                 235                 240

Thr Gly Gly Ala Ala Cys Thr Cys Gly Gly Gly Thr Gly Cys Cys Cys
            245                 250                 255

Thr Gly Ala Ala Gly Ala Gly Cys Gly Gly Cys Gly Thr Gly Cys Ala
        260                 265                 270
```

```
Cys Ala Cys Cys Thr Thr Cys Cys Cys Gly Gly Cys Cys Gly Thr Cys
    275                 280                 285

Cys Gly Gly Cys Ala Gly Thr Cys Cys Thr Cys Thr Gly Gly Gly Cys
    290                 295                 300

Thr Gly Thr Ala Cys Thr Cys Thr Cys Thr Cys Ala Gly Cys Ala Gly
305                 310                 315                 320

Cys Ala Thr Gly Gly Thr Gly Ala Cys Thr Gly Thr Gly Cys Cys Cys
                325                 330                 335

Gly Cys Cys Ala Gly Cys Ala Gly Cys Thr Cys Ala Gly Ala Ala Ala
            340                 345                 350

Cys Cys Cys Ala Gly Ala Cys Cys Thr Thr Cys Ala Cys Cys Thr Gly
            355                 360                 365

Cys Ala Ala Cys Gly Thr Ala Gly Cys Cys Ala Cys Cys Cys Cys Gly
    370                 375                 380

Gly Cys Cys Ala Gly Cys Ala Gly Cys Ala Cys Cys Ala Ala Gly Gly
385                 390                 395                 400

Thr Gly Gly Ala Cys Ala Ala Gly Gly Cys Thr Gly Thr Cys Ala Cys
                405                 410                 415

Thr Gly Cys Ala Ala Gly Gly Cys Gly Thr Cys Cys Ala Gly Thr Cys
            420                 425                 430

Cys Cys Gly Ala Cys Gly Ala Cys Gly Cys Ala Ala Ala Gly Thr Ala
            435                 440                 445

Cys Ala Ala Cys Thr Ala Thr Cys Cys Cys Thr Cys Cys Thr Gly Gly
    450                 455                 460

Ala Ala Ala Ala Cys Cys Ala Cys Ala Cys Cys Cys Cys Thr Cys Ala
465                 470                 475                 480

Ala Gly Thr Ala Thr Gly Thr Ala Ala Thr Cys Cys Cys Ala Ala Cys
                485                 490                 495

Ala Cys Thr Cys Cys Thr Gly Cys Cys Thr Gly Cys Ala Gly Gly Gly
            500                 505                 510

Gly Cys Cys Thr Cys Ala Gly Cys Cys Ala Gly Gly Gly Gly Gly Thr
            515                 520                 525

Gly Cys Thr Gly Thr Gly Ala Ala Cys Ala Gly Cys Cys Gly Cys Cys
    530                 535                 540

Ala Gly Cys Gly Thr Gly Thr Cys Ala Gly Gly Gly Ala Gly Gly Gly
545                 550                 555                 560

Cys Cys Cys Thr Gly Thr Cys Thr Gly Thr Cys Thr Cys Thr Cys Thr
                565                 570                 575

Cys Thr Cys Cys Thr Gly Ala Ala Gly Gly Thr Cys Thr Cys Ala Cys
            580                 585                 590

Ala Gly Gly Cys Thr Thr Gly Gly Gly Ala Gly Gly Gly Gly Gly Thr
    595                 600                 605

Gly Thr Thr Gly Gly Ala Cys Thr Thr Cys Cys Ala Cys Gly Gly Ala
            610                 615                 620

Thr Gly Thr Cys Cys Ala Gly Gly Cys Thr Gly Cys Thr Gly Cys Ala
625                 630                 635                 640

Gly Gly Cys Thr Gly Gly Ala Thr Gly Ala Cys Gly Cys Cys Thr Cys
                645                 650                 655

Gly Gly Cys Cys Cys Thr Gly Gly Cys Cys Cys Ala Cys Ala
            660                 665                 670

Gly Ala Gly Gly Cys Gly Gly Cys Cys Cys Thr Cys Gly Gly Cys
    675                 680                 685
```

```
Thr Cys Gly Gly Ala Cys Thr Ala Cys Cys Ala Ala Ala Cys Thr
            690                 695                 700
Thr Gly Thr Cys Cys Thr Gly Cys Cys Thr Ala Ala Gly Cys
705                 710                 715                 720
Cys Cys Ala Gly Ala Cys Cys Ala Cys Ala Gly Cys Thr Thr Cys Cys
                725                 730                 735
Thr Gly Cys Cys Cys Cys Thr Gly Gly Thr Ala Ala Cys Cys Cys Cys
            740                 745                 750
Cys Gly Gly Thr Cys Thr Gly Cys Thr Cys Thr Cys Thr Gly
            755                 760                 765
Cys Ala Gly Ala Gly Thr Cys Thr Gly Ala Ala Gly Thr Thr Gly Ala
            770                 775                 780
Ala Ala Ala Gly Ala Cys Ala Cys Cys Thr Gly Cys Cys Ala Gly
785                 790                 795                 800
Thr Gly Thr Thr Cys Cys Ala Ala Thr Gly Cys Cys Cys Ala Gly
                805                 810                 815
Gly Thr Ala Ala Gly Thr Cys Ala Gly Cys Thr Gly Gly Cys Thr Thr
            820                 825                 830
Cys Ala Thr Cys Cys Thr Cys Thr Gly Thr Cys Thr Gly Ala Cys Ala
                835                 840                 845
Cys Thr Gly Gly Cys Gly Ala Ala Cys Ala Gly Cys Ala Cys Thr Cys
            850                 855                 860
Ala Gly Gly Gly Cys Ala Gly Cys Cys Gly Gly Thr Gly Gly Ala
865                 870                 875                 880
Gly Gly Ala Cys Gly Cys Gly Gly Thr Cys Cys Ala Ala Ala Gly
                885                 890                 895
Gly Ala Gly Gly Thr Thr Thr Cys Cys Ala Gly Gly Thr Gly Cys
            900                 905                 910
Ala Gly Ala Ala Cys Cys Cys Cys Ala Cys Ala Thr Gly Cys
            915                 920                 925
Thr Thr Thr Cys Thr Cys Ala Cys Cys Ala Ala Cys Cys Ala
930                 935                 940
Gly Ala Ala Cys Cys Thr Cys Thr Gly Gly Gly Ala Gly Gly Ala Cys
945                 950                 955                 960
Thr Gly Thr Cys Thr Gly Thr Cys Thr Cys Ala Thr Cys Thr Thr
                965                 970                 975
Cys Cys Cys Ala Cys Cys Gly Ala Ala Ala Cys Cys Cys Ala Ala Gly
                980                 985                 990
Gly Ala Cys Ala Cys Cys Cys  Cys Ala Cys Ala Ala  Thr Cys Thr
            995                 1000                1005
Cys Gly  Gly Gly Ala Ala Cys  Gly Cys Cys Cys Gly  Ala Gly Gly
            1010                1015                1020
Thr  Cys Ala Cys Gly Thr Gly  Thr Gly Thr Gly Thr  Gly Thr Gly
            1025                1030                1035
Thr Gly  Gly Ala Cys Gly Thr  Gly Gly Gly Cys Cys  Ala Gly Gly
            1040                1045                1050
Ala Thr  Gly Ala Cys Cys Cys  Gly Ala Gly Gly Thr  Gly Thr Cys
            1055                1060                1065
Ala Gly  Thr Thr Cys Thr Cys  Cys Thr Gly Gly Thr  Thr Cys Gly
            1070                1075                1080
Thr Gly  Gly Ala Cys Gly Ala  Cys Gly Thr Gly Gly  Ala Gly Gly
            1085                1090                1095
Thr Gly  Cys Ala Cys Ala Cys  Gly Gly Cys Cys Ala  Gly Gly Ala
```

```
              1100                1105                1110

Cys Gly Ala Ala Gly Cys Cys Gly Ala Gly Ala Gly Gly
    1115                1120                1125

Ala Gly Cys Ala Gly Thr Thr Cys Ala Ala Cys Ala Gly Cys Ala
    1130                1135                1140

Cys Cys Thr Ala Cys Cys Gly Cys Gly Thr Gly Gly Thr Cys Ala
    1145                1150                1155

Gly Cys Gly Cys Cys Cys Thr Gly Cys Gly Cys Ala Thr Cys Cys
    1160                1165                1170

Ala Gly Cys Ala Cys Cys Ala Gly Gly Ala Cys Thr Gly Gly Cys
    1175                1180                1185

Thr Gly Cys Ala Gly Gly Gly Ala Ala Ala Gly Ala Gly Thr
    1190                1195                1200

Thr Cys Ala Ala Gly Thr Gly Cys Ala Ala Gly Gly Thr Cys Ala
    1205                1210                1215

Ala Cys Ala Ala Cys Ala Ala Ala Gly Gly Cys Cys Thr Cys Cys
    1220                1225                1230

Cys Gly Gly Cys Cys Cys Cys Ala Thr Thr Gly Thr Gly Ala
    1235                1240                1245

Gly Gly Ala Cys Cys Ala Thr Cys Thr Cys Cys Ala Gly Gly Ala
    1250                1255                1260

Cys Cys Ala Ala Ala Gly Gly Thr Gly Gly Gly Cys Cys Ala Gly
    1265                1270                1275

Gly Thr Gly Gly Ala Cys Thr Gly Gly Ala Cys Cys Gly Gly Gly
    1280                1285                1290

Ala Gly Gly Gly Thr Cys Cys Cys Gly Thr Gly Gly Gly Cys Cys
    1295                1300                1305

Ala Ala Thr Cys Ala Gly Ala Gly Thr Gly Ala Cys Cys Gly Cys
    1310                1315                1320

Thr Gly Thr Ala Cys Gly Gly Gly Ala Cys Cys Gly Gly Gly Cys
    1325                1330                1335

Cys Cys Thr Gly Thr Gly Gly Gly Cys Cys Ala Ala Thr Cys Ala
    1340                1345                1350

Gly Ala Gly Thr Gly Ala Cys Cys Gly Cys Thr Gly Gly Ala Cys
    1355                1360                1365

Gly Gly Gly Ala Cys Cys Gly Gly Ala Gly Gly Gly Thr Cys
    1370                1375                1380

Cys Cys Gly Thr Gly Gly Gly Cys Cys Ala Ala Thr Cys Ala Gly
    1385                1390                1395

Ala Gly Thr Gly Ala Cys Cys Gly Cys Thr Gly Thr Gly Cys Thr
    1400                1405                1410

Ala Ala Cys Ala Gly Cys Cys Thr Thr Cys Cys Thr Gly Thr Cys
    1415                1420                1425

Cys Cys Cys Ala Cys Ala Gly Gly Gly Cys Ala Gly Gly Cys Cys
    1430                1435                1440

Cys Gly Gly Gly Ala Gly Cys Cys Gly Cys Ala Gly Gly Thr Gly
    1445                1450                1455

Thr Ala Thr Gly Thr Cys Cys Thr Gly Gly Cys Cys Cys Cys Ala
    1460                1465                1470

Cys Cys Cys Cys Gly Gly Gly Ala Ala Gly Ala Gly Cys Thr Cys
    1475                1480                1485

Ala Gly Cys Ala Ala Ala Ala Gly Cys Ala Cys Gly Cys Thr Cys
    1490                1495                1500
```

```
Ala Gly Cys Cys Thr Cys Ala Cys Cys Thr Gly Cys Cys Thr Gly
    1505                1510                1515

Ala Thr Cys Ala Cys Cys Gly Gly Thr Thr Thr Cys Thr Ala Cys
    1520                1525                1530

Cys Cys Ala Gly Ala Ala Gly Ala Gly Ala Thr Ala Gly Ala Cys
    1535                1540                1545

Gly Thr Gly Gly Ala Gly Thr Gly Gly Cys Ala Gly Ala Gly Ala
    1550                1555                1560

Ala Ala Thr Gly Gly Gly Cys Ala Gly Cys Cys Thr Gly Ala Gly
    1565                1570                1575

Thr Cys Gly Gly Ala Gly Gly Ala Cys Ala Ala Gly Thr Ala Cys
    1580                1585                1590

Cys Ala Cys Ala Cys Gly Ala Cys Cys Gly Cys Ala Cys Cys Cys
    1595                1600                1605

Cys Ala Gly Cys Thr Gly Gly Ala Thr Gly Cys Thr Gly Ala Cys
    1610                1615                1620

Gly Gly Cys Thr Cys Cys Thr Ala Cys Thr Thr Cys Cys Thr Gly
    1625                1630                1635

Thr Ala Cys Ala Gly Cys Ala Ala Gly Cys Thr Cys Ala Gly Gly
    1640                1645                1650

Gly Thr Gly Ala Ala Cys Ala Ala Gly Ala Gly Cys Ala Gly Cys
    1655                1660                1665

Thr Gly Gly Cys Ala Gly Gly Ala Ala Gly Gly Ala Gly Ala Cys
    1670                1675                1680

Cys Ala Cys Thr Ala Cys Ala Cys Gly Thr Gly Thr Gly Cys Ala
    1685                1690                1695

Gly Thr Gly Ala Thr Gly Cys Ala Cys Gly Ala Ala Gly Cys Thr
    1700                1705                1710

Thr Thr Ala Cys Gly Gly Ala Ala Thr Cys Ala Cys Thr Ala Cys
    1715                1720                1725

Ala Ala Ala Gly Ala Gly Ala Ala Gly Thr Cys Cys Ala Thr Cys
    1730                1735                1740

Thr Cys Gly Ala Gly Gly Thr Cys Thr Cys Cys Gly Gly Gly Thr
    1745                1750                1755

Ala Ala Ala Thr Gly Ala
    1760

<210> SEQ ID NO 32
<211> LENGTH: 405
<212> TYPE: PRT
<213> ORGANISM: Bos taurus

<400> SEQUENCE: 32

Met Thr Arg Thr Ser Leu Lys Lys Val Phe Ser Cys Cys Val Leu
1               5                   10                  15

Ile Phe Leu Leu Phe Ala Ile Ile Cys Val Trp Lys Glu Lys Lys
                20                  25                  30

Gly Asn Tyr Tyr Glu Phe Leu Lys Leu Gln Asn Lys Glu Tyr Gln Val
            35                  40                  45

Leu Gln Gly Leu Glu Lys Leu Ala Val Ser Ser Ser Gln Pro Val
        50                  55                  60

Ser Ser Ser Ser Thr His Asn Pro Gln Arg Asn Ile Gln Ala Leu Gly
65                  70                  75                  80

Gly Pro Lys Ala Lys Leu Lys Ala Thr Phe Gln Val Trp Asp Lys Asp
```

```
                    85                  90                  95
        Ser Ser Ser Lys Asn Leu Ala Pro Arg Leu Gln Thr Ile Arg Lys Asn
                    100                 105                 110

Tyr Leu Asn Met Asn Lys Tyr Lys Val Thr Tyr Lys Gly Pro Gly Pro
                    115                 120                 125

Gly Val Lys Phe Ser Ala Glu Ala Leu Leu Cys His Leu Arg Asp His
                    130                 135                 140

Val Asn Ile Ser Met Ile Glu Ala Thr Asp Phe Pro Phe Asn Thr Ser
        145                 150                 155                 160

Asp Trp Glu Gly Tyr Leu Pro Gln Glu Asp Ile Arg Thr Lys Ala Gly
                    165                 170                 175

Pro Trp Gly Arg Cys Ala Val Val Ser Ser Ala Gly Ser Leu Lys Ser
                    180                 185                 190

Ser Arg Leu Gly Arg Glu Ile Asp Asp His Asp Ala Val Leu Arg Phe
                    195                 200                 205

Asn Gly Ala Pro Thr Val Lys Phe Gln Gln Asp Val Gly Thr Lys Thr
                    210                 215                 220

Thr Ile Arg Leu Val Asn Ser Gln Leu Val Thr Thr Glu Ala Gly Phe
        225                 230                 235                 240

Leu Lys Asp Ser Leu Tyr Asn Glu Gly Ile Leu Ile Val Trp Asp Pro
                    245                 250                 255

Ser Val Tyr His Ser Asp Ile Pro Lys Trp Tyr Arg Asn Pro Asp Tyr
                    260                 265                 270

Ser Phe Phe Asn Asn Phe Lys Ser Tyr Arg Lys Leu His Pro Asp Gln
                    275                 280                 285

Pro Phe Tyr Ile Leu Lys Pro Gln Met Pro Trp Glu Leu Trp Asp Ile
                    290                 295                 300

Ile Gln Glu Ile Ser Ser Glu Leu Ile Gln Pro Asn Pro Pro Ser Ser
        305                 310                 315                 320

Gly Met Leu Gly Ile Ala Ile Met Met Ser Leu Cys Asp Gln Val Asp
                    325                 330                 335

Ile Tyr Glu Phe Leu Pro Ser Lys Arg Lys Thr Asp Val Cys Tyr Tyr
                    340                 345                 350

Tyr Gln Arg Tyr Phe Asp Ser Ala Cys Thr Met Gly Ala Tyr His Pro
                    355                 360                 365

Leu Leu Phe Glu Lys Asn Met Val Lys Tyr Leu Asn Leu Gly Thr Asp
                    370                 375                 380

Glu Asp Ile Tyr Leu Leu Gly Lys Ala Thr Leu Pro Gly Phe Arg Thr
        385                 390                 395                 400

Ile Arg Cys Gly Ala
                    405

<210> SEQ ID NO 33
<211> LENGTH: 402
<212> TYPE: PRT
<213> ORGANISM: Bos taurus

<400> SEQUENCE: 33

Met Lys Phe Arg Glu Pro Leu Leu Gly Gly Ser Ala Ala Met Pro Gly
        1               5                   10                  15

Ala Ser Leu Gln Arg Ala Cys Arg Leu Leu Val Ala Val Cys Ala Leu
                    20                  25                  30

His Leu Gly Val Thr Leu Val Tyr Tyr Leu Ala Gly Arg Asp Leu Arg
                    35                  40                  45
```

```
Arg Leu Pro Gln Leu Val Gly Val His Pro Pro Leu Gln Gly Ser Ser
 50                  55                  60
His Gly Ala Ala Ala Ile Gly Gln Pro Ser Gly Glu Leu Arg Leu Arg
 65                  70                  75                  80
Gly Val Ala Pro Pro Pro Leu Gln Asn Ser Ser Lys Pro Arg Ser
                 85                  90                  95
Arg Ala Pro Ser Asn Leu Asp Ala Tyr Ser His Pro Gly Pro Gly Pro
                100                 105                 110
Gly Pro Gly Ser Asn Leu Thr Ser Ala Pro Val Pro Ser Thr Thr Thr
            115                 120                 125
Arg Ser Leu Thr Ala Cys Pro Glu Ser Pro Leu Leu Val Gly Pro
130                 135                 140
Met Leu Ile Glu Phe Asn Ile Pro Val Asp Leu Lys Leu Val Glu Gln
145                 150                 155                 160
Gln Asn Pro Lys Val Lys Leu Gly Gly Arg Tyr Thr Pro Met Asp Cys
                165                 170                 175
Ile Ser Pro His Lys Val Ala Ile Ile Ile Pro Phe Arg Asn Arg Gln
            180                 185                 190
Glu His Leu Lys Tyr Trp Leu Tyr Tyr Leu His Pro Ile Leu Gln Arg
        195                 200                 205
Gln Gln Leu Asp Tyr Gly Ile Tyr Val Ile Asn Gln Ala Gly Glu Ser
    210                 215                 220
Met Phe Asn Arg Ala Lys Leu Leu Asn Val Gly Phe Lys Glu Ala Leu
225                 230                 235                 240
Lys Asp Tyr Asp Tyr Asn Cys Phe Val Phe Ser Asp Val Asp Leu Ile
                245                 250                 255
Pro Met Asn Asp His Asn Thr Tyr Arg Cys Phe Ser Gln Pro Arg His
            260                 265                 270
Ile Ser Val Ala Met Asp Lys Phe Gly Phe Ser Leu Pro Tyr Val Gln
        275                 280                 285
Tyr Phe Gly Gly Val Ser Ala Leu Ser Lys Gln Gln Phe Leu Ser Ile
    290                 295                 300
Asn Gly Phe Pro Asn Asn Tyr Trp Gly Trp Gly Gly Glu Asp Asp Asp
305                 310                 315                 320
Ile Tyr Asn Arg Leu Ala Phe Arg Gly Met Ser Val Ser Arg Pro Asn
                325                 330                 335
Ala Val Ile Gly Lys Cys Arg Met Ile Arg His Ser Arg Asp Lys Lys
            340                 345                 350
Asn Glu Pro Asn Pro Gln Arg Phe Asp Arg Ile Ala His Thr Lys Glu
        355                 360                 365
Thr Met Leu Ser Asp Gly Leu Asn Ser Leu Thr Tyr Met Val Leu Glu
    370                 375                 380
Val Gln Arg Tyr Pro Leu Tyr Thr Lys Ile Thr Val Asp Ile Gly Thr
385                 390                 395                 400
Pro Ser

<210> SEQ ID NO 34
<211> LENGTH: 337
<212> TYPE: PRT
<213> ORGANISM: Equus caballus

<400> SEQUENCE: 34

Ala Ser Thr Thr Ala Pro Lys Val Phe Ala Leu Ala Pro Gly Cys Gly
 1               5                  10                  15
```

Thr Thr Ser Asp Ser Thr Val Ala Leu Gly Cys Leu Val Ser Gly Tyr
            20                  25                  30

Phe Pro Glu Pro Val Lys Val Ser Trp Asn Ser Gly Ser Leu Thr Ser
        35                  40                  45

Gly Val His Thr Phe Pro Ser Val Leu Gln Ser Ser Gly Phe Tyr Ser
    50                  55                  60

Leu Ser Ser Met Val Thr Val Pro Ala Ser Thr Trp Thr Ser Glu Thr
65                  70                  75                  80

Tyr Ile Cys Asn Val Val His Ala Ala Ser Asn Phe Lys Val Asp Lys
                85                  90                  95

Arg Ile Glu Pro Ile Pro Asp Asn His Gln Lys Val Cys Asp Met Ser
            100                 105                 110

Lys Cys Pro Lys Cys Pro Ala Pro Glu Leu Leu Gly Gly Pro Ser Val
        115                 120                 125

Phe Ile Phe Pro Pro Asn Pro Lys Asp Thr Leu Met Ile Thr Arg Thr
    130                 135                 140

Pro Glu Val Thr Cys Val Val Val Asp Val Ser Gln Glu Asn Pro Asp
145                 150                 155                 160

Val Lys Phe Asn Trp Tyr Met Asp Gly Val Glu Val Arg Thr Ala Thr
                165                 170                 175

Thr Arg Pro Lys Glu Glu Gln Phe Asn Ser Thr Tyr Arg Val Val Ser
            180                 185                 190

Val Leu Arg Ile Gln His Gln Asp Trp Leu Ser Gly Lys Glu Phe Lys
        195                 200                 205

Cys Lys Val Asn Asn Gln Ala Leu Pro Gln Pro Ile Glu Arg Thr Ile
    210                 215                 220

Thr Lys Thr Lys Gly Arg Ser Gln Glu Pro Gln Val Tyr Val Leu Ala
225                 230                 235                 240

Pro His Pro Asp Glu Leu Ser Lys Ser Lys Val Ser Val Thr Cys Leu
                245                 250                 255

Val Lys Asp Phe Tyr Pro Pro Glu Ile Asn Ile Glu Trp Gln Ser Asn
            260                 265                 270

Gly Gln Pro Glu Leu Glu Thr Lys Tyr Ser Thr Thr Gln Ala Gln Gln
        275                 280                 285

Asp Ser Asp Gly Ser Tyr Phe Leu Tyr Ser Lys Leu Ser Val Asp Arg
    290                 295                 300

Asn Arg Trp Gln Gln Gly Thr Thr Phe Thr Cys Gly Val Met His Glu
305                 310                 315                 320

Ala Leu His Asn His Tyr Thr Gln Lys Asn Val Ser Lys Asn Pro Gly
                325                 330                 335

Lys

<210> SEQ ID NO 35
<211> LENGTH: 342
<212> TYPE: PRT
<213> ORGANISM: Equus caballus

<400> SEQUENCE: 35

Ala Ser Thr Thr Ala Pro Lys Tyr Phe Gln Leu Thr Pro Ser Cys Gly
1               5                   10                  15

Ile Thr Ser Asp Ala Thr Val Ala Leu Gly Cys Leu Val Ser Asp Tyr
            20                  25                  30

Tyr Pro Glu Pro Val Thr Val Ser Trp Asn Ser Gly Ala Leu Thr Ser
        35                  40                  45

```
Gly Val His Thr Phe Pro Ser Val Leu Gln Ser Ser Gly Leu Tyr Ala
 50                  55                  60

Leu Ser Ser Met Val Thr Val Pro Ala Ser Trp Thr Ser Glu Thr
 65                  70                  75                  80

Tyr Ile Cys Asn Val Ala His Pro Ala Ser Ser Thr Lys Val Asp Lys
                 85                  90                  95

Arg Ile Pro Pro Cys Val Leu Ser Ala Glu Gly Val Ile Pro Ile Pro
            100                 105                 110

Ser Val Pro Lys Pro Gln Cys Pro Tyr Thr His Ser Lys Phe Leu
            115                 120                 125

Gly Gly Pro Ser Val Phe Ile Phe Pro Pro Asn Pro Lys Asp Ala Leu
        130                 135                 140

Met Ile Ser Arg Thr Pro Val Val Thr Cys Val Val Val Asn Leu Ser
145                 150                 155                 160

Asp Gln Tyr Pro Asp Val Gln Phe Ser Trp Tyr Val Asp Asn Thr Glu
                165                 170                 175

Val His Ser Ala Ile Thr Lys Gln Arg Glu Ala Gln Phe Asn Ser Thr
            180                 185                 190

Tyr Arg Val Val Ser Val Leu Pro Ile Gln His Gln Asp Trp Leu Ser
        195                 200                 205

Gly Lys Glu Phe Lys Cys Ser Val Thr Asn Val Gly Val Pro Gln Pro
210                 215                 220

Ile Ser Arg Ala Ile Ser Arg Gly Lys Gly Pro Ser Arg Val Pro Gln
225                 230                 235                 240

Val Tyr Val Leu Pro Pro His Pro Asp Glu Leu Ala Lys Ser Lys Val
                245                 250                 255

Ser Val Thr Cys Leu Val Lys Asp Phe Tyr Pro Pro Asp Ile Ser Val
            260                 265                 270

Glu Trp Gln Ser Asn Arg Trp Pro Glu Leu Glu Gly Lys Tyr Ser Thr
        275                 280                 285

Thr Pro Ala Gln Leu Asp Gly Asp Gly Ser Tyr Phe Leu Tyr Ser Lys
290                 295                 300

Leu Ser Leu Glu Thr Ser Arg Trp Gln Gln Val Glu Ser Phe Thr Cys
305                 310                 315                 320

Ala Val Met His Glu Ala Leu His Asn His Phe Thr Lys Thr Asp Ile
                325                 330                 335

Ser Glu Ser Leu Gly Lys
            340

<210> SEQ ID NO 36
<211> LENGTH: 354
<212> TYPE: PRT
<213> ORGANISM: Equus caballus

<400> SEQUENCE: 36

Ala Ser Thr Thr Ala Pro Lys Val Phe Pro Leu Ala Pro Ser Cys Gly
 1               5                  10                  15

Thr Thr Ser Asp Ser Thr Val Ala Leu Gly Cys Leu Val Ser Ser Tyr
                 20                  25                  30

Phe Pro Glu Pro Val Thr Val Ser Trp Asn Ser Gly Thr Leu Thr Ser
            35                  40                  45

Gly Val Arg Thr Phe Pro Ser Val Leu Gln Ser Ser Gly Leu Tyr Ser
        50                  55                  60

Leu Ser Ser Met Val Thr Val Pro Ala Ser Ser Leu Glu Ser Lys Thr
 65                  70                  75                  80
```

-continued

```
Tyr Ile Cys Asn Val Ala His Pro Ala Ser Ser Thr Lys Val Asp Lys
                 85                  90                  95

Arg Ile Glu Pro Val Leu Pro Lys Pro Thr Thr Pro Ala Pro Thr Val
            100                 105                 110

Pro Leu Thr Thr Thr Val Pro Val Glu Thr Thr Thr Pro Pro Cys Pro
            115                 120                 125

Cys Glu Cys Pro Lys Cys Pro Ala Pro Glu Leu Leu Gly Gly Pro Ser
        130                 135                 140

Val Phe Ile Phe Pro Pro Lys Pro Lys Asp Val Leu Met Ile Thr Arg
145                 150                 155                 160

Thr Pro Glu Val Thr Cys Leu Val Val Asp Val Ser His Asp Ser Ser
                165                 170                 175

Asp Val Leu Phe Thr Trp Tyr Val Asp Gly Thr Glu Val Lys Thr Ala
            180                 185                 190

Lys Thr Met Pro Asn Glu Glu Gln Asn Ser Thr Tyr Arg Val Val
            195                 200                 205

Ser Val Leu Arg Ile Gln His Gln Asp Trp Leu Asn Gly Lys Lys Phe
        210                 215                 220

Lys Cys Lys Val Asn Asn Gln Ala Leu Pro Ala Pro Val Glu Arg Thr
225                 230                 235                 240

Ile Ser Lys Ala Thr Gly Gln Thr Arg Val Pro Gln Val Tyr Val Leu
                245                 250                 255

Ala Pro His Pro Asp Glu Leu Ser Lys Asn Lys Val Ser Val Thr Cys
            260                 265                 270

Leu Val Lys Asp Phe Leu Pro Thr Asp Ile Thr Val Glu Trp Gln Ser
        275                 280                 285

Asn Glu His Pro Glu Pro Glu Gly Lys Tyr Arg Thr Thr Glu Ala Gln
290                 295                 300

Lys Asp Ser Asp Gly Ser Tyr Phe Leu Tyr Ser Lys Leu Thr Val Glu
305                 310                 315                 320

Thr Asp Arg Trp Gln Gln Gly Thr Thr Phe Thr Cys Val Val Met His
                325                 330                 335

Glu Ala Leu His Asn His Val Met Gln Lys Asn Val Ser His Ser Pro
            340                 345                 350

Gly Lys

<210> SEQ ID NO 37
<211> LENGTH: 335
<212> TYPE: PRT
<213> ORGANISM: Equus caballus
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid

<400> SEQUENCE: 37

Ala Ser Thr Thr Ala Pro Lys Val Phe Pro Leu Ala Ser His Ser Ala
1               5                   10                  15

Ala Thr Ser Gly Ser Thr Val Ala Leu Gly Cys Leu Val Ser Ser Tyr
            20                  25                  30

Phe Pro Glu Pro Val Thr Val Ser Trp Asn Ser Gly Ala Leu Thr Ser
        35                  40                  45
```

Gly Val His Thr Phe Pro Ser Val Leu Gln Ser Ser Gly Leu Tyr Ser
            50                  55                  60

Leu Ser Ser Met Val Thr Val Pro Ala Ser Ser Leu Lys Ser Gln Thr
65                  70                  75                  80

Tyr Ile Cys Asn Val Ala His Pro Ala Ser Ser Thr Lys Val Asp Lys
                85                  90                  95

Lys Ile His Leu Ser Val Leu Ser Ala Val Ile Lys Glu Cys Asn Gly
            100                 105                 110

Gly Cys Pro Ala Pro Glu Cys Leu Gln Val Gly Pro Ser Val Phe Ile
        115                 120                 125

Phe Pro Pro Lys Pro Lys Asp Val Leu Met Ile Ser Arg Thr Pro Thr
130                 135                 140

Val Thr Cys Val Val Val Asp Val Gly His Asp Phe Pro Asp Val Gln
145                 150                 155                 160

Phe Asn Trp Tyr Val Asp Gly Val Glu Thr His Thr Ala Thr Thr Glu
                165                 170                 175

Pro Lys Gln Glu Gln Phe Asn Ser Thr Tyr Arg Val Val Ser Val Leu
            180                 185                 190

Pro Ile Gln His Lys Asp Trp Leu Ser Gly Lys Glu Phe Lys Cys Lys
        195                 200                 205

Val Asn Asn Lys Ala Leu Pro Ala Pro Val Glu Arg Thr Ile Ser Lys
210                 215                 220

Pro Thr Gly Gln Pro Arg Glu Pro Gln Val Tyr Val Leu Ala Pro His
225                 230                 235                 240

Arg Asp Glu Leu Xaa Arg Xaa Asn Val Ser Val Thr Cys Leu Val Lys
                245                 250                 255

Asp Phe Tyr Pro Thr Asp Ile Asp Ile Glu Trp Lys Ser Asn Gly Gln
            260                 265                 270

Pro Glu Pro Glu Thr Lys Tyr Ser Thr Thr Pro Ala Gln Leu Asp Ser
        275                 280                 285

Asp Gly Ser Tyr Phe Leu Tyr Ser Lys Leu Thr Val Gly Thr Asn Arg
290                 295                 300

Trp Gln Gln Gly Thr Thr Phe Thr Cys Ala Val Met His Glu Ala Leu
305                 310                 315                 320

His Asn His Tyr Thr Glu Lys Ser Val Ser Lys Ser Pro Gly Lys
                325                 330                 335

<210> SEQ ID NO 38
<211> LENGTH: 326
<212> TYPE: PRT
<213> ORGANISM: Equus caballus

<400> SEQUENCE: 38

Glu Ser Pro Lys Ala Pro Asp Val Phe Pro Leu Thr Ile Cys Gly Asn
1               5                   10                  15

Thr Pro Asp Pro Thr Val Pro Val Gly Cys Leu Val Ser Asn Tyr Phe
            20                  25                  30

Pro Glu Pro Val Thr Val Ser Trp Asn Cys Asp Ala Leu Lys Gly Asp
        35                  40                  45

Ile His Thr Phe Pro Leu Asp Leu Ser Asn Ser Ala His His Ser Leu
50                  55                  60

Ser Ser Met Met Ala Val Pro Arg Ser Ser Leu Asn Gln Thr Tyr Ile
65                  70                  75                  80

Cys Ser Val Ala His Pro Ala Ser Ser Thr Lys Val Asp Lys Arg Ile
                85                  90                  95

```
Val Val Lys Gly Ser Pro Cys Pro Lys Cys Pro Ala Pro Glu Leu Pro
             100                 105                 110

Gly Gly Pro Ser Val Phe Ile Phe Pro Pro Lys Pro Lys Asp Val Leu
             115                 120                 125

Lys Ile Ser Arg Lys Pro Glu Val Thr Cys Val Val Asp Leu Gly
             130                 135                 140

His Asp Pro Asp Val Gln Phe Thr Trp Phe Val Asp Gly Val Glu
145                 150                 155                 160

Thr His Thr Ala Thr Thr Glu Pro Lys Glu Glu Gln Phe Asn Ser Thr
                 165                 170                 175

Tyr Arg Val Val Ser Val Leu Pro Ile Gln His Gln Asp Trp Leu Ser
             180                 185                 190

Gly Lys Glu Phe Lys Cys Ser Val Thr Asn Lys Ala Leu Pro Ala Pro
             195                 200                 205

Val Glu Arg Thr Thr Ser Lys Ala Lys Gly Gln Leu Arg Val Pro Gln
             210                 215                 220

Val Tyr Val Leu Ala Pro His Pro Asp Glu Leu Ala Lys Asn Thr Val
225                 230                 235                 240

Ser Val Thr Cys Leu Val Lys Asp Phe Tyr Pro Pro Glu Ile Asp Val
                 245                 250                 255

Glu Trp Gln Ser Asn Glu His Pro Glu Pro Glu Gly Lys Tyr Ser Thr
             260                 265                 270

Thr Pro Ala Gln Leu Asn Ser Asp Gly Ser Tyr Phe Leu Tyr Ser Lys
             275                 280                 285

Leu Ser Val Glu Thr Ser Arg Trp Lys Gln Gly Glu Ser Phe Thr Cys
             290                 295                 300

Gly Val Met His Glu Ala Val Glu Asn His Tyr Thr Gln Lys Asn Val
305                 310                 315                 320

Ser His Ser Pro Gly Lys
                 325

<210> SEQ ID NO 39
<211> LENGTH: 324
<212> TYPE: PRT
<213> ORGANISM: Equus caballus

<400> SEQUENCE: 39

Ala Ser Thr Thr Ala Pro Lys Val Phe Gln Leu Ala Ser His Ser Ala
1               5                   10                  15

Gly Thr Ser Asp Ser Thr Val Ala Leu Gly Cys Leu Val Ser Ser Tyr
             20                  25                  30

Phe Pro Glu Pro Val Thr Val Ser Trp Asn Ser Gly Ala Leu Thr Ser
             35                  40                  45

Gly Val His Thr Phe Pro Ser Val Arg Gln Ser Ser Gly Leu Tyr Ser
     50                  55                  60

Leu Ser Ser Met Val Thr Val Pro Ala Ser Ser Leu Lys Ser Gln Thr
65                  70                  75                  80

Tyr Ile Cys Asn Val Ala His Pro Ala Ser Ser Thr Lys Val Asp Lys
                 85                  90                  95

Arg Ile Val Ile Lys Glu Pro Cys Cys Cys Pro Lys Cys Pro Gly Arg
             100                 105                 110

Pro Ser Val Phe Ile Phe Pro Pro Asn Pro Lys Asp Thr Leu Met Ile
             115                 120                 125

Ser Arg Thr Pro Glu Val Thr Cys Val Val Val Asp Val Ser Gln Glu
```

```
                 130                 135                 140
Asn Pro Asp Val Lys Phe Asn Trp Tyr Val Asp Gly Val Glu Ala His
145                 150                 155                 160

Thr Ala Thr Thr Lys Ala Lys Glu Lys Gln Asp Asn Ser Thr Tyr Arg
                165                 170                 175

Val Val Ser Val Leu Pro Ile Gln His Gln Asp Trp Arg Arg Gly Lys
            180                 185                 190

Glu Phe Lys Cys Lys Val Asn Asn Arg Ala Leu Pro Ala Pro Val Glu
        195                 200                 205

Arg Thr Ile Thr Lys Ala Lys Gly Glu Leu Gln Asp Pro Lys Val Tyr
    210                 215                 220

Ile Leu Ala Pro His Arg Glu Glu Val Thr Lys Asn Thr Val Ser Val
225                 230                 235                 240

Thr Cys Leu Val Lys Asp Phe Tyr Pro Pro Asp Ile Asn Val Glu Trp
                245                 250                 255

Gln Ser Asn Glu Glu Pro Glu Pro Glu Val Lys Tyr Ser Thr Thr Pro
            260                 265                 270

Ala Gln Leu Asp Gly Asp Gly Ser Tyr Phe Leu Tyr Ser Lys Leu Thr
        275                 280                 285

Val Glu Thr Asp Arg Trp Glu Gln Gly Glu Ser Phe Thr Cys Val Val
    290                 295                 300

Met His Glu Ala Ile Arg His Thr Tyr Arg Gln Lys Ser Ile Thr Asn
305                 310                 315                 320

Phe Pro Gly Lys

<210> SEQ ID NO 40
<211> LENGTH: 406
<212> TYPE: PRT
<213> ORGANISM: Equus caballus

<400> SEQUENCE: 40

Met Ile His Ser Ser Leu Lys Lys Lys Phe Ser Phe Cys Val Leu Val
1               5                   10                  15

Phe Leu Leu Phe Ala Val Ile Cys Val Trp Lys Glu Lys Lys Lys Gly
            20                  25                  30

Ser Tyr Tyr Glu Ser Leu Lys Leu Gln Thr Lys Glu Leu Gln Met Pro
        35                  40                  45

Arg Ser Pro Glu Lys Arg Ala Ile Gly Ser Gly Ser Lys Phe Ala Ser
    50                  55                  60

Ser Ser Ser Thr Gln Asp Pro His Arg Asn Thr Gln Gly Leu Ser Asn
65                  70                  75                  80

Pro Arg Ser Pro Ala Lys Ala Lys Pro Glu Gly Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Val Lys Phe Ser Ala Asp Val Leu Arg Cys Arg Leu
    130                 135                 140

Arg Asp Glu Val Asn Val Ser Met Val Glu Ala Thr Asp Phe Pro Phe
145                 150                 155                 160

Asn Thr Ser Glu Trp Glu Gly Tyr Leu Pro Met Glu Asp Ile Arg Thr
                165                 170                 175

Lys Ala Gly Pro Trp Gly Lys Cys Ala Val Val Ser Ser Ala Gly Ser
```

```
            180                 185                 190
Leu Lys Ser Ser Gln Leu Gly Gln Glu Ile Asp Asp His Asp Ala Val
        195                 200                 205

Met Arg Phe Asn Gly Ala Pro Thr Ala Ser Phe Gln Gln Asp Val Gly
    210                 215                 220

Thr Lys Thr Thr Ile Arg Leu Met Asn Ser Gln Leu Val Thr Thr Glu
225                 230                 235                 240

Gly Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Lys Asn
            260                 265                 270

Pro Asp Tyr Ser Phe Phe Asp Asn Tyr Lys Ser Tyr Arg Lys Leu His
        275                 280                 285

Pro Asp Gln Pro Phe Tyr Ile Leu Lys Pro Gln Met Pro Trp Glu Leu
    290                 295                 300

Trp Asp Ile Ile Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Tyr Phe Asp Thr Ala Cys Thr Met Gly Ala
        355                 360                 365

Tyr His Pro Leu Leu Phe Glu Lys Asn Met Val Lys His Leu Asn Gln
    370                 375                 380

Gly Thr Asp Glu Asp Ile Tyr Leu Phe Gly Lys Ala Thr Leu Pro Gly
385                 390                 395                 400

Phe Arg Ser Ile Arg Cys
                405

<210> SEQ ID NO 41
<211> LENGTH: 266
<212> TYPE: PRT
<213> ORGANISM: Equus caballus

<400> SEQUENCE: 41

Ser Ser Thr Ser Leu Val Gly Pro Met Met Ile Glu Phe Asn Met Ala
1               5                   10                  15

Val Asp Leu Asn Arg Val Ala Glu Glu Asn Pro Glu Val Lys Leu Gly
            20                  25                  30

Gly Arg Tyr Thr Pro Lys Asp Cys Ile Ser Pro His Lys Val Ala Ile
        35                  40                  45

Ile Ile Pro Phe Arg Asn Arg Gln Glu His Leu Lys Tyr Trp Leu Tyr
    50                  55                  60

Tyr Leu His Pro Ile Leu Gln Arg Gln Gln Leu Asp Tyr Gly Ile Tyr
65                  70                  75                  80

Val Ile Asn Gln Ala Gly Glu Ala Met Phe Asn Arg Ala Lys Leu Leu
                85                  90                  95

Asn Val Gly Phe Gln Glu Ala Leu Lys Asp Tyr Asp Tyr Asn Cys Phe
            100                 105                 110

Val Phe Ser Asp Val Asp Leu Ile Pro Met Asn Asp His Asn Ala Tyr
        115                 120                 125

Arg Cys Phe Ser Gln Pro Arg His Ile Ser Val Ala Met Asp Lys Phe
    130                 135                 140
```

-continued

Gly Phe Ser Leu Pro Tyr Val Gln Tyr Phe Gly Val Ser Ala Leu
145                 150                 155                 160

Ser Lys Glu Gln Phe Leu Thr Ile Asn Gly Phe Pro Asn Asn Tyr Trp
                165                 170                 175

Gly Trp Gly Gly Glu Asp Asp Asp Ile Phe Asn Arg Leu Val Phe Lys
            180                 185                 190

Gly Met Ser Leu Ser Arg Pro Asn Ala Val Ile Gly Lys Cys Arg Met
        195                 200                 205

Ile Arg His Ser Arg Asp Lys Lys Asn Glu Pro Asn Pro Gln Arg Phe
210                 215                 220

Asp Arg Ile Ala His Thr Lys Glu Thr Met Phe Leu Asp Gly Leu Asn
225                 230                 235                 240

Thr Leu Phe Tyr Asn Val Leu Asp Val Gln Arg Tyr Pro Leu Tyr Thr
                245                 250                 255

Lys Val Thr Val Asp Ile Gly Thr Pro Ser
                260                 265

<210> SEQ ID NO 42
<211> LENGTH: 619
<212> TYPE: PRT
<213> ORGANISM: Artificial Sequence
<220> FEATURE:
<223> OTHER INFORMATION: Fc -B4GALT1 fusion protein

<400> SEQUENCE: 42

Met Tyr Arg Met Gln Leu Leu Ser Cys Ile Ala Leu Ser Leu Ala Leu
1               5                   10                  15

Val Thr Asn Ser Met Pro Arg Gly Pro Pro Lys Ser Cys Asp Lys Thr
                20                  25                  30

His Thr Cys Pro Pro Cys Pro Ala Pro Glu Leu Leu Gly Gly Pro Ser
            35                  40                  45

Val Phe Leu Phe Pro Pro Lys Pro Lys Asp Thr Leu Met Ile Ser Arg
50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
130                 135                 140

Ile Ser Lys Ala Lys Gly Gln Pro Arg Glu Pro Gln Val Cys Thr Leu
145                 150                 155                 160

Pro Pro Ser Arg Asp Glu Leu Thr Lys Asn Gln Val Ser Leu Ser Cys
                165                 170                 175

Ala Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Val Ser Lys Leu Thr Val Asp Lys Ser
210                 215                 220

Arg Trp Gln Gln Gly Asn Val Phe Ser Cys Ser Val Met His Glu Ala
225                 230                 235                 240

```
Leu His Asn His Tyr Thr Gln Lys Ser Leu Ser Leu Ser Pro Gly Lys
                245                 250                 255

Gly Ala Pro Asp Leu Lys Leu Met Gly Arg Asp Leu Ser Arg Leu Pro
            260                 265                 270

Gln Leu Val Gly Val Ser Thr Pro Leu Gln Gly Gly Ser Asn Ser Ala
        275                 280                 285

Ala Ala Ile Gly Gln Ser Ser Gly Glu Leu Arg Thr Gly Gly Ala Arg
    290                 295                 300

Pro Pro Pro Leu Gly Ala Ser Ser Gln Pro Arg Pro Gly Gly Asp
305                 310                 315                 320

Ser Ser Pro Val Val Asp Ser Gly Pro Gly Pro Ala Ser Asn Leu Thr
                325                 330                 335

Ser Val Pro Val Pro His Thr Thr Ala Leu Ser Leu Pro Ala Cys Pro
            340                 345                 350

Glu Glu Ser Pro Leu Leu Val Gly Pro Met Leu Ile Glu Phe Asn Met
        355                 360                 365

Pro Val Asp Leu Glu Leu Val Ala Lys Gln Asn Pro Asn Val Lys Met
    370                 375                 380

Gly Gly Arg Tyr Ala Pro Arg Asp Cys Val Ser Pro His Lys Val Ala
385                 390                 395                 400

Ile Ile Ile Pro Phe Arg Asn Arg Gln Glu His Leu Lys Tyr Trp Leu
                405                 410                 415

Tyr Tyr Leu His Pro Val Leu Gln Arg Gln Gln Leu Asp Tyr Gly Ile
            420                 425                 430

Tyr Val Ile Asn Gln Ala Gly Asp Thr Ile Phe Asn Arg Ala Lys Leu
        435                 440                 445

Leu Asn Val Gly Phe Gln Glu Ala Leu Lys Asp Tyr Asp Tyr Thr Cys
    450                 455                 460

Phe Val Phe Ser Asp Val Asp Leu Ile Pro Met Asn Asp His Asn Ala
465                 470                 475                 480

Tyr Arg Cys Phe Ser Gln Pro Arg His Ile Ser Val Ala Met Asp Lys
                485                 490                 495

Phe Gly Phe Ser Leu Pro Tyr Val Gln Tyr Phe Gly Gly Val Ser Ala
            500                 505                 510

Leu Ser Lys Gln Gln Phe Leu Thr Ile Asn Gly Phe Pro Asn Asn Tyr
        515                 520                 525

Trp Gly Trp Gly Gly Glu Asp Asp Ile Phe Asn Arg Leu Val Phe
            530                 535                 540

Arg Gly Met Ser Ile Ser Arg Pro Asn Ala Val Val Gly Arg Cys Arg
545                 550                 555                 560

Met Ile Arg His Ser Arg Asp Lys Lys Asn Glu Pro Asn Pro Gln Arg
                565                 570                 575

Phe Asp Arg Ile Ala His Thr Lys Glu Thr Met Leu Ser Asp Gly Leu
            580                 585                 590

Asn Ser Leu Thr Tyr Gln Val Leu Asp Val Gln Arg Tyr Pro Leu Tyr
        595                 600                 605

Thr Gln Ile Thr Val Asp Ile Gly Thr Pro Ser
    610                 615
```

<210> SEQ ID NO 43
<211> LENGTH: 627
<212> TYPE: PRT
<213> ORGANISM: Artificial Sequence
<220> FEATURE:
<223> OTHER INFORMATION: Fc-ST6GAL1 fusion protein

<400> SEQUENCE: 43

```
Met Tyr Arg Met Gln Leu Leu Ser Cys Ile Ala Leu Ser Leu Ala Leu
1               5                   10                  15

Val Thr Asn Ser Met Pro Arg Gly Pro Pro Lys Ser Cys Asp Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
145                 150                 155                 160

Pro Pro Cys Arg Asp Glu Leu Thr Lys Asn Gln Val Ser Leu Trp Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Tyr Ser Lys Leu Thr Val Asp Lys Ser
    210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255

Gly Ala Pro Asp Leu Lys Leu Met Glu Phe Gln Val Leu Lys Ser Leu
            260                 265                 270

Gly Lys Leu Ala Met Gly Ser Asp Ser Gln Ser Val Ser Ser Ser Ser
        275                 280                 285

Thr Gln Asp Pro His Arg Gly Arg Gln Thr Leu Gly Ser Leu Arg Gly
    290                 295                 300

Leu Ala Lys Ala Lys Pro Glu Ala Ser Phe Gln Val Trp Asn Lys Asp
305                 310                 315                 320

Ser Ser Ser Lys Asn Leu Ile Pro Arg Leu Gln Lys Ile Trp Lys Asn
                325                 330                 335

Tyr Leu Ser Met Asn Lys Tyr Lys Val Ser Tyr Lys Gly Pro Gly Pro
            340                 345                 350

Gly Ile Lys Phe Ser Ala Glu Ala Leu Arg Cys His Leu Arg Asp His
        355                 360                 365

Val Asn Val Ser Met Val Glu Val Thr Asp Phe Pro Phe Asn Thr Ser
    370                 375                 380

Glu Trp Glu Gly Tyr Leu Pro Lys Glu Ser Ile Arg Thr Lys Ala Gly
385                 390                 395                 400

Pro Trp Gly Arg Cys Ala Val Val Ser Ser Ala Gly Ser Leu Lys Ser
```

-continued

```
                405                 410                 415
Ser Gln Leu Gly Arg Glu Ile Asp Asp His Asp Ala Val Leu Arg Phe
            420                 425                 430

Asn Gly Ala Pro Thr Ala Asn Phe Gln Gln Asp Val Gly Thr Lys Thr
            435                 440                 445

Thr Ile Arg Leu Met Asn Ser Gln Leu Val Thr Thr Glu Lys Arg Phe
    450                 455                 460

Leu Lys Asp Ser Leu Tyr Asn Glu Gly Ile Leu Ile Val Trp Asp Pro
465                 470                 475                 480

Ser Val Tyr His Ser Asp Ile Pro Lys Trp Tyr Gln Asn Pro Asp Tyr
            485                 490                 495

Asn Phe Phe Asn Asn Tyr Lys Thr Tyr Arg Lys Leu His Pro Asn Gln
            500                 505                 510

Pro Phe Tyr Ile Leu Lys Pro Gln Met Pro Trp Glu Leu Trp Asp Ile
            515                 520                 525

Leu Gln Glu Ile Ser Pro Glu Glu Ile Gln Pro Asn Pro Pro Ser Ser
            530                 535                 540

Gly Met Leu Gly Ile Ile Ile Met Met Thr Leu Cys Asp Gln Val Asp
545                 550                 555                 560

Ile Tyr Glu Phe Leu Pro Ser Lys Arg Lys Thr Asp Val Cys Tyr Tyr
            565                 570                 575

Tyr Gln Lys Phe Phe Asp Ser Ala Cys Thr Met Gly Ala Tyr His Pro
            580                 585                 590

Leu Leu Tyr Glu Lys Asn Leu Val Lys His Leu Asn Gln Gly Thr Asp
            595                 600                 605

Glu Asp Ile Tyr Leu Leu Gly Lys Ala Thr Leu Pro Gly Phe Arg Thr
    610                 615                 620

Ile His Cys
625
```